US008298771B2

(12) United States Patent
Smith et al.

(10) Patent No.: US 8,298,771 B2
(45) Date of Patent: *Oct. 30, 2012

(54) EPITOPE REGIONS OF A THYROTROPHIN (TSH) RECEPTOR, USES THEREOF AND ANTIBODIES THERETO

(75) Inventors: Bernard Rees Smith, Cardiff (GB); Jadwiga Furmaniak, Cardiff (GB); Jane Fina Sanders, Cardiff (GB)

(73) Assignee: RSR Limited, Pentwyn, Cardiff (GB)

(*) Notice: Subject to any disclaimer, the term of this patent is extended or adjusted under 35 U.S.C. 154(b) by 0 days.

This patent is subject to a terminal disclaimer.

(21) Appl. No.: 12/333,740

(22) Filed: Dec. 12, 2008

(65) Prior Publication Data
US 2009/0203036 A1    Aug. 13, 2009

Related U.S. Application Data

(63) Continuation of application No. 10/488,074, filed as application No. PCT/GB02/03831 on Aug. 21, 2002.

(30) Foreign Application Priority Data

Aug. 23, 2001 (GB) .................................. 0120649.9
Jul. 1, 2002 (GB) .................................. 0215212.2

(51) Int. Cl.
G01N 33/53 (2006.01)

(52) U.S. Cl. ....................................................... 435/7.1

(58) Field of Classification Search ........................ None
See application file for complete search history.

(56) References Cited

U.S. PATENT DOCUMENTS

| 4,244,940 | A | 1/1981 | Jeong et al. |
| 4,472,508 | A | 9/1984 | Ingbar |
| 4,609,622 | A | 9/1986 | Kohn et al. |
| 5,578,496 | A | 11/1996 | Atassi et al. |
| 5,614,363 | A | 3/1997 | Cone |
| 5,639,627 | A | 6/1997 | Tanaka |
| 5,705,400 | A | 1/1998 | Furmaniak-Wehr |
| 5,744,348 | A | 4/1998 | Cone |
| 5,814,461 | A | 9/1998 | Bergmann et al. |
| 5,919,632 | A | 7/1999 | Bergmann |
| 6,066,475 | A | 5/2000 | Maclaren et al. |
| 6,228,597 | B1 | 5/2001 | Parmentier et al. |
| 6,261,800 | B1 | 7/2001 | Nikolics et al. |
| 6,284,491 | B1 | 9/2001 | Wondisford et al. |
| 6,537,760 | B1 | 3/2003 | Bergmann et al. |
| 7,001,775 | B1 | 2/2006 | Burne et al. |
| 8,110,664 | B2 | 2/2012 | Sanders et al. |

FOREIGN PATENT DOCUMENTS

| DE | 196 51 093 | 6/1998 |
| EP | 0 153 114 | 8/1985 |
| EP | 0 218 587 | 11/1990 |
| EP | 0 482 598 | 4/1992 |
| EP | 0 139 676 | 11/1992 |
| EP | 0 095 346 | 4/1993 |
| EP | 0 719 858 | 7/1996 |
| EP | 0 909 816 | 4/1999 |
| EP | 1 078 986 | 2/2001 |
| JP | 4-149197 | 5/1992 |
| JP | 6-220089 | 8/1994 |
| JP | 7-89991 | 4/1995 |
| WO | 90/13643 | 11/1990 |
| WO | 91/09137 | 6/1991 |
| WO | 93/15750 | 8/1993 |
| WO | 94/02748 | 2/1994 |
| WO | 95/06258 | 3/1995 |
| WO | 97/00447 | 1/1997 |
| WO | 98/20345 | 5/1998 |
| WO | 98/26294 | 6/1998 |
| WO | 99/64865 | 12/1999 |
| WO | 00/05345 | 2/2000 |
| WO | 01/27634 | 4/2001 |
| WO | 01/44300 | 6/2001 |
| WO | 01/63296 | 8/2001 |
| WO | 01/66754 | 9/2001 |
| WO | WO 01/90192 | 11/2001 |
| WO | 03/018632 | 3/2003 |

OTHER PUBLICATIONS

Janeway and Travers, 1997, Immunobiology, p. 2:10.*
Oda, et al., :"Epitope Analysis of the Human Tyrotropin (TSH) Receptor Using Monoclonal Antibodies", Thyroid, vol. 10, No. 12, 2000, 1051-1059.
Kosugi, et al., "At the Cutting Edge Epitope analysis of the thyrotropin receptor, 1997", Molecular and Cellular Endocrinology, 128, 1997 11-18.
Vlase, et al., "Defining the Major Antibody Epitopes on the Human Thyrotropin Receptor in Immunized Mice: Evidence for Intramolecular Epitope Spreading" Endocrinology, vol. 136, No. 10, 1995, 4415-4423.
Seetharamaiah, et al., "Generation and Characterization of Monoclonal Antibodies to the Human Thyrotropin (TSH) Receptor: Antibodies Can Bind to Discrete Conformational or Linear Epitopes and Block TSH Binding", Endo, vol. 136, No. 7, 1995 2817-2824.
Nicholson, et al., "Monoclnoal antibodies to the human TSH receptor: Epitope mapping and binding to the native receptor on the basolateral plasma membrane of thyroid follicular cells", Journal of Molecular Endocrinology, vol. 16, 1996, 159-170.
Morgenthaler, Nils G., "New Assay systems for thyrotropin receptor antibodies", Current Opinion in Endocrinology & Diabetes, 1999, 6:251-260.
Rapoport, et al., "The Thyrotropin (TSH) Receptor: Interaction with TSH and Autoantibodies", Endocrine Reviews 19(6): 673-716, 1998.
Costagliola, et al., "Genetic immunization of outbread mice with thyrotropin receptor cDNA provides a model of Graves' disease, " The Journal of ;Clinical Investigation, Mar. 2000, vol. 105, No. 6, 803-811.
Byun, et al., "Identification of the Peptides that inhibit the Function of Human Monoclonal Thyroid-stimulating antibodies from Phage-Displayed Peptide Library", The Journal of Clinical Endocrinology & Metabolism, vol. 86, No. 7, 3311-3318, 2001.
Fan, et al., "Analysis of Autoantibody Reactivity in Patients with Graves' Disease using Recombinant Extracellular Domain of the Human Thyrotropin Receptor and Synthetic Peptides", Autoimmunity, 1193, vol. 15, 285-291, 1993.

(Continued)

Primary Examiner — Amy Juedes
(74) Attorney, Agent, or Firm — Merchant & Gould P.C.

(57) ABSTRACT

The present invention is concerned with epitope regions of a thyrotrophin (TSH) receptor, uses thereof and antibodies thereto.

24 Claims, 52 Drawing Sheets

OTHER PUBLICATIONS

Sanders, et al., "Thyroid-Stimulating Monoclonal Antibodies", Thyroid, vol. 12, No. 12, 2002, 1043-1050.
Jeffreys, et al., "Characterization of the Thyrotropin Binding Pocket", Thyroid, vol. 12, No. 12, 2002, 1051-1061.
Van Der Heijden, et al., "Limitations of the semisynthetic library approach for obtaining human monoclonal autoantibodies to the thyrotropin receptor of Graves' disease", Clin. Exp. Immunol., vol. 118:205-212, 1999.
Akamizu, et al., Characterization of Recombinant Monoclonal Antithyrotripin Receptor Antibodies (TshrAbs) Derived from Lymphocytes of Patients with Graves' Disease: Epitope and Binding Study of Two Stimulatory TSHRAbs Endocrinology, 140(4):1594-1601, 1999.
Shepherd, et al., "Identification of an important thyrotrophin binding site on the human thyrotrophin receptor using monoclonal antibodies", Molecular and Cellular Endocrinology 149 (1999) 197-206.
Sanders, et al., "The Interaction of TSH Receptor Antoantibodies with $^{125}$I-Labelled TSH Receptor", The Journal of Clinical Endocrinology & Metabolism, 84(10):3797-3802, 1999.
Valente, et al., "Monoclonal antibodies to the thyrotropin receptor: Stimulating and blocking antibodies derived from the lymphocytes of patients with Graves' disease", Proc. Natl. Acad. Sci. 79 (1982) 6680-6684.
Misrahi, et al., Cloning, sequencing and expression of human TSH receptor, Biochem. Biophys. Res. Commun. 166 (1), 394-403 (1990).
Southgate, et al., "A Receptor Assay for the Measurement of the TSH Receptor Antibodies in Unextracted Serum", Clinical Endocrinology (1984) 20, 539-548.
Matsuba, et al., "Expression of recombinant human thyrotropin", J. Biochem. (Tokyo) (1995), 118(2), 265-70.
Ludgate, et al., "Use of the recombinant human thyrotropin receptor (TSH-R) expressed in mammalian cell lines to assay TSH-R autoantibodies", Mol. Cell. Endocrinol. (1990), 73(1), R13-R18.
Miura, et al., "Fundamental and clinical evaluation of TSH antibody (TRAb) assay kit", Igaku to Yakugaku (1993), 30(2), 341-8.
Sanders, et al., "Understanding the thyrotropin receptor function-structure relationship", Bailliere's Clinical Endocrinology and Metabolism, 11(3) 1997, 451-479.
Smith, B. Rees, "Development of a Luminescent Bioassay for Thyrotropin-Receptor Antibodies", J. Endocrinol. Invest. 21, 1998, 69.
Furmaniak, et al., "Immunity to the thyroid-stimulating hormone receptor", Springer Semin Immunopathol (1993) 14:309-321.
Oda, et al., "Binding characteristics of antibodies to the TSH receptor", J. of Mol. Endocrinology (1998) 20, 233-244.
Prentice, et al., "Thyrotropin (TSH) Receptor Autoantibodies Do Not Appear to Bind to the TSH Receptor Produced in an in Vitro Transcription/Translation System", JCE & M, 82(4) 1997, 1288-1292.
Evans et al., 1990. *Journal of Clinical Endocrinology and Metabolism*. p. 374-377. vol. 84, No. 1.
Martin et al., 1997. *J. Clin. End. Met.* vol. 82: 3361-3366.
Bobovnikova et al., 1997, *Endocrinology*. vol. 138: 588-593.
Marion et al., Characterization of monoclonal antibodies to the human thyrotropin receptor, *Endocrinology* (1992) 130: 967-975.
Szkudlinski et al., Thyroid-stimulating hormone and thyroid-stimulating hormone receptor structure-function relationships, *Physiol. Res.* (2002) 82: 473-502.
Klimka et al., "Human anti-CD30 recombinant antibodies by guided phage antibody selection using cell planning" *Brit. J. Cancer* (2000) 82 (2): 252-260.
Bradley-Mullen, *Activation of Distinct Subsets of T Suppressor Cells with Type III Pneutnococcal Polysaccharide Coupled to Syngeneic Spleen Cells*, in: Immunological Tolerance to Self and Non-Self, Buttisto et al, eds., Annals N. Y. Acad. Sci. vol. 392, pp. 156-166, 1982.
Sinha et al., "Autoimmune diseases: The failure of self tolerance," *Science* (1990) 248: 1380-1388.
Hendry et al., "X-ray structure of a monoclonal antibody that binds to a major autoantigenic epitope on thyroid peroxidase," *Thyroid* (2001) 11 (12): 1091-1099.
Kita et al., "Regulation and transfer of a murine model of thyrotropin receptor antibody mediated Graves' Disease," *Endocrinology* (1999) 140 (3): 1392-1398.
Kettleborough et al., "Optimization of primers for cloning libraries of mouse immunoglobulin genes using the polymerase chain reaction," *Eur. J. Immunol.* (1993) 23: 206-211.
Smith et al., "A New Assay for Thyrotropin Receptor Autoantibodies." *Thyroid*, vol. 14, No. 10, 2004, pp. 830-835.
Hellmark et al., "Point mutations of single amino acids abolish ability of $\alpha_3$ NCI domain to elicit experimental autoimmune glomerulonephritis in rats," *The Journal of Biological Chemistry* (2003) 47 (21): 46516-46522.
Akamizu et al. "Molecular Analysis of Stimulatory Anti-Thyrotropin Receptor Antibodies (TSAbs) Involved in Graves' Disease." *J. of Immun.* 1996. pp. 3148-3152.
Ando et al. "A monoclonal thyroid-stimulating antibody." *J. of Clin. Invest.* vol. 110. No. 11. 2002. pp. 1667-1674.
Ando et al. "Monoclonal antibodies to the thyrotropin receptor." *Clinical & Develop. Immunology*. vol. 12. No. 2. 2005. pp. 137-143.
Borrebaeck et al. "Kinetic Analysis of Recombinant Antibody—Antigen Interactions: Relations Between Structural domains and antigen binding." *BNS*. 1992. 2 pages.
Costagliola et al. "Guest Editorial: Monoclonal Antibodies with Thyroid Stimulating Activity, at Last." *Thyroid*. vol. 12. No. 12. 2002. pp. 1039-1041.
Davies et al. "Affinity improvement of single antibody VH domains: residues in all three hypervariable regions affect antigen binding." *Immunol*. vol. 2. 1996. pp. 169-1793.
Davies. "Editorial: A New Story About "Monoclonal Thyroid Stimulating Antibodies."" *Thyroid*. vol. 12. No. 12. 2002. pp. 1037.
Dayan. "Human monoclonal thyroid-stimulating autoantibody: how useful is a holy grail?" *The Lancet* vol. 362. 2003. pp. 92-128.
Holt et al. "Domain antibodies: proteins for therapy." *TRENDS* vol. 21. No. 11. 2003. pp. 484-490.
Kabat et al. "Sequence of proteins of immunological interest." *US Public Health Service*. vol. 1. 1991. pp. 662, 653, 654, 658, 718.
Knappik et al. "Fully Synthetic Human Combinatorial Antibody Libraries (HuCAL) Based on Modular Consensus Frameworks and CDRs Randomized with Trinucleotides." *JMB*. vol. 296. 2000. pp. 57-86.
Kohn et al. "Characterization of Monoclonal Thyroid-Stimulating and Thyrotropin Binding-Inhibiting Autoantibodies from a Hashimoto's Patient Whose Children had Intrauterine and Neonatal Thyroid Disease." *J. of Clin. Endo & Meta*. vol. 82. No. 12. 1997. 3998-4008.
Kouki et al. "Demonstration of thyroid stimulating activity within H chain fragments of TSAb-IgG by proteaste digestion and reduction." *Clin. Endo*. vol. 48. 1997. pp. 183-188.
Liang et al. "Baculovirus expression cassette vectors for rapid production of complete human IgG from phage display selected antibody fragments." *J. of Imm. Methods*. vol. 247. 2001. pp. 119-130.
Little et al. "Of mice and men; hybridoma and recombinant antibodies." *Review Immunology Today*. vol. 21. No. 8. pp. 364-370.
Nucleotide—Mus musculus anti-DNA antibody Ig kappa chain mRNA, V-J region, hybridoma 84.26, partial cds. http://www.ncbi.nlm.nih.gov/nuccore/89619.
Pedersen et al. "TSH-receptor antibody measurement for differentiation of hyperthyroidism into Graves' disease and multinodular toxic goiter: a comparison of two competitive binding assays." *Clin. Endo*. vol. 55. 2001. pp. 381-390.
Rapaport et al. "Editorial: Whither TSH Receptor Blocking Antibodies in the Treatment of Graves' Disease?" *Thyroid*. vol. 18.2008. pp. 695-696.
Smith et al. "The Thyroid-Stimulating Properties of Long-Acting Thyroid Stimulator γG-Globulin subunits." *Biochem et Biophysics Acta*. vol. 192. 1969. pp. 277-285.
Smith et al. "TSH-Receptor-Autoantibody Interactions." *Horm. Metabl. Res*. vol. 41. 2009. pp. 448-455.
Yoshida et al. "Monoclonal Antibodies to the Thyrotropin Receptor Bind to a 56-kDa Subunit of the Thyrotropin Receptor and Show Heterogeneous Bioactivities." *J. of Bio Chem*. vol. 263. No. 31. 1988. pp. 16341-16347.

\* cited by examiner

```
          MRPTPLLQLALLALPRSLGGKGCPSPPCECHQEDDFRVT    Majority

1      MRPADLLQLVLLLDLPRDLGGMGCSSPPCECHQEEDFRVT    HTSHR.PRO
   1      MSLTPLLQLALVLALPRSLRGKGCPSPPCECHQEDDFRVT    PTSHR.PRO
   1      MRPTPLLRLALFLVLPSSLGGERCPSPPCECRQEDDFRVT    BTSHR.PRO
   1      MRQTPLLQLALLLSLPRSLGGKGCPSPPCECHQEDDFRVT    CTSHR.PRO
   1      MRPPPLLHLALLLALPRSLGGKGCPSPPCECHQEDDFRVT    DTSHR.PRO
   1      MRPGSLLLLVLLLALSRSLRGKECASPPCECHQEDDFRVT    MTSHR.PRO
   1      MRPGSLLQLTLLLALPRSLWGRGCTSPPCECHQEDDFRVT    RTSHR.PRO
   1      MRPTPLLRLALLLVLPSSLWGERCPSPPCECRQEDDFRVT    STSHRP.PRO

CKDIHRIPSLPPSTQTLKFIETHLKTIPSRAFSNLPNISR    Majority

41      CKDIQRIPSLPPSTQTLKLIETHLRTIPSHAFSNLPNISR    HTSHR.PRO
  41      CKDIHSIPPLPPNTQTLKFIETHLKTIPSRAFSNLPNISR    PTSHR.PRO
  41      CKDIQSIPSLPPSTQTLKFIETHLKTIPSRAFSNLPNISR    BTSHS.PRO
  41      CKDIHRIPSLPPSTQTLKFIETHLKTIPSRAFSNLPNISR    CTSHR.PRO
  41      CKDIHRIPTLPPSTQTLKFIETQLKTIPSRAFSNLPNISR    DTSHR.PRO
  41      CKELHRIPSLPPSTQTLKLIETHLKTIPSLAFSSLPNISR    MTSHR.PRO
  41      CKELHQIPSLPPSTQTLKLIETHLKTIPSLAFSSLPNISR    RTSHS.PRO
  41      CKDIQRIPSLPPSTQTLKFIETHLKTIPSRAFSNLPNISR    STSHRP.PRO

IYLSIDATLQQLESHSFYNLSKMTHIEIRNTRSLTYIDPG    Majority

81      IYVSIDVTLQQLESHSFYNLSKVTHIEIRNTRNLTYIDPD    HTSHR.PRO
  81      IYLSIDATLQQLESQSFYNLSKMTHIEIRNTRSLTYINPG    PTSHR.PRO
  81      IYLSIDATLQQLESHSFYNLSKVTHIEIRNTRSLTYIDSG    BTSHR.PRO
  81      IYLSIDATLQRLESHSFYNLSKMTHIEIRNTRSLTYIDPG    CTSHR.PRO
  81      IYLSIDATLQRLESHSFYNLSKMTHIEIRNTRSLTSIDPD    DTSHR.PRO
  81      IYLSIDATLQRLEPHSFYNLSKMTHIEIRNTRSLTYIDPD    MTSHR.PRO
  81      IYLSIDATLQRLEPHSFYNLSKMTHIEIRNTRSLTYIDPD    RTSHR.PRO
  81      IYLSIDATLQQLESHSFYNLSKVTHIEIRNTRSLTYIDSG    STSHRP.PRO

ALKELPLLKFLGIFNTGLRVFPDLTKVYSTDVFFILEITD    Majority

121      ALKELPLLKFLGIFNTGLKMFPDLTKVYSTDIFFILEITD    HTSHR.PRO
 121      ALKDLPLLKFLGIFNTGLRIFPDLTKVYSTDVFFILEITD    PTSHR.PRO
 121      ALKELPLLKFLGIFNTGLRVFPDLTKIYSTDVFFILEITD    BTSHR.PRO
 121      ALKELPLLKFLGIFNTGLGVFPDLTKVYSTDVFFILEITD    CTSHR.PRO
 121      ALKELPLLKFLGIFNTGLGVFPDVTKVYSTDVFFILEITD    DTSHR.PRO
 121      ALTELPLLKFLGIFNTGLRIFPDLTKIYSTDIFFILEITD    MTSHR.PRO
 121      ALTELPLLKFLGIFNTGLRIFPDLTKIYSTDVFFILEITD    RTSHR.PRO
 121      ALKELPLLKFLGIFNTGLRVFPDLTKIYSTDVFFILEITD    STSHRP.PRO

NPYMTSIPANAFQGLCNETLTLKLYNNGFTSIQGHAFNGT    Majority

161      NPYMTSIPVNAFQGLCNETLTLKLYNNGFTSVQGYAFNGT    HTSHR.PRO
 161      NPYMTSIPANAFQGLCNETLTLKLYNNGFTSVQGHAFNGT    PTSHR.PRO
 161      NPYMTSIPANAFQGLCNETLTLKLYNNGFTSIQGHAFNGT    BTSHR.PRO
 161      NPYMTSIPANAFQGLCNETLTLKLYNNGFTSIQGHAFNGT    CTSHR.PRO
 161      NPYMASIPANAFQGLCNETLTLKLYNNGFTSIQGHAFNGT    DTSHR.PRO
 161      NPYMTSVPENAFQGLCNETLTLKLYNNGFTSVQGHAFNGT    MTSHR.PRO
 161      NPYMTSVPENAFQGLCNETLTLKLYNNGFTSIQGHAFNGT    RTSHR.PRO
 161      NPYMTSVPANAFQGLSNETLTLKLYNNGFTSIQGHAFNGT    STSHRP.PRO
```

FIG. 1

```
         ATGAGGCCGACGCCCCTGCTGCAGCTGGCGCTGCTTCTCG    Majority

1     ATGAGGCAGACGCCCCTGCTGCAGCTGGCGTTACTTCTCT    CAT.SEQ
   1     ATGCGGCCGACGCCCCTCCTGCGGCTGGCGCTGTTTCTGG    COW.SEQ
   1     ATGAGGCCGCCGCCCTGCTGCACCTGGCGCTGCTTCTCG     DOG.SEQ
   1     ATGAGGCCAGGGTCCCTGCTGCTGCTTGTTCTGCTGCTCG    MOUSE.SEQ
   1     ATGAGTCTGACGCCCTGTTGCAGCTGGCGCTCGTTCTCG     PTSHR.SEQ
   1     ATGAGGCCAGGGTCCCTGCTCCAGCTCACTCTGCTGCTCG    RAT.SEQ
   1     ATGCGGCCGACGCCCCTCCTGCGGTTGGCGCTGCTTCTGG    SHEEP.SEQ
   1     ATGAGGCCGGCGGACTTGCTGCAGCTGGTGCTGCTGCTCG    HTSHR.SEQ

CCCTGCCCAGGAGCCTGGGGGGGAAGGGGTGTCCGTCTCC    Majority

41     CCCTGCCCAGGAGCCTGGGGGGGAAAGGGTGTCCGTCTCC    CAT.SEQ
  41     TCCTGCCCAGCAGCCTCGGTGGGGAGAGGTGTCCGTCTCC    COW.SEQ
  41     CCCTGCCCAGGAGCCTGGGGGGGAAGGGGTGTCCTTCTCC    DOG.SEQ
  41     CCCTGTCCAGGAGCCTGCGGGGCAAAGAGTGTGCGTCTCC    MOUSE.SEQ
  41     CCCTGCCCAGGAGCCTCAGGGGGAAAGGGTGTCCGTCTCC    PTSHR.SEQ
  41     CCCTGCCCAGGAGCCTCTGGGGCAGAGGGTGTACTTCTCC    RAT.SEQ
  41     TCCTGCCCAGCAGCCTCTGGGGGGAGAGGTGTCCGTCTCC    SHEEP.SEQ
  41     ACCTGCCCAGGGACCTGGGCGGAATGGGGTGTTCGTCTCC    HTSHR.SEQ

GCCCTGCGAGTGCCACCAGGAGGACGACTTCAGAGTCACC    Majority

81     GCCCTGCGAGTGTCACCAGGAAGATGACTTCAGAGTCACC    CAT.SEQ
  81     GCCCTGCGAATGCCGCCAGGAGGACGACTTCAGAGTCACC    COW.SEQ
  81     CCCCTGTGAGTGCCACCAGGAGGATGACTTCAGAGTCACC    DOG.SEQ
  81     ACCCTGTGAGTGTCACCAGGAGGACGACTTCAGAGTCACC    MOUSE.SEQ
  81     GCCCTGCGAATGCCACCAGGAGGACGACTTCAGAGTCACC    PTSHR.SEQ
  81     ACCCTGCGAATGCCACCAGGAGGACGACTTCAGAGTCACC    RAT.SEQ
  81     GCCCTGCGAATGCCGCCAGGAGGACGACTTCAGAGTCACC    SHEEP.SEQ
  81     ACCCTGCGAGTGCCATCAGGAGGAGGACTTCAGAGTCACC    HTSHR.SEQ

TGCAAGGATATCCACCGCATCCCCAGCTTACCGCCCAGCA    Majority

121     TGCAAGGATATTCACCGTATCCCCAGCCTACCGCCCAGCA    CAT.SEQ
 121     TGCAAGGACATCCAGAGCATCCCTAGCTTACCCCCCAGCA    COW.SEQ
 121     TGCAAGGATATCCACCGCATCCCCACCCTACCACCCAGCA    DOG.SEQ
 121     TGCAAGGAGCTCCACCGAATCCCCAGCCTGCCGCCCAGCA    MOUSE.SEQ
 121     TGCAAGGATATCCACAGCATCCCCCCCTTACCACCCAATA    PTSHR.SEQ
 121     TGCAAGGAACTCCACCAAATCCCCAGCCTACCGCCCAGCA    RAT.SEQ
 121     TGCAAGGACATCCAGCGCATCCCTAGCTTACCCCCCAGCA    SHEEP.SEQ
 121     TGCAAGGATATTCAACGCATCCCCAGCTTACCGCCCAGTA    HTSHR.SEQ

CGCAGACTCTGAAGTTTATAGAGACTCATCTGAAAACCAT    Majority

161     CGCAGACTCTGAAATTTATAGAGACTCATCTGAAAACCAT    CAT.SEQ
 161     CGCAGACCCTGAAGTTTATAGAGACTCATCTGAAAACCAT    COW.SEQ
 161     CGCAGACTCTGAAGTTTATAGAGACTCAGCTGAAAACCAT    DOG.SEQ
 161     CCCAGACTCTGAAGCTCATCGAGACTCATCTGAAGACCAT    MOUSE.SEQ
 161     CTCAGACACTAAAGTTTATAGAGACTCATCTGAAAACCAT    PTSHR.SEQ
 161     CCCAGACTCTGAAGCTCATCGAGACTCACCTGAAGACCAT    RAT.SEQ
 161     CGCAGACCCTGAAGTTTATAGAGACTCATCTGAAAACCAT    SHEEP.SEQ
 161     CGCAGACTCTGAAGCTTATTGAGACTCACCTGAGAACTAT    HTSHR.SEQ
```

FIG. 2

```
        TCCCAGTCGTGCATTTTCAAATCTGCCCAATATTTCCAGG    Majority

201     TCCCAGTCGTGCATTTTCAAATCTGCCCAATATTTCCAGG    CAT.SEQ
201     TCCCAGTCGTGCGTTCTCAAATCTGCCCAATATTTCCAGG    COW.SEQ
201     TCCCAGTCGTGCATTTTCAAATCTGCCCAATATTTCCAGG    DOG.SEQ
201     ACCCAGTCTTGCATTTTCGAGTCTGCCCAATATTTCCAGG    MOUSE.SEQ
201     CCCCAGTCGTGCATTTTCAAATCTGCCCAATATTTCCAGG    PTSHR.SEQ
201     TCCCAGTCTTGCCTTTTCGAGCCTGCCCAATATTTCCAGG    RAT.SEQ
201     TCCCAGTCGTGCGTTCTCAAATTTGCCCAATATTTCCAGG    SHEEP.SEQ
201     TCCAAGTCATGCATTTTCTAATCTGCCCAATATTTCCAGA    HTSHR.SEQ

ATCTACTTGTCAATAGATGCAACTCTGCAGCGGCTGGAAT    Majority

241     ATCTACTTGTCAATAGATGCAACTCTGCAGCGACTGGAAT    CAT.SEQ
241     ATCTACTTGTCAATAGATGCAACTCTGCAGCAGCTGGAAT    COW.SEQ
241     ATCTACTTGTCAATAGATGCAACTCTGCAGCGGCTGGAAT    DOG.SEQ
241     ATCTATTTATCTATAGATGCAACTCTGCAGCGGCTGGAAC    MOUSE.SEQ
241     ATCTACCTGTCAATAGATGCAACTCTACAGCAGCTGGAAT    PTSHR.SEQ
241     ATCTATCTATCCATAGATGCCACTCTGCAGCGACTGGAGC    RAT.SEQ
241     ATCTACTTGTCAATAGATGCGACTTTGCAGCAACTGGAAT    SHEEP.SEQ
241     ATCTACGTATCTATAGATGTGACTCTGCAGCAGCTGGAAT    HTSHR.SEQ

CACATTCCTTCTACAATTTG                        Majority

281     CACATTCCTTCTACAATTTG                        CAT.SEQ
281     CACATTCCTTCTACAATTTA                        COW.SEQ
281     CACATTCCTTCTACAATTTA                        DOG.SEQ
281     CACATTCTTTCTACAATTTG                        MOUSE.SEQ
281     CACAGTCCTTCTACAATTTG                        PTSHR.SEQ
281     CACATTCTTTCTACAATTTG                        RAT.SEQ
281     CACATTCCTTCTACAATTTA                        SHEEP.SEQ
281     CACACTCCTTCTACAATTTG                        HTSHR.SEQ
```

FIG. 2 CONT'D

```
      TKLDAVYLNKNKYLTAIDKDAFGGVYSGFTLLDVSYTSVT      Majority

200   TKLDAVYLNKNKYLTVIDKDAFGGVYSGPSLLDVSQTSVT      HTSHR.PRO
200   TKLDAVYLNKNKYLTVIDKDAFGGVFSGPTLLDVSYTSVT      PTSHR.PRO
200   TKLDAVYLNKNKYLTVIGQDAFAGVYSGPTLLDISYTSVT      BTSHR.PRO
200   TKLDAVYLNKNKYLTAIDQDAFGGVYSGPTLLDVSYTSVT      CTSHR.PRO
200   TKLDAVYLNKNKYLSAIDKDAFGGVYSGPTLLDVSYTSVT      DTSHR.PRO
200   TKLDAVYLNKNKYLTAIDNDAFGGVYSGPTLLDVSSTSVT      MTSHR.PRO
200   TKLDAVYLNKNKYLTAIDKDAFGGVYSGPTLLDVSSTSVT      RTSHR.PRO
200   TKLDAVYLNKNKYLTVIDQDAFAGVYSGPTLLDISYTSVT      STSHRP.PRO

ALPSKGLEHLKELIARNTWTLKKLPLSPSFLHLTRADLSY      Majority

240   ALPSKGLEHLKELIARNTWTLKKLPLSLSFLHLTRADLSY      HTSHR.PRO
240   ALPPKGLEHLKELIARNTWTLKKLPLSLSFLHLTRADLSY      PTSHR.PRO
240   ALPSKGLEHLKELIARNTWTLRKLPLSLSFLHLTRADLSY      BTSHS.PRO
240   ALPSKGLEHLKELIARNTWTLKKLPLTLSFLHLTRADLSY      CTSHR.PRO
240   ALPSKGLEHLKELIARNTWTLKKLPLSLSFLHLTRADLSY      DTSHR.PRO
240   ALPSKGLEHLKELIAKDTWTLKKLPLSLSFLHLTRADLSY      MTSHR.PRO
240   ALPSKGLEHLKELIAKNTWTLKKLPLSLSFLHLTRADLSY      RTSHS.PRO
240   ALPSKGLEHLKELIARNTWTLKKLPLSLSFLHLTRADLSY      STSHRP.PRO

PSHCCAFKNQKKIRGILESLM                         Majority

280   PSHCCAFKNQKKIRGILESLM                         HTSHR.PRO
280   PSHCCAFKNQKKIRGILESLM                         PTSHR.PRO
280   PSHCCAFKNQKKIRGILQSLM                         BTSHR.PRO
280   PSHCCAFKNQKKIRGILESFM                         CTSHR.PRO
280   PSHCCAFKNQKKIRGILESLM                         DTSHR.PRO
280   PSHCCAFKNQKKIRGILESLM                         MTSHR.PRO
280   PSHCCAFKNQKKIRGILESLM                         RTSHR.PRO
280   PSHCCAFKNQKNIRGILQSLM                         STSHRP.PRO
```

FIG. 3

```
      TCTTACACCAGTGTCACTGCCCTTCCATCCAAAGGCCTGG  Majority

700   TCTTACACCAGTGTCACTGCCCTGCCATCCAAAGGCCTGG  CAT.SEQ
700   TCTTATACCAGTGTCACAGCCCTACCATCCAAAGGCCTGG  COW.SEQ
700   TCTTACACCAGTGTTACTGCCCTGCCATCCAAAGGCCTGG  DOG.SEQ
700   TCTTCCACCAGCGTCACTGCCCTTCCTTCCAAAGGCCTGG  MOUSE.SEQ
700   TCTTATACCAGTGTTACTGCCCTGCCACCCAAAGGCCTGG  PTSHR.SEQ
700   TCTTCCACCAGCGTTACTGCTCTTCCTTCCAAAGGCCTGG  RAT.SEQ
700   TCTTATACCAGTGTCACTGCCCTACCATCCAAAGGCCTGG  SHEEP.SEQ
700   TCTCAAACCAGTGTCACTGCCCTTCCATCCAAAGGCCTGG  HTSHR.SEQ

AGCACCTGAAGGAACTGATACCAAGAAACACTTGGACTCT  Majority

740   AGCACCTGAAGGAATTGATAGCAAGAAACACTTGGACTCT  CAT.SEQ
740   AACACCTGAAGGAATTGATAGCAAGAAACACTTGGACTCT  COW.SEQ
740   AGCATCTAAAGGAGCTGATAGCAAGAAACACTTGGACTCT  DOG.SEQ
740   AGCACCTCAAAGAACTGATCGCAAAAGACACCTGGACTCT  MOUSE.SEQ
740   AACACCTGAAGGAACTGATAGCAAGAAATACTTGGACTCT  PTSHR.SEQ
740   AGCACCTCAAAGAGCTGATCGCGAAGAACACCTGGACTCT  RAT.SEQ
740   AACACCTGAAGGAATTGATAGCAAGAAACACTTGGACTCT  SHEEP.SEQ
740   AGCACCTGAAGGAACTGATAGCAAGAAACACCTGGACTCT  HTSHR.SEQ

AAAGAAACTTCCACTTTCCTTGAGTTTCCTTCACCTCACA  Majority

780   AAAGAAACTTCCACTTACCTTGAGTTTCCTTCACCTCACA  CAT.SEQ
780   AAGGAAACTTCCTCTTTCCTTGAGTTTCCTTCACCTCACA  COW.SEQ
780   AAAGAAACTCCCACTTTCCTTGAGTTTCCTTCACCTTACA  DOG.SEQ
780   CAAAAAGCTCCCGCTGTCGTTGAGTTTCCTCCACCTCACT  MOUSE.SEQ
780   AAAGAAACTTCCACTGTCCTTGAGTTTCCTTCACCTCACA  PTSHR.SEQ
780   CAAAAAGCTCCCCCTGTCCTTGAGCTTCCTCCACCTCACT  RAT.SEQ
780   AAAGAAACTTCCTCTTTCCTTGAGTTTCCTTCACCTCACA  SHEEP.SEQ
780   TAAGAAACTTCCACTTTCCTTGAGTTTCCTTCACCTCACA  HTSHR.SEQ

CGGGCTGACCTTTCTTATCCAAGCCACTGCTGTGCTTTTA  Majority

820   CGGGCTGACCTTTCTTATCCAAGCCACTGCTGTGCTTTTA  CAT.SEQ
820   CGGGCTGACCTTTCTTATCCGAGCCACTGCTGCGCTTTTA  COW.SEQ
820   CGGGCTGACCTTTCTTATCCAAGCCACTGCTGTGCTTTTA  DOG.SEQ
820   CGGGCTGACCTCTCTTACCCGAGCCACTGCTGCGCTTTTA  MOUSE.SEQ
820   CGAGCTGACCTTTCTTATCCAAGCCACTGCTGTGCTTTTA  PTSHR.SEQ
820   CGGGCTGACCTCTCTTACCCAAGTCACTGCTGTGCTTTTA  RAT.SEQ
820   CGGGCTGACCTTTCTTATCCGAGCCACTGCTGTGCTTTTA  SHEEP.SEQ
820   CGGGCTGACCTTTCTTACCCAAGCCACTGCTGTGCCTTTA  HTSHR.SEQ

AGAATCAGAAGAAAATCAGACCAATCCTTGACTCTTTAAT  Majority

860   AGAATCAGAAGAAAATCAGAGGAATCCTTGAGTCCTTCAT  CAT.SEQ
860   AGAATCAGAAGAAAATCAGAGGAATCCTTGAGTCTTTAAT  COW.SEQ
860   AGAATCAGAAGAAAATCAGAGGAATCCTTGAGTCCTTAAT  DOG.SEQ
860   AGAACCAGAAGAAAATCAGGGGAATCCTGGAGTCTTTGAT  MOUSE.SEQ
860   AGAATCAGAAGAAGATCAGAGGAATCCTTGAGTCTTTAAT  PTSHR.SEQ
860   AGAACCAGAAGAAAATCAGGGGAATCCTAGAGTCTTTGAT  RAT.SEQ
860   AGAATCAGAAGAATATCAGAGGAATCCTTGAGTCTTTAAT  SHEEP.SEQ
860   AGAATCAGAAGAAAATCAGAGGAATCCTTGAGTCCTTGAT  HTSHR.SEQ
```

FIG. 4

```
      KELIARNTWTLKKLPLSLSFLHLTRADLSYPSHCCAFKNQ  Majority

250   KELIARNTWTLKKLPLSLSFLHLTRADLSYPSHCCAFKNQ  HTSHR.PRO
250   KELIARNTWTLKKLPLSLSFLHLTRADLSYPSHCCAFKNQ  PTSHR.PRO
250   KELIARNTWTLRKLPLSLSFLHLTRADLSYPSHCCAFKNQ  BTSHR.PRO
250   KELIARNTWTLKKLPLTLSFLHLTRADLSYPSHCCAFKNQ  CTSHR.PRO
250   KELIARNTWTLKKLPLSLSFLHLTRADLSYPSHCCAFKNQ  DTSHR.PRO
250   KELIAKDTWTLKKLPLSLSFLHLTRADLSYPSHCCAFKNQ  MTSHR.PRO
250   KELIAKNTWTLKKLPLSLSFLHLTRADLSYPSHCCAFKNQ  RTSHR.PRO
250   KELIARNTWTLKKLPLSLSFLHLTRADLSYPSHCCAFKNQ  STSHRP.PRO

KKIRGILESLMCNESSIRSLRQRKSVNALNGPFYQEYEED  Majority

290   KKIRGILESLMCNESSMQSLRQRKSVNALNSPLHQEYEEN  HTSHR.PRO
290   KKIRGILESLMCNESSIRSLRQRKSVNAVNGPFYQEYEED  PTSHR.PRO
290   KKIRGILQSLMCNESSIRGLRQRKSASALNGPFYQEYEDX  BTSHS.PRO
290   KKIRGILESFMCNDSSIRSLRQRKSVNALNGPFDQEYEEY  CTSHR.PRO
290   KKIRGILESLMCNESSIRSLRQRKSVNTLNGPFDQEYEEY  DTSHR.PRO
290   KKIRGILESLMCNESSIRNLRQRKSVNILRGPIYQEYEED  MTSHR.PRO
290   KKIRGILESLMCNESSIRNLRQRKSVNVMRGPVYQEYEEG  RTSHS.PRO
290   KNIRGILQSLMCNESSIWGLRQRKSASALNGPFYQEYEED  STSHRP.PRO

LDGSSAGYKENSKFQDTHSNSHYYVFFEEQEDEIIGFGQE  Majority

330   LGDSIVGYKEKSKFQDTHNNAHYYVFFEEQEDEIIGFGQE  HTSHR.PRO
330   LGDTSVGNKENSKFQDTHSNSHYYVFFEEQEDEIIGFGQE  PTSHR.PRO
330   LGDGSAGYKENSKFQDTQSNSHYYVFFEEQEDEIIGFGQQ  BTSHR.PRO
330   LGDSHAGYKDNSKFQDTRSNSHYYVFFEEQXDEILGFGQE  CTSHR.PRO
330   LGDSHAGYKDNSQFQDTDSNSHYYVFFEEQEDEILGFGQE  DTSHR.PRO
330   PGDNSVGYKQNSKFQESPSNSHYYVFFEEQEDEVVGFGQE  MTSHR.PRO
330   LGDNHVGYKQNSKFQEGPSNSHYYVFFEEQEDEIIGFGQE  RTSHR.PRO
330   LGDGSAGYKENSKFQDTHSNSHYYVFFEDQEDEIIGFGQE  STSHRP.PRO

LKNPQEETLQAFDSHYDYTVCGGSEDMVCTPKSDEFNPCE  Majority

370   LKNPQEETLQAFDSHYDYTICGDSEDMVCTPKSDEFNPCE  HTSHR.PRO
370   LKNPQEETLQAFDSHYDYTVCGGSEDMVCTPKSDEFNPCE  PTSHR.PRO
370   LKNPQEETLQAFDSHYDYTVCGGSEDMVCTPKSDEFNPCE  BTSHR.PRO
370   LKNPQEETLQAFDSHYDYTVCGGNEDMVCTPKSDEFNPCE  CTSHR.PRO
370   LKNPQEETLQAFDSHYDYTVCGGNEDMVCTPKSDEFNPCE  DTSHR.PRO
370   LKNPQEETLQAFESHYDYTVCGDNEDMVCTPKSDEFNPCE  MTSHR.PRO
370   LKNPQEETLQAFDSHYDYTVCGDNEDMVCTPKSDEFNPCE  RTSHR.PRO
370   LKNPQEETLQAFDNHYDYTVCGGSEEMVCTPKSDEFNPCE  STSHRP.PRO

DIMGYKFLRIVVWFVSLLALLGNVFVLVILLTSHYKLTVP  Majority

410   DIMGYKFLRIVVWFVSLLALLGNVFVLLILLTSHYKLNVP  HTSHR.PRO
410   DIMGYRFLRIVVWFVSLLALLGNVFVLVILLTSHYKLTVP  PTSHR.PRO
410   DIMGYKFLRIVVWFVSLLALLGNVFVLVILLTSHYKLTVP  BTSHR.PRO
410   DIMGYKFLRIVVWFVSLLALLGNVFVLIILLTSHYKLTVP  CTSHR.PRO
410   DIMGYKFLRIVVWFVSLLALLGNVFVLIVLLTSHYKLTVP  DTSHR.PRO
410   DIMGYRFLRIVVWFVSLLALLGNIFVLLILLTSHYKLTVP  MTSHR.PRO
410   DIMGYKFLRIVVWFVSPMALLGNVFVLFVLLTSHYKLTVP  RTSHR.PRO
410   DIMGYKFLRIVVWFVSLLALLGNVFVLVILLTSHYKLTVP  STSHRP.PRO
```

FIG. 5

```
        GGAACTGATAGCAAGAAACACTTGGACTCTAAAGAAACTT  Majority

750 GGAATTGATAGCAAGAAACACTTGGACTCTAAAGAAACTT  CAT.SEQ
    750 GGAATTGATAGCAAGAAACACTTGGACTCTAAGGAAACTT  COW.SEQ
    750 GGAGCTGATAGCAAGAAACACTTGGACTCTAAAGAAACTC  DOG.SEQ
    750 AGAACTGATCGCAAAAGACACCTGGACTCTCAAAAAGCTC  MOUSE.SEQ
    750 GGAACTGATAGCAAGAAATACTTGGACTCTAAAGAAACTT  PTSHR.SEQ
    750 AGAGCTGATCGCGAAGAACACCTGGACTCTCAAAAAGCTC  RAT.SEQ
    750 GGAATTGATAGCAAGAAACACTTGGACTCTAAAGAAACTT  SHEEP.SEQ
    750 GGAACTGATAGCAAGAAACACCTGGACTCTTAAGAAACTT  HTSHR.SEQ

CCACTTTCCTTGAGTTTCCTTCACCTCACACGGGCTGACC  Majority

790 CCACTTACCTTGAGTTTCCTTCACCTCACACGGGCTGACC  CAT.SEQ
    790 CCTCTTTCCTTGAGTTTCCTTCACCTCACACGGGCTGACC  COW.SEQ
    790 CCACTTTCCTTGAGTTTCCTTCACCTTACACGGGCTGACC  DOG.SEQ
    790 CCGCTGTCGTTGAGTTTCCTCCACCTCACTCGGGCTGACC  MOUSE.SEQ
    790 CCACTGTCCTTGAGTTTCCTTCACCTCACACGAGCTGACC  PTSHR.SEQ
    790 CCCCTGTCCTTGAGCTTCCTCCACCTCACTCGGGCTGACC  RAT.SEQ
    790 CCTCTTTCCTTGAGTTTCCTTCACCTCACACGGGCTGACC  SHEEP.SEQ
    790 CCACTTTCCTTGAGTTTCCTTCACCTCACACGGGCTGACC  HTSHR.SEQ

TTTCTTATCCAAGCCACTGCTGTGCTTTTAAGAATCAGAA  Majority

830 TTTCTTATCCAAGCCACTGCTGTGCTTTTAAGAATCAGAA  CAT.SEQ
    830 TTTCTTATCCGAGCCACTGCTGCGCTTTTAAGAATCAGAA  COW.SEQ
    830 TTTCTTATCCAAGCCACTGCTGTGCTTTTAAGAATCAGAA  DOG.SEQ
    830 TCTCTTACCCGAGCCACTGCTGCGCTTTTAAGAACCAGAA  MOUSE.SEQ
    830 TTTCTTATCCAAGCCACTGCTGTGCTTTTAAGAATCAGAA  PTSHR.SEQ
    830 TCTCTTACCCAAGTCACTGCTGTGCTTTTAAGAACCAGAA  RAT.SEQ
    830 TTTCTTATCCGAGCCACTGCTGTGCTTTTAAGAATCAGAA  SHEEP.SEQ
    830 TTTCTTACCCAAGCCACTGCTGTGCCTTTAAGAATCAGAA  HTSHR.SEQ

GAAAATCAGAGGAATCCTTGAGTCTTTAATGTGTAATGAG  Majority

870 GAAAATCAGAGGAATCCTTGAGTCCTTCATGTGTAATGAC  CAT.SEQ
    870 GAAAATCAGAGGAATCCTTCAGTCTTTAATGTGTAACGAG  COW.SEQ
    870 GAAAATCAGAGGAATCCTTGAGTCCTTAATGTGTAATGAA  DOG.SEQ
    870 GAAAATCAGGGGAATCCTGGAGTCTTTGATGTGTAATGAG  MOUSE.SEQ
    870 GAAGATCAGAGGAATCCTTGAGTCTTTAATGTGTAATGAG  PTSHR.SEQ
    870 GAAAATCAGGGGAATCCTAGAGTCTTTGATGTGTAATGAG  RAT.SEQ
    870 GAATATCAGAGGAATCCTTCAGTCTTTAATGTGTAACGAG  SHEEP.SEQ
    870 GAAAATCAGAGGAATCCTTGAGTCCTTGATGTGTAATGAG  HTSHR.SEQ

AGCAGTATTCGGAGCCTGCGTCAGAGAAAATCTGTGAATG  Majority

910 AGCAGTATTCGGAGCCTGCGTCAGAGAAAATCTGTGAATG  CAT.SEQ
    910 AGCAGTATTCGGGGCCTGCGTCAGAGAAAATCCGCAAGTG  COW.SEQ
    910 AGCAGTATTCGGAGCCTGCGCCAGAGAAAATCTGTGAATA  DOG.SEQ
    910 AGCAGTATCCGGAACCTTCGTCAAAGGAAATCAGTGAACA  MOUSE.SEQ
    910 AGCAGTATTCGGAGCCTGCGTCAGAGAAAATCTGTGAATG  PTSHR.SEQ
    910 AGTAGTATCCGGAACCTGCGTCAAAGAAAGTCAGTGAACG  RAT.SEQ
    910 AGCAGTATTTGGGGCCTGCGTCAGAGAAAATCCGCGAGTG  SHEEP.SEQ
    910 AGCAGTATGCAGAGCTTGCGCCAGAGAAAATCTGTGAATG  HTSHR.SEQ
```

FIG. 6

```
         CTTTGAATGGTCCCTTCTACCAGGAATATGAAGAGGATCT    Majority

950     CTTTGAATGGTCCCTTCGACCAGGAATATGAAGAGTATCT    CAT.SEQ
 950     CTTTGAATGGTCCCTTCTACCAGGAATATGAGGATNNNCT    COW.SEQ
 950     CTTTGAATGGCCCCTTTGACCAGGAATATGAAGAGTATCT    DOG.SEQ
 950     TCTTGAGGGGTCCCATCTACCAGGAATATGAAGAAGATCC    MOUSE.SEQ
 950     CTGTAAATGGTCCCTTTTACCAAGAATATGAAGAGGATCT    PTSHR.SEQ
 950     TCATGAGGGGTCCCGTCTACCAGGAATATGAAGAAGGTCT    RAT.SEQ
 950     CTTTGAATGGTCCCTTCTACCAGGAATATGAAGAGGATCT    SHEEP.SEQ
 950     CCTTGAATAGCCCCCTCCACCAGGAATATGAAGAGAATCT    HTSHR.SEQ

GGGTGACAGCAGTGTTGGGTACAAGGAAAACTCCAAGTTC    Majority

990     AGGTGACAGCCATGCTGGATATAAGGACAACTCTAAGTTC    CAT.SEQ
 990     GGGTGATGGCAGTGCTGGGTACAAGGAGAACTCCAAGTTC    COW.SEQ
 990     GGGTGACAGCCATGCTGGGTACAAGGACAACTCTCAGTTC    DOG.SEQ
 990     GGGTGACAACAGTGTTGGGTACAAACAAAACTCCAAGTTC    MOUSE.SEQ
 990     GGGCGACACGAGTGTTGGGAATAAGGAAAACTCCAAGTTC    PTSHR.SEQ
 990     GGGTGACAACCATGTTGGGTACAAACAAAACTCCAAGTTC    RAT.SEQ
 990     GGGTGATGGCAGTGCTGGGTACAAGGAGAACTCCAAGTTC    SHEEP.SEQ
 990     GGGTGACAGCATTGTTGGGTACAAGGAAAAGTCCAAGTTC    HTSHR.SEQ

CAGGATACCCATAGCAACTCTCATTATTATGTCTTCTTTG    Majority

1030     CAGGATACTCGCAGCAACTCTCATTATTATGTCTTCTTTG    CAT.SEQ
1030     CAAGATACCCAAAGCAACTCTCATTACTATGTCTTCTTTG    COW.SEQ
1030     CAGGATACCGATAGCAATTCTCATTATTATGTCTTCTTCG    DOG.SEQ
1030     CAGGAGAGCCCAAGCAACTCTCACTATTACGTCTTCTTTG    MOUSE.SEQ
1030     CAGGATACCCATAGCAACTCCATTACTACGTCTTCTTTG     PTSHR.SEQ
1030     CAGGAGGGCCCAAGCAACTCTCACTATTACGTCTTCTTTG    RAT.SEQ
1030     CAAGATACCCACAGCAACTCTCATTACTATGTCTTCTTTG    SHEEP.SEQ
1030     CAGGATACTCATAACAACGCTCATTATTACGTCTTCTTTG    HTSHR.SEQ

AAGAACAAGAGGATGAGATCATTGGTTTTGG             Majority

1070     AAGAACAANNNGACGAGATCCTTGGTTTTGG             CAT.SEQ
1070     AGGAGCAAGAAGATGAGATCATCGGTTTTGG             COW.SEQ
1070     AAGAACAAGAAGATGAGATCCTCGGTTTTGG             DOG.SEQ
1070     AAGAACAAGAGGATGAGGTCGTTGGTTTCGG             MOUSE.SEQ
1070     AAGAACAAGAGGATGAGATCATTGGTTTTGG             PTSHR.SEQ
1070     AAGAACAAGAGGACGAGATCATCGGTTTCGG             RAT.SEQ
1070     AGGATCAAGAAGATGAGATCATCGGTTTTGG             SHEEP.SEQ
1070     AAGAACAAGAGGATGAGATCATTGGTTTTGG             HTSHR.SEQ
```

FIG. 6CONT'D

```
          SHYYVFFEEQEDEIIGFGQELKNPQEETLQAFDSHYDYTV   Majority

750   AHYYVFFEEQEDEIIGFGQELKNPQEETLQAFDSHYDYTI       CAT.SEQ
750   SHYYVFFEEQEDEIIGFGQELKNPQEETLQAFDSHYDYTV       COW.SEQ
750   SHYYVFFEEQEDEIIGFGQQLKNPQEETLQAFDSHYDYTV       DOG.SEQ
750   SHYYVFFEEQXDEILGFGQELKNPQEETLQAFDSHYDYTV       MOUSE.SEQ
750   SHYYVFFEEQEDEILGFGQELKNPQEETLQAFDSHYDYTV       PTSHR.SEQ
750   SHYYVFFEEQEDEVVGFGQELKNPQEETLQAFESHYDYTV       RAT.SEQ
750   SHYYVFFEEQEDEIIGFGQELKNPQEETLQAFDSHYDYTV       SHEEP.SEQ
750   SHYYVFFEDQEDEIIGFGQELKNPQEETLQAFDNHYDYTV       HTSHR.SEQ

CGGSEDMVCTPKSDEFNPCEDIMGYKFLRIVVWFVSLLAL   Majority

790   CGDSEDMVCTPKSDEFNPCEDIMGYKFLRIVVWFVSLLAL       CAT.SEQ
790   CGGSEDMVCTPKSDEFNPCEDIMGYRFLRIVVWFVSLLAL       COW.SEQ
790   CGGSEDMVCTPKSDEFNPCEDIMGYKFLRIVVWFVSLLAL       DOG.SEQ
790   CGGNEDMVCTPKSDEFNPCEDIMGYKFLRIVVWFVSLLAL       MOUSE.SEQ
790   CGGNEDMVCTPKSDEFNPCEDIMGYKFLRIVVWFVSLLAL       PTSHR.SEQ
790   CGDNEDMVCTPKSDEFNPCEDIMGYRFLRIVVWFVSLLAL       RAT.SEQ
790   CGDNEDMVCTPKSDEFNPCEDIMGYKFLRIVVWFVSPMAL       SHEEP.SEQ
790   CGGSEEMVCTPKSDEFNPCEDIMGYKFLRIVVWFVSLLAL       HTSHR.SEQ

LGNVFVLVILLTSHYKLTVPRFLMCNLAFADFCMGMYLLL   Majority

830   LGNVFVLLILLTSHYKLNVPRFLMCNLAFADFCMGMYLLL       CAT.SEQ
830   LGNVFVLVILLTSHYKLTVPRFLMCNLAFADFCMGMYLLL       COW.SEQ
830   LGNVFVLVILLTSHYKLTVPRFLMCNLAFADFCMGLYLLL       DOG.SEQ
830   LGNVFVLIILLTSHYKLTVPRFLMCNLAFADFCMGMYLLL       MOUSE.SEQ
830   LGNVFVLIVLLTSHYKLTVPRFLMCNLAFADFCMGMYLLL       PTSHR.SEQ
830   LGNIFVLLILLTSHYKLTVPRFLMCNLAFADFCMGVYLLL       RAT.SEQ
830   LGNVFVLFVLLTSHYKLTVPRFLMCNLAFADFCMGVYLLL       SHEEP.SEQ
830   LGNVFVLVILLTSHYKLTVPRFLMCNLAFADFCMGLYLLL       HTSHR.SEQ

IASVDLYTHSEYYNHAIDWQTGPGCNTAGFF            Majority

870   IASVDLYTHSEYYNHAIDWQTGPGCNTAGFF                CAT.SEQ
870   IASVDLYTQSEYYNHAIDWQTGPGCNTAGFF                COW.SEQ
870   IASVDLYTQSEYYNHAIDWQTGPGCNTAGFF                DOG.SEQ
870   IASVDLYTHSEYYNHAIDWQTGPGCNAAGFF                MOUSE.SEQ
870   IASVDLYTHSEYYNHAIDWQTGPGCNTAGFF                PTSHR.SEQ
870   IASVDLYTHSEYYNHAIDWQTGPGCNTAGFF                RAT.SEQ
870   IASVDLYTHTEYYNHAIDWQTGPGCNTAGFF                SHEEP.SEQ
870   IASVDLYTQSEYYNHAIDWQTGPGCNTAGFF                HTSHR.SEQ
```

FIG. 7

```
          GCCAAGAGCTCAAAAACCCCCAGGAAGAGACCCTCCAGGC  Majority

700 GCCAGGAGCTTAAAAACCCACAAGAAGAGACCCTACAGGC  CAT.SEQ
      700 GCCAACAGCTCAAAAACCCCCAGGAGGAGACCCTGCAGGC  COW.SEQ
      700 GGCAGGAGCTTAAAAACCCACAGGAAGAGACCCTCCAGGC  DOG.SEQ
      700 GCCAAGAGCTCAAAAATCCTCAGGAAGAGACTCTCCAAGC  MOUSE.SEQ
      700 GCCAAGAGCTCAAAAACCCCCAGGAAGAGACCCTCCAGGC  PTSHR.SEQ
      700 GCCAAGAGCTCAAAAATCCTCAGGAAGAGACTCTCCAAGC  RAT.SEQ
      700 GCCAAGAGCTTAAAAACCCCCAGGAGGAGACCCTGCAGGC  SHEEP.SEQ
      700 GCCAGGAGCTCAAAAACCCCCAGGAAGAGACTCTACAAGC  HTSHR.SEQ

CTTTGACAGCCATTATGACTACACCGTGTGTCGGGGCAGT  Majority

740 CTTCGATAGCCATTATGACTACACTGTGTGTGGAGGCAAT  CAT.SEQ
      740 CTTTGACAGCCATTACGACTATACCGTGTGTGGGGGCAGT  COW.SEQ
      740 CTTTGATAGCCATTATGACTACACTGTGTGTGGTGGCAAT  DOG.SEQ
      740 CTTCGAGAGCCACTATGACTACACGGTGTGTGGGGACAAC  MOUSE.SEQ
      740 CTTTGACAGCCATTACGACTACACCGTGTGTGGGGGCAGT  PTSHR.SEQ
      740 CTTCGACAGCCACTATGACTACACTGTGTGTGGGGACAAC  RAT.SEQ
      740 CTTTGACAACCATTACGACTATACCGTGTGCGGGGGGAGT  SHEEP.SEQ
      740 TTTTGACAGCCATTATGACTACACCATATGTGGGGACAGT  HTSHR.SEQ

GAGGACATGGTGTGTACCCCCAAGTCAGATCAGTTCAACC  Majority

780 GAAGACATGGTGTGTACTCCCAAGTCAGATGAGTTCAACC  CAT.SEQ
      780 GAGGACATGGTGTGTACCCCCAAGTCGGATGAGTTCAACC  COW.SEQ
      780 GAAGACATGGTGTGTACTCCTAAGTCAGATGAGTTCAACC  DOG.SEQ
      780 GAGGACATGGTGTGTACCCCCAAGTCGGACGAGTTTAACC  MOUSE.SEQ
      780 GAAGACATGGTGTGCACCCCCAAGTCAGATGAGTTCAACC  PTSHR.SEQ
      780 GAGGACATGGTGTGTACCCCCAAGTCAGACGAGTTTAACC  RAT.SEQ
      780 GAGGAGATGGTGTGTACCCCCAAGTCGGATGAGTTCAACC  SHEEP.SEQ
      780 GAAGACATGGTGTGTACCCCCAAGTCCGATGAGTTCAACC  HTSHR.SEQ

CCTGTGAAGACATCATGGGCTACAAGTTCCTGAGAATTGT  Majority

820 CCTGTGAAGACATAATGGGCTACAAGTTCCTGAGAATTGT  CAT.SEQ
      820 CCTGTGAGGACATCATGGGCTACAAGTTCCTGAGAATCGT  COW.SEQ
      820 CCTGTGAAGACATAATGGGCTACAAGTTCCTGAGGATTGT  DOG.SEQ
      820 CCTGTGAAGATATCATGGGCTACAGGTTCCTGAGAATCGT  MOUSE.SEQ
      820 CCTGTGAAGACATAATGGGCTACAGGTTCCTGAGAATCGT  PTSHR.SEQ
      820 CCTGTGAAGATATCATGGGCTACAAGTTCCTGAGAATCGT  RAT.SEQ
      820 CCTGTGAGGACATCATGGGCTACAAGTTCCTGAGAATTGT  SHEEP.SEQ
      820 CGTGTGAAGACATAATGGGCTACAAGTTCCTGAGAATTGT  HTSHR.SEQ

GGTGTGGTTTGTTAGTCTGCTGGCTCTCCTGGGCAATGTC  Majority

860 GGTGTGGTTTGTTAGTCTGCTGGCTCTCCTGGGCAATGTC  CAT.SEQ
      860 GGTGTGGTTTGTGAGTCTGCTGGCTCTCCTGGGCAACGTC  COW.SEQ
      860 GGTGTGGTTTGTTAGTCTGCTGGCTCTCCTGGGCAATGTC  DOG.SEQ
      860 GGTGTGGTTTGTCAGTCTGCTGGCTCTCCTGGGCAATATC  MOUSE.SEQ
      860 GGTGTGGTTCGTTAGCCTGCTGGCTCTCCTGGGCAATGTC  PTSHR.SEQ
      860 GGTATGGTTTGTCAGTCCGATGGCTCTCCTGGGCAACGTC  RAT.SEQ
      860 GGTGTGGTTTGTGAGTCTGCTGGCTCTCCTGGGCAACGTC  SHEEP.SEQ
      860 GGTGTGGTTCGTTAGTCTGCTGGCTCTCCTGGGCAATGTC  HTSHR.SEQ
```

FIG. 8

4D7 - HC

DVQLKHSGPELVKPGASMKISCKASGYSFTGYTMNWVKQSHGKNLEWIGL
INPYTGGTNYNQKFKGKAKLTVDKSSSTAFMELLSLTSEDSAVYYCARDG
NLDYWGQGTTLTVSSAKTTPPSVYPLAPGSAAQTNSMVTLGCLVKGYFPE
PVTVTWNSGSLSSGVHTFPAVLQSDLYTLSSSVTVPSSTWPSETVTCNVA
HPASKTKVD

FIG. 9

4D7 - HC

DVQLKHSGPELVKPGASMKISCKASGYSFT GYTMN WVKQSHGKNLEWIG L      50
PCR primer                      CDR I INPYTGGTNYNQKFKG KAKLTVDKSSSTAFMELLSLTSEDSAVYYCAR DG        100
CDR II                                             CDR III NLDY WGQGTTLTVSS AKTTPPSVYPLAPGSAAQTNSMVTLGCLVKGYFPE        150
            constant region

PVTVTWNSGSLSSGVHTFPAVLQSDLYTLSSSVTVPSSTWPSETVTCNVA         200

HPASKTKVD                                                  209
PCR primer

FIG. 10

4D7 - LC

SIVMSQSPASLAVSLGQRATISCRASETVDNYGFSFMHWFQQIPGQPPKL
LIYAASNQGSGVPARFSGSGSGTDFSLNIHPMEEDDTAMYFCQQSKEVPY
TFGGGTKLEIKRADAAPTVSIFPPSSEQLTSGGASVVCFLNNFYPKDINV
KWKIDGSERQNGVLNSWTDQDSKDSTYSMSSTLTLTKDEYERHNSYTCEA
THKTSTSPIVKSFNRNEC

FIG. 11

4D7 - LC

| | |
|---|---|
| SIVMSQSPASLAVSLGQRATISC<span style="border:1px solid">RASETVDNYGFSFMH</span>WFQQIPGQPPKL<br>PCR primer                        CDR I | 50 |
| LIY<span style="border:1px solid">AASNQGS</span>GVPARFSGSGSGTDFSLNIHPMEEDDTAMYF<span style="border:1px solid">CQQSKEVPY</span><br>   CDR II                                         CDR III | 100 |
| <span style="border:1px solid">T</span>FGGGTKLEIKRADAAPTVSIFPPSSEQLTSGGASVVCFLNNFYPKDINV<br>              constant region | 150 |
| KWKIDGSERQNGVLNSWTDQDSKDSTYSMSSTLTLTKDEYERHNSYTCEA | 200 |
| THKTSTSPIVKSFNRNEC<br>             PCR primer | 218 |

FIG. 12

16E5 - HC

DVQLVQSGPELVKPGASVKMSCKASGYSFTGYNMHWVKQSHGKSLEWIGY
IDPYNGATSYNQKFEDKATLTVDKSSSTAYMQLNSLTSEDSAVYYCARRW
DWDPYAMDYWGQGTSVTVSSAKTTAPSVYPLAPVCGDTSGSSVTLGCLVK
GYFPEPVTLTWNSGSLSSGVHTSPAVLQSDLYTLSSSVTVTSSTWPSQSI
TCNVAHPASKTKVD

FIG. 13

16E5 - HC

<u>DVQLVQSGPELVKPGASVKMSCKASGYSFT</u>GYNMHWVKQSHGKSLEWIGY  50
<u>PCR primer</u>                    CDR I

IDPYNGATSYNQKFEDKATLTVDKSSSTAYMQLNSLTSEDSAVYYCARRW  100
  CDR II

DWDPYAMDYWGQGTSVTVSSAKTTAPSVYPLAPVCGDTSGSSVTLGCLVK  150
  CDR III         constant region

GYFPEPVTLTWNSGSLSSGVHTSPAVLQSDLYTLSSSVTVTSSTWPSQSI  200

TCNVA<u>HPASKTKVD</u>  214
      <u>PCR primer</u>

FIG. 14

16E5 - LC

DILLTQSPAILSVSPGERVSFSCRASQSIGTSIHWYQQRTNGSPRLLIKY
ASESISGIFSRFSGSGSGTDFTLTINSVESEDIADYYCQQSNRWPLTFGA
GTKLELKRADAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC

FIG. 15

16E5 - LC

DILLTQSPAILSVSPGERVSFSC RASQSIGTSIH WYQQRTNGSPRLLIK Y        50
PCR primer              CDR I ASESIS GIFSRFSGSGSGTDFTLTINSVESEDIADYYC QQSNRWPLT FGA       100
CDR II                                  CDR III GTKLELKRADAAPTVSIFPPSSEQLTSGGASVVCFLNNFYPKDINVKWKI         150
        constant region

DGSERQNGVLNSWTDQDSKDSTYSMSSTLTLTKDEYERHNSYTCEATHKT         200

STSPIVK SFNRNEC                                            214
        PCR primer

FIG. 16

17D2 - HC

DVQIQQSGPELVKPGASVKMSCKASGYSFTAYNMHWVKQTHGKSLEWIGY
IDPYSGATSYHQKFKGKATLTVDKSSSTAYMRLNSLTSEDSAVYYCARRW
DWDPYAMDYWGQGTSVTVSSAKTTPPSVYPLAPGCGDTTGSSVTLGCLVK
GYFPESVTVTWNSGSLSSSVHTFPALLQSGLYTMSSSVTVPSSAWPSQTV
TCSVAHPASNTTVD

FIG. 17

17D2 - HC

DVQIQQSGPELVKPGASVKMSCKASGYSFT AYNMH WVKQTHGKSLEWIG Y    50
PCR primer                      CDR I

IDPYSGATSYHQKFKG KATLTVDKSSSTAYMRLNSLTSEDSAVYYCAR RW    100
    CDR II

DWDPYAMDY WGQGTSVTVSS AKTTPPSVYPLAPGCGDTTGSSVTLGCLVK    150
 CDR III              constant region

GYFPESVTVTWNSGSLSSSVHTFPALLQSGLYTMSSSVTVPSSAWPSQTV     200

TCSVAHPASNTTVD                                         214
 PCR primer

FIG. 18

17D2 - LC

SVEMSQSPAILSVSPGERISFSCRASQSIGTSIHWYQQRTNGSPRLLIKY
ASASISGIPSRFSGSGSGTDFTLSINSVESEDIADYYCQQSNSWPLTFGA
GTKLELKRADAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC

FIG. 19

17D2 - LC

| | |
|---|---|
| <u>SVEMSQSPAILSVSPGERISFSC</u>`RASQSIGTSIH`WYQQRTNGSPRLLIK`Y` | 50 |
|     PCR primer                             CDR I | |
| `ASASIS`GIPSRFSGSGSGTDFTLSINSVESEDIADYYC`QQSNSWPLT`FGA | 100 |
| CDR II                                      CDR III | |
| GTKLELKRADAAPTVSIFPPSSEQLTSGGASVVCFLNNFYPKDINVKWKI | 150 |
|         constant region | |
| DGSERQNGVLNSWTDQDSKDSTYSMSSTLTLTKDEYERHNSYTCEATHKT | 200 |
| STSPIV<u>KSFNRNEC</u> | 214 |
|        PCR primer | |

FIG. 20

14D3 - HC

DVQMQQPGPELVKPGASLKMSCKASGYSFTGYNMHWVKQSHGKSLEWIGY
IDPYSGATSYNQKFEGKATLTVDKSSSTAYMQLNSLTSEDSAVYYCARRW
DWDPYAMDYWGQGTSVTVSSAKTTAPSVYPLAPVCGDTSGSSVTLGCLVK
GYFPEPVTLTWNSGSLSSGVHTFPAVLQSDLYTLSSSVTVTSSTWPSQSI
TCNVAHPASNTKVD

FIG. 21

14D3 - HC

DVQMQQPGPELVKPGASLKMSCKASGYSFT GYNMH WVKQSHGKSLEWIG Y          50
PCR primer                      CDR I

IDPYSGATSYNQKFEG KATLTVDKSSSTAYMQLNSLTSEDSAVYYCAR RW           100
     CDR II

DWDPYAMDY WGQGTSVTVSSAKTTAPSVYPLAPVCGDTSGSSVTLGCLVK         150
  CDR III              constant region

GYFPEPVTLTWNSGSLSSGVHTFPAVLQSDLYTLSSSVTVTSSTWPSQSI          200

TCNVAHPASNTKVD                                              214
    PCR primer

FIG. 22

14D3 - LC

NILMTQSPAILSVSPGERVSFACRASQSIGTSIHWYQQRTNGSPRLLIKY
ASESISGIPSRFSGSGSGTDFTLSINSVESEDIADYYCQQTNRWPLTFGA
GTKLELKRADAAPTVSIFPPSSEQLTSGGASVVCFLNNFYPKDINVKWKI
DGSERQNGVLNSWTDQDSKDSTYSMSSTLTLTKDEYERHNSYTCEATHKT
STSPIVKSFNRNEC

FIG. 23

14D3 - LC

NILMTQSPAILSVSPGERVSFAC|RASQSIGTSIH|WYQQRTNGSPRLLIK|Y|     50
PCR primer         CDR I

|ASESIS|GIPSRFSGSGSGTDFTLSINSVESEDIADYYC|QQTNRWPLT|FGA     100
CDR II                             CDR III

GTKLELKRADAAPTVSIFPPSSEQLTSGGASVVCFLNNFYPKDINVKWKI     150
      constant region

DGSERQNGVLNSWTDQDSKDSTYSMSSTLTLTKDEYERHNSYTCEATHKT     200

STSPIVKSFNRNEC     214
    PCR primer

FIG. 24

4D7 - HC gacgtccagctgaagcactcaggacctgagctggtgaagcctggagcttc
aatgaagatatcctgtaaggcttctggttactcattcactggctacacca
tgaactgggtgaagcagagccatggaaagaaccttgagtggattggactt
attaatccttacactggtggtactaactacaaccagaagttcaagggcaa
ggccaaattaactgtagacaagtcatccagcacagccttcatggagctcc
tcagtctgacatctgaggactctgcagtctattactgtgcaagagatggt
aaccttgactactggggccaaggcaccactctcacagtctcctcagccaa
aacgacaccccatctgtctatccactggcccctggatctgctgcccaaa
ctaactccatggtgaccctgggatgcctggtcaagggctatttccctgag
ccagtgacagtgacctggaactctggatccctgtccagcggtgtgcacac
cttccagctgtcctgcagtctgacctctacactctgagcagctcagtga
ctgtcccctccagcacctggcccagcgagaccgtcacctgcaacgttgcc
cacccagccagcaagaccaaggtcgac

FIG. 25

4D7 - HC

| | |
|---|---|
| gacgtccagctgaagcactcaggacctgagctggtgaagcctggagcttc<br>PCR primer | 50 |
| aatgaagatatcctgtaaggcttctggttactcattcactggctacacca<br>                                              CDR I | 100 |
| tgaactgggtgaagcagagccatggaaagaaccttgagtggattggactt | 150 |
| attaatccttacactggtggtactaactacaaccagaagttcaagggcaa<br>  CDR II | 200 |
| ggccaaattaactgtagacaagtcatccagcacagccttcatggagctcc | 250 |
| tcagtctgacatctgaggactctgcagtctattactgtgcaagagatggt<br>                                                   CDR III | 300 |
| aaccttgactactggggccaaggcaccactctcacagtctcctcagccaa | 350 |
| aacgacaccccatctgtctatccactggccctggatctgctgcccaaa<br>  constant region | 400 |
| ctaactccatggtgaccctgggatgcctggtcaagggctatttccctgag | 450 |
| ccagtgacagtgacctggaactctggatccctgtccagcggtgtgcacac | 500 |
| cttcccagctgtcctgcagtctgacctctacactctgagcagctcagtga | 550 |
| ctgtcccctccagcacctggcccagcgagaccgtcacctgcaacgttgcc | 600 |
| cacccagccagcaagaccaaggtcgac<br>PCR primer | 627 |

FIG. 26

4D7 - LC agcattgtgatgtcacagtcgccagcttctttggctgtgtctctagggca
gagggccaccatctcctgcagagccagcgaaactgttgataattatggct
ttagttttatgcactggttccaacagataccgggacagccacccaaactc
ctcatctatgctgcatccaaccaaggatccggggtccctgccaggtttag
tggcagtgggtctgggacagacttcagcctcaacatccatcctatggagg
aggatgatactgcaatgtatttctgtcagcaaagtaaggaggttccgtac
acgttcggaggggggaccaagctggaaataaaacgggctgatgctgcacc
aactgtatccatcttcccaccatccagtgagcagttaacatctggaggtg
cctcagtcgtgtgcttcttgaacaacttctaccccaaagacatcaatgtc
aagtggaagattgatggcagtgaacgacaaaatggcgtcctgaacagttg
gactgatcaggacagcaaagacagcacctacagcatgagcagcaccctca
cgttgaccaaggacgagtatgaacgacataacagctatacctgtgaggcc
actcacaagacatcaacttcacccattgtcaagagcttcaacaggaatga
gtgt

FIG. 27

4D7 - LC

<u>agcattgtgatgtcacagtcgccagcttctttggctgtgtctctagggca</u>      50
   PCR primer gagggccaccatctcctgc<span style="border:1px solid">agagccagcgaaactgttgataattatggct</span>      100
                    CDR I <span style="border:1px solid">ttagttttatgcac</span>tggttccaacagataccgggacagccacccaaactc      150 ctcatctat<span style="border:1px solid">gctgcatccaaccaaggatcc</span>ggggtccctgccaggtttag      200
          CDR II tggcagtgggtctgggacagacttcagcctcaacatccatcctatggagg      250 aggatgatactgcaatgtatttctgt<span style="border:1px solid">cagcaaagtaaggaggttccgtac</span>      300
                           CDR III <span style="border:1px solid">acg</span>ttcggaggggggaccaagctggaaataaaacgggctgatgctgcacc      350
                                     constant region aactgtatccatcttcccaccatccagtgagcagttaacatctggaggtg      400 cctcagtcgtgtgcttcttgaacaacttctaccccaaagacatcaatgtc      450 aagtggaagattgatggcagtgaacgacaaaatggcgtcctgaacagttg      500 gactgatcaggacagcaaagacagcacctacagcatgagcagcaccctca      550 cgttgaccaaggacgagtatgaacgacataacagctatacctgtgaggcc      600 actcacaagacatcaacttcacccattgtcaaga<u>gcttcaacaggaatga</u>      650
                                       PCR primer <u>gtgt</u>                                                      654

FIG. 28

16E5 - HC gacgtccagttggtgcaatctggacctgagctggtgaagcctggagcttc
agtgaagatgtcctgcaaggcttctggttactcattcactggctacaaca
tgcactgggtgaagcagagccatggaaagagccttgagtggattgggtat
attgatccttacaatggtgctactagctacaaccagaaattcgaggacaa
ggccacattgactgtagacaaatcttccagcacagcctacatgcagctca
acagcctgacatctgaggactctgcagtctattactgtgcaagaagatgg
gactgggacccttatgctatggactactggggtcaaggaacctcagtcac
cgtctcctcagccaaaacaacagccccatcggtctatccactggcccctg
tgtgtggagatacaagtggctcctcggtgactctaggatgcctggtcaag
ggttatttccctgagccagtgaccttgacctggaactctggatccctgtc
cagtggtgtgcacacctccccagctgtcctgcagtctgacctctacaccc
tcagcagctcagtgactgtaacctcgagcacctggcccagccagtccatc
acctgcaatgtggcccacccggccagcaagaccaaggtcgac

FIG. 29

16E5 - HC

| | |
|---|---|
| gacgtccagttggtgcaatctggacctgagctggtgaagcctggagcttc<br>PCR primer | 50 |
| agtgaagatgtcctgcaaggcttctggttactcattcactggctacaaca<br>                                           CDR I | 100 |
| tgcactgggtgaagcagagccatggaaagagccttgagtggattgggtat<br>CDR I (cont) | 150 |
| attgatccttacaatggtgctactagctacaaccagaaattcgaggacaa<br>CDR II | 200 |
| ggccacattgactgtagacaaatcttccagcacagcctacatgcagctca | 250 |
| acagcctgacatctgaggactctgcagtctattactgtcaagaagatgg<br>                                                CDR III | 300 |
| gactgggacccttatgctatggactactggggtcaaggaacctcagtcac<br>CDR III (cont) | 350 |
| cgtctcctcagccaaaacaacagccccatcggtctatccactggcccctg<br>            constant region | 400 |
| tgtgtggagatacaagtggctcctcggtgactctaggatgcctggtcaag | 450 |
| ggttatttccctgagccagtgaccttgacctggaactctggatccctgtc | 500 |
| cagtggtgtgcacacctccccagctgtcctgcagtctgacctctacaccc | 550 |
| tcagcagctcagtgactgtaacctcgagcacctggcccagccagtccatc | 600 |
| acctgcaatgtggcccacccggccagcaagaccaaggtcgac<br>PCR primer | 642 |

FIG. 30

16E5 - LC gacatcttgctgactcagtctccagccatcctgtctgtgagtccaggaga
aagagtcagtttctcctgcagggccagtcagagcattggcacaagcatac
actggtatcagcaaagaacaaatggttctccaaggcttctcataaagtat
gcttctgagtccatctctgggatatttctaggtttagtggcagtggatc
agggacagattttactcttaccatcaacagtgtggagtctgaagatattg
cagattattactgtcaacaaagtaataggtggccgctcacgttcggagct
gggaccaagctggagctgaaacgggctgatgctgcaccaactgtatccat
cttcccaccatccagtgagcagttaacatctggaggtgcctcagtcgtgt
gcttcttgaacaacttctaccccaaagacatcaatgtcaagtggaagatt
gatggcagtgaacgacaaaatggcgtcctgaacagttggactgatcagga
cagcaaagacagcacctacagcatgagcagcaccctcacgttgaccaagg
acgagtatgaacgacataacagctatacctgtgaggccactcacaagaca
tcaacttcacccattgtcaagagcttcaacaggaatgagtgt

FIG. 31

16E5 - LC

| | |
|---|---|
| <u>gacatcttgctgactcagtctcc</u>agccatcctgtctgtgagtccaggaga<br>PCR primer | 50 |
| aagagtcagtttctcctgcagggccagtcagagcattggcacaagcatac<br>　　　　　　　　　　　　　　CDR I | 100 |
| ac tggtatcagcaaagaacaaatggttctccaaggcttctcataaag tat | 150 |
| gcttctgagtccatctct gggatattttctaggtttagtggcagtggatc<br>CDR II | 200 |
| agggacagattttactcttaccatcaacagtgtggagtctgaagatattg | 250 |
| cagattattactgt caacaaagtaataggtggccgctcacg ttcggagct<br>　　　　　　　　　CDR III | 300 |
| gggaccaagctggagctgaaacgggctgatgctgcaccaactgtatccat<br>　　　　　　　　　　　constant region | 350 |
| cttccaccatccagtgagcagttaacatctggaggtgcctcagtcgtgt | 400 |
| gcttcttgaacaacttctaccccaaagacatcaatgtcaagtggaagatt | 450 |
| gatggcagtgaacgacaaaatggcgtcctgaacagttggactgatcagga | 500 |
| cagcaaagacagcacctacagcatgagcagcaccctcacgttgaccaagg | 550 |
| acgagtatgaacgacataacagctatacctgtgaggccactcacaagaca | 600 |
| tcaacttcacccattgtcaaga<u>gcttcaacaggaatgagtgt</u><br>　　　　　　　　　　　　PCR primer | 642 |

FIG. 32

17D2 - HC

```
gacgtccagatccagcagtctgggcctgagctggtgaagcctggagcttc
agtgaagatgtcctgcaaggcttctggttactcattcactgcctacaaca
tgcactgggtgaagcagacccatggaaagagccttgagtggattggttat
attgatccttacagtggtgctactagctaccaccagaaattcaagggcaa
ggccacattgactgttgacaaatcttccagcacagcctacatgcgcctca
acagcctgacatctgaggactctgcagtctattactgtgcaagaagatgg
gactgggacccttatgctatggactactggggtcaaggaacctcagtcac
cgtctcctcagccaaaacaacaccccatcagtctatccactggcccctg
ggtgtggagatacaactggttcctccgtgactctgggatgcctggtcaag
ggctacttccctgagtcagtgactgtgacttggaactctggatccctgtc
cagcagtgtgcacaccttcccagctctcctgcagtctggactctacacta
tgagcagctcagtgactgtcccctccagcgcctggccaagtcagaccgtc
acctgcagcgttgctcacccggccagcaacaccacggtcgac
```

FIG. 33

17D2 - HC

| | |
|---|---|
| <u>gacgtccagatccagcagtctgggcctgagctggtgaagcctggagcttc</u><br>    PCR primer | 50 |
| agtgaagatgtcctgcaaggcttctggttactcattcact`gcctacaaca`<br>                                                        CDR I | 100 |
| `tgcac`tgggtgaagcagacccatggaaagagccttgagtggattggt`tat` | 150 |
| `attgatccttacagtggtgctactagctaccaccagaaattcaagggc`aa<br>    CDR II | 200 |
| ggccacattgactgttgacaaatcttccagcacagcctacatgcgcctca | 250 |
| acagcctgacatctgaggactctgcagtctattactgtcaaga`agatgg` | 300 |
| `gactgggaccttatgctatggactac`tggggtcaaggaacctcagtcac<br>    CDR III | 350 |
| cgtctcctcagccaaaacaacaccccatcagtctatccactggcccctg<br>           constant region | 400 |
| ggtgtggagatacaactggttcctccgtgactctgggatgcctggtcaag | 450 |
| ggctacttccctgagtcagtgactgtgacttggaactctggatccctgtc | 500 |
| cagcagtgtgcacaccttcccagctctcctgcagtctggactctacacta | 550 |
| tgagcagctcagtgactgtcccctccagcgcctggccaagtcagaccgtc | 600 |
| acctgcagcgttgct<u>cacccggccagcaacaccacggtcgac</u><br>                     PCR primer | 642 |

FIG. 34

17D2 - LC agcgttgagatgtcacagtcgccagccatcctgtctgtgagtccaggaga
aagaatcagtttctcctgcagggccagtcagagcattggcacaagcatac
actggtatcagcaaagaacaaatggttctccaaggcttctcattaagtat
gcttctgcgtctatctctgggatcccttccaggtttagtggcagtggatc
agggacagattttactcttagcatcaacagtgtggagtctgaagatattg
cagattattactgtcaacaaagtaatagctggccgctcacgttcggtgct
gggaccaagctggagctgaaacgggctgatgctgcaccaactgtatccat
cttcccaccatccagtgagcagttaacatctggaggtgcctcagtcgtgt
gcttcttgaacaacttctaccccaaagacatcaatgtcaagtggaagatt
gatggcagtgaacgacaaaatggcgtcctgaacagttggactgatcagga
cagcaaagacagcacctacagcatgagcagcaccctcacgttgaccaagg
acgagtatgaacgacataacagctatacctgtgaggccactcacaagaca
tcaacttcacccattgtcaagagcttcaacaggaatgagtgt

FIG. 35

| | |
|---|---:|
| <u>agcgttgagatgtcacagtcgccagccatcctgtctgtgagtccaggaga</u><br>   PCR primer | 50 |
| aagaatcagtttctcctgc`agggccagtcagagcattggcacaagcatac` | 100 |
|                               CDR I | |
| `ac`tggtatcagcaaagaacaaatggttctccaaggcttctcattaag`tat` | 150 |
| `gcttctgcgtctatctct`gggatcccttccaggtttagtggcagtggatc | 200 |
|    CDR II | |
| agggacagattttactcttagcatcaacagtgtggagtctgaagatattg | 250 |
| cagattattactgt`caacaaagtaatagctggccgctcacg`ttcggtgct | 300 |
|                    CDR III | |
| gggaccaagctggagctgaaacgggctgatgctgcaccaactgtatccat | 350 |
|                    constant region | |
| cttcccaccatccagtgagcagttaacatctggaggtgcctcagtcgtgt | 400 |
| gcttcttgaacaacttctaccccaaagacatcaatgtcaagtggaagatt | 450 |
| gatggcagtgaacgacaaaatggcgtcctgaacagttggactgatcagga | 500 |
| cagcaaagacagcacctacagcatgagcagcaccctcacgttgaccaagg | 550 |
| acgagtatgaacgacataacagctatacctgtgaggccactcacaagaca | 600 |
| tcaacttcacccattgtcaaga<u>gcttcaacaggaatgagtgt</u> | 642 |
|                    PCR primer | |

FIG. 36

14D3 - HC gacgtccagatgcagcagcctgggcctgagctggtgaagcctggagcttc
actaaagatgtcctgcaaggcttctggttactcattcactggctacaaca
tgcactgggtgaagcagagccatggaaagagccttgagtggattggatat
attgatccttacagtggtgctactagctacaaccagaaattcgagggcaa
ggccacattgactgtagacaaatcttccagcacagcctacatgcagctca
acagcctgacatctgaggactctgcagtctattactgtgcaagaagatgg
gactgggacccttatgctatggactactggggtcaaggaacctcagtcac
cgtctcctcagccaaaacaacagccccatcggtctatccactggcccctg
tgtgtggagatacaagtggctcctcggtgactctaggatgcctggtcaag
ggttatttccctgagccagtgaccttgacctggaactctggatccctgtc
cagtggtgtgcacaccttccagctgtcctgcagtctgacctctacaccc
tcagcagctcagtgactgtaacctcgagcacctggcccagccagtccatc
acctgcaatgtggcccacccagccagcaacaccaaggtcgac

FIG. 37

14D3 — HC

```
gacgtccagatgcagcagcctgggcctgagctggtgaagcctggagcttc          50
    PCR primer
actaaagatgtcctgcaaggcttctggttactcattcactggctacaaca         100
                                            CDR I
tgcactgggtgaagcagagccatggaagagccttgagtggattggatat          150 attgatccttacagtggtgctactagctacaaccagaaattcgagggcaa         200
    CDR II
ggccacattgactgtagacaaatcttccagcacagcctacatgcagctca         250 acagcctgacatctgaggactctgcagtctattactgtgcaagaagatgg         300
                                                CDR III
gactgggacccttatgctatggactactggggtcaaggaacctcagtcac         350 cgtctcctcagccaaaacaacagccccatcggtctatccactggcccctg         400
         constant
tgtgtggagatacaagtggctcctcggtgactctaggatgcctggtcaag         450 ggttatttccctgagccagtgaccttgacctggaactctggatccctgtc         500 cagtggtgtgcacaccttcccagctgtcctgcagtctgacctctacaccc         550 tcagcagctcagtgactgtaacctcgagcacctggcccagccagtccatc         600 acctgcaatgtggcccacccagccagcaacaccaaggtcgac                 642
                              PCR primer
```

FIG. 38

14D3 — LC aacattctgatgacacagtctccagccatcttgtctgtgagtccaggaga
aagagtcagtttcgcctgcagggccagtcagagcattggcacaagcatac
actggtatcagcaaagaacaaatggttctccaaggcttctcataaagtat
gcttctgagtctatctctgggatccttccaggtttagtggcagtggatc
agggacagattttactcttagcatcaacagtgtggagtctgaagatattg
cagattattactgtcaacaaactaataggtggccgctcacgttcggtgct
gggaccaagctggagctgaaacgggctgatgctgcaccaactgtatccat
cttcccaccatccagtgagcagttaacatctggaggtgcctcagtcgtgt
gcttcttgaacaacttctaccccaaagacatcaatgtcaagtggaagatt
gatggcagtgaacgacaaaatggcgtcctgaacagttggactgatcagga
cagcaaagacagcacctacagcatgagcagcaccctcacgttgaccaagg
acgagtatgaacgacataacagctatacctgtgaggccactcacaagaca
tcaacttcacccattgtcaagagcttcaacaggaatgagtgt

FIG. 39

14D3 - LC

| | |
|---|---|
| aacattctgatgacacagtctccagccatcttgtctgtgagtccaggaga<br>PCR primer | 50 |
| aagagtcagtttcgcctgcagggccagtcagagcattggcacaagcatac<br>CDR I | 100 |
| actggtatcagcaaagaacaaatggttctccaaggcttctcataaagtat | 150 |
| gcttctgagtctatctctgggatcccttccaggtttagtggcagtggatc<br>CDR II | 200 |
| agggacagattttactcttagcatcaacagtgtggagtctgaagatattg | 250 |
| cagattattactgtcaacaaactaataggtggccgctcacgttcggtgct<br>CDR III | 300 |
| gggaccaagctggagctgaaacgggctgatgctgcaccaactgtatccat<br>constant region | 350 |
| cttcccaccatccagtgagcagttaacatctggaggtgcctcagtcgtgt | 400 |
| gcttcttgaacaacttctaccccaaagacatcaatgtcaagtggaagatt | 450 |
| gatggcagtgaacgacaaaatggcgtcctgaacagttggactgatcagga | 500 |
| cagcaaagacagcacctacagcatgagcagcaccctcacgttgaccaagg | 550 |
| acgagtatgaacgacataacagctatacctgtgaggccactcacaagaca | 600 |
| tcaacttcacccattgtcaagagcttcaacaggaatgagtgt<br>PCR primer | 642 |

FIG. 40

3B3 - HC

DVQLQQPGAELVKPGASVKLSCTTSGVNIKDTYMHWMKQRPEQGLEWIGR
IDPANGNTKYDPKFRGKATITADTSSNTVYVQLRSLTSEDTAVYYCAYDG
YWGQGTLVTVSAAKTTPPSVYPLAPGSAAQTNSMVTLGCLVKGYFPEPVT
VTWNSGSLSSGVHTFPAVLQSDLYTLSSSVTVPSSTWPSETVTCNVAHPA
SSTKVD

FIG. 41

3B3 - HC

<u>DVQLQQ</u>PGAELVKPGASVKLSCTTSGVNIK<span style="border:1px solid">DTYMH</span>WMKQRPEQGLEWIG<span style="border:1px solid">R</span>  50
  PCR primer                            CDR I <span style="border:1px solid">IDPANGNTKYDPKFRG</span>KATITADTSSNTVYVQLRSLTSEDTAVYYCAY<span style="border:1px solid">DG</span>  100
    CDR II                                                CDR III <span style="border:1px solid">Y</span>WGQGTLVTVSAAKTTPPSVYPLAPGSAAQTNSMVTLGCLVKGYFPEPVT  150
         constant region VTWNSGSLSSGVHTFPAVLQSDLYTLSSSVTVPSSTWPSETVTCNV<u>AHPA</u>200
                                                                           PCR primer <u>SSTKVD</u>  206

FIG. 42

3B3 - LC

NIVMTQTPASLAVSLGQRATISCRASESVDSYGNNFMHWYQQKPGQSPRL
LIYRASNLESGIPARFSGSGSRTDFTLTTNPVEADDVATYYCQQSHKDPL
TFGAGTKLELKRADAAPTVSIFPPSSEQLTSGGASVVCFLNNFYPKDINV
KWKIDGSERQNGVLNSWTDQDSKDSTYSMSSTLTLTKDEYERHNSYTCEA
THKTSTSPIVKSFKANEC

FIG. 43

3B3 - LC

| | |
|---|---|
| NIVMTQTPASLAVSLGQRATISC RASESVDSYGNNFMH WYQQKPGQSPRL<br>PCR primer                    CDR I | 50 |
| LIY RASNLES GIPARFSGSGSRTDFTLTTNPVEADDVATYYC QQSHKDPL<br>    CDR II                                              CDR III | 100 |
| T FGAGTKLELKRADAAPTVSIFPPSSEQLTSGGASVVCFLNNFYPKDINV<br>       constant region | 150 |
| KWKIDGSERQNGVLNSWTDQDSKDSTYSMSSTLTLTKDEYERHNSYTCEA | 200 |
| THKTSTSPIVK SFKANEC<br>          PCR primer | 218 |

FIG. 44

3C7 - HC

DVQLKHSGPELVKPGASMKISCKASGYSFTGYTMNWVKQSHGKNLDWIGL
INPYNGGTSYDQKFKGKATLTVDKSSSTAYMELLSLTSEDSAVYYCARDG
LMDYWGQGTSVTVSSAKTTPPSVYPLAPGSAAQTNSMVTLGCLVKGYFPE
PVTVTWNSGSLSSGVHTFPAVLQSDLYTLSSSVTVPSSTWPSETVTCNVA
HPASKTKVD

FIG. 45

3C7 - HC

<u>DVQLKHSGPELVKPGASMKISCKASGYSFT</u>GYTMN WVKQSHGKNLDWIGL    50
    PCR primer                     CDR I

INPYNGGTSYDQKFKG KATLTVDKSSSTAYMELLSLTSEDSAVYYCAR DG    100
      CDR II

LMDY WGQGTSVTVSSAKTTPPSVYPLAPGSAAQTNSMVTLGCLVKGYFPE    150
CDR III          constant region

PVTVTWNSGSLSSGVHTFPAVLQSDLYTLSSSVTVPSSTWPSETVTCNVA    200

<u>HPASKTKVD</u>    209
  PCR primer

FIG. 46

3C7 - LC

DIVMTQTPASLAVSLGQRATIFCRASQSVDYNGISYMHWFQQKPGQPPKL
LIYAASNLESGIPARFSGSGSGTDFTLNIHPVEEEDAATYYCQQSFEDPH
TFGGGTKLEIKRADAAPTVSIFPPSSEQLTSGGASVVCFLNNFYPKDINV
KWKIDGSERQNGVLNSWTDQDSKDSTYSMSSTLTLTKDEYERHNSYTCEA
THKTSTSPIVKSFNRNEC

FIG. 47

3C7 - LC

DIVMTQTPASLAVSLGQRATIFC RASQSVDYNGISYMH WFQQKPGQPPKL      50
PCR primer                  CDR I LIY AASNLES GIPARFSGSGSGTDFTLNIHPVEEEDAATYYC QQSFEDPH      100
    CDR II                                   CDR III T FGGGTKLEIKRADAAPTVSIFPPSSEQLTSGGASVVCFLNNFYPKDINV        150
         constant region

KWKIDGSERQNGVLNSWTDQDSKDSTYSMSSTLTLTKDEYERHNSYTCEA         200

THKTSTSPIVK SFNRNEC                                        218
            PCR primer

FIG. 48

2B4 - HC

DVQLQQSGTVLARPGASVRMSCKASGYSFTRYWIHWLKQRPGQGLEWIGA
IFPGNRDTSYNQRFKGKAEVTAVTSASTAYLDLSSLTNEDSAVYYCTRWP
YYGSIYVNFDYWGQGTTLTVSSAKTTPPSVYPLAPGSAAQTNSMVTLGCL
VKGYFPEPVTVTWNSGSLSSGVHTFPAVLQSDLYTLSSSVTVPSSTWPSE
TVTCNVAHPASSTKVD

FIG. 49

2B4 - HC

DVQLQQSGTVLARPGASVRMSCKASGYSFTRYWIHWLKQRPGQGLEWIGA     50
PCR primer                         CDR I

IFPGNRDTSYNQRFKGKAEVTAVTSASTAYLDLSSLTNEDSAVYYCTRWP     100
CDR II

YYGSIYVNFDYWGQGTTLTVSSAKTTPPSVYPLAPGSAAQTNSMVTLGCL     150
CDR III             constant region

VKGYFPEPVTVTWNSGSLSSGVHTFPAVLQSDLYTLSSSVTVPSSTWPSE     200

TVTCNVAHPASSTKVD     216
PCR primer

FIG. 50

2B4 – LC

DIVMTQSPLSLPVSLGDQASISCRTSQNLVHRNGNTYLHWYLQKPGQSPK
LLIYKISNRFSGVPDRFSGSGSGTDFTLKISRVEAEDLGVYFCSQGTHVP
PTFGGGTKLEIKRADAAPTVSIFPPSSEQLTSGGASVVCFLNNFYPKDIN
VKWKIDGSERQNGVLNSWTDQDSKDSTYSMSSTLTLTKDEYERHNSYTCE
ATHKTSTSPIVKSFNRNEC

FIG. 51

2B4 – LC

DIVMTQSPLSLPVSLGDQASISCRTSQNLVHRNGNTYLHWYLQKPGQSPK     50
  PCR primer                CDR I LLIYKISNRFSGVPDRFSGSGSGTDFTLKISRVEAEDLGVYFCSQGTHVP     100
                            CDR II          CDR III PTFGGGTKLEIKRADAAPTVSIFPPSSEQLTSGGASVVCFLNNFYPKDIN     150
            constant region

VKWKIDGSERQNGVLNSWTDQDSKDSTYSMSSTLTLTKDEYERHNSYTCE     200

ATHKTSTSPIVKSFNRNEC                                    219
           PCR primer

FIG. 52

3B3 – HC gacgtccagctccagcagcctggagcagagcttgtgaagccaggggcctc
agtcaagttgtcctgcaccacttctggcgtcaacattaaagacacctata
tgcactggatgaagcagaggcctgaacagggcctggagtggattggaagg
attgatcctgcgaatggtaatactaaatatgacccgaaattccggggcaa
ggccactataacagcagacacatcctcaacacggtctacgtgcaactca
gaagcctgacatctgaggacactgccgtctattactgtgcctatgatggt
tactggggccaagggactctggtcactgtctctgcagccaaaacgacacc
cccatctgtctatccactggccctggatctgctgcccaaactaactcca
tggtgaccctgggatgcctggtcaagggctatttccctgagccagtgaca
gtgacctggaactctggatccctgtccagcggtgtgcacaccttcccagc
tgtcctgcagtctgacctctacactctgagcagctcagtgactgtccct
ccagcacctggcccagcgagaccgtcacctgcaacgttgcccacccggcc
agcagcaccaaggtcgac

FIG. 53

3B3 - HC

| | |
|---|---|
| <u>gacgtccagctccagcagcctg</u>gagcagagcttgtgaagccagggggcctc<br>     PCR primer | 50 |
| agtcaagttgtcctgcaccacttctggcgtcaacattaaa<span style="background:#ccc">gacacctata</span><br>                                                  CDR I | 100 |
| <span style="background:#ccc">tgcac</span>tggatgaagcagaggcctgaacagggcctggagtggattgga<span style="background:#ccc">agg</span> | 150 |
| <span style="background:#ccc">attgatcctgcgaatggtaatactaaatatgacccgaaattccggggc</span>aa<br>    CDR II | 200 |
| ggccactataacagcagacacatcctccaacacggtctacgtgcaactca | 250 |
| gaagcctgacatctgaggacactgccgtctattactgtgccta<span style="background:#ccc">tgatggt</span><br>                                                        CDR III | 300 |
| <span style="background:#ccc">tac</span>tggggccaagggactctggtcactgtctctgcagccaaaacgacacc<br>                                        constant region | 350 |
| cccatctgtctatccactggcccctggatctgctgcccaaactaactcca | 400 |
| tggtgaccctgggatgcctggtcaagggctatttccctgagccagtgaca | 450 |
| gtgacctggaactctggatccctgtccagcggtgtgcacaccttcccagc | 500 |
| tgtcctgcagtctgacctctacactctgagcagctcagtgactgtcccct | 550 |
| ccagcacctggcccagcgagaccgtcacctgcaacgttgcc<u>cacccggcc</u><br>                                                          PCR primer | 600 |
| <u>agcagcaccaaggtcgac</u> | 618 |

FIG. 54

3B3 — LC aacattgtgatgacccaaactccagcctctttggctgtgtctctagggca
gagggccaccatatcctgcagagccagtgaaagtgttgatagttatggca
ataattttatgcactggtaccagcagaaaccaggacagtcacccagactc
ctcatctatcgtgcatccaacctagaatctgggatccctgccaggttcag
tggcagtgggtctaggacagacttcaccctcaccactaatcctgtggagg
ctgatgatgttgcaacctattactgtcagcaaagtcataaggatccgctc
acgttcggtgctgggaccaagctggagctgaaacgggctgatgctgcacc
aactgtatccatcttcccaccatccagtgagcagttaacatctggaggtg
cctcagtcgtgtgcttcttgaacaacttctaccccaaagacatcaatgtc
aagtggaagattgatggcagtgaacgacaaaatggcgtcctgaacagttg
gactgatcaggacagcaaagacagcacctacagcatgagcagcaccctca
cgttgaccaaggacgagtatgaacgacataacagctatacctgtgaggcc
actcacaagacatcaacttcacccattgtcaagagcttcaaggaacatga
gtgt

FIG. 55

3B3 – LC aacattgtgatgacccaaactccagcctctttggctgtgtctctagggca    50
    PCR primer gagggccaccatatcctgcagagccagtgaaagtgttgatagttatggca    100
                         CDR I ataattttatgcactggtaccagcagaaaccaggacagtcacccagactc    150 ctcatctatcgtgcatccaacctagaatctgggatccctgccaggttcag    200
            CDR II tggcagtgggtctaggacagacttcaccctcaccactaatcctgtggagg    250 ctgatgatgttgcaacctattactgtcagcaaagtcataaggatccgctc    300
                             CDR III acgttcggtgctgggaccaagctggagctgaaacgggctgatgctgcacc    350
                             constant region aactgtatccatcttcccaccatccagtgagcagttaacatctggaggtg    400 cctcagtcgtgtgcttcttgaacaacttctaccccaaagacatcaatgtc    450 aagtggaagattgatggcagtgaacgacaaaatggcgtcctgaacagttg    500 gactgatcaggacagcaaagacagcacctacagcatgagcagcaccctca    550 cgttgaccaaggacgagtatgaacgacataacagctatacctgtgaggcc    600 actcacaagacatcaacttcacccattgtcaagagcttcaacaggaatga    650
                                              PCR primer gtgt    652

FIG. 56

3C7 - HC gacgtccagctgaagcatcaggacctgagctggtgaagcctggagcttca
atgaagatatcctgcaaggcttctggttactcattcactggctacaccat
gaactgggtgaagcagagccatggaaagaaccttgagtggattggactta
ttaatccttacaatggtggtactagctacgaccagaagttcaagggcaag
gccacattaactgtagacaagtcatccagcacagcctacatggagctcct
cagtctgacatctgaggactctgcagtctattactgtgcaagagatggcc
tgatggactactggggtcaaggaacctcagtcaccgtctcctcagccaaa
acgacaccccatctgtctatccactggccctggatctgctgcccaaac
taactccatggtgaccctgggatgcctggtcaagggctatttccctgagc
cagtgacagtgacctggaactctggatccctgtccagcggtgtgcacacc
ttcccagctgtcctgcagtctgacctctacactctgagcagctcagtgac
tgtcccctccagcacctggcccagcgagaccgtcacctgcaacgttgccc
acccggccagcaagaccaaggtcgac

FIG. 57

3C7 - HC

| | |
|---|---|
| <u>gacgtccagctgaagcatcaggacct</u>gagctggtgaagcctggagcttca | 50 |
|     PCR primer | |
| atgaagatatcctgcaaggcttctggttactcattcact`ggctacaccat` | 100 |
|                                                  CDR I | |
| `gaac`tgggtgaagcagagccatggaagaaccttgagtggattgga`ctta` | 150 |
|                                                     CDR II | |
| `ttaatccttacaatggtggtactagctacgaccagaagttcaagggc`aag | 200 |
| gccacattaactgtagacaagtcatccagcacagcctacatggagctcct | 250 |
| cagtctgacatctgaggactctgcagtctattactgtgcaaga`gatggcc` | 300 |
|                                                     CDR III | |
| `tgatggactac`tggggtcaaggaacctcagtcaccgtctcctcagccaaa | 350 |
|                                                    constant region | |
| acgacaccccatctgtctatccactggccctggatctgctgcccaaac | 400 |
| taactccatggtgaccctgggatgcctggtcaagggctatttccctgagc | 450 |
| cagtgacagtgacctggaactctggatccctgtccagcggtgtgcacacc | 500 |
| ttcccagctgtcctgcagtctgacctctacactctgagcagctcagtgac | 550 |
| tgtcccctccagcacctggcccagcgagaccgtcacctgcaacgttgc<u>c</u> | 600 |
| <u>acccggccagcaagaccaaggtcgac</u> | 626 |
|     PCR primer | |

FIG. 58

3C7 - LC gatattgtgatgacccaaactccagcttctttggctgtgtctctaggaca
gagagccactatcttctgcagagccagccagagtgtcgattataatggaa
ttagttatatgcactggttccaacagaaaccaggacagccacccaaactc
ctcatctatgctgcatccaacctagaatctgggatccctgccaggttcag
tggcagtgggtctgggacagacttcaccctcaacatccatcctgtggagg
aggaagatgctgcaacctattactgtcagcaaagttttgaggatccgcac
acgttcggagggggaccaagctggaaataaaacgggctgatgctgcacc
aactgtatccatcttcccaccatccagtgagcagttaacatctggaggtg
cctcagtcgtgtgcttcttgaacaacttctacccaaagacatcaatgtc
aagtggaagattgatggcagtgaacgacaaaatggcgtcctgaacagttg
gactgatcaggacagcaaagacagcacctacagcatgagcagcaccctca
cgttgaccaaggacgagtatgaacgacataacagctatacctgtgaggcc
actcacaagacatcaacttcacccattgtcaagagcttcaacaggaatga
gtgt

FIG. 59

3C7 - LC

| | |
|---|---|
| <u>gatattgtgatgacccaaactccagcttctttggctgtgtctctaggaca</u><br>　　　PCR primer | 50 |
| gagagccactatcttctgc<span style="border:1px solid">agagccagccagagtgtcgattataatggaa</span><br>　　　　　　　　　　　　　CDR I | 100 |
| <span style="border:1px solid">ttagttatatgcac</span>tggttccaacagaaaccaggacagccacccaaactc | 150 |
| ctcatctat<span style="border:1px solid">gctgcatccaacctagaatct</span>gggatccctgccaggttcag<br>　　　　　　　　　CDR II | 200 |
| tggcagtgggtctgggacagacttcaccctcaacatccatcctgtggagg | 250 |
| aggaagatgctgcaacctattactgt<span style="border:1px solid">cagcaaagttttgaggatccgcac</span><br>　　　　　　　　　　　　　　　　CDR III | 300 |
| <span style="border:1px solid">acg</span>ttcggaggggggaccaagctggaaataaaacgggctgatgctgcacc<br>　　　　　　　　　　　　　　　　constant region | 350 |
| aactgtatccatcttcccaccatccagtgagcagttaacatctggaggtg | 400 |
| cctcagtcgtgtgcttcttgaacaacttctaccccaaagacatcaatgtc | 450 |
| aagtggaagattgatggcagtgaacgacaaaatggcgtcctgaacagttg | 500 |
| gactgatcaggacagcaaagacagcacctacagcatgagcagcaccctca | 550 |
| cgttgaccaaggacgagtatgaacgacataacagctatacctgtgaggcc | 600 |
| actcacaagacatcaacttcacccattgtcaaga<u>gcttcaacaggaatga</u><br>　　　　　　　　　　　　　　　　　　PCR primer | 650 |
| <u>gtgt</u> | 654 |

FIG. 60

2B4 - HC gacgtccagctgcagcagtctgggactgtgctggcaaggcctggggcttc
cgtgaggatgtcctgcaaggcttctggctacagctttaccaggtactgga
tacactggttaaaacagaggcctggacagggtctagaatggattggtgct
atttttcctggaaatcgtgataccagttacaaccagaggttcaagggcaa
ggccgaagtgactgcagtcacatccgccagcactgcctacttggacctca
gtagcctgacaaatgaggactctgcggtctattactgtacaagatggcct
tactatggttccatctacgttaactttgactactggggccaaggcaccac
tctcacagtctcctcagccaaaacgacaccccatctgtctatccactgg
cccctggatctgctgcccaaactaactccatggtgaccctgggatgcctg
gtcaagggctatttcctgagccagtgacagtgacctggaactctggatc
cctgtccagcggtgtgcacaccttccagctgtcctgcagtctgacctct
acactctgagcagctcagtgactgtcccctccagcacctggcccagcgag
accgtcacctgcaacgttgcccacccagccagcagcaccaaggtcgac

FIG. 61

2B4 - HC

| | |
|---|---|
| <u>gacgtccagctgcagcagtctggg</u>actgtgctggcaaggcctggggcttc<br>　　　PCR primer | 50 |
| cgtgaggatgtcctgcaaggcttctggctacagctttacc<span style="background:#ddd">aggtactgga</span><br>　　　　　　　　　　　　　　　　　　　　　　　CDR I | 100 |
| <span style="background:#ddd">tacac</span>tggttaaaacagaggcctggacagggtctagaatggattggt<span style="background:#ddd">gct</span> | 150 |
| <span style="background:#ddd">attttccctggaaatcgtgataccagttacaaccagaggttcaagggc</span>aa<br>　　　CDR II | 200 |
| ggccgaagtgactgcagtcacatccgccagcactgcctacttggacctca | 250 |
| gtagcctgacaaatgaggactctgcggtctattactgtacaaga<span style="background:#ddd">tggcct</span> | 300 |
| <span style="background:#ddd">tactatggttccatctacgttaactttgactac</span>tggggccaaggcaccac<br>　　　CDR III | 350 |
| tctcacagtctcctcagccaaaacgacacccccatctgtctatccactgg<br>　　　　　　　　　　　constant region | 400 |
| cccctggatctgctgcccaaactaactccatggtgaccctgggatgcctg | 450 |
| gtcaagggctatttccctgagccagtgacagtgacctggaactctggatc | 500 |
| cctgtccagcggtgtgcacaccttccagctgtcctgcagtctgacctct | 550 |
| acactctgagcagctcagtgactgtcccctccagcacctggcccagcgag | 600 |
| accgtcacctgcaacgttgcc<u>cacccagccagcagcaccaaggtcgac</u><br>　　　　　　　　　　　　PCR primer | 648 |

FIG. 62

2B4 - LC gatattgtgatgacccagtctcctctctccctgcctgtcagtcttggaga
tcaagcctccatctcttgcagaactagtcagaaccttgtacacaggaatg
gaaacacctatttacattggtacctgcagaagccaggccagtctccaaag
ctcctgatttacaaaatttccaaccgattttctggggtcccagacaggtt
cagtggcagtggatcagggacagatttcacactcaagatcagcagagtgg
aggctgaggatctggagtttatttctgctctcaaggtacacatgttcct
ccgacgttcggtggaggcaccaagctggaaatcaaacgggctgatgctgc
accaactgtatccatcttcccaccatccagtgagcagttaacatctggag
gtgcctcagtcgtgtgcttcttgaacaacttctaccccaaagacatcaat
gtcaagtggaagattgatggcagtgaacgacaaaatggcgtcctgaacag
ttggactgatcaggacagcaaagacagcacctacagcatgagcagcaccc
tcacgttgaccaaggacgagtatgaacgacataacagctatacctgtgag
gccactcacaagacatcaacttcaccattgtcaagagcttcaacaggaa
tgagtgt

FIG. 63

2B4 - LC

| | |
|---|---|
| gatattgtgatgacccagtctcctctctccctgcctgtcagtcttggaga | 50 |
| PCR primer | |
| tcaagcctccatctcttgcagaactagtcagaaccttgtacacaggaatg | 100 |
| CDR I | |
| gaaacacctatttacattggtacctgcagaagccaggccagtctccaaag | 150 |
| ctcctgatttacaaaatttccaaccgatttctggggtcccagacaggtt | 200 |
| CDR II | |
| cagtggcagtggatcagggacagatttcacactcaagatcagcagagtgg | 250 |
| aggctgaggatctgggagtttatttctgctctcaaggtacacatgttcct | 300 |
| CDR III | |
| ccgacgttcggtggaggcaccaagctggaaatcaaacgggctgatgctgc | 350 |
| constant region | |
| accaactgtatccatcttcccaccatccagtgagcagttaacatctggag | 400 |
| gtgcctcagtcgtgtgcttcttgaacaacttctaccccaaagacatcaat | 450 |
| gtcaagtggaagattgatggcagtgaacgacaaaatggcgtcctgaacag | 500 |
| ttggactgatcaggacagcaaagacagcacctacagcatgagcagcaccc | 550 |
| tcacgttgaccaaggacgagtatgaacgacataacagctatacctgtgag | 600 |
| gccactcacaagacatcaacttcacccattgtcaagagcttcaacaggaa | 650 |
| PCR primer | |
| tgagtgt | 657 |

FIG. 64

SEQUENCE LISTING

```
<160> NUMBER OF SEQ ID NOS: 92

<210> SEQ ID NO 1
<211> LENGTH: 200
<212> TYPE: PRT
<213> ORGANISM: Homo sapiens
<220> FEATURE:
<221> NAME/KEY: misc_feature
<223> OTHER INFORMATION: Figure 1

<400> SEQUENCE: 1

Met Arg Pro Ala Asp Leu Leu Gln Leu Val Leu Leu Leu Asp Leu Pro
1               5                   10                  15

Arg Asp Leu Gly Gly Met Gly Cys Ser Ser Pro Pro Cys Glu Cys His
            20                  25                  30
```

```
Gln Glu Glu Asp Phe Arg Val Thr Cys Lys Asp Ile Gln Arg Ile Pro
            35                  40                  45

Ser Leu Pro Pro Ser Thr Gln Thr Leu Lys Leu Ile Glu Thr His Leu
 50                  55                  60

Arg Thr Ile Pro Ser His Ala Phe Ser Asn Leu Pro Asn Ile Ser Arg
 65                  70                  75                  80

Ile Tyr Val Ser Ile Asp Val Thr Leu Gln Gln Leu Glu Ser His Ser
                 85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
            115                 120                 125

Lys Phe Leu Gly Ile Phe Asn Thr Gly Leu Lys Met Phe Pro Asp Leu
            130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr
            195                 200

<210> SEQ ID NO 2
<211> LENGTH: 200
<212> TYPE: PRT
<213> ORGANISM: Sus scrofa
<220> FEATURE:
<221> NAME/KEY: misc_feature
<223> OTHER INFORMATION: Figure 1

<400> SEQUENCE: 2

Met Ser Leu Thr Pro Leu Leu Gln Leu Ala Leu Val Leu Ala Leu Pro
 1               5                  10                  15

Arg Ser Leu Arg Gly Lys Gly Cys Pro Ser Pro Cys Glu Cys His
            20                  25                  30

Gln Glu Asp Asp Phe Arg Val Thr Cys Lys Asp Ile His Ser Ile Pro
            35                  40                  45

Pro Leu Pro Pro Asn Thr Gln Thr Leu Lys Phe Ile Glu Thr His Leu
 50                  55                  60

Lys Thr Ile Pro Ser Arg Ala Phe Ser Asn Leu Pro Asn Ile Ser Arg
 65                  70                  75                  80

Ile Tyr Leu Ser Ile Asp Ala Thr Leu Gln Gln Leu Glu Ser Gln Ser
                 85                  90                  95

Phe Tyr Asn Leu Ser Lys Met Thr His Ile Glu Ile Arg Asn Thr Arg
            100                 105                 110

Ser Leu Thr Tyr Ile Asn Pro Gly Ala Leu Lys Asp Leu Pro Leu Leu
            115                 120                 125

Lys Phe Leu Gly Ile Phe Asn Thr Gly Leu Arg Ile Phe Pro Asp Leu
            130                 135                 140

Thr Lys Val Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Val
            180                 185                 190
```

```
Gln Gly His Ala Phe Asn Gly Thr
        195                 200

<210> SEQ ID NO 3
<211> LENGTH: 200
<212> TYPE: PRT
<213> ORGANISM: Bos taurus
<220> FEATURE:
<221> NAME/KEY: misc_feature
<223> OTHER INFORMATION: Figure 1

<400> SEQUENCE: 3

Met Arg Pro Thr Pro Leu Leu Arg Leu Ala Leu Phe Leu Val Leu Pro
1               5                   10                  15

Ser Ser Leu Gly Gly Glu Arg Cys Pro Ser Pro Cys Glu Cys Arg
            20                  25                  30

Gln Glu Asp Asp Phe Arg Val Thr Cys Lys Asp Ile Gln Ser Ile Pro
            35                  40                  45

Ser Leu Pro Pro Ser Thr Gln Thr Leu Lys Phe Ile Glu Thr His Leu
        50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Ser Leu Thr Tyr Ile Asp Ser Gly Ala Leu Lys Glu Leu Pro Leu Leu
        115                 120                 125

Lys Phe Leu Gly Ile Phe Asn Thr Gly Leu Arg Val Phe Pro Asp Leu
    130                 135                 140

Thr Lys Ile Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr
        195                 200

<210> SEQ ID NO 4
<211> LENGTH: 200
<212> TYPE: PRT
<213> ORGANISM: Felis catus
<220> FEATURE:
<221> NAME/KEY: misc_feature
<223> OTHER INFORMATION: Figure 1

<400> SEQUENCE: 4

Met Arg Gln Thr Pro Leu Leu Gln Leu Ala Leu Leu Leu Ser Leu Pro
1               5                   10                  15

Arg Ser Leu Gly Gly Lys Gly Cys Pro Ser Pro Cys Glu Cys His
            20                  25                  30

Gln Glu Asp Asp Phe Arg Val Thr Cys Lys Asp Ile His Arg Ile Pro
            35                  40                  45

Ser Leu Pro Pro Ser Thr Gln Thr Leu Lys Phe Ile Glu Thr His Leu
        50                  55                  60

Lys Thr Ile Pro Ser Arg Ala Phe Ser Asn Leu Pro Asn Ile Ser Arg
65                  70                  75                  80
```

```
Ile Tyr Leu Ser Ile Asp Ala Thr Leu Gln Arg Leu Glu Ser His Ser
                85                  90                  95

Phe Tyr Asn Leu Ser Lys Met Thr His Ile Glu Ile Arg Asn Thr Arg
            100                 105                 110

Ser Leu Thr Tyr Ile Asp Pro Gly Ala Leu Lys Glu Leu Pro Leu Leu
        115                 120                 125

Lys Phe Leu Gly Ile Phe Asn Thr Gly Leu Gly Val Phe Pro Asp Leu
    130                 135                 140

Thr Lys Val Tyr Ser Thr Asp Val Phe Phe Ile Leu Glu Ile Thr Asp
145                 150                 155                 160

Asn Pro Tyr Met Thr Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr
        195                 200

<210> SEQ ID NO 5
<211> LENGTH: 200
<212> TYPE: PRT
<213> ORGANISM: Canis familiaris
<220> FEATURE:
<221> NAME/KEY: misc_feature
<223> OTHER INFORMATION: Figure 1

<400> SEQUENCE: 5

Met Arg Pro Pro Pro Leu Leu His Leu Ala Leu Leu Ala Leu Pro
1               5                   10                  15

Arg Ser Leu Gly Gly Lys Gly Cys Pro Ser Pro Cys Glu Cys His
            20                  25                  30

Gln Glu Asp Asp Phe Arg Val Thr Cys Lys Asp Ile His Arg Ile Pro
        35                  40                  45

Thr Leu Pro Pro Ser Thr Gln Thr Leu Lys Phe Ile Glu Thr Gln Leu
    50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Arg Leu Glu Ser His Ser
                85                  90                  95

Phe Tyr Asn Leu Ser Lys Met Thr His Ile Glu Ile Arg Asn Thr Arg
            100                 105                 110

Ser Leu Thr Ser Ile Asp Pro Asp Ala Leu Lys Glu Leu Pro Leu Leu
        115                 120                 125

Lys Phe Leu Gly Ile Phe Asn Thr Gly Leu Gly Val Phe Pro Asp Val
    130                 135                 140

Thr Lys Val Tyr Ser Thr Asp Val Phe Phe Ile Leu Glu Ile Thr Asp
145                 150                 155                 160

Asn Pro Tyr Met Ala Ser Ile Pro Ala Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr
        195                 200

<210> SEQ ID NO 6
<211> LENGTH: 200
<212> TYPE: PRT
<213> ORGANISM: Mus musculus
<220> FEATURE:
```

```
<221> NAME/KEY: misc_feature
<223> OTHER INFORMATION: Figure 1

<400> SEQUENCE: 6
```

| | | | | | | | | | | | | | | |
|---|---|---|---|---|---|---|---|---|---|---|---|---|---|---|
Met Arg Pro Gly Ser Leu Leu Leu Val Leu Leu Ala Leu Ser
1               5                   10                  15

Arg Ser Leu Arg Gly Lys Glu Cys Ala Ser Pro Cys Glu Cys His
            20                  25                  30

Gln Glu Asp Asp Phe Arg Val Thr Cys Lys Glu Leu His Arg Ile Pro
        35                  40                  45

Ser Leu Pro Pro Ser Thr Gln Thr Leu Lys Leu Ile Glu Thr His Leu
    50                  55                  60

Lys Thr Ile Pro Ser Leu Ala Phe Ser Ser Leu Pro Asn Ile Ser Arg
65                  70                  75                  80

Ile Tyr Leu Ser Ile Asp Ala Thr Leu Gln Arg Leu Glu Pro His Ser
                85                  90                  95

Phe Tyr Asn Leu Ser Lys Met Thr His Ile Glu Ile Arg Asn Thr Arg
            100                 105                 110

Ser Leu Thr Tyr Ile Asp Pro Asp Ala Leu Thr Glu Leu Pro Leu Leu
        115                 120                 125

Lys Phe Leu Gly Ile Phe Asn Thr Gly Leu Arg Ile Phe Pro Asp Leu
    130                 135                 140

Thr Lys Ile Tyr Ser Thr Asp Ile Phe Phe Ile Leu Glu Ile Thr Asp
145                 150                 155                 160

Asn Pro Tyr Met Thr Ser Val Pro Glu Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly His Ala Phe Asn Gly Thr
        195                 200

```
<210> SEQ ID NO 7
<211> LENGTH: 200
<212> TYPE: PRT
<213> ORGANISM: Rattus norvegicus
<220> FEATURE:
<221> NAME/KEY: misc_feature
<223> OTHER INFORMATION: Figure 1

<400> SEQUENCE: 7
```

Met Arg Pro Gly Ser Leu Leu Gln Leu Thr Leu Leu Ala Leu Pro
1               5                   10                  15

Arg Ser Leu Trp Gly Arg Gly Cys Thr Ser Pro Cys Glu Cys His
            20                  25                  30

Gln Glu Asp Asp Phe Arg Val Thr Cys Lys Glu Leu His Gln Ile Pro
        35                  40                  45

Ser Leu Pro Pro Ser Thr Gln Thr Leu Lys Leu Ile Glu Thr His Leu
    50                  55                  60

Lys Thr Ile Pro Ser Leu Ala Phe Ser Ser Leu Pro Asn Ile Ser Arg
65                  70                  75                  80

Ile Tyr Leu Ser Ile Asp Ala Thr Leu Gln Arg Leu Glu Pro His Ser
                85                  90                  95

Phe Tyr Asn Leu Ser Lys Met Thr His Ile Glu Ile Arg Asn Thr Arg
            100                 105                 110

Ser Leu Thr Tyr Ile Asp Pro Asp Ala Leu Thr Glu Leu Pro Leu Leu
        115                 120                 125

Lys Phe Leu Gly Ile Phe Asn Thr Gly Leu Arg Ile Phe Pro Asp Leu

```
              130                 135                 140
Thr Lys Ile Tyr Ser Thr Asp Val Phe Phe Ile Leu Glu Ile Thr Asp
145                 150                 155                 160

Asn Pro Tyr Met Thr Ser Val Pro Glu Asn Ala Phe Gln Gly Leu Cys
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr
        195                 200

<210> SEQ ID NO 8
<211> LENGTH: 200
<212> TYPE: PRT
<213> ORGANISM: Ovis aries
<220> FEATURE:
<221> NAME/KEY: misc_feature
<223> OTHER INFORMATION: Figure 1

<400> SEQUENCE: 8

Met Arg Pro Thr Pro Leu Leu Arg Leu Ala Leu Leu Val Leu Pro
1               5                   10                  15

Ser Ser Leu Trp Gly Glu Arg Cys Pro Ser Pro Cys Glu Cys Arg
            20                  25                  30

Gln Glu Asp Asp Phe Arg Val Thr Cys Lys Asp Ile Gln Arg Ile Pro
        35                  40                  45

Ser Leu Pro Pro Ser Thr Gln Thr Leu Lys Phe Ile Glu Thr His Leu
    50                  55                  60

Lys Thr Ile Pro Ser Arg Ala Phe Ser Asn Leu Pro Asn Ile Ser Arg
65                  70                  75                  80

Ile Tyr Leu Ser Ile Asp Ala Thr Leu Gln Gln Leu Gly Ser His Ser
                85                  90                  95

Phe Tyr Asn Leu Ser Lys Val Thr His Ile Glu Ile Arg Asn Thr Arg
            100                 105                 110

Ser Leu Thr Tyr Ile Asp Ser Gly Ala Leu Lys Glu Leu Pro Leu Leu
        115                 120                 125

Lys Phe Leu Gly Ile Phe Asn Thr Gly Leu Arg Val Phe Pro Asp Leu
    130                 135                 140

Thr Lys Ile Tyr Ser Thr Asp Val Phe Phe Ile Leu Glu Ile Thr Asp
145                 150                 155                 160

Asn Pro Tyr Met Thr Ser Val Pro Ala Asn Ala Phe Gln Gly Leu Ser
                165                 170                 175

Asn Glu Thr Leu Thr Leu Lys Leu Tyr Asn Asn Gly Phe Thr Ser Ile
            180                 185                 190

Gln Gly His Ala Phe Asn Gly Thr
        195                 200

<210> SEQ ID NO 9
<211> LENGTH: 300
<212> TYPE: DNA
<213> ORGANISM: Felis catus
<220> FEATURE:
<221> NAME/KEY: misc_feature
<223> OTHER INFORMATION: Figure 2

<400> SEQUENCE: 9
atgaggcaga cgcccctgct gcagctggcg ttacttctct ccctgcccag gagcctgggg     60
gggaaagggt gtccgtctcc gccctgcgag tgtcaccagg aagatgactt cagagtcacc    120
tgcaaggata ttcaccgtat ccccagccta ccgcccagca cgcagactct gaaatttata    180
```

```
gagactcatc tgaaaaccat tcccagtcgt gcattttcaa atctgcccaa tatttccagg    240
atctacttgt caatagatgc aactctgcag cgactggaat cacattcctt ctacaatttg    300
```

<210> SEQ ID NO 10
<211> LENGTH: 300
<212> TYPE: DNA
<213> ORGANISM: Bos taurus
<220> FEATURE:
<221> NAME/KEY: misc_feature
<223> OTHER INFORMATION: Figure 2

<400> SEQUENCE: 10

```
atgcggccga cgcccctcct gcggctggcg ctgtttctgg tcctgcccag cagcctcggt     60
ggggagaggt gtccgtctcc gccctgcgaa tgccgccagg aggacgactt cagagtcacc    120
tgcaaggaca tccagagcat ccctagctta ccccccagca cgcagaccct gaagtttata    180
gagactcatc tgaaaaccat tcccagtcgt gcgttctcaa atctgcccaa tatttccagg    240
atctacttgt caatagatgc aactctgcag cagctggaat cacattcctt ctacaattta    300
```

<210> SEQ ID NO 11
<211> LENGTH: 300
<212> TYPE: DNA
<213> ORGANISM: Canis familiaris
<220> FEATURE:
<221> NAME/KEY: misc_feature
<223> OTHER INFORMATION: Figure 2

<400> SEQUENCE: 11

```
atgaggccgc cgcccctgct gcacctggcg ctgcttctcg ccctgcccag gagcctgggg     60
gggaaggggt gtccttctcc cccctgtgag tgccaccagg aggatgactt cagagtcacc    120
tgcaaggata tccaccgcat ccccacccta ccacccagca cgcagactct gaagtttata    180
gagactcagc tgaaaaccat tcccagtcgt gcattttcaa atctgcccaa tatttccagg    240
atctacttgt caatagatgc aactctgcag cggctggaat cacattcctt ctacaattta    300
```

<210> SEQ ID NO 12
<211> LENGTH: 300
<212> TYPE: DNA
<213> ORGANISM: Mus musculus
<220> FEATURE:
<221> NAME/KEY: misc_feature
<223> OTHER INFORMATION: Figure 2

<400> SEQUENCE: 12

```
atgaggccag ggtccctgct gctgcttgtt ctgctgctcg ccctgtccag gagcctgcgg     60
ggcaaagagt gtgcgtctcc accctgtgag tgtcaccagg aggacgactt cagagtcacc    120
tgcaaggagc tccaccgaat ccccagcctg ccgcccagca cccagactct gaagctcatc    180
gagactcatc tgaagaccat acccagtctt gcattttcga gtctgcccaa tatttccagg    240
atctatttat ctatagatgc aactctgcag cggctggaac cacattcttt ctacaatttg    300
```

<210> SEQ ID NO 13
<211> LENGTH: 300
<212> TYPE: DNA
<213> ORGANISM: Sus scrofa
<220> FEATURE:
<221> NAME/KEY: misc_feature
<223> OTHER INFORMATION: Figure 2

<400> SEQUENCE: 13

```
atgagtctga cgcccctgtt gcagctggcg ctcgttctcg ccctgcccag gagcctcagg     60
```

```
gggaaagggt gtccgtctcc gccctgcgaa tgccaccagg aggacgactt cagagtcacc    120
tgcaaggata tccacagcat ccccccctta ccacccaata ctcagacact aaagtttata    180
gagactcatc tgaaaaccat ccccagtcgt gcattttcaa atctgcccaa tatttccagg    240
atctacctgt caatagatgc aactctacag cagctggaat cacagtcctt ctacaatttg    300
```

<210> SEQ ID NO 14
<211> LENGTH: 300
<212> TYPE: DNA
<213> ORGANISM: Rattus norvegicus
<220> FEATURE:
<221> NAME/KEY: misc_feature
<223> OTHER INFORMATION: Figure 2

<400> SEQUENCE: 14

```
atgaggccag ggtccctgct ccagctcact ctgctgctcg ccctgcccag gagcctctgg    60
ggcagagggt gtacttctcc accctgcgaa tgccaccagg aggacgactt cagagtcacc    120
tgcaaggaac tccaccaaat ccccagccta ccgcccagca cccagactct gaagctcatc    180
gagactcacc tgaagaccat tcccagtctt gccttttcga gcctgcccaa tatttccagg    240
atctatctat ccatagatgc cactctgcag cgactggagc acattctttt ctacaatttg    300
```

<210> SEQ ID NO 15
<211> LENGTH: 300
<212> TYPE: DNA
<213> ORGANISM: Ovis aries
<220> FEATURE:
<221> NAME/KEY: misc_feature
<223> OTHER INFORMATION: Figure 2

<400> SEQUENCE: 15

```
atgcggccga cgcccctcct gcggttggcg ctgcttctgg tcctgcccag cagcctctgg    60
ggggagaggt gtccgtctcc gccctgcgaa tgccgccagg aggacgactt cagagtcacc    120
tgcaaggaca tccagcgcat ccctagctta ccccccagca cgcagaccct gaagtttata    180
gagactcatc tgaaaaccat tcccagtcgt gcgttctcaa atttgcccaa tatttccagg    240
atctacttgt caatagatgc gactttgcag caactggaat cacattcctt ctacaattta    300
```

<210> SEQ ID NO 16
<211> LENGTH: 300
<212> TYPE: DNA
<213> ORGANISM: Homo sapiens
<220> FEATURE:
<221> NAME/KEY: misc_feature
<223> OTHER INFORMATION: Figure 2

<400> SEQUENCE: 16

```
atgaggccgg cggacttgct gcagctggtg ctgctgctcg acctgcccag ggacctgggc    60
ggaatggggt gttcgtctcc accctgcgag tgccatcagg aggaggactt cagagtcacc    120
tgcaaggata ttcaacgcat ccccagctta ccgcccagta cgcagactct gaagcttatt    180
gagactcacc tgagaactat tccaagtcat gcattttcta atctgcccaa tatttccaga    240
atctacgtat ctatagatgt gactctgcag cagctggaat cacactcctt ctacaatttg    300
```

<210> SEQ ID NO 17
<211> LENGTH: 101
<212> TYPE: PRT
<213> ORGANISM: Homo sapiens
<220> FEATURE:
<221> NAME/KEY: misc_feature
<223> OTHER INFORMATION: Figure 3

<400> SEQUENCE: 17

Thr Lys Leu Asp Ala Val Tyr Leu Asn Lys Asn Lys Tyr Leu Thr Val
1               5                   10                  15

Ile Asp Lys Asp Ala Phe Gly Gly Val Tyr Ser Gly Pro Ser Leu Leu
            20                  25                  30

Asp Val Ser Gln Thr Ser Val Thr Ala Leu Pro Ser Lys Gly Leu Glu
        35                  40                  45

His Leu Lys Glu Leu Ile Ala Arg Asn Thr Trp Thr Leu Lys Lys Leu
    50                  55                  60

Pro Leu Ser Leu Ser Phe Leu His Leu Thr Arg Ala Asp Leu Ser Tyr
65                  70                  75                  80

Pro Ser His Cys Cys Ala Phe Lys Asn Gln Lys Lys Ile Arg Gly Ile
                85                  90                  95

Leu Glu Ser Leu Met
            100

<210> SEQ ID NO 18
<211> LENGTH: 101
<212> TYPE: PRT
<213> ORGANISM: Sus scrofa
<220> FEATURE:
<221> NAME/KEY: misc_feature
<223> OTHER INFORMATION: Figure 3

<400> SEQUENCE: 18

Thr Lys Leu Asp Ala Val Tyr Leu Asn Lys Asn Lys Tyr Leu Thr Val
1               5                   10                  15

Ile Asp Lys Asp Ala Phe Gly Gly Val Phe Ser Gly Pro Thr Leu Leu
            20                  25                  30

Asp Val Ser Tyr Thr Ser Val Thr Ala Leu Pro Pro Lys Gly Leu Glu
        35                  40                  45

His Leu Lys Glu Leu Ile Ala Arg Asn Thr Trp Thr Leu Lys Lys Leu
    50                  55                  60

Pro Leu Ser Leu Ser Phe Leu His Leu Thr Arg Ala Asp Leu Ser Tyr
65                  70                  75                  80

Pro Ser His Cys Cys Ala Phe Lys Asn Gln Lys Lys Ile Arg Gly Ile
                85                  90                  95

Leu Glu Ser Leu Met
            100

<210> SEQ ID NO 19
<211> LENGTH: 101
<212> TYPE: PRT
<213> ORGANISM: Bos taurus
<220> FEATURE:
<221> NAME/KEY: misc_feature
<223> OTHER INFORMATION: Figure 3

<400> SEQUENCE: 19

Thr Lys Leu Asp Ala Val Tyr Leu Asn Lys Asn Lys Tyr Leu Thr Val
1               5                   10                  15

Ile Gly Gln Asp Ala Phe Ala Gly Val Tyr Ser Gly Pro Thr Leu Leu
            20                  25                  30

Asp Ile Ser Tyr Thr Ser Val Thr Ala Leu Pro Ser Lys Gly Leu Glu
        35                  40                  45

His Leu Lys Glu Leu Ile Ala Arg Asn Thr Trp Thr Leu Arg Lys Leu
    50                  55                  60

Pro Leu Ser Leu Ser Phe Leu His Leu Thr Arg Ala Asp Leu Ser Tyr

```
                65                  70                  75                  80
Pro Ser His Cys Cys Ala Phe Lys Asn Gln Lys Lys Ile Arg Gly Ile
                    85                  90                  95

Leu Gln Ser Leu Met
            100

<210> SEQ ID NO 20
<211> LENGTH: 101
<212> TYPE: PRT
<213> ORGANISM: Felis catus
<220> FEATURE:
<221> NAME/KEY: misc_feature
<223> OTHER INFORMATION: Figure 3

<400> SEQUENCE: 20

Thr Lys Leu Asp Ala Val Tyr Leu Asn Lys Asn Lys Tyr Leu Thr Ala
1               5                   10                  15

Ile Asp Gln Asp Ala Phe Gly Gly Val Tyr Ser Gly Pro Thr Leu Leu
                20                  25                  30

Asp Val Ser Tyr Thr Ser Val Thr Ala Leu Pro Ser Lys Gly Leu Glu
            35                  40                  45

His Leu Lys Glu Leu Ile Ala Arg Asn Thr Trp Thr Leu Lys Lys Leu
        50                  55                  60

Pro Leu Thr Leu Ser Phe Leu His Leu Thr Arg Ala Asp Leu Ser Tyr
65                  70                  75                  80

Pro Ser His Cys Cys Ala Phe Lys Asn Gln Lys Lys Ile Arg Gly Ile
                    85                  90                  95

Leu Glu Ser Phe Met
            100

<210> SEQ ID NO 21
<211> LENGTH: 101
<212> TYPE: PRT
<213> ORGANISM: Canis familiaris
<220> FEATURE:
<221> NAME/KEY: misc_feature
<223> OTHER INFORMATION: Figure 3

<400> SEQUENCE: 21

Thr Lys Leu Asp Ala Val Tyr Leu Asn Lys Asn Lys Tyr Leu Ser Ala
1               5                   10                  15

Ile Asp Lys Asp Ala Phe Gly Gly Val Tyr Ser Gly Pro Thr Leu Leu
                20                  25                  30

Asp Val Ser Tyr Thr Ser Val Thr Ala Leu Pro Ser Lys Gly Leu Glu
            35                  40                  45

His Leu Lys Glu Leu Ile Ala Arg Asn Thr Trp Thr Leu Lys Lys Leu
        50                  55                  60

Pro Leu Ser Leu Ser Phe Leu His Leu Thr Arg Ala Asp Leu Ser Tyr
65                  70                  75                  80

Pro Ser His Cys Cys Ala Phe Lys Asn Gln Lys Lys Ile Arg Gly Ile
                    85                  90                  95

Leu Glu Ser Leu Met
            100

<210> SEQ ID NO 22
<211> LENGTH: 101
<212> TYPE: PRT
<213> ORGANISM: Mus musculus
<220> FEATURE:
<221> NAME/KEY: misc_feature
<223> OTHER INFORMATION: Figure 3
```

-continued

<400> SEQUENCE: 22

Thr Lys Leu Asp Ala Val Tyr Leu Asn Lys Asn Lys Tyr Leu Thr Ala
1               5                   10                  15

Ile Asp Asn Asp Ala Phe Gly Gly Val Tyr Ser Gly Pro Thr Leu Leu
            20                  25                  30

Asp Val Ser Ser Thr Ser Val Thr Ala Leu Pro Ser Lys Gly Leu Glu
        35                  40                  45

His Leu Lys Glu Leu Ile Ala Lys Asp Thr Trp Thr Leu Lys Lys Leu
    50                  55                  60

Pro Leu Ser Leu Ser Phe Leu His Leu Thr Arg Ala Asp Leu Ser Tyr
65                  70                  75                  80

Pro Ser His Cys Cys Ala Phe Lys Asn Gln Lys Lys Ile Arg Gly Ile
                85                  90                  95

Leu Glu Ser Leu Met
            100

<210> SEQ ID NO 23
<211> LENGTH: 101
<212> TYPE: PRT
<213> ORGANISM: Rattus norvegicus
<220> FEATURE:
<221> NAME/KEY: misc_feature
<223> OTHER INFORMATION: Figure 3

<400> SEQUENCE: 23

Thr Lys Leu Asp Ala Val Tyr Leu Asn Lys Asn Lys Tyr Leu Thr Ala
1               5                   10                  15

Ile Asp Lys Asp Ala Phe Gly Gly Val Tyr Ser Gly Pro Thr Leu Leu
            20                  25                  30

Asp Val Ser Ser Thr Ser Val Thr Ala Leu Pro Ser Lys Gly Leu Glu
        35                  40                  45

His Leu Lys Glu Leu Ile Ala Lys Asn Thr Trp Thr Leu Lys Lys Leu
    50                  55                  60

Pro Leu Ser Leu Ser Phe Leu His Leu Thr Arg Ala Asp Leu Ser Tyr
65                  70                  75                  80

Pro Ser His Cys Cys Ala Phe Lys Asn Gln Lys Lys Ile Arg Gly Ile
                85                  90                  95

Leu Glu Ser Leu Met
            100

<210> SEQ ID NO 24
<211> LENGTH: 101
<212> TYPE: PRT
<213> ORGANISM: Ovis aries
<220> FEATURE:
<221> NAME/KEY: misc_feature
<223> OTHER INFORMATION: Figure 3

<400> SEQUENCE: 24

Thr Lys Leu Asp Ala Val Tyr Leu Asn Lys Asn Lys Tyr Leu Thr Val
1               5                   10                  15

Ile Asp Gln Asp Ala Phe Ala Gly Val Tyr Ser Gly Pro Thr Leu Leu
            20                  25                  30

Asp Ile Ser Tyr Thr Ser Val Thr Ala Leu Pro Ser Lys Gly Leu Glu
        35                  40                  45

His Leu Lys Glu Leu Ile Ala Arg Asn Thr Trp Thr Leu Lys Lys Leu
    50                  55                  60

Pro Leu Ser Leu Ser Phe Leu His Leu Thr Arg Ala Asp Leu Ser Tyr

```
                65                  70                  75                  80
Pro Ser His Cys Cys Ala Phe Lys Asn Gln Lys Asn Ile Arg Gly Ile
                85                  90                  95

Leu Gln Ser Leu Met
            100

<210> SEQ ID NO 25
<211> LENGTH: 200
<212> TYPE: DNA
<213> ORGANISM: Felis catus
<220> FEATURE:
<221> NAME/KEY: misc_feature
<223> OTHER INFORMATION: Figure 4

<400> SEQUENCE: 25
tcttacacca gtgtcactgc cctgccatcc aaaggcctgg agcacctgaa ggaattgata      60
gcaagaaaca cttggactct aaagaaactt ccacttacct tgagtttcct tcacctcaca     120
cgggctgacc tttcttatcc aagccactgc tgtgctttta agaatcagaa gaaaatcaga     180
ggaatccttg agtccttcat                                                 200

<210> SEQ ID NO 26
<211> LENGTH: 200
<212> TYPE: DNA
<213> ORGANISM: Bos taurus
<220> FEATURE:
<221> NAME/KEY: misc_feature
<223> OTHER INFORMATION: Figure 4

<400> SEQUENCE: 26
tcttatacca gtgtcacagc cctaccatcc aaaggcctgg aacacctgaa ggaattgata      60
gcaagaaaca cttggactct aaggaaactt cctctttcct tgagtttcct tcacctcaca     120
cgggctgacc tttcttatcc gagccactgc tgcgctttta agaatcagaa gaaaatcaga     180
ggaatccttc agtctttaat                                                 200

<210> SEQ ID NO 27
<211> LENGTH: 200
<212> TYPE: DNA
<213> ORGANISM: Canis familiaris
<220> FEATURE:
<221> NAME/KEY: misc_feature
<223> OTHER INFORMATION: Figure 4

<400> SEQUENCE: 27
tcttacacca gtgttactgc cctgccatcc aaaggcctgg agcatctaaa ggagctgata      60
gcaagaaaca cttggactct aaagaaactc ccactttcct tgagtttcct tcaccttaca     120
cgggctgacc tttcttatcc aagccactgc tgtgctttta agaatcagaa gaaaatcaga     180
ggaatccttg agtccttaat                                                 200

<210> SEQ ID NO 28
<211> LENGTH: 200
<212> TYPE: DNA
<213> ORGANISM: Mus musculus
<220> FEATURE:
<221> NAME/KEY: misc_feature
<223> OTHER INFORMATION: Figure 4

<400> SEQUENCE: 28
tcttccacca gcgtcactgc ccttccttcc aaaggcctgg agcacctcaa agaactgatc      60
gcaaaagaca cctggactct caaaaagctc ccgctgtcgt tgagtttcct ccacctcact     120
```

```
cgggctgacc tctcttaccc gagccactgc tgcgctttta agaaccagaa gaaaatcagg    180
ggaatcctgg agtctttgat                                                200

<210> SEQ ID NO 29
<211> LENGTH: 200
<212> TYPE: DNA
<213> ORGANISM: Sus scrofa
<220> FEATURE:
<221> NAME/KEY: misc_feature
<223> OTHER INFORMATION: Figure 4

<400> SEQUENCE: 29
tcttatacca gtgttactgc cctgccaccc aaaggcctgg aacacctgaa ggaactgata    60
gcaagaaata cttggactct aaagaaactt ccactgtcct tgagtttcct tcacctcaca    120
cgagctgacc tttcttatcc aagccactgc tgtgctttta agaatcagaa gaagatcaga    180
ggaatccttg agtctttaat                                                200

<210> SEQ ID NO 30
<211> LENGTH: 200
<212> TYPE: DNA
<213> ORGANISM: Rattus norvegicus
<220> FEATURE:
<221> NAME/KEY: misc_feature
<223> OTHER INFORMATION: Figure 4

<400> SEQUENCE: 30
tcttccacca gcgttactgc tcttccttcc aaaggcctgg agcacctcaa agagctgatc    60
gcgaagaaca cctggactct caaaaagctc ccctgtcct tgagcttcct ccacctcact    120
cgggctgacc tctcttaccc aagtcactgc tgtgctttta agaaccagaa gaaaatcagg    180
ggaatcctag agtctttgat                                                200

<210> SEQ ID NO 31
<211> LENGTH: 200
<212> TYPE: DNA
<213> ORGANISM: Ovis aries
<220> FEATURE:
<221> NAME/KEY: misc_feature
<223> OTHER INFORMATION: Figure 4

<400> SEQUENCE: 31
tcttatacca gtgtcactgc cctaccatcc aaaggcctgg aacacctgaa ggaattgata    60
gcaagaaaca cttggactct aaagaaactt cctctttcct tgagtttcct tcacctcaca    120
cgggctgacc tttcttatcc gagccactgc tgtgctttta agaatcagaa gaatatcaga    180
ggaatccttc agtctttaat                                                200

<210> SEQ ID NO 32
<211> LENGTH: 200
<212> TYPE: DNA
<213> ORGANISM: Homo sapiens
<220> FEATURE:
<221> NAME/KEY: misc_feature
<223> OTHER INFORMATION: Figure 4

<400> SEQUENCE: 32
tctcaaacca gtgtcactgc ccttccatcc aaaggcctgg agcacctgaa ggaactgata    60
gcaagaaaca cctggactct taagaaactt ccactttcct tgagtttcct tcacctcaca    120
cgggctgacc tttcttaccc aagccactgc tgtgccttta agaatcagaa gaaaatcaga    180
ggaatccttg agtcctttgat                                               200
```

-continued

<210> SEQ ID NO 33
<211> LENGTH: 200
<212> TYPE: PRT
<213> ORGANISM: Homo sapiens
<220> FEATURE:
<221> NAME/KEY: misc_feature
<223> OTHER INFORMATION: Figure 5

<400> SEQUENCE: 33

```
Lys Glu Leu Ile Ala Arg Asn Thr Trp Thr Leu Lys Lys Leu Pro Leu
1               5                   10                  15

Ser Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Glu
        35                  40                  45

Ser Leu Met Cys Asn Glu Ser Ser Met Gln Ser Leu Arg Gln Arg Lys
    50                  55                  60

Ser Val Asn Ala Leu Asn Ser Pro Leu His Gln Glu Tyr Glu Glu Asn
65                  70                  75                  80

Leu Gly Asp Ser Ile Val Gly Tyr Lys Glu Lys Ser Lys Phe Gln Asp
                85                  90                  95

Thr His Asn Asn Ala His Tyr Tyr Val Phe Glu Glu Gln Glu Asp
            100                 105                 110

Glu Ile Ile Gly Phe Gly Gln Glu Leu Lys Asn Pro Gln Glu Glu Thr
        115                 120                 125

Leu Gln Ala Phe Asp Ser His Tyr Asp Tyr Thr Ile Cys Gly Asp Ser
    130                 135                 140

Glu Asp Met Val Cys Thr Pro Lys Ser Asp Glu Phe Asn Pro Cys Glu
145                 150                 155                 160

Asp Ile Met Gly Tyr Lys Phe Leu Arg Ile Val Val Trp Phe Val Ser
                165                 170                 175

Leu Leu Ala Leu Leu Gly Asn Val Phe Val Leu Leu Ile Leu Leu Thr
            180                 185                 190

Ser His Tyr Lys Leu Asn Val Pro
        195                 200
```

<210> SEQ ID NO 34
<211> LENGTH: 200
<212> TYPE: PRT
<213> ORGANISM: Sus scrofa
<220> FEATURE:
<221> NAME/KEY: misc_feature
<223> OTHER INFORMATION: Figure 5

<400> SEQUENCE: 34

```
Lys Glu Leu Ile Ala Arg Asn Thr Trp Thr Leu Lys Lys Leu Pro Leu
1               5                   10                  15

Ser Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Glu
        35                  40                  45

Ser Leu Met Cys Asn Glu Ser Ser Ile Arg Ser Leu Arg Gln Arg Lys
    50                  55                  60

Ser Val Asn Ala Val Asn Gly Pro Phe Tyr Gln Glu Tyr Glu Glu Asp
65                  70                  75                  80

Leu Gly Asp Thr Ser Val Gly Asn Lys Glu Asn Ser Lys Phe Gln Asp
                85                  90                  95

Thr His Ser Asn Ser His Tyr Tyr Val Phe Phe Glu Glu Gln Glu Asp
```

```
                        100                 105                 110
Glu Ile Ile Gly Phe Gly Gln Glu Leu Lys Asn Pro Gln Glu Thr
            115                 120                 125

Leu Gln Ala Phe Asp Ser His Tyr Asp Tyr Thr Val Cys Gly Gly Ser
        130                 135                 140

Glu Asp Met Val Cys Thr Pro Lys Ser Asp Glu Phe Asn Pro Cys Glu
145                 150                 155                 160

Asp Ile Met Gly Tyr Arg Phe Leu Arg Ile Val Val Trp Phe Val Ser
            165                 170                 175

Leu Leu Ala Leu Leu Gly Asn Val Phe Val Leu Val Ile Leu Leu Thr
        180                 185                 190

Ser His Tyr Lys Leu Thr Val Pro
        195                 200

<210> SEQ ID NO 35
<211> LENGTH: 200
<212> TYPE: PRT
<213> ORGANISM: Bos taurus
<220> FEATURE:
<221> NAME/KEY: misc_feature
<223> OTHER INFORMATION: Figure 5
<220> FEATURE:
<221> NAME/KEY: MISC_FEATURE
<222> LOCATION: (80)..(80)
<223> OTHER INFORMATION: spacer for sequence alignment of figure 5

<400> SEQUENCE: 35

Lys Glu Leu Ile Ala Arg Asn Thr Trp Thr Leu Arg Lys Leu Pro Leu
1               5                   10                  15

Ser Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Gln
        35                  40                  45

Ser Leu Met Cys Asn Glu Ser Ser Ile Arg Gly Leu Arg Gln Arg Lys
    50                  55                  60

Ser Ala Ser Ala Leu Asn Gly Pro Phe Tyr Gln Glu Tyr Glu Asp Xaa
65                  70                  75                  80

Leu Gly Asp Gly Ser Ala Gly Tyr Lys Glu Asn Ser Lys Phe Gln Asp
            85                  90                  95

Thr Gln Ser Asn Ser His Tyr Tyr Val Phe Phe Glu Glu Gln Glu Asp
        100                 105                 110

Glu Ile Ile Gly Phe Gly Gln Gln Leu Lys Asn Pro Gln Glu Thr
            115                 120                 125

Leu Gln Ala Phe Asp Ser His Tyr Asp Tyr Thr Val Cys Gly Gly Ser
        130                 135                 140

Glu Asp Met Val Cys Thr Pro Lys Ser Asp Glu Phe Asn Pro Cys Glu
145                 150                 155                 160

Asp Ile Met Gly Tyr Lys Phe Leu Arg Ile Val Val Trp Phe Val Ser
            165                 170                 175

Leu Leu Ala Leu Leu Gly Asn Val Phe Val Leu Val Ile Leu Leu Thr
        180                 185                 190

Ser His Tyr Lys Leu Thr Val Pro
        195                 200

<210> SEQ ID NO 36
<211> LENGTH: 200
<212> TYPE: PRT
<213> ORGANISM: Felis catus
<220> FEATURE:
```

```
<221> NAME/KEY: misc_feature
<223> OTHER INFORMATION: Figure 5
<220> FEATURE:
<221> NAME/KEY: MISC_FEATURE
<222> LOCATION: (111)..(111)
<223> OTHER INFORMATION: spacer for sequence alignment of Figure 5

<400> SEQUENCE: 36

Lys Glu Leu Ile Ala Arg Asn Thr Trp Thr Leu Lys Lys Leu Pro Leu
1               5                   10                  15

Thr Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Glu
        35                  40                  45

Ser Phe Met Cys Asn Asp Ser Ser Ile Arg Ser Leu Arg Gln Arg Lys
    50                  55                  60

Ser Val Asn Ala Leu Asn Gly Pro Phe Asp Gln Glu Tyr Glu Glu Tyr
65                  70                  75                  80

Leu Gly Asp Ser His Ala Gly Tyr Lys Asp Asn Ser Lys Phe Gln Asp
                85                  90                  95

Thr Arg Ser Asn Ser His Tyr Tyr Val Phe Phe Glu Glu Gln Xaa Asp
            100                 105                 110

Glu Ile Leu Gly Phe Gly Gln Glu Leu Lys Asn Pro Gln Glu Glu Thr
        115                 120                 125

Leu Gln Ala Phe Asp Ser His Tyr Asp Tyr Thr Val Cys Gly Gly Asn
    130                 135                 140

Glu Asp Met Val Cys Thr Pro Lys Ser Asp Glu Phe Asn Pro Cys Glu
145                 150                 155                 160

Asp Ile Met Gly Tyr Lys Phe Leu Arg Ile Val Val Trp Phe Val Ser
                165                 170                 175

Leu Leu Ala Leu Leu Gly Asn Val Phe Val Leu Ile Ile Leu Leu Thr
            180                 185                 190

Ser His Tyr Lys Leu Thr Val Pro
        195                 200

<210> SEQ ID NO 37
<211> LENGTH: 200
<212> TYPE: PRT
<213> ORGANISM: Canis familiaris
<220> FEATURE:
<221> NAME/KEY: misc_feature
<223> OTHER INFORMATION: Figure 5

<400> SEQUENCE: 37

Lys Glu Leu Ile Ala Arg Asn Thr Trp Thr Leu Lys Lys Leu Pro Leu
1               5                   10                  15

Ser Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Glu
        35                  40                  45

Ser Leu Met Cys Asn Glu Ser Ser Ile Arg Ser Leu Arg Gln Arg Lys
    50                  55                  60

Ser Val Asn Thr Leu Asn Gly Pro Phe Asp Gln Glu Tyr Glu Glu Tyr
65                  70                  75                  80

Leu Gly Asp Ser His Ala Gly Tyr Lys Asp Asn Ser Gln Phe Gln Asp
                85                  90                  95

Thr Asp Ser Asn Ser His Tyr Tyr Val Phe Phe Glu Glu Gln Glu Asp
            100                 105                 110
```

```
Glu Ile Leu Gly Phe Gly Gln Glu Leu Lys Asn Pro Gln Glu Thr
        115                 120                 125

Leu Gln Ala Phe Asp Ser His Tyr Asp Tyr Thr Val Cys Gly Gly Asn
    130                 135                 140

Glu Asp Met Val Cys Thr Pro Lys Ser Asp Glu Phe Asn Pro Cys Glu
145                 150                 155                 160

Asp Ile Met Gly Tyr Lys Phe Leu Arg Ile Val Val Trp Phe Val Ser
                165                 170                 175

Leu Leu Ala Leu Leu Gly Asn Val Phe Val Leu Ile Val Leu Leu Thr
            180                 185                 190

Ser His Tyr Lys Leu Thr Val Pro
        195                 200

<210> SEQ ID NO 38
<211> LENGTH: 200
<212> TYPE: PRT
<213> ORGANISM: Mus musculus
<220> FEATURE:
<221> NAME/KEY: misc_feature
<223> OTHER INFORMATION: Figure 5

<400> SEQUENCE: 38

Lys Glu Leu Ile Ala Lys Asp Thr Trp Thr Leu Lys Lys Leu Pro Leu
1               5                   10                  15

Ser Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Glu
        35                  40                  45

Ser Leu Met Cys Asn Glu Ser Ser Ile Arg Asn Leu Arg Gln Arg Lys
    50                  55                  60

Ser Val Asn Ile Leu Arg Gly Pro Ile Tyr Gln Glu Tyr Glu Glu Asp
65                  70                  75                  80

Pro Gly Asp Asn Ser Val Gly Tyr Lys Gln Asn Ser Lys Phe Gln Glu
                85                  90                  95

Ser Pro Ser Asn Ser His Tyr Tyr Val Phe Phe Glu Glu Gln Glu Asp
            100                 105                 110

Glu Val Val Gly Phe Gly Gln Glu Leu Lys Asn Pro Gln Glu Thr
        115                 120                 125

Leu Gln Ala Phe Glu Ser His Tyr Asp Tyr Thr Val Cys Gly Asp Asn
    130                 135                 140

Glu Asp Met Val Cys Thr Pro Lys Ser Asp Glu Phe Asn Pro Cys Glu
145                 150                 155                 160

Asp Ile Met Gly Tyr Arg Phe Leu Arg Ile Val Val Trp Phe Val Ser
                165                 170                 175

Leu Leu Ala Leu Leu Gly Asn Ile Phe Val Leu Leu Ile Leu Leu Thr
            180                 185                 190

Ser His Tyr Lys Leu Thr Val Pro
        195                 200

<210> SEQ ID NO 39
<211> LENGTH: 200
<212> TYPE: PRT
<213> ORGANISM: Rattus norvegicus
<220> FEATURE:
<221> NAME/KEY: misc_feature
<223> OTHER INFORMATION: Figure 5

<400> SEQUENCE: 39

Lys Glu Leu Ile Ala Lys Asn Thr Trp Thr Leu Lys Lys Leu Pro Leu
```

```
                1               5                   10                  15
Ser Leu Ser Phe Leu His Leu Thr Arg Ala Asp Leu Ser Tyr Pro Ser
            20                  25                  30

His Cys Cys Ala Phe Lys Asn Gln Lys Lys Ile Arg Gly Ile Leu Glu
            35                  40                  45

Ser Leu Met Cys Asn Glu Ser Ser Ile Arg Asn Leu Arg Gln Arg Lys
50                  55                  60

Ser Val Asn Val Met Arg Gly Pro Val Tyr Gln Glu Tyr Glu Glu Gly
65                  70                  75                  80

Leu Gly Asp Asn His Val Gly Tyr Lys Gln Asn Ser Lys Phe Gln Glu
                85                  90                  95

Gly Pro Ser Asn Ser His Tyr Tyr Val Phe Glu Glu Gln Glu Asp
            100                 105                 110

Glu Ile Ile Gly Phe Gly Gln Glu Leu Lys Asn Pro Gln Glu Thr
            115                 120                 125

Leu Gln Ala Phe Asp Ser His Tyr Asp Tyr Thr Val Cys Gly Asp Asn
            130                 135                 140

Glu Asp Met Val Cys Thr Pro Lys Ser Asp Glu Phe Asn Pro Cys Glu
145                 150                 155                 160

Asp Ile Met Gly Tyr Lys Phe Leu Arg Ile Val Val Trp Phe Val Ser
                165                 170                 175

Pro Met Ala Leu Leu Gly Asn Val Phe Val Leu Phe Val Leu Leu Thr
            180                 185                 190

Ser His Tyr Lys Leu Thr Val Pro
            195                 200

<210> SEQ ID NO 40
<211> LENGTH: 200
<212> TYPE: PRT
<213> ORGANISM: Ovis aries
<220> FEATURE:
<221> NAME/KEY: misc_feature
<223> OTHER INFORMATION: Figure 5

<400> SEQUENCE: 40

Lys Glu Leu Ile Ala Arg Asn Thr Trp Thr Leu Lys Lys Leu Pro Leu
1               5                   10                  15

Ser Leu Ser Phe Leu His Leu Thr Arg Ala Asp Leu Ser Tyr Pro Ser
            20                  25                  30

His Cys Cys Ala Phe Lys Asn Gln Lys Asn Ile Arg Gly Ile Leu Gln
            35                  40                  45

Ser Leu Met Cys Asn Glu Ser Ser Ile Trp Gly Leu Arg Gln Arg Lys
50                  55                  60

Ser Ala Ser Ala Leu Asn Gly Pro Phe Tyr Gln Glu Tyr Glu Glu Asp
65                  70                  75                  80

Leu Gly Asp Gly Ser Ala Gly Tyr Lys Glu Asn Ser Lys Phe Gln Asp
                85                  90                  95

Thr His Ser Asn Ser His Tyr Tyr Val Phe Phe Glu Asp Gln Glu Asp
            100                 105                 110

Glu Ile Ile Gly Phe Gly Gln Glu Leu Lys Asn Pro Gln Glu Thr
            115                 120                 125

Leu Gln Ala Phe Asp Asn His Tyr Asp Tyr Thr Val Cys Gly Gly Ser
            130                 135                 140

Glu Glu Met Val Cys Thr Pro Lys Ser Asp Glu Phe Asn Pro Cys Glu
145                 150                 155                 160

Asp Ile Met Gly Tyr Lys Phe Leu Arg Ile Val Val Trp Phe Val Ser
```

```
                          165                 170                 175
Leu Leu Ala Leu Leu Gly Asn Val Phe Val Leu Val Ile Leu Leu Thr
            180                 185                 190

Ser His Tyr Lys Leu Thr Val Pro
        195                 200

<210> SEQ ID NO 41
<211> LENGTH: 351
<212> TYPE: DNA
<213> ORGANISM: Felis catus
<220> FEATURE:
<221> NAME/KEY: misc_feature
<223> OTHER INFORMATION: Figure 6
<220> FEATURE:
<221> NAME/KEY: misc_feature
<222> LOCATION: (329)..(331)
<223> OTHER INFORMATION: spacers for sequence alignment of figure 6

<400> SEQUENCE: 41
ggaattgata gcaagaaaca cttggactct aaagaaactt ccacttacct tgagtttcct      60
tcacctcaca cgggctgacc tttcttatcc aagccactgc tgtgctttta agaatcagaa     120
gaaaatcaga ggaatccttg agtccttcat gtgtaatgac agcagtattc ggagcctgcg     180
tcagagaaaa tctgtgaatg ctttgaatgg tcccttcgac caggaatatg aagagtatct     240
aggtgacagc catgctggat ataaggacaa ctctaagttc caggatactc gcagcaactc     300
tcattattat gtcttctttg aagaacaann ngacgagatc cttggttttg g              351

<210> SEQ ID NO 42
<211> LENGTH: 351
<212> TYPE: DNA
<213> ORGANISM: Bos taurus
<220> FEATURE:
<221> NAME/KEY: misc_feature
<223> OTHER INFORMATION: Figure 6
<220> FEATURE:
<221> NAME/KEY: misc_feature
<222> LOCATION: (236)..(238)
<223> OTHER INFORMATION: spacers for sequence alignment of figure 6

<400> SEQUENCE: 42
ggaattgata gcaagaaaca cttggactct aaggaaactt cctctttcct tgagtttcct      60
tcacctcaca cgggctgacc tttcttatcc gagccactgc tgcgctttta agaatcagaa     120
gaaaatcaga ggaatccttc agtctttaat gtgtaacgag agcagtattc ggggcctgcg     180
tcagagaaaa tccgcaagtg ctttgaatgg tcccttctac caggaatatg aggatnnnct     240
gggtgatggc agtgctgggt acaaggagaa ctccaagttc caagataccc aaagcaactc     300
tcattactat gtcttctttg aggagcaaga agatgagatc atcggttttg g              351

<210> SEQ ID NO 43
<211> LENGTH: 351
<212> TYPE: DNA
<213> ORGANISM: Canis familiaris
<220> FEATURE:
<221> NAME/KEY: misc_feature
<223> OTHER INFORMATION: Figure 6

<400> SEQUENCE: 43
ggagctgata gcaagaaaca cttggactct aaagaaactc ccactttcct tgagtttcct      60
tcaccttaca cgggctgacc tttcttatcc aagccactgc tgtgctttta agaatcagaa     120
gaaaatcaga ggaatccttg agtccttaat gtgtaatgaa agcagtattc ggagcctgcg     180
ccagagaaaa tctgtgaata ctttgaatgg ccccttcgac caggaatatg aagagtatct     240
```

```
gggtgacagc catgctgggt acaaggacaa ctctcagttc caggataccg atagcaattc    300
tcattattat gtcttcttcg aagaacaaga agatgagatc ctcggttttg g            351
```

<210> SEQ ID NO 44
<211> LENGTH: 351
<212> TYPE: DNA
<213> ORGANISM: Mus musculus
<220> FEATURE:
<221> NAME/KEY: misc_feature
<223> OTHER INFORMATION: Figure 6

<400> SEQUENCE: 44

```
agaactgatc gcaaaagaca cctggactct caaaaagctc ccgctgtcgt tgagtttcct    60
ccacctcact cgggctgacc tctcttaccc gagccactgc tgcgctttta agaaccagaa   120
gaaaatcagg ggaatcctgg agtctttgat gtgtaatgag agcagtatcc ggaaccttcg   180
tcaaaggaaa tcagtgaaca tcttgagggg tcccatctac caggaatatg aagaagatcc   240
gggtgacaac agtgttgggt acaaacaaaa ctccaagttc caggagagcc caagcaactc   300
tcactattac gtcttctttg aagaacaaga ggatgaggtc gttggtttcg g            351
```

<210> SEQ ID NO 45
<211> LENGTH: 351
<212> TYPE: DNA
<213> ORGANISM: Sus scrofa
<220> FEATURE:
<221> NAME/KEY: misc_feature
<223> OTHER INFORMATION: Figure 6

<400> SEQUENCE: 45

```
ggaactgata gcaagaaata cttggactct aaagaaactt ccactgtcct tgagtttcct    60
tcacctcaca cgagctgacc tttcttatcc aagccactgc tgtgctttta agaatcagaa   120
gaagatcaga ggaatccttg agtctttaat gtgtaatgag agcagtattc ggagcctgcg   180
tcagagaaaa tctgtgaatg ctgtaaatgg tcccttttac caagaatatg aagaggatct   240
gggcgacacg agtgttggga ataaggaaaa ctccaagttc caggataccc atagcaactc   300
ccattactac gtcttctttg aagaacaaga ggatgagatc attggttttg g            351
```

<210> SEQ ID NO 46
<211> LENGTH: 351
<212> TYPE: DNA
<213> ORGANISM: Rattus norvegicus
<220> FEATURE:
<221> NAME/KEY: misc_feature
<223> OTHER INFORMATION: Figure 6

<400> SEQUENCE: 46

```
agagctgatc gcgaagaaca cctggactct caaaaagctc ccctgtcct tgagcttcct     60 ccacctcact cgggctgacc tctcttaccc aagtcactgc tgtgctttta agaaccagaa   120
gaaaatcagg ggaatcctag agtctttgat gtgtaatgag agtagtatcc ggaacctgcg   180
tcaaagaaag tcagtgaacg tcatgagggg tcccgtctac caggaatatg aagaaggtct   240
gggtgacaac catgttgggt acaaacaaaa ctccaagttc caggagggcc caagcaactc   300
tcactattac gtcttctttg aagaacaaga ggacgagatc atcggtttcg g            351
```

<210> SEQ ID NO 47
<211> LENGTH: 351
<212> TYPE: DNA
<213> ORGANISM: Ovis aries
<220> FEATURE:

<221> NAME/KEY: misc_feature
<223> OTHER INFORMATION: Figure 6

<400> SEQUENCE: 47

```
ggaattgata gcaagaaaca cttggactct aaagaaactt cctctttcct tgagtttcct    60
tcacctcaca cgggctgacc tttcttatcc gagccactgc tgtgctttta agaatcagaa   120
gaatatcaga ggaatccttc agtctttaat gtgtaacgag agcagtattt ggggcctgcg   180
tcagagaaaa tccgcgagtg ctttgaatgg tcccttctac caggaatatg aagaggatct   240
gggtgatggc agtgctgggt acaaggagaa ctccaagttc caagataccc acagcaactc   300
tcattactat gtcttctttg aggatcaaga agatgagatc atcggttttg g            351
```

<210> SEQ ID NO 48
<211> LENGTH: 351
<212> TYPE: DNA
<213> ORGANISM: Homo sapiens
<220> FEATURE:
<221> NAME/KEY: misc_feature
<223> OTHER INFORMATION: Figure 6

<400> SEQUENCE: 48

```
ggaactgata gcaagaaaca cctggactct taagaaactt ccactttcct tgagtttcct    60
tcacctcaca cgggctgacc tttcttaccc aagccactgc tgtgccttta agaatcagaa   120
gaaaatcaga ggaatccttg agtccttgat gtgtaatgag agcagtatgc agagcttgcg   180
ccagagaaaa tctgtgaatg ccttgaatag ccccctccac caggaatatg aagagaatct   240
gggtgacagc attgttgggt acaaggaaaa gtccaagttc caggatactc ataacaacgc   300
tcattattac gtcttctttg aagaacaaga ggatgagatc attggttttg g            351
```

<210> SEQ ID NO 49
<211> LENGTH: 151
<212> TYPE: PRT
<213> ORGANISM: Homo sapiens
<220> FEATURE:
<221> NAME/KEY: misc_feature
<223> OTHER INFORMATION: Figure 7

<400> SEQUENCE: 49

```
Ala His Tyr Tyr Val Phe Phe Glu Glu Gln Glu Asp Glu Ile Ile Gly
1               5                   10                  15

Phe Gly Gln Glu Leu Lys Asn Pro Gln Glu Thr Leu Gln Ala Phe
            20                  25                  30

Asp Ser His Tyr Asp Tyr Thr Ile Cys Gly Asp Ser Glu Asp Met Val
        35                  40                  45

Cys Thr Pro Lys Ser Asp Glu Phe Asn Pro Cys Glu Asp Ile Met Gly
    50                  55                  60

Tyr Lys Phe Leu Arg Ile Val Val Trp Phe Val Ser Leu Leu Ala Leu
65                  70                  75                  80

Leu Gly Asn Val Phe Val Leu Leu Ile Leu Leu Thr Ser His Tyr Lys
                85                  90                  95

Leu Asn Val Pro Arg Phe Leu Met Cys Asn Leu Ala Phe Ala Asp Phe
            100                 105                 110

Cys Met Gly Met Tyr Leu Leu Leu Ile Ala Ser Val Asp Leu Tyr Thr
        115                 120                 125

His Ser Glu Tyr Tyr Asn His Ala Ile Asp Trp Gln Thr Gly Pro Gly
    130                 135                 140

Cys Asn Thr Ala Gly Phe Phe
145             150
```

```
<210> SEQ ID NO 50
<211> LENGTH: 151
<212> TYPE: PRT
<213> ORGANISM: Sus scrofa
<220> FEATURE:
<221> NAME/KEY: misc_feature
<223> OTHER INFORMATION: Figure 7

<400> SEQUENCE: 50

Ser His Tyr Tyr Val Phe Phe Glu Glu Gln Glu Asp Glu Ile Ile Gly
 1               5                  10                  15

Phe Gly Gln Glu Leu Lys Asn Pro Gln Glu Glu Thr Leu Gln Ala Phe
            20                  25                  30

Asp Ser His Tyr Asp Tyr Thr Val Cys Gly Gly Ser Glu Asp Met Val
        35                  40                  45

Cys Thr Pro Lys Ser Asp Glu Phe Asn Pro Cys Glu Asp Ile Met Gly
    50                  55                  60

Tyr Arg Phe Leu Arg Ile Val Val Trp Phe Val Ser Leu Leu Ala Leu
65                  70                  75                  80

Leu Gly Asn Val Phe Val Leu Val Ile Leu Leu Thr Ser His Tyr Lys
                85                  90                  95

Leu Thr Val Pro Arg Phe Leu Met Cys Asn Leu Ala Phe Ala Asp Phe
            100                 105                 110

Cys Met Gly Met Tyr Leu Leu Leu Ile Ala Ser Val Asp Leu Tyr Thr
        115                 120                 125

Gln Ser Glu Tyr Tyr Asn His Ala Ile Asp Trp Gln Thr Gly Pro Gly
    130                 135                 140

Cys Asn Thr Ala Gly Phe Phe
145                 150

<210> SEQ ID NO 51
<211> LENGTH: 151
<212> TYPE: PRT
<213> ORGANISM: Bos taurus
<220> FEATURE:
<221> NAME/KEY: misc_feature
<223> OTHER INFORMATION: Figure 7

<400> SEQUENCE: 51

Ser His Tyr Tyr Val Phe Phe Glu Glu Gln Glu Asp Glu Ile Ile Gly
 1               5                  10                  15

Phe Gly Gln Gln Leu Lys Asn Pro Gln Glu Glu Thr Leu Gln Ala Phe
            20                  25                  30

Asp Ser His Tyr Asp Tyr Thr Val Cys Gly Gly Ser Glu Asp Met Val
        35                  40                  45

Cys Thr Pro Lys Ser Asp Glu Phe Asn Pro Cys Glu Asp Ile Met Gly
    50                  55                  60

Tyr Lys Phe Leu Arg Ile Val Val Trp Phe Val Ser Leu Leu Ala Leu
65                  70                  75                  80

Leu Gly Asn Val Phe Val Leu Val Ile Leu Leu Thr Ser His Tyr Lys
                85                  90                  95

Leu Thr Val Pro Arg Phe Leu Met Cys Asn Leu Ala Phe Ala Asp Phe
            100                 105                 110

Cys Met Gly Leu Tyr Leu Leu Leu Ile Ala Ser Val Asp Leu Tyr Thr
        115                 120                 125

Gln Ser Glu Tyr Tyr Asn His Ala Ile Asp Trp Gln Thr Gly Pro Gly
    130                 135                 140
```

```
Cys Asn Thr Ala Gly Phe Phe
145                 150
```

<210> SEQ ID NO 52
<211> LENGTH: 151
<212> TYPE: PRT
<213> ORGANISM: Felis catus
<220> FEATURE:
<221> NAME/KEY: misc_feature
<223> OTHER INFORMATION: Figure 7
<220> FEATURE:
<221> NAME/KEY: misc_feature
<222> LOCATION: (11)..(11)
<223> OTHER INFORMATION: spacer for sequence alignment of figure 7

<400> SEQUENCE: 52

```
Ser His Tyr Tyr Val Phe Phe Glu Glu Gln Xaa Asp Glu Ile Leu Gly
1               5                   10                  15

Phe Gly Gln Glu Leu Lys Asn Pro Gln Glu Glu Thr Leu Gln Ala Phe
                20                  25                  30

Asp Ser His Tyr Asp Tyr Thr Val Cys Gly Gly Asn Glu Asp Met Val
            35                  40                  45

Cys Thr Pro Lys Ser Asp Glu Phe Asn Pro Cys Glu Asp Ile Met Gly
        50                  55                  60

Tyr Lys Phe Leu Arg Ile Val Val Trp Phe Val Ser Leu Leu Ala Leu
65                  70                  75                  80

Leu Gly Asn Val Phe Val Leu Ile Ile Leu Leu Thr Ser His Tyr Lys
                85                  90                  95

Leu Thr Val Pro Arg Phe Leu Met Cys Asn Leu Ala Phe Ala Asp Phe
                100                 105                 110

Cys Met Gly Met Tyr Leu Leu Leu Ile Ala Ser Val Asp Leu Tyr Thr
            115                 120                 125

His Ser Glu Tyr Tyr Asn His Ala Ile Asp Trp Gln Thr Gly Pro Gly
        130                 135                 140

Cys Asn Ala Ala Gly Phe Phe
145                 150
```

<210> SEQ ID NO 53
<211> LENGTH: 151
<212> TYPE: PRT
<213> ORGANISM: Canis familiaris
<220> FEATURE:
<221> NAME/KEY: misc_feature
<223> OTHER INFORMATION: Figure 7

<400> SEQUENCE: 53

```
Ser His Tyr Tyr Val Phe Phe Glu Glu Gln Glu Asp Glu Ile Leu Gly
1               5                   10                  15

Phe Gly Gln Glu Leu Lys Asn Pro Gln Glu Glu Thr Leu Gln Ala Phe
                20                  25                  30

Asp Ser His Tyr Asp Tyr Thr Val Cys Gly Gly Asn Glu Asp Met Val
            35                  40                  45

Cys Thr Pro Lys Ser Asp Glu Phe Asn Pro Cys Glu Asp Ile Met Gly
        50                  55                  60

Tyr Lys Phe Leu Arg Ile Val Val Trp Phe Val Ser Leu Leu Ala Leu
65                  70                  75                  80

Leu Gly Asn Val Phe Val Leu Ile Val Leu Leu Thr Ser His Tyr Lys
                85                  90                  95

Leu Thr Val Pro Arg Phe Leu Met Cys Asn Leu Ala Phe Ala Asp Phe
                100                 105                 110
```

Cys Met Gly Met Tyr Leu Leu Ile Ala Ser Val Asp Leu Tyr Thr
              115                 120                 125

His Ser Glu Tyr Tyr Asn His Ala Ile Asp Trp Gln Thr Gly Pro Gly
        130                 135                 140

Cys Asn Thr Ala Gly Phe Phe
145                 150

<210> SEQ ID NO 54
<211> LENGTH: 151
<212> TYPE: PRT
<213> ORGANISM: Mus musculus
<220> FEATURE:
<221> NAME/KEY: misc_feature
<223> OTHER INFORMATION: Figure 7

<400> SEQUENCE: 54

Ser His Tyr Tyr Val Phe Phe Glu Glu Gln Glu Asp Glu Val Val Gly
1               5                   10                  15

Phe Gly Gln Glu Leu Lys Asn Pro Gln Glu Glu Thr Leu Gln Ala Phe
            20                  25                  30

Glu Ser His Tyr Asp Tyr Thr Val Cys Gly Asp Asn Glu Asp Met Val
        35                  40                  45

Cys Thr Pro Lys Ser Asp Glu Phe Asn Pro Cys Glu Asp Ile Met Gly
    50                  55                  60

Tyr Arg Phe Leu Arg Ile Val Val Trp Phe Val Ser Leu Leu Ala Leu
65                  70                  75                  80

Leu Gly Asn Ile Phe Val Leu Leu Ile Leu Leu Thr Ser His Tyr Lys
                85                  90                  95

Leu Thr Val Pro Arg Phe Leu Met Cys Asn Leu Ala Phe Ala Asp Phe
            100                 105                 110

Cys Met Gly Val Tyr Leu Leu Leu Ile Ala Ser Val Asp Leu Tyr Thr
        115                 120                 125

His Ser Glu Tyr Tyr Asn His Ala Ile Asp Trp Gln Thr Gly Pro Gly
    130                 135                 140

Cys Asn Thr Ala Gly Phe Phe
145                 150

<210> SEQ ID NO 55
<211> LENGTH: 151
<212> TYPE: PRT
<213> ORGANISM: Rattus norvegicus
<220> FEATURE:
<221> NAME/KEY: misc_feature
<223> OTHER INFORMATION: Figure 7

<400> SEQUENCE: 55

Ser His Tyr Tyr Val Phe Phe Glu Glu Gln Glu Asp Glu Ile Ile Gly
1               5                   10                  15

Phe Gly Gln Glu Leu Lys Asn Pro Gln Glu Glu Thr Leu Gln Ala Phe
            20                  25                  30

Asp Ser His Tyr Asp Tyr Thr Val Cys Gly Asp Asn Glu Asp Met Val
        35                  40                  45

Cys Thr Pro Lys Ser Asp Glu Phe Asn Pro Cys Glu Asp Ile Met Gly
    50                  55                  60

Tyr Lys Phe Leu Arg Ile Val Val Trp Phe Val Ser Pro Met Ala Leu
65                  70                  75                  80

Leu Gly Asn Val Phe Val Leu Phe Val Leu Leu Thr Ser His Tyr Lys
                85                  90                  95

Leu Thr Val Pro Arg Phe Leu Met Cys Asn Leu Ala Phe Ala Asp Phe

```
                    100                 105                 110
Cys Met Gly Val Tyr Leu Leu Ile Ala Ser Val Asp Leu Tyr Thr
            115                 120                 125

His Thr Glu Tyr Tyr Asn His Ala Ile Asp Trp Gln Thr Gly Pro Gly
        130                 135                 140

Cys Asn Thr Ala Gly Phe Phe
145                 150

<210> SEQ ID NO 56
<211> LENGTH: 151
<212> TYPE: PRT
<213> ORGANISM: Ovis aries
<220> FEATURE:
<221> NAME/KEY: misc_feature
<223> OTHER INFORMATION: Figure 7

<400> SEQUENCE: 56

Ser His Tyr Tyr Val Phe Phe Glu Asp Gln Glu Asp Glu Ile Ile Gly
1               5                   10                  15

Phe Gly Gln Glu Leu Lys Asn Pro Gln Glu Thr Leu Gln Ala Phe
            20                  25                  30

Asp Asn His Tyr Asp Tyr Thr Val Cys Gly Gly Ser Glu Glu Met Val
        35                  40                  45

Cys Thr Pro Lys Ser Asp Glu Phe Asn Pro Cys Glu Asp Ile Met Gly
    50                  55                  60

Tyr Lys Phe Leu Arg Ile Val Val Trp Phe Val Ser Leu Leu Ala Leu
65                  70                  75                  80

Leu Gly Asn Val Phe Val Leu Val Ile Leu Leu Thr Ser His Tyr Lys
                85                  90                  95

Leu Thr Val Pro Arg Phe Leu Met Cys Asn Leu Ala Phe Ala Asp Phe
            100                 105                 110

Cys Met Gly Leu Tyr Leu Leu Leu Ile Ala Ser Val Asp Leu Tyr Thr
            115                 120                 125

Gln Ser Glu Tyr Tyr Asn His Ala Ile Asp Trp Gln Thr Gly Pro Gly
        130                 135                 140

Cys Asn Thr Ala Gly Phe Phe
145                 150

<210> SEQ ID NO 57
<211> LENGTH: 200
<212> TYPE: DNA
<213> ORGANISM: Felis catus
<220> FEATURE:
<221> NAME/KEY: misc_feature
<223> OTHER INFORMATION: Figure 8

<400> SEQUENCE: 57
gccaggagct taaaaaccca caagaagaga ccctacaggc cttcgatagc cattatgact     60
acactgtgtg tggaggcaat gaagacatgg tgtgtactcc caagtcagat gagttcaacc   120
cctgtgaaga cataatgggc tacaagttcc tgagaattgt ggtgtggttt gttagtctgc   180
tggctctcct gggcaatgtc                                                200

<210> SEQ ID NO 58
<211> LENGTH: 200
<212> TYPE: DNA
<213> ORGANISM: Bos taurus
<220> FEATURE:
<221> NAME/KEY: misc_feature
<223> OTHER INFORMATION: Figure 8
```

-continued

```
<400> SEQUENCE: 58
gccaacagct caaaaacccc caggaggaga ccctgcaggc ctttgacagc cattacgact      60
ataccgtgtg tgggggcagt gaggacatgg tgtgtacccc caagtcggat gagttcaacc    120
cctgtgagga catcatgggc tacaagttcc tgagaatcgt ggtgtggttt gtgagtctgc    180
tggctctcct gggcaacgtc                                                 200

<210> SEQ ID NO 59
<211> LENGTH: 200
<212> TYPE: DNA
<213> ORGANISM: Canis familiaris
<220> FEATURE:
<221> NAME/KEY: misc_feature
<223> OTHER INFORMATION: Figure 8

<400> SEQUENCE: 59
ggcaggagct taaaaaccca caggaagaga ccctccaggc ctttgatagc cattatgact      60
acactgtgtg tggtggcaat gaagacatgg tgtgtactcc taagtcagat gagttcaacc    120
cctgtgaaga cataatgggc tacaagttcc tgaggattgt ggtgtggttt gttagtctgc    180
tggctctcct gggcaatgtc                                                 200

<210> SEQ ID NO 60
<211> LENGTH: 200
<212> TYPE: DNA
<213> ORGANISM: Mus musculus
<220> FEATURE:
<221> NAME/KEY: misc_feature
<223> OTHER INFORMATION: Figure 8

<400> SEQUENCE: 60
gccaagagct caaaaatcct caggaagaga ctctccaagc cttcgagagc cactatgact      60
acacggtgtg tggggacaac gaggacatgg tgtgtacccc caagtcggac gagtttaacc    120
cctgtgaaga tatcatgggc tacaggttcc tgagaatcgt ggtgtggttt gtcagtctgc    180
tggctctcct gggcaatatc                                                 200

<210> SEQ ID NO 61
<211> LENGTH: 200
<212> TYPE: DNA
<213> ORGANISM: Sus scrofa
<220> FEATURE:
<221> NAME/KEY: misc_feature
<223> OTHER INFORMATION: Figure 8

<400> SEQUENCE: 61
gccaagagct caaaaacccc caggaagaga ccctccaggc ctttgacagc cattacgact      60
acaccgtgtg tgggggcagt gaagacatgg tgtgcacccc caagtcagat gagttcaacc    120
cctgtgaaga cataatgggc tacaggttcc tgagaatcgt ggtgtggttc gttagcctgc    180
tggctctcct gggcaatgtc                                                 200

<210> SEQ ID NO 62
<211> LENGTH: 200
<212> TYPE: DNA
<213> ORGANISM: Rattus norvegicus
<220> FEATURE:
<221> NAME/KEY: misc_feature
<223> OTHER INFORMATION: Figure 8

<400> SEQUENCE: 62
gccaagagct caaaaatcct caggaagaga ctctccaagc cttcgacagc cactatgact      60
```

```
acactgtgtg tggggacaac gaggacatgg tgtgtacccc caagtcagac gagtttaacc      120
cctgtgaaga tatcatgggc tacaagttcc tgagaatcgt ggtatggttt gtcagtccga      180
tggctctcct gggcaacgtc                                                   200
```

<210> SEQ ID NO 63
<211> LENGTH: 200
<212> TYPE: DNA
<213> ORGANISM: Ovis aries
<220> FEATURE:
<221> NAME/KEY: misc_feature
<223> OTHER INFORMATION: Figure 8

<400> SEQUENCE: 63

```
gccaagagct taaaacccc caggaggaga ccctgcaggc ctttgacaac cattacgact        60
ataccgtgtg cgggggagt gaggagatgg tgtgtacccc caagtcggat gagttcaacc       120
cctgtgagga catcatgggc tacaagttcc tgagaattgt ggtgtggttt gtgagtctgc      180
tggctctcct gggcaacgtc                                                   200
```

<210> SEQ ID NO 64
<211> LENGTH: 200
<212> TYPE: DNA
<213> ORGANISM: Homo sapiens
<220> FEATURE:
<221> NAME/KEY: misc_feature
<223> OTHER INFORMATION: Figure 8

<400> SEQUENCE: 64

```
gccaggagct caaaaacccc caggaagaga ctctacaagc ttttgacagc cattatgact       60
acaccatatg tggggacagt gaagacatgg tgtgtacccc caagtccgat gagttcaacc      120
cgtgtgaaga cataatgggc tacaagttcc tgagaattgt ggtgtggttc gttagtctgc      180
tggctctcct gggcaatgtc                                                   200
```

<210> SEQ ID NO 65
<211> LENGTH: 209
<212> TYPE: PRT
<213> ORGANISM: Mus musculus
<220> FEATURE:
<221> NAME/KEY: misc_feature
<223> OTHER INFORMATION: Figures 9 & 10

<400> SEQUENCE: 65

```
Asp Val Gln Leu Lys His Ser Gly Pro Glu Leu Val Lys Pro Gly Ala
1               5                   10                  15

Ser Met Lys Ile Ser Cys Lys Ala Ser Gly Tyr Ser Phe Thr Gly Tyr
            20                  25                  30

Thr Met Asn Trp Val Lys Gln Ser His Gly Lys Asn Leu Glu Trp Ile
        35                  40                  45

Gly Leu Ile Asn Pro Tyr Thr Gly Gly Thr Asn Tyr Asn Gln Lys Phe
    50                  55                  60

Lys Gly Lys Ala Lys Leu Thr Val Asp Lys Ser Ser Ser Thr Ala Phe
65                  70                  75                  80

Met Glu Leu Leu Ser Leu Thr Ser Glu Asp Ser Ala Val Tyr Tyr Cys
                85                  90                  95

Ala Arg Asp Gly Asn Leu Asp Tyr Trp Gly Gln Gly Thr Thr Leu Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
```

```
            130                 135                 140
Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Val Thr Val Pro Ser Ser Thr Trp Pro Ser
            180                 185                 190

Glu Thr Val Thr Cys Asn Val Ala His Pro Ala Ser Lys Thr Lys Val
            195                 200                 205

Asp

<210> SEQ ID NO 66
<211> LENGTH: 218
<212> TYPE: PRT
<213> ORGANISM: Mus musculus
<220> FEATURE:
<221> NAME/KEY: misc_feature
<223> OTHER INFORMATION: Figures 11 & 12

<400> SEQUENCE: 66

Ser Ile Val Met Ser Gln Ser Pro Ala Ser Leu Ala Val Ser Leu Gly
1               5                   10                  15

Gln Arg Ala Thr Ile Ser Cys Arg Ala Ser Glu Thr Val Asp Asn Tyr
            20                  25                  30

Gly Phe Ser Phe Met His Trp Phe Gln Gln Ile Pro Gly Gln Pro Pro
        35                  40                  45

Lys Leu Leu Ile Tyr Ala Ala Ser Asn Gln Gly Ser Gly Val Pro Ala
50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Tyr Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
        210                 215

<210> SEQ ID NO 67
<211> LENGTH: 214
<212> TYPE: PRT
<213> ORGANISM: Mus musculus
<220> FEATURE:
<221> NAME/KEY: misc_feature
<223> OTHER INFORMATION: Figures 13 & 14

<400> SEQUENCE: 67
```

```
Asp Val Gln Leu Val Gln Ser Gly Pro Glu Leu Val Lys Pro Gly Ala
1               5                   10                  15

Ser Val Lys Met Ser Cys Lys Ala Ser Gly Tyr Ser Phe Thr Gly Tyr
            20                  25                  30

Asn Met His Trp Val Lys Gln Ser His Gly Lys Ser Leu Glu Trp Ile
        35                  40                  45

Gly Tyr Ile Asp Pro Tyr Asn Gly Ala Thr Ser Tyr Asn Gln Lys Phe
    50                  55                  60

Glu Asp Lys Ala Thr Leu Thr Val Asp Lys Ser Ser Thr Ala Tyr
65                  70                  75                  80

Met Gln Leu Asn Ser Leu Thr Ser Glu Asp Ser Ala Val Tyr Tyr Cys
            85                  90                  95

Ala Arg Arg Trp Asp Trp Asp Pro Tyr Ala Met Asp Tyr Trp Gly Gln
            100                 105                 110

Gly Thr Ser Val Thr Val Ser Ser Ala Lys Thr Thr Ala Pro Ser Val
            115                 120                 125

Tyr Pro Leu Ala Pro Val Cys Gly Asp Thr Ser Gly Ser Ser Val Thr
    130                 135                 140

Leu Gly Cys Leu Val Lys Gly Tyr Phe Pro Glu Pro Val Thr Leu Thr
145                 150                 155                 160

Trp Asn Ser Gly Ser Leu Ser Ser Gly Val His Thr Ser Pro Ala Val
            165                 170                 175

Leu Gln Ser Asp Leu Tyr Thr Leu Ser Ser Val Thr Val Thr Ser
            180                 185                 190

Ser Thr Trp Pro Ser Gln Ser Ile Thr Cys Asn Val Ala His Pro Ala
            195                 200                 205

Ser Lys Thr Lys Val Asp
    210

<210> SEQ ID NO 68
<211> LENGTH: 214
<212> TYPE: PRT
<213> ORGANISM: Mus musculus
<220> FEATURE:
<221> NAME/KEY: misc_feature
<223> OTHER INFORMATION: Figures 15 & 16

<400> SEQUENCE: 68

Asp Ile Leu Leu Thr Gln Ser Pro Ala Ile Leu Ser Val Ser Pro Gly
1               5                   10                  15

Glu Arg Val Ser Phe Ser Cys Arg Ala Ser Gln Ser Ile Gly Thr Ser
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Phe Ser Arg Phe Ser Gly
    50                  55                  60

Ser Gly Ser Gly Thr Asp Phe Thr Leu Thr Ile Asn Ser Val Glu Ser
65                  70                  75                  80

Glu Asp Ile Ala Asp Tyr Tyr Cys Gln Gln Ser Asn Arg Trp Pro Leu
            85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
            115                 120                 125

Gly Ala Ser Val Val Cys Phe Leu Asn Asn Phe Tyr Pro Lys Asp Ile
    130                 135                 140
```

-continued

```
Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210
```

<210> SEQ ID NO 69
<211> LENGTH: 214
<212> TYPE: PRT
<213> ORGANISM: Mus musculus
<220> FEATURE:
<221> NAME/KEY: misc_feature
<223> OTHER INFORMATION: Figures 17 & 18

<400> SEQUENCE: 69

```
Asp Val Gln Ile Gln Gln Ser Gly Pro Glu Leu Val Lys Pro Gly Ala
1               5                   10                  15

Ser Val Lys Met Ser Cys Lys Ala Ser Gly Tyr Ser Phe Thr Ala Tyr
            20                  25                  30

Asn Met His Trp Val Lys Gln Thr His Gly Lys Ser Leu Glu Trp Ile
        35                  40                  45

Gly Tyr Ile Asp Pro Tyr Ser Gly Ala Thr Ser Tyr His Gln Lys Phe
    50                  55                  60

Lys Gly Lys Ala Thr Leu Thr Val Asp Lys Ser Ser Ser Thr Ala Tyr
65                  70                  75                  80

Met Arg Leu Asn Ser Leu Thr Ser Glu Asp Ser Ala Val Tyr Tyr Cys
                85                  90                  95

Ala Arg Arg Trp Asp Trp Asp Pro Tyr Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Cys Gly Asp Thr Thr Gly Ser Ser Val Thr
    130                 135                 140

Leu Gly Cys Leu Val Lys Gly Tyr Phe Pro Glu Ser Val Thr Val Thr
145                 150                 155                 160

Trp Asn Ser Gly Ser Leu Ser Ser Val His Thr Phe Pro Ala Leu
                165                 170                 175

Leu Gln Ser Gly Leu Tyr Thr Met Ser Ser Ser Val Thr Val Pro Ser
            180                 185                 190

Ser Ala Trp Pro Ser Gln Thr Val Thr Cys Ser Val Ala His Pro Ala
        195                 200                 205

Ser Asn Thr Thr Val Asp
    210
```

<210> SEQ ID NO 70
<211> LENGTH: 214
<212> TYPE: PRT
<213> ORGANISM: Mus musculus
<220> FEATURE:
<221> NAME/KEY: misc_feature
<223> OTHER INFORMATION: Figures 19 & 20

<400> SEQUENCE: 70

Ser Val Glu Met Ser Gln Ser Pro Ala Ile Leu Ser Val Ser Pro Gly

```
            1               5                  10                 15
    Glu Arg Ile Ser Phe Ser Cys Arg Ala Ser Gln Ser Ile Gly Thr Ser
                    20                  25                  30

Ile His Trp Tyr Gln Gln Arg Thr Asn Gly Ser Pro Arg Leu Leu Ile
                    35                  40                  45

Lys Tyr Ala Ser Ala Ser Ile Ser Gly Ile Pro Ser Arg Phe Ser Gly
                    50                  55                  60

Ser Gly Ser Gly Thr Asp Phe Thr Leu Ser Ile Asn Ser Val Glu Ser
    65                  70                  75                  80

Glu Asp Ile Ala Asp Tyr Tyr Cys Gln Gln Ser Asn Ser Trp Pro Leu
                    85                  90                  95

Thr Phe Gly Ala Gly Thr Lys Leu Glu Leu Lys Arg Ala Asp Ala Ala
                    100                 105                 110

Pro Thr Val Ser Ile Phe Pro Pro Ser Ser Glu Gln Leu Thr Ser Gly
                    115                 120                 125

Gly Ala Ser Val Val Cys Phe Leu Asn Asn Phe Tyr Pro Lys Asp Ile
                    130                 135                 140

Asn Val Lys Trp Lys Ile Asp Gly Ser Glu Arg Gln Asn Gly Val Leu
    145                 150                 155                 160

Asn Ser Trp Thr Asp Gln Asp Ser Lys Asp Ser Thr Tyr Ser Met Ser
                    165                 170                 175

Ser Thr Leu Thr Leu Thr Lys Asp Glu Tyr Glu Arg His Asn Ser Tyr
                    180                 185                 190

Thr Cys Glu Ala Thr His Lys Thr Ser Thr Ser Pro Ile Val Lys Ser
                    195                 200                 205

Phe Asn Arg Asn Glu Cys
                    210

<210> SEQ ID NO 71
<211> LENGTH: 214
<212> TYPE: PRT
<213> ORGANISM: Mus musculus
<220> FEATURE:
<221> NAME/KEY: misc_feature
<223> OTHER INFORMATION: Figures 21 & 22

<400> SEQUENCE: 71

Asp Val Gln Met Gln Gln Pro Gly Pro Glu Leu Val Lys Pro Gly Ala
    1               5                   10                  15

Ser Leu Lys Met Ser Cys Lys Ala Ser Gly Tyr Ser Phe Thr Gly Tyr
                    20                  25                  30

Asn Met His Trp Val Lys Gln Ser His Gly Lys Ser Leu Glu Trp Ile
                    35                  40                  45

Gly Tyr Ile Asp Pro Tyr Ser Gly Ala Thr Ser Tyr Asn Gln Lys Phe
                    50                  55                  60

Glu Gly Lys Ala Thr Leu Thr Val Asp Lys Ser Ser Ser Thr Ala Tyr
    65                  70                  75                  80

Met Gln Leu Asn Ser Leu Thr Ser Glu Asp Ser Ala Val Tyr Tyr Cys
                    85                  90                  95

Ala Arg Arg Trp Asp Trp Asp Pro Tyr Ala Met Asp Tyr Trp Gly Gln
                    100                 105                 110

Gly Thr Ser Val Thr Val Ser Ser Ala Lys Thr Thr Ala Pro Ser Val
                    115                 120                 125

Tyr Pro Leu Ala Pro Val Cys Gly Asp Thr Ser Gly Ser Ser Val Thr
                    130                 135                 140

Leu Gly Cys Leu Val Lys Gly Tyr Phe Pro Glu Pro Val Thr Leu Thr
```

```
                145                 150                 155                 160
Trp Asn Ser Gly Ser Leu Ser Gly Val His Thr Phe Pro Ala Val
                165                 170                 175

Leu Gln Ser Asp Leu Tyr Thr Leu Ser Ser Val Thr Val Thr Ser
            180                 185                 190

Ser Thr Trp Pro Ser Gln Ser Ile Thr Cys Asn Val Ala His Pro Ala
        195                 200                 205

Ser Asn Thr Lys Val Asp
    210

<210> SEQ ID NO 72
<211> LENGTH: 214
<212> TYPE: PRT
<213> ORGANISM: Mus musculus
<220> FEATURE:
<221> NAME/KEY: misc_feature
<223> OTHER INFORMATION: Figures 23 & 24

<400> SEQUENCE: 72

Asn Ile Leu Met Thr Gln Ser Pro Ala Ile Leu Ser Val Ser Pro Gly
1               5                   10                  15

Glu Arg Val Ser Phe Ala Cys Arg Ala Ser Gln Ser Ile Gly Thr Ser
                20                  25                  30

Ile His Trp Tyr Gln Gln Arg Thr Asn Gly Ser Pro Arg Leu Leu Ile
            35                  40                  45

Lys Tyr Ala Ser Glu Ser Ile Ser Gly Ile Pro Ser Arg Phe Ser Gly
        50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Thr Asn Arg Trp Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210

<210> SEQ ID NO 73
<211> LENGTH: 627
<212> TYPE: DNA
<213> ORGANISM: Mus musculus
<220> FEATURE:
<221> NAME/KEY: misc_feature
<223> OTHER INFORMATION: Figures 25 & 26

<400> SEQUENCE: 73
gacgtccagc tgaagcactc aggacctgag ctggtgaagc ctggagcttc aatgaagata    60
```

| | |
|---|---:|
| tcctgtaagg cttctggtta ctcattcact ggctacacca tgaactgggt gaagcagagc | 120 |
| catggaaaga accttgagtg gattggactt attaatcctt acactggtgg tactaactac | 180 |
| aaccagaagt tcaagggcaa ggccaaatta actgtagaca agtcatccag cacagccttc | 240 |
| atggagctcc tcagtctgac atctgaggac tctgcagtct attactgtgc aagagatggt | 300 |
| aaccttgact actggggcca aggcaccact ctcacagtct cctcagccaa acgacaccc | 360 |
| ccatctgtct atccactggc ccctggatct gctgcccaaa ctaactccat ggtgaccctg | 420 |
| ggatgcctgg tcaagggcta tttccctgag ccagtgacag tgacctggaa ctctggatcc | 480 |
| ctgtccagcg gtgtgcacac cttcccagct gtcctgcagt ctgacctcta cactctgagc | 540 |
| agctcagtga ctgtcccctc agcacctgg cccagcgaga ccgtcacctg caacgttgcc | 600 |
| cacccagcca gcaagaccaa ggtcgac | 627 |

```
<210> SEQ ID NO 74
<211> LENGTH: 654
<212> TYPE: DNA
<213> ORGANISM: Mus musculus
<220> FEATURE:
<221> NAME/KEY: misc_feature
<223> OTHER INFORMATION: Figures 27 & 28

<400> SEQUENCE: 74
```

| | |
|---|---:|
| agcattgtga tgtcacagtc gccagcttct ttggctgtgt ctctagggca gagggccacc | 60 |
| atctcctgca gagccagcga aactgttgat aattatggct ttagttttat gcactggttc | 120 |
| caacagatac cgggacagcc acccaaactc ctcatctatg ctgcatccaa ccaaggatcc | 180 |
| ggggtccctg ccaggtttag tggcagtggg tctgggacag acttcagcct caacatccat | 240 |
| cctatggagg aggatgatac tgcaatgtat ttctgtcagc aaagtaagga ggttccgtac | 300 |
| acgttcggag gggggaccaa gctggaaata aaacggctg atgctgcacc aactgtatcc | 360 |
| atcttcccac catccagtga gcagttaaca tctggaggtg cctcagtcgt gtgcttcttg | 420 |
| aacaacttct accccaaaga catcaatgtc aagtggaaga ttgatggcag tgaacgacaa | 480 |
| aatggcgtcc tgaacagttg gactgatcag gacagcaaag acagcaccta cagcatgagc | 540 |
| agcacccta cgttgaccaa ggacgagtat gaacgacata cagctatac ctgtgaggcc | 600 |
| actcacaaga catcaacttc acccattgtc aagagcttca caggaatga gtgt | 654 |

```
<210> SEQ ID NO 75
<211> LENGTH: 642
<212> TYPE: DNA
<213> ORGANISM: Mus musculus
<220> FEATURE:
<221> NAME/KEY: misc_feature
<223> OTHER INFORMATION: Figures 29 & 30

<400> SEQUENCE: 75
```

| | |
|---|---:|
| gacgtccagt tggtgcaatc tggacctgag ctggtgaagc ctggagcttc agtgaagatg | 60 |
| tcctgcaagg cttctggtta ctcattcact ggctacaaca tgcactgggt gaagcagagc | 120 |
| catggaaaga gccttgagtg gattgggtat attgatcctt acaatggtgc tactagctac | 180 |
| aaccagaaat tcgaggacaa ggccacattg actgtagaca atcttccag cacagcctac | 240 |
| atgcagctca acagcctgac atctgaggac tctgcagtct attactgtgc aagaagatgg | 300 |
| gactgggacc cttatgctat ggactactgg ggtcaaggaa cctcagtcac cgtctcctca | 360 |
| gccaaaacaa cagcccatc ggtctatcca ctggcccctg tgtgtggaga tacaagtggc | 420 |
| tcctcggtga ctctaggatg cctggtcaag ggttatttcc ctgagccagt gaccttgacc | 480 |

```
tggaactctg gatccctgtc cagtggtgtg cacacctccc cagctgtcct gcagtctgac        540
ctctacaccc tcagcagctc agtgactgta acctcgagca cctggcccag ccagtccatc        600
acctgcaatg tggcccaccc ggccagcaag accaaggtcg ac                          642
```

```
<210> SEQ ID NO 76
<211> LENGTH: 642
<212> TYPE: DNA
<213> ORGANISM: Mus musculus
<220> FEATURE:
<221> NAME/KEY: misc_feature
<223> OTHER INFORMATION: Figures 31 & 32

<400> SEQUENCE: 76
gacatcttgc tgactcagtc tccagccatc ctgtctgtga gtccaggaga aagagtcagt         60
ttctcctgca gggccagtca gagcattggc acaagcatac actggtatca gcaaagaaca       120
aatggttctc caaggcttct cataaagtat gcttctgagt ccatctctgg gatattttct       180
aggtttagtg gcagtggatc agggacagat tttactctta ccatcaacag tgtggagtct       240
gaagatattg cagattatta ctgtcaacaa agtaataggt ggccgctcac gttcggagct       300
gggaccaagc tggagctgaa acgggctgat gctgcaccaa ctgtatccat cttcccacca       360
tccagtgagc agttaacatc tggaggtgcc tcagtcgtgt gcttcttgaa caacttctac       420
cccaaagaca tcaatgtcaa gtggaagatt gatggcagtg aacgacaaaa tggcgtcctg       480
aacagttgga ctgatcagga cagcaaagac agcacctaca gcatgagcag cacctcacg        540 ttgaccaagg acgagtatga acgacataac agctatacct gtgaggccac tcacaagaca       600
tcaacttcac ccattgtcaa gagcttcaac aggaatgagt gt                          642
```

```
<210> SEQ ID NO 77
<211> LENGTH: 642
<212> TYPE: DNA
<213> ORGANISM: Mus musculus
<220> FEATURE:
<221> NAME/KEY: misc_feature
<223> OTHER INFORMATION: Figures 33 & 34

<400> SEQUENCE: 77
gacgtccaga tccagcagtc tgggcctgag ctggtgaagc ctggagcttc agtgaagatg        60
tcctgcaagg cttctggtta ctcattcact gcctacaaca tgcactgggt gaagcagacc       120
catggaaaga gccttgagtg gattggttat attgatcctt acagtggtgc tactagctac       180
caccagaaat tcaagggcaa ggccacattg actgttgaca aatcttccag cacagcctac       240
atgcgcctca acagcctgac atctgaggac tctgcagtct attactgtgc aagaagatgg       300
gactgggacc cttatgctat ggactactgg ggtcaaggaa cctcagtcac cgtctcctca       360
gccaaaacaa cacccccatc agtctatcca ctggcccctg ggtgtggaga taaactggt        420 tcctccgtga ctctgggatg cctggtcaag ggctacttcc ctgagtcagt gactgtgact       480
tggaactctg gatccctgtc cagcagtgtg cacaccttcc cagctctcct gcagtctgga       540
ctctacacta tgagcagctc agtgactgtc cctccagcg cctggccaag tcagaccgtc        600
acctgcagcg ttgctcaccc ggccagcaac accacggtcg ac                          642
```

```
<210> SEQ ID NO 78
<211> LENGTH: 642
<212> TYPE: DNA
<213> ORGANISM: Mus musculus
<220> FEATURE:
<221> NAME/KEY: misc_feature
<223> OTHER INFORMATION: Figures 35 & 36
```

<400> SEQUENCE: 78

```
agcgttgaga tgtcacagtc gccagccatc ctgtctgtga gtccaggaga aagaatcagt    60
ttctcctgca gggccagtca gagcattggc acaagcatac actggtatca gcaaagaaca   120
aatggttctc caaggcttct cattaagtat gcttctgcgt ctatctctgg gatcccttcc   180
aggtttagtg gcagtggatc agggacagat tttactctta gcatcaacag tgtggagtct   240
gaagatattg cagattatta ctgtcaacaa agtaatagct ggccgctcac gttcggtgct   300
gggaccaagc tggagctgaa acgggctgat gctgcaccaa ctgtatccat cttcccacca   360
tccagtgagc agttaacatc tggaggtgcc tcagtcgtgt gcttcttgaa caacttctac   420
cccaaagaca tcaatgtcaa gtggaagatt gatggcagtg aacgacaaaa tggcgtcctg   480
aacagttgga ctgatcagga cagcaaagac agcacctaca gcatgagcag caccctcacg   540
ttgaccaagg acgagtatga cgacataaac agctatacct gtgaggccac tcacaagaca   600
tcaacttcac ccattgtcaa gagcttcaac aggaatgagt gt                      642
```

<210> SEQ ID NO 79
<211> LENGTH: 642
<212> TYPE: DNA
<213> ORGANISM: Mus musculus
<220> FEATURE:
<221> NAME/KEY: misc_feature
<223> OTHER INFORMATION: Figures 37 & 38

<400> SEQUENCE: 79

```
gacgtccaga tgcagcagcc tgggcctgag ctggtgaagc ctggagcttc actaaagatg    60
tcctgcaagg cttctggtta ctcattcact ggctacaaca tgcactgggt gaagcagagc   120
catggaaaga gccttgagtg gattggatat attgatcctt acagtggtgc tactagctac   180
aaccagaaat tcgagggcaa ggccacattg actgtagaca atctcttccag cacagcctac   240
atgcagctca cagcctgac atctgaggac tctgcagtct attactgtgc aagaagatgg   300
gactgggacc cttatgctat ggactactgg ggtcaaggaa cctcagtcac cgtctcctca   360
gccaaaacaa cagccccatc ggtctatcca ctggcccctg tgtgtggaga tacaagtggc   420
tcctcggtga ctctaggatg cctggtcaag ggttatttcc ctgagccagt gaccttgacc   480
tggaactctg gatccctgtc cagtggtgtg cacaccttcc cagctgtcct gcagtctgac   540
ctctacaccc tcagcagctc agtgactgta acctcgagca cctggcccag ccagtccatc   600
acctgcaatg tggcccaccc agccagcaac accaaggtcg ac                      642
```

<210> SEQ ID NO 80
<211> LENGTH: 642
<212> TYPE: DNA
<213> ORGANISM: Mus musculus
<220> FEATURE:
<221> NAME/KEY: misc_feature
<223> OTHER INFORMATION: Figures 39 & 40

<400> SEQUENCE: 80

```
aacattctga tgacacagtc tccagccatc ttgtctgtga gtccaggaga aagagtcagt    60
ttcgcctgca gggccagtca gagcattggc acaagcatac actggtatca gcaaagaaca   120
aatggttctc caaggcttct cataaagtat gcttctgagt ctatctctgg gatcccttcc   180
aggtttagtg gcagtggatc agggacagat tttactctta gcatcaacag tgtggagtct   240
gaagatattg cagattatta ctgtcaacaa actaataggg gccgctcac gttcggtgct   300
gggaccaagc tggagctgaa acgggctgat gctgcaccaa ctgtatccat cttcccacca   360
```

```
tccagtgagc agttaacatc tggaggtgcc tcagtcgtgt gcttcttgaa caacttctac    420
cccaaagaca tcaatgtcaa gtggaagatt gatggcagtg aacgacaaaa tggcgtcctg    480
aacagttgga ctgatcagga cagcaaagac agcacctaca gcatgagcag caccctcacg    540
ttgaccaagg acgagtatga acgacataac agctataccT gtgaggccac tcacaagaca    600
tcaacttcac ccattgtcaa gagcttcaac aggaatgagt gt                       642
```

<210> SEQ ID NO 81
<211> LENGTH: 206
<212> TYPE: PRT
<213> ORGANISM: Mus musculus
<220> FEATURE:
<221> NAME/KEY: misc_feature
<223> OTHER INFORMATION: Figures 41 & 42

<400> SEQUENCE: 81

```
Asp Val Gln Leu Gln Gln Pro Gly Ala Glu Leu Val Lys Pro Gly Ala
1               5                   10                  15

Ser Val Lys Leu Ser Cys Thr Thr Ser Gly Val Asn Ile Lys Asp Thr
            20                  25                  30

Tyr Met His Trp Met Lys Gln Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Arg Gly Lys Ala Thr Ile Thr Ala Asp Thr Ser Ser Asn Thr Val Tyr
65                  70                  75                  80

Val Gln Leu Arg Ser Leu Thr Ser Glu Asp Thr Ala Val Tyr Tyr Cys
                85                  90                  95

Ala Tyr Asp Gly Tyr Trp Gly Gln Gly Thr Leu Val Thr Val Ser Ala
            100                 105                 110

Ala Lys Thr Thr Pro Pro Ser Val Tyr Pro Leu Ala Pro Gly Ser Ala
        115                 120                 125

Ala Gln Thr Asn Ser Met Val Thr Leu Gly Cys Leu Val Lys Gly Tyr
    130                 135                 140

Phe Pro Glu Pro Val Thr Val Thr Trp Asn Ser Gly Ser Leu Ser Ser
145                 150                 155                 160

Gly Val His Thr Phe Pro Ala Val Leu Gln Ser Asp Leu Tyr Thr Leu
                165                 170                 175

Ser Ser Ser Val Thr Val Pro Ser Ser Thr Trp Pro Ser Glu Thr Val
            180                 185                 190

Thr Cys Asn Val Ala His Pro Ala Ser Ser Thr Lys Val Asp
        195                 200                 205
```

<210> SEQ ID NO 82
<211> LENGTH: 218
<212> TYPE: PRT
<213> ORGANISM: Mus musculus
<220> FEATURE:
<221> NAME/KEY: misc_feature
<223> OTHER INFORMATION: Figures 43 & 44

<400> SEQUENCE: 82

```
Asn Ile Val Met Thr Gln Thr Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Gly Asn Asn Phe Met His Trp Tyr Gln Gln Lys Pro Gly Gln Ser Pro
        35                  40                  45
```

```
Arg Leu Leu Ile Tyr Arg Ala Ser Asn Leu Glu Ser Gly Ile Pro Ala
     50                  55                  60

Arg Phe Ser Gly Ser Gly Ser Arg Thr Asp Phe Thr Leu Thr Thr Asn
 65                  70                  75                  80

Pro Val Glu Ala Asp Asp Val Ala Thr Tyr Tyr Cys Gln Gln Ser His
                 85                  90                  95

Lys Asp Pro Leu Thr Phe Gly Ala Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Lys Ala Asn Glu Cys
210                 215

<210> SEQ ID NO 83
<211> LENGTH: 209
<212> TYPE: PRT
<213> ORGANISM: Mus musculus
<220> FEATURE:
<221> NAME/KEY: misc_feature
<223> OTHER INFORMATION: Figures 45 & 46

<400> SEQUENCE: 83

Asp Val Gln Leu Lys His Ser Gly Pro Glu Leu Val Lys Pro Gly Ala
 1               5                  10                  15

Ser Met Lys Ile Ser Cys Lys Ala Ser Gly Tyr Ser Phe Thr Gly Tyr
             20                  25                  30

Thr Met Asn Trp Val Lys Gln Ser His Gly Lys Asn Leu Asp Trp Ile
         35                  40                  45

Gly Leu Ile Asn Pro Tyr Asn Gly Gly Thr Ser Tyr Asp Gln Lys Phe
     50                  55                  60

Lys Gly Lys Ala Thr Leu Thr Val Asp Lys Ser Ser Thr Ala Tyr
 65                  70                  75                  80

Met Glu Leu Leu Ser Leu Thr Ser Glu Asp Ser Ala Val Tyr Tyr Cys
                 85                  90                  95

Ala Arg Asp Gly Leu Met Asp Tyr Trp Gly Gln Gly Thr Ser Val Thr
            100                 105                 110

Val Ser Ser Ala Lys Thr Thr Pro Pro Ser Val Tyr Pro Leu Ala Pro
        115                 120                 125

Gly Ser Ala Ala Gln Thr Asn Ser Met Val Thr Leu Gly Cys Leu Val
130                 135                 140

Lys Gly Tyr Phe Pro Glu Pro Val Thr Val Thr Trp Asn Ser Gly Ser
145                 150                 155                 160

Leu Ser Ser Gly Val His Thr Phe Pro Ala Val Leu Gln Ser Asp Leu
                165                 170                 175

Tyr Thr Leu Ser Ser Ser Val Thr Val Pro Ser Ser Thr Trp Pro Ser
            180                 185                 190
```

Glu Thr Val Thr Cys Asn Val Ala His Pro Ala Ser Lys Thr Lys Val
        195                 200                 205
Asp

<210> SEQ ID NO 84
<211> LENGTH: 218
<212> TYPE: PRT
<213> ORGANISM: Mus musculus
<220> FEATURE:
<221> NAME/KEY: misc_feature
<223> OTHER INFORMATION: Figures 47 & 48

<400> SEQUENCE: 84

Asp Ile Val Met Thr Gln Thr Pro Ala Ser Leu Ala Val Ser Leu Gly
1               5                   10                  15

Gln Arg Ala Thr Ile Phe Cys Arg Ala Ser Gln Ser Val Asp Tyr Asn
            20                  25                  30

Gly Ile Ser Tyr Met His Trp Phe Gln Gln Lys Pro Gly Gln Pro Pro
        35                  40                  45

Lys Leu Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Phe
                85                  90                  95

Glu Asp Pro His Thr Phe Gly Gly Gly Thr Lys Leu Glu Ile Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 85
<211> LENGTH: 216
<212> TYPE: PRT
<213> ORGANISM: Mus musculus
<220> FEATURE:
<221> NAME/KEY: misc_feature
<223> OTHER INFORMATION: Figures 49 & 50

<400> SEQUENCE: 85

Asp Val Gln Leu Gln Gln Ser Gly Thr Val Leu Ala Arg Pro Gly Ala
1               5                   10                  15

Ser Val Arg Met Ser Cys Lys Ala Ser Gly Tyr Ser Phe Thr Arg Tyr
            20                  25                  30

Trp Ile His Trp Leu Lys Gln Arg Pro Gly Gln Gly Leu Glu Trp Ile
        35                  40                  45

Gly Ala Ile Phe Pro Gly Asn Arg Asp Thr Ser Tyr Asn Gln Arg Phe

```
                    50                   55                    60
Lys Gly Lys Ala Glu Val Thr Ala Val Thr Ser Ala Ser Thr Ala Tyr
 65                  70                   75                    80

Leu Asp Leu Ser Ser Leu Thr Asn Glu Asp Ser Ala Val Tyr Tyr Cys
                     85                   90                    95

Thr Arg Trp Pro Tyr Tyr Gly Ser Ile Tyr Val Asn Phe Asp Tyr Trp
                100                  105                  110

Gly Gln Gly Thr Thr Leu Thr Val Ser Ser Ala Lys Thr Thr Pro Pro
                115                  120                  125

Ser Val Tyr Pro Leu Ala Pro Gly Ser Ala Ala Gln Thr Asn Ser Met
                130                  135                  140

Val Thr Leu Gly Cys Leu Val Lys Gly Tyr Phe Pro Glu Pro Val Thr
145                 150                  155                  160

Val Thr Trp Asn Ser Gly Ser Leu Ser Ser Gly Val His Thr Phe Pro
                165                  170                  175

Ala Val Leu Gln Ser Asp Leu Tyr Thr Leu Ser Ser Ser Val Thr Val
                180                  185                  190

Pro Ser Ser Thr Trp Pro Ser Glu Thr Val Thr Cys Asn Val Ala His
                195                  200                  205

Pro Ala Ser Ser Thr Lys Val Asp
                210                  215

<210> SEQ ID NO 86
<211> LENGTH: 219
<212> TYPE: PRT
<213> ORGANISM: Mus musculus
<220> FEATURE:
<221> NAME/KEY: misc_feature
<223> OTHER INFORMATION: Figures 51 & 52

<400> SEQUENCE: 86

Asp Ile Val Met Thr Gln Ser Pro Leu Ser Leu Pro Val Ser Leu Gly
  1               5                  10                  15

Asp Gln Ala Ser Ile Ser Cys Arg Thr Ser Gln Asn Leu Val His Arg
                 20                  25                  30

Asn Gly Asn Thr Tyr Leu His Trp Tyr Leu Gln Lys Pro Gly Gln Ser
             35                  40                  45

Pro Lys Leu Leu Ile Tyr Lys Ile Ser Asn Arg Phe Ser Gly Val Pro
         50                  55                  60

Asp Arg Phe Ser Gly Ser Gly Ser Gly Thr Asp Phe Thr Leu Lys Ile
 65                  70                  75                   80

Ser Arg Val Glu Ala Glu Asp Leu Gly Val Tyr Phe Cys Ser Gln Gly
                 85                  90                  95

Thr His Val Pro Pro Thr Phe Gly Gly Gly Thr Lys Leu Glu Ile Lys
                100                 105                 110

Arg Ala Asp Ala Ala Pro Thr Val Ser Ile Phe Pro Pro Ser Ser Glu
                115                 120                 125

Gln Leu Thr Ser Gly Gly Ala Ser Val Val Cys Phe Leu Asn Asn Phe
            130                 135                 140

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
                180                 185                 190

Arg His Asn Ser Tyr Thr Cys Glu Ala Thr His Lys Thr Ser Thr Ser
```

```
                195             200             205
Pro Ile Val Lys Ser Phe Asn Arg Asn Glu Cys
    210             215
```

<210> SEQ ID NO 87
<211> LENGTH: 618
<212> TYPE: DNA
<213> ORGANISM: Mus musculus
<220> FEATURE:
<221> NAME/KEY: misc_feature
<223> OTHER INFORMATION: Figures 53 & 54

<400> SEQUENCE: 87

```
gacgtccagc tccagcagcc tggagcagag cttgtgaagc caggggcctc agtcaagttg      60
tcctgcacca cttctggcgt caacattaaa gacacctata tgcactggat gaagcagagg     120
cctgaacagg gcctggagtg gattggaagg attgatcctg cgaatggtaa tactaaatat     180
gacccgaaat tccggggcaa ggccactata acagcagaca catcctccaa cacggtctac     240
gtgcaactca gaagcctgac atctgaggac actgccgtct attactgtgc ctatgatggt     300
tactggggcc aagggactct ggtcactgtc tctgcagcca aaacgacacc cccatctgtc     360
tatccactgg cccctggatc tgctgcccaa actaactcca tggtgaccct gggatgcctg     420
gtcaagggct atttccctga ccagtgaca gtgacctgga actctggatc cctgtccagc     480
ggtgtgcaca ccttcccagc tgtcctgcag tctgacctct acactctgag cagctcagtg     540
actgtcccct ccagcacctg gcccagcgag accgtcacct gcaacgttgc ccacccggcc     600
agcagcacca aggtcgac                                                   618
```

<210> SEQ ID NO 88
<211> LENGTH: 654
<212> TYPE: DNA
<213> ORGANISM: Mus musculus
<220> FEATURE:
<221> NAME/KEY: misc_feature
<223> OTHER INFORMATION: Figures 55 & 56

<400> SEQUENCE: 88

```
aacattgtga tgacccaaac tccagcctct ttggctgtgt ctctagggca gagggccacc      60
atatcctgca gagccagtga aagtgttgat agttatggca ataattttat gcactggtac     120
cagcagaaac caggacagtc acccagactc ctcatctatc gtgcatccaa cctagaatct     180
gggatccctg ccaggttcag tggcagtggg tctaggacag acttcaccct caccactaat     240
cctgtggagg ctgatgatgt tgcaacctat tactgtcagc aaagtcataa ggatccgctc     300
acgttcggtg ctgggaccaa gctggagctg aaacgggctg atgctgcacc aactgtatcc     360
atcttcccac catccagtga gcagttaaca tctggaggtg cctcagtcgt gtgcttcttg     420
aacaacttct accccaaaga catcaatgtc aagtggaaga ttgatggcag tgaacgacaa     480
aatggcgtcc tgaacagttg gactgatcag gacagcaaag acagcaccta cagcatgagc     540
agcaccctca cgttgaccaa ggacgagtat gaacgacata acagctatac ctgtgaggcc     600
actcacaaga catcaacttc acccattgtc aagagcttca ggaacatga gtgt            654
```

<210> SEQ ID NO 89
<211> LENGTH: 626
<212> TYPE: DNA
<213> ORGANISM: Mus musculus
<220> FEATURE:
<221> NAME/KEY: misc_feature
<223> OTHER INFORMATION: Figures 57 & 58

-continued

<400> SEQUENCE: 89

```
gacgtccagc tgaagcatca ggacctgagc tggtgaagcc tggagcttca atgaagatat      60
cctgcaaggc ttctggttac tcattcactg gctacaccat gaactgggtg aagcagagcc     120
atggaaagaa ccttgagtgg attggactta ttaatcctta caatggtggt actagctacg     180
accagaagtt caagggcaag gccacattaa ctgtagacaa gtcatccagc acagcctaca     240
tggagctcct cagtctgaca tctgaggact ctgcagtcta ttactgtgca agagatggcc     300
tgatggacta ctggggtcaa ggaacctcag tcaccgtctc ctcagccaaa acgacacccc     360
catctgtcta tccactggcc cctggatctg ctgcccaaac taactccatg gtgaccctgg     420
gatgcctggt caagggctat ttccctgagc cagtgacagt gacctggaac tctggatccc     480
tgtccagcgg tgtgcacacc ttcccagctg tcctgcagtc tgacctctac actctgagca     540
gctcagtgac tgtcccctcc agcacctggc ccagcgagac cgtcacctgc aacgttgccc     600
acccggccag caagaccaag gtcgac                                          626
```

<210> SEQ ID NO 90
<211> LENGTH: 654
<212> TYPE: DNA
<213> ORGANISM: Mus musculus
<220> FEATURE:
<221> NAME/KEY: misc_feature
<223> OTHER INFORMATION: Figures 59 & 60

<400> SEQUENCE: 90

```
gatattgtga tgacccaaac tccagcttct ttggctgtgt ctctaggaca gagagccact      60
atcttctgca gagccagcca gagtgtcgat tataatggaa ttagttatat gcactggttc     120
caacagaaac caggacagcc acccaaactc ctcatctatg ctgcatccaa cctagaatct     180
gggatccctg ccaggttcag tggcagtggg tctgggacag acttcaccct caacatccat     240
cctgtggagg aggaagatgc tgcaacctat tactgtcagc aaagttttga ggatccgcac     300
acgttcggag gggggaccaa gctggaaata aaacggctg atgctgcacc aactgtatcc     360
atcttcccac catccagtga gcagttaaca tctggaggtg cctcagtcgt gtgcttcttg     420
aacaacttct accccaaaga catcaatgtc aagtggaaga ttgatggcag tgaacgacaa     480
aatggcgtcc tgaacagttg gactgatcag gacagcaaag acagcaccta cagcatgagc     540
agcaccctca cgttgaccaa ggacgagtat gaacgacata cagctatac ctgtgaggcc     600 actcacaaga catcaacttc acccattgtc aagagcttca caggaatga gtgt            654
```

<210> SEQ ID NO 91
<211> LENGTH: 648
<212> TYPE: DNA
<213> ORGANISM: Mus musculus
<220> FEATURE:
<221> NAME/KEY: misc_feature
<223> OTHER INFORMATION: Figures 61 & 62

<400> SEQUENCE: 91

```
gacgtccagc tgcagcagtc tgggactgtg ctggcaaggc ctggggcttc cgtgaggatg      60
tcctgcaagg cttctggcta cagctttacc aggtactgga tacactggtt aaaacagagg     120
cctggacagg gtctagaatg gattggtgct atttttcctg gaaatcgtga taccagttac     180
aaccagaggt tcaagggcaa ggccgaagtg actgcagtca catccgccag cactgcctac     240
ttggacctca gtagcctgac aaatgaggac tctgcggtct attactgtac aagatggcct     300
tactatggtt ccatctacgt taactttgac tactggggcc aaggcaccac tctcacagtc     360
```

```
tcctcagcca aaacgacacc cccatctgtc tatccactgg cccctggatc tgctgcccaa    420
actaactcca tggtgaccct gggatgcctg gtcaagggct atttccctga gccagtgaca    480
gtgacctgga actctggatc cctgtccagc ggtgtgcaca ccttcccagc tgtcctgcag    540
tctgacctct acactctgag cagctcagtg actgtccct ccagcacctg gcccagcgag     600
accgtcacct gcaacgttgc ccacccagcc agcagcacca aggtcgac                 648

<210> SEQ ID NO 92
<211> LENGTH: 657
<212> TYPE: DNA
<213> ORGANISM: Mus musculus
<220> FEATURE:
<221> NAME/KEY: misc_feature
<223> OTHER INFORMATION: Figures 63 & 64

<400> SEQUENCE: 92
gatattgtga tgacccagtc tcctctctcc ctgcctgtca gtcttggaga tcaagcctcc     60
atctcttgca gaactagtca gaaccttgta cacaggaatg gaaacaccta tttacattgg    120
tacctgcaga agccaggcca gtctccaaag ctcctgattt acaaaatttc caaccgattt    180
tctggggtcc cagacaggtt cagtggcagt ggatcaggga cagatttcac actcaagatc    240
agcagagtgg aggctgagga tctgggagtt tatttctgct ctcaaggtac acatgttcct    300
ccgacgttcg gtggaggcac caagctggaa atcaaacggg ctgatgctgc accaactgta    360
tccatcttcc caccatccag tgagcagtta acatctggag gtgcctcagt cgtgtgcttc    420
ttgaacaact ctaccccaa agacatcaat gtcaagtgga gattgatgg cagtgaacga     480 caaaatggcg tcctgaacag ttggactgat caggacagca agacagcac ctacagcatg     540 agcagcaccc tcacgttgac caaggacgag tatgaacgac ataacagcta tacctgtgag    600
gccactcaca agacatcaac ttcacccatt gtcaagagct caacaggaa tgagtgt        657
```

EPITOPE REGIONS OF A THYROTROPHIN (TSH) RECEPTOR, USES THEREOF AND ANTIBODIES THERETO

This application is a Continuation of U.S. application Ser. No. 10/488,074, filed Jun. 17, 2004, which is a National Stage Application of PCT/GB2002/03831, filed Aug. 21, 2002, which claims benefit of Serial No. 0215212.2, filed Jul. 1, 2002 in Great Britain, and also claims benefit of Serial No. 0120649.9, filed Aug. 23, 2001 in Great Britain and which application(s) are incorporated herein by reference. A claim of priority to all, to the extent appropriate is made.

The present invention is concerned with epitope regions of a thyrotrophin (TSH) receptor, uses thereof and antibodies thereto.

Thyrotrophin or thyroid stimulating hormone (TSH) is a pituitary hormone which plays a key role in regulating the function of the thyroid. Its release is stimulated by the hormone TRH formed in the hypothalamus and controls the formation and release of the important thyroid hormones thyroxine (T4) and tri-iodothyronine (T3). On the basis of a feedback mechanism, the thyroid hormone content of the serum controls the release of TSH. The formation of T3 and T4 by the thyroid cells is stimulated by TSH by a procedure in which the TSH released by the pituitary binds to the TSH receptor of the thyroid cell membrane.

In certain pathological conditions, various types of autoantibodies against this TSH receptor can also be formed. Depending on the type of these autoantibodies, either inhibition of the formation and release of T3 and T4 may occur at the TSH receptor owing to the shielding of the TSH molecules, or, on the other hand, these thyroid hormones may be released in an uncontrolled manner because the anti-TSH receptor autoantibodies mimic the action of the TSH and stimulate the synthesis and release of thyroid hormones.

Autoimmune thyroid disease (AMD) is the most common autoimmune disease affecting different populations worldwide. A proportion of patients with AITD, principally those with Graves' disease, have autoantibodies to the TSH receptor substantially as hereinbefore described. The autoantibodies bind to the TSH receptor and usually mimic the actions of TSH, stimulating the thyroid gland to produce high levels of thyroid hormones. These autoantibodies are described as having stimulating activity. In some patients, autoantibodies bind to the TSH receptor but do not stimulate thyroid hormone production and are described as having blocking activity [J Sanders, Y Oda, S-A Roberts, M Maruyama, J Furmaniak, B Rees Smith "Understanding the thyrotrophin receptor function-structure relationship." Bailliere's Clinical Endocrinology and Metabolism. Ed. T F Davies 1997 11(3): 451-479. Pub. Bailliere Tindall, London].

Measurements of TSH receptor autoantibodies are important in the diagnosis and management of AMTD, particularly Graves' disease. Currently three types of assays are used to measure TSH receptor autoantibodies:

(a) competitive binding assays which measure the ability of TSH receptor autoantibodies to inhibit the binding of TSH to preparations of TSH receptor;

(b) bioassays which measure the ability of TSH receptor autoantibodies to stimulate cells expressing the TSH receptor in culture; and (c) immunoprecipitation of TSH receptor preparations with TSH receptor autoantibodies.

Measurement of TSH receptor autoantibodies using such assays are described in references J Sanders, Y Oda, S-A Roberts, M Maruyama, J Furmaniak, B Rees Smith "Understanding the thyrotrophin receptor function-structure relationship." Bailliere's Clinical Endocrinology and Metabolism. Ed. T F Davies 1997 11(3): 451-479. Pub. Bailliere Tindall, London, and J Sanders, Y Oda, S Roberts, A Kiddie, T Richards, J Bolton, V McGrath, S Walters, D Jaskolski, J Furmaniak, B Rees Smith "The interaction of TSH receptor autoantibodies with $^{125}$I-labelled TSH receptor." Journal of Clinical Endocrinology and Metabolism 1999 84(10):3797-3802.

There are, however, a number of limitations associated with the use of the above described currently available assays for measuring TSH receptor autoantibodies. The competitive assays of type (a) which are available in different formats are generally sensitive, relatively easy to perform and adaptable for routine use. However, competitive radioreceptor assays known to date for detecting TSH receptor autoantibodies have fundamental disadvantages of a practical nature which can be ascribed to the fact that the binding ability of TSH receptor preparations generally react very sensitively to changes in the receptor or in a biomolecule bound by it. The binding of biomolecules which are peptides or protein in nature, for example hormones or autoantibodies, to receptors is as a rule very complicated in nature, and the specific binding between receptor and bio-molecule is very much more sensitive to structural alterations, in particular of the receptor, than is the case with a usual antigen/antibody binding pair which is the basis of most immunoassays in which receptors are involved. Attempts to immobilise and/or to label the TSH receptor have as a rule led to structural alterations which have greatly impaired the functionality of the receptor.

As far as bioassays of the type mentioned in (b) are concerned, these tend to be expensive, time-consuming, require highly skilled staff and are essentially unsuitable for routine use.

With respect to the direct immunoprecipitation assays of type (c), currently available such immunoprecipitation assays do not in practice have the required sensitivity for TSH receptor autoantibody detection.

The present invention alleviates the problems hitherto associated with the prior art detection of TSH receptor autoantibodies. More particularly, the present invention provides diagnostic methods and kits for screening for TSH receptor autoantibodies, with improved sensitivity compared to prior art diagnostic methods and kits, and which, if desired, allow the use of one or more competitive binding partners or competitors for a TSH receptor in competitive assays of the type described above. In particular the present invention is concerned with the use of one or more identified epitope regions of TSH receptor in diagnostic methods and kits for screening for TSH receptor auto antibodies.

There is provided by the present invention, therefore, for use in diagnosis or therapy of autoimmune disease associated with an immune reaction to a TSH receptor, a polypeptide sequence comprising part or all of the primary structural conformation (that is a continuous sequence of amino acid residues) of one or more TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of one or more of the following, or one or more variants, analogs, derivatives or fragments thereof, or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

(in particular said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and/or the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments);

wherein autoantibodies and/or lymphocytes produced in response to a TSH receptor interact (suitably under conditions that allow interaction of a TSH receptor with such autoantibodies or lymphocytes) with said polypeptide sequence, so as to enable said diagnosis or therapy.

More particularly, there is provided by the present invention for use in diagnosis or therapy of autoimmune disease associated with an immune reaction to a TSH receptor, a polypeptide sequence comprising, consisting of or consisting essentially of part or all of the primary structural conformation of one or more TSH receptor epitopes with which autoantibodies produced in response to a TSH receptor interact (suitably under conditions that allow interaction of a TSH receptor with such autoantibodies), said polypeptide sequence comprising, consisting of or consisting essentially of the primary structural conformation of one or more of the following, or one or more variants, analogs, derivatives or fragments thereof, or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

(in particular said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and/or the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments);

wherein autoantibodies produced in response to a TSH receptor interact (suitably under conditions that allow interaction of a TSH receptor with such autoantibodies) with said polypeptide sequence, so as to enable said diagnosis or therapy.

Alternatively, there is provided by the present invention for use in diagnosis or therapy of autoimmune disease associated with an immune reaction to a TSH receptor, a polypeptide sequence comprising, consisting of or consisting essentially of part or all of the primary structural conformation of one or more TSH receptor epitopes with which lymphocytes produced in response to a TSH receptor interact (suitably under conditions that allow interaction of a TSH receptor with such lymphocytes), said polypeptide sequence comprising, consisting of or consisting essentially of the primary structural conformation of one or more of the following, or one or more variants, analogs, derivatives or fragments thereof or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

(in-particular said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and/or the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments);

wherein lymphocytes produced in response to a TSH receptor interact (suitably under conditions that allow interaction of a TSH receptor with such lymphocytes) with said polypeptide sequence, so as to enable said diagnosis or therapy.

The present invention further provides for use in diagnosis or therapy of autoimmune disease associated with an immune reaction to a TSH receptor, a polypeptide sequence comprising, consisting of or consisting essentially of part or all of the primary structural conformation of one or more TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of one or more of the following, or one or more variants, analogs, derivatives or fragments thereof, or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

as depicted in any one of the amino acid sequences of any of FIGS. 1, 3, 5 and 7, (in particular said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and/or the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments);

wherein autoantibodies and/or lymphocytes produced in response to a TSH receptor interact (suitably under conditions that allow interaction of a TSH receptor with such autoantibodies or lymphocytes) with said polypeptide sequence, so as to enable said diagnosis or therapy.

More particularly, the present invention further provides for use in diagnosis or therapy of autoimmune disease associated with an immune reaction to a TSH receptor, a polypeptide sequence comprising, consisting of or consisting essentially of part or all of the primary structural conformation of one or more TSH receptor epitopes with which autoantibodies produced in response to a TSH receptor interact (suitably under conditions that allow interaction of a TSH receptor with such autoantibodies), said polypeptide sequence comprising, consisting of or consisting essentially of the primary structural conformation of one or more of the following, or one or more variants, analogs, derivatives or fragments thereof or variants, analogs or derivatives of such fragments:

amino acid numbers 22 to 91 of a TSH receptor;
amino acid numbers 246 to 260 of a TSH receptor;

amino acid numbers 260 to 363 of a TSH receptor; and
amino acid numbers 380 to 418 of a TSH receptor;
as depicted in any one of the amino acid sequences of any of FIGS. 1, 3, 5 and 7, (in particular said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and/or the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments);
wherein autoantibodies produced in response to a TSH receptor interact (suitably under conditions that allow interaction of a TSH receptor with such autoantibodies) with said polypeptide sequence, so as to enable said diagnosis or therapy.

The present invention further provides for use in diagnosis or therapy of autoimmune disease associated with an immune reaction to a TSH receptor, a polypeptide sequence comprising, consisting of or consisting essentially of part or all of the primary structural conformation of one or more TSH receptor epitopes with which lymphocytes produced in response to a TSH receptor interact (suitably under conditions that allow interaction of a TSH receptor with such lymphocytes), said polypeptide sequence comprising, consisting of or consisting essentially of the primary structural conformation of one or more of the following, or one or more variants, analogs, derivatives or fragments thereof, or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

as depicted in any one of the amino acid sequences of any of FIGS. 1, 3, 5 and 7, (in particular said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and/or the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments);

wherein lymphocytes produced in response to a TSH receptor interact (suitably under conditions that allow interaction of a TSH receptor with such lymphocytes) with said polypeptide sequence, so as to enable said diagnosis or therapy.

More preferably, it is generally preferred that such diagnostic or therapeutic use employs a polypeptide sequence or sequences comprising, consisting of or consisting essentially of the primary structural conformation of one or more of the following, or one or more variants, analogs, derivatives or fragments thereof, or variants, analogs or derivatives of such fragments:

amino acid numbers 32 to 41 of a TSH receptor;
    amino acid numbers 36 to 42 of a TSH receptor;
    amino acid numbers 247 to 260 of a TSH receptor;
    amino acid numbers 277 to 296 of a TSH receptor; and
    amino acid numbers 381 to 385 of a TSH receptor;

(in particular said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and/or the primary structural conformation of amino acid numbers 247 to 260 of a TSH receptor, or one or more variants, analogs, derivatives or fragments of amino acid numbers 247 to 260 of a TSH receptor, or variants, analogs or derivatives of such fragments).

In particular, it is generally preferred according to the present invention that such diagnostic or therapeutic use employs amino acid numbers 277 to 296 of a TSH receptor, or one or more variants, analogs, derivatives or fragments thereof, or variants, analogs or derivatives of such fragments.

In particular, it is generally preferred according to the present invention that such diagnostic or therapeutic use employs amino acid numbers 246 to 260 of a TSH receptor, or one or more variants, analogs, derivatives or fragments thereof, or variants, analogs or derivatives of such fragments.

In particular, it is generally preferred according to the present invention that such diagnostic or therapeutic use employs amino acid numbers 247 to 260 of a TSH receptor, or one or more variants, analogs, derivatives or fragments thereof, or variants, analogs or derivatives of such fragments.

A particularly preferred such diagnostic or therapeutic use according to the present invention, comprises for use in diagnosis or therapy of autoimmune disease associated with an immune reaction to a TSH receptor:

(i) a polypeptide sequence comprising, consisting of or consisting essentially of part or all of the primary structural conformation of one or more TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and (ii) a polypeptide sequence comprising, consisting of or consisting essentially of part or all of the primary structural conformation of one or more further TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments;

wherein autoantibodies and/or lymphocytes produced in response to a TSH receptor interact (suitably under conditions that allow interaction of a TSH receptor with such autoantibodies or lymphocytes) with said polypeptide sequences, so as to enable said diagnosis or therapy.

More particularly, such diagnostic or therapeutic use may comprise:
(i) a polypeptide sequence comprising, consisting of or consisting essentially of part or all of the primary structural conformation of one or more TSH receptor epitopes with which autoantibodies produced in response to a TSH receptor interact (suitably under conditions that allow interaction of a TSH receptor with such autoantibodies), said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and
(ii) a polypeptide sequence comprising, consisting of or consisting essentially of part or all of the primary structural conformation of one or more further TSH receptor epitopes with which autoantibodies produced in response to a TSH receptor interact (suitably under conditions that allow interaction of a TSH receptor with such autoantibodies), said polypeptide sequence comprising, consisting of or consisting essentially of the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments;
wherein autoantibodies produced in response to a TSH receptor interact (suitably under conditions that allow interaction of a TSH receptor with such autoantibodies) with said polypeptide sequences, so as to enable said diagnosis or therapy.

Alternatively, such diagnostic or therapeutic use may comprise:
(i) a polypeptide sequence comprising, consisting of or consisting essentially of part or all of the primary structural conformation of one or more TSH receptor epitopes with which lymphocytes produced in response to a TSH receptor interact (suitably under conditions that allow interaction of a TSH receptor with such lymphocytes), said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and
(ii) a polypeptide sequence comprising, consisting of or consisting essentially of part or all of the primary structural conformation of one or more further TSH receptor epitopes with which lymphocytes produced in response to a TSH receptor interact (suitably under conditions that allow interaction of a TSH receptor with such lymphocytes), said polypeptide sequence comprising, consisting of or consisting essentially of the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments;
wherein lymphocytes produced in response to a TSH receptor interact (suitably under conditions that allow interaction of a TSH receptor with such lymphocytes) with said polypeptide sequences, so as to enable said diagnosis or therapy.

A particularly preferred diagnostic or therapeutic use according to the present invention, comprises for use in diagnosis or therapy of autoimmune disease associated with an immune reaction to a TSH receptor:
(i) a polypeptide sequence comprising, consisting of or consisting essentially of part or all of the primary structural conformation of one or more TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and
(ii) a polypeptide sequence comprising, consisting of or consisting essentially of part or all of the primary structural conformation of one or more filter TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments;
wherein autoantibodies and/or lymphocytes produced in response to a TSH receptor interact (suitably under conditions that allow interaction of a TSH receptor with such autoantibodies or lymphocytes) with said polypeptide sequences, so as to enable said diagnosis or therapy.

More particularly, such diagnostic or therapeutic use may comprise:
(i) a polypeptide sequence comprising, consisting of or consisting essentially of part or all of the primary structural conformation of one or more TSH receptor epitopes with which autoantibodies produced in response to a TSH receptor interact (suitably under conditions that allow interaction of a TSH receptor with such autoantibodies), said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and
(ii) a polypeptide sequence comprising, consisting of or consisting essentially of part or all of the primary structural conformation of one or more flirter TSH receptor epitopes with which autoantibodies produced in response to a TSH receptor interact (suitably under conditions that allow interaction of a TSH receptor with such autoantibodies), said polypeptide sequence comprising, consisting of or consisting essentially of the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments;

wherein autoantibodies produced in response to a TSH receptor interact (suitably under conditions that allow interaction of a TSH receptor with such autoantibodies) with said polypeptide sequences, so as to enable said diagnosis or therapy.

Alternatively, such diagnostic or therapeutic use may comprise:

(i) a polypeptide sequence comprising, consisting of or consisting essentially of part or all of the primary structural conformation of one or more TSH receptor epitopes with which lymphocytes produced in response to a TSH receptor interact (suitably under conditions that allow interaction of a TSH receptor with such lymphocytes), said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and (ii) a polypeptide sequence comprising, consisting of or consisting essentially of part or all of the primary structural conformation of one or more further TSH receptor epitopes with which lymphocytes produced in response to a TSH receptor interact (suitably under conditions that allow interaction of a TSH receptor with such lymphocytes), said polypeptide sequence comprising, consisting of or consisting essentially of the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments;

wherein lymphocytes produced in response to a TSH receptor interact (suitably under conditions that allow interaction of a TSH receptor with such lymphocytes) with said polypeptide sequences, so as to enable said diagnosis or therapy.

It may also be further preferred that the above mentioned diagnostic or therapeutic use employing:

(i) a polypeptide sequence comprising, consisting of or consisting essentially of part or all of the primary structural conformation of one or more TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments; and (ii) a polypeptide sequence comprising, consisting of or consisting essentially of part or all of the primary structural conformation of one or more further TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments;

further employs:

(iii) a polypeptide sequence comprising, consisting of or consisting essentially of part or all of the primary structural conformation of one or more further TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 381 to 385 of a TSH receptor, or one or more variants, analogs, derivatives or fragments of amino acid numbers 381 to 385 of a TSH receptor, or variants, analogs or derivatives of such fragments.

More particularly, such preferred diagnostic or therapeutic use employs:

(i) a polypeptide sequence comprising, consisting of or consisting essentially of part or all of the primary structural conformation of one or more TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments;

(ii) a polypeptide sequence comprising, consisting of or consisting essentially of part or all of the primary structural conformation of one or more further TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments; and (iii) a polypeptide sequence comprising, consisting of or consisting essentially of part or all of the primary structural conformation of one or more further TSH receptor epitopes with which autoantibodies and/or lymphocytes produced in response to a TSH receptor interact (suitably under conditions that allow interaction of a TSH receptor with such autoantibodies or lymphocytes), said polypeptide sequence comprising, consisting of or consisting essentially of the primary structural conformation of amino acid numbers 381 to 385 of a TSH receptor as depicted in any one of the amino acid sequences of FIG. 7, or one or more variants, analogs, derivatives or fragments of amino acid numbers 381 to 385 of a TSH receptor as depicted in any one of the amino acid sequences of FIG. 7, or variants, analogs or derivatives of such fragments.

As will be appreciated from the accompanying Figures, the above mentioned amino acid sequences can be of human, porcine, bovine, canine, feline, mouse, rat or ovine origin, and the specific amino acid sequences in each of the above mentioned species are hereinafter described in greater detail with reference to FIGS. 1, 3, 5, and 7.

There also provided by the present invention one or more TSH receptor epitopes with which autoantibodies and/or lymphocytes produced in response to a TSH receptor interact (suitably under conditions that allow interaction of a TSH receptor with such autoantibodies or lymphocytes), said one or more TSH receptor epitopes comprising, consisting of or consisting essentially of one or more of the following, or one or more variants, analogs, derivatives or fragments thereof or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

(in particular amino acid numbers 277 to 296 of a TSH receptor, or one or more variants, analogs, derivatives or fragments of amino acid numbers 277 to 296 of a TSH receptor, or variants, analogs or derivatives of such fragments; or amino acid numbers 246 to 260 of a TSH receptor, or one or more variants, analogs, derivatives or fragments of amino acid numbers 246 to 260 of a TSH receptor, or variants, analogs or derivatives of such fragments).

More particularly, there is provided by the present invention one or more TSH receptor epitopes with which autoantibodies produced in response to a TSH receptor interact (suitably under conditions that allow interaction of a TSH receptor with such autoantibodies), said one or more TSH receptor epitopes comprising, consisting of or consisting essentially of one or more of the following, or one or more variants, analogs, derivatives or fragments thereof, or variants, analogs or derivatives of such fragments:
amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

(in particular amino acid numbers 277 to 296 of a TSH receptor, or one or more variants, analogs, derivatives or fragments of amino acid numbers 277 to 296 of a TSH receptor, or variants, analogs or derivatives of such fragments; or amino acid numbers 246 to 260 of a TSH receptor, or one or more variants, analogs, derivatives or fragments of amino acid numbers 246 to 260 of a TSH receptor, or variants, analogs or derivatives of such fragments).

Alternatively, there is provided by the present invention one or more TSH receptor epitopes with which lymphocytes produced in response to a TSH receptor interact (suitably under conditions that allow interaction of a TSH receptor with such lymphocytes), said one or more TSH receptor epitopes comprising, consisting of or consisting essentially of one or more of the following, or one or more variants, analogs, derivatives or fragments thereof, or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

(in particular amino acid numbers 277 to 296 of a TSH receptor, or one or more variants, analogs, derivatives or fragments of amino acid numbers 277 to 296 of a TSH receptor, or variants, analogs or derivatives of such fragments; or amino acid numbers 246 to 260 of a TSH receptor, or one or more variants, analogs, derivatives or fragments of amino acid numbers 246 to 260 of a TSH receptor, or variants, analogs or derivatives of such fragments).

The present invention further provides one or more TSH receptor epitopes with which autoantibodies and/or lymphocytes produced in response to a TSH receptor interact (suitably under conditions that allow interaction of a TSH receptor with such autoantibodies or lymphocytes), said one or more TSH receptor epitopes comprising, consisting of or consisting essentially of one or more of the following, or one or more variants, analogs, derivatives or fragments thereof, or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

as depicted in any one of the amino acid sequences of any of FIGS. 1, 3, 5 and 7, (in particular amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; or amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments).

More particularly, the present invention further provides one or more TSH receptor epitopes with which autoantibodies produced in response to a TSH receptor interact (suitably under conditions that allow interaction of a TSH receptor with such autoantibodies), said one or more TSH receptor epitopes comprising, consisting of or consisting essentially of one or more of the following, or one or more variants, analogs, derivatives or fragments thereof or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

as depicted in any one of the amino acid sequences of any of FIGS. 1, 3, 5 and 7, (in particular amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; or amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments).

The present invention further provides one or more TSH receptor epitopes with which lymphocytes produced in response to a TSH receptor interact (suitably under conditions that allow interaction of a TSH receptor with such lymphocytes), said TSH receptor epitopes comprising, consisting of or consisting essentially of one or more of the following, or one or more variants, analogs, derivatives or fragments thereof, or variants, analogs or derivatives of such fragments:
    amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;
as depicted in any one of the amino acid sequences of any of FIGS. 1, 3, 5 and 7, (in particular amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; or amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments).

More preferably, it is generally preferred that one or more TSH receptor epitopes comprise one or more of the following, or one or more variants, analogs, derivatives or fragments thereof, or variants, analogs or derivatives of such fragments:
    amino acid numbers 32 to 41 of a TSH receptor;
    amino acid numbers 36 to 42 of a TSH receptor;
    amino acid numbers 247 to 260 of a TSH receptor;
    amino acid numbers 277 to 296 of a TSH receptor; and
    amino acid numbers 381 to 385 of a TSH receptor;
(in particular amino acid numbers 277 to 296 of a TSH receptor, or one or more variants, analogs, derivatives or fragments of amino acid numbers 277 to 296 of a TSH receptor, or variants, analogs or derivatives of such fragments; or amino acid numbers 247 to 260 of a TSH receptor, or one or more variants, analogs, derivatives or fragments of amino acid numbers 247 to 260 of a TSH receptor, or variants, analogs or derivatives of such fragments).

A particularly preferred TSH receptor epitope according to the present invention comprises, consists of or consists essentially of amino acid numbers 277 to 296 of a TSH receptor, or one or more variants, analogs, derivatives or fragments thereof, or variants, analogs or derivatives of such fragments, with which autoantibodies and/or lymphocytes produced in response to a TSH receptor can interact (suitably under conditions that allow interaction of a TSH receptor with such autoantibodies or lymphocytes).

A particularly preferred TSH receptor epitope according to the present invention comprises, consists of or consists essentially of amino acid numbers 246 to 260 of a TSH receptor, or one or more variants, analogs, derivatives or fragments thereof, or variants, analogs or derivatives of such fragments, with which autoantibodies and/or lymphocytes produced in response to a TSH receptor can interact (suitably under conditions that allow interaction of a TSH receptor with such autoantibodies or lymphocytes).

A particularly preferred TSH receptor epitope according to the present invention comprises, consists of or consists essentially of amino acid numbers 247 to 260 of a TSH receptor, or one or more variants, analogs, derivatives or fragments thereof, or variants, analogs or derivatives of such fragments, with which autoantibodies and/or lymphocytes produced in response to a TSH receptor can interact (suitably under conditions that allow interaction of a TSH receptor with such autoantibodies or lymphocytes).

There is also provided by the present invention a polypeptide with which autoantibodies and/or lymphocytes produced in response to a TSH receptor can interact (suitably under conditions that allow interaction of a TSH receptor with such autoantibodies or lymphocytes) and which comprises, consists of or consists essentially of part or all of the primary structural conformation of one or more epitopes of a TSH receptor with which autoantibodies and/or lymphocytes produced in response to a TSH receptor can interact (suitably under conditions that allow interaction of a TSH receptor with such autoantibodies or lymphocytes), which polypeptide comprises, consists of or consists essentially of the primary structural conformation of one or more of the following, or one or more variants, analogs, derivatives or fragments thereof, or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

(in particular amino acid numbers 277 to 296 of a TSH receptor, or one or more variants, analogs, derivatives or fragments of amino acid numbers 277 to 296 of a TSH receptor, or variants, analogs or derivatives of such fragments; and/or amino acid numbers 246 to 260 of a TSH receptor, or one or more variants, analogs, derivatives or fragments of amino acid numbers 246 to 260 of a TSH receptor, or variants, analogs or derivatives of such fragments), with which autoantibodies and/or lymphocytes produced in response to a TSH receptor can interact (suitably under conditions that allow interaction of a TSH receptor with such autoantibodies or lymphocytes), with the exception of a full length TSH receptor.

More particularly, there is provided by the present invention a polypeptide with which autoantibodies produced in response to a TSH receptor can interact (suitably under conditions that allow interaction of a TSH receptor with such autoantibodies) and which comprises, consists of or consists essentially of part or all of the primary structural conformation (that is a continuous sequence of amino acid residues) of one or more epitopes of a TSH receptor with which autoantibodies produced in response to a TSH receptor can interact (suitably under conditions that allow interaction of a TSH receptor with such autoantibodies), which polypeptide comprises, consists of or consists essentially of the primary structural conformation of one or more of the following, or one or more variants, analogs, derivatives or fragments thereof, or variants, analogs or derivatives of such fragments:

amino acid numbers 22 to 91 of a TSH receptor;
amino acid numbers 246 to 260 of a TSH receptor;
amino acid numbers 260 to 363 of a TSH receptor; and
amino acid numbers 380 to 418 of a TSH receptor;

(in particular amino acid numbers 277 to 296 of a TSH receptor, or one or more variants, analogs, derivatives or fragments of amino acid numbers 277 to 296 of a TSH receptor, or variants, analogs or derivatives of such fragments; and/or amino acid numbers 246 to 260 of a TSH receptor, or one or more variants, analogs, derivatives or fragments of amino acid numbers 246 to 260 of a TSH receptor, or variants, analogs or derivatives of such fragments), with which autoantibodies produced in response to a TSH receptor can interact (suitably under conditions that allow interaction of a TSH receptor with such autoantibodies), with the exception of a full length TSH receptor. Alternatively, there is provided by the present invention a polypeptide with which lymphocytes produced in response to a TSH receptor can interact (suitably under conditions that allow interaction of a TSH receptor with such lymphocytes) and which comprises, consists of or consists essentially of part or all of the primary structural conformation (that is a continuous sequence of amino acid residues) of one or more epitopes of a TSH receptor with which lymphocytes produced in response to a TSH receptor can interact (suitably under conditions that allow interaction of a TSH receptor with such lymphocytes), which polypeptide comprises, consists of or consists essentially of the primary structural conformation of one or more of the following, or one or more variants, analogs, derivatives or fragments thereof, or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

(in particular amino acid numbers 277 to 296 of a TSH receptor, or one or more variants, analogs, derivatives or fragments of amino acid numbers 277 to 296 of a TSH receptor, or variants, analogs or derivatives of such fragments; and/or amino acid numbers 246 to 260 of a TSH receptor, or one or more variants, analogs, derivatives or fragments of amino acid numbers 246 to 260 of a TSH receptor, or variants, analogs or derivatives of such fragments), with which lymphocytes produced in response to a TSH receptor can interact (suitably under conditions that allow interaction of a TSH receptor with such lymphocytes), with the exception of a full length TSH receptor.

The present invention further provides a polypeptide with which autoantibodies and/or lymphocytes produced in response to a TSH receptor can interact (suitably under conditions that allow interaction of a TSH receptor with such autoantibodies or lymphocytes) and which comprises, consists of or consists essentially of part or all of the primary structural conformation of one or more epitopes of a TSH receptor with which autoantibodies and/or lymphocytes produced in response to a TSH receptor can interact (suitably under conditions that allow interaction of a TSH receptor with such autoantibodies or lymphocytes), which polypeptide comprises, consists of or consists essentially of the primary structural conformation of one or more of the following, or one or more variants, analogs, derivatives or fragments thereof or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

as depicted in any one of the amino acid sequences of any of FIGS. 1, 3, 5 and 7, (in particular amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and/or amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments), with which autoantibodies and/or lymphocytes produced in response to a TSH receptor can interact (suitably under conditions that allow interaction of a TSH receptor with such autoantibodies or lymphocytes), with the exception of a full length TSH receptor.

More particularly, the present invention further provides a polypeptide with which autoantibodies produced in response to a TSH receptor can interact (suitably under conditions that allow interaction of a TSH receptor with such autoantibodies) and which comprises, consists of or consists essentially of part or all of the primary structural conformation of one or more epitopes of a TSH receptor with which autoantibodies produced in response to a TSH receptor can interact (suitably under conditions that allow interaction of a TSH receptor with such autoantibodies), which polypeptide comprises, consists of or consists essentially of the primary structural conformation of one or more of the following, or one or more variants, analogs, derivatives or fragments thereof, or variants, analogs or derivatives of such fragments:

amino acid numbers 22 to 91 of a TSH receptor;
    amino acid numbers 246 to 260 of a TSH receptor;
    amino acid numbers 260 to 363 of a TSH receptor; and
    amino acid numbers 380 to 418 of a TSH receptor;

as depicted in any one of the amino acid sequences of any of FIGS. 1, 3, 5 and 7, (in particular amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and/or amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments), with which autoantibodies produced in response to a TSH receptor can interact (suitably under conditions that allow interaction of a TSH receptor with such autoantibodies), with the exception of a full length TSH receptor.

The present invention further provides a polypeptide with which lymphocytes produced in response to a TSH receptor can interact (suitably under conditions that allow interaction of a TSH receptor with such lymphocytes) and which comprises, consists of or consists essentially of part or all of the primary structural conformation of one or more epitopes of a TSH receptor with which lymphocytes produced in response to a TSH receptor can interact (suitably under conditions that allow interaction of a TSH receptor with such lymphocytes), which polypeptide comprises, consists of or consists essentially of the primary structural conformation of one or more of the following, or one or more variants, analogs, derivatives or fragments thereof or variants, analogs or derivatives of such fragments:

amino acid numbers 22 to 91 of a TSH receptor,
    amino acid numbers 246 to 260 of a TSH receptor,
    amino acid numbers 260 to 363 of a TSH receptor; and
    amino acid numbers 380 to 418 of a TSH receptor;

as depicted in any one of the amino acid sequences of any of FIGS. 1, 3, 5 and 7, (in particular amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments; and/or amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments), with which lymphocytes produced in response to a TSH receptor can interact (suitably under conditions that allow interaction of a TSH receptor with such lymphocytes), with the exception of a full length TSH receptor.

More preferably, it is generally preferred that a polypeptide according to the present invention can comprise part or all of the primary structural conformation of one or more epitopes of a TSH receptor with which autoantibodies and/or lymphocytes produced in response to a TSH receptor can interact (suitably under conditions that allow interaction of a TSH receptor with such autoantibodies or lymphocytes) and as such comprises, consists of or consists essentially of the primary structural conformation of one or more of the following, or one or more variants, analogs, derivatives or fragments thereof or variants, analogs or derivatives of such fragments, with which autoantibodies and/or lymphocytes produced in response to a TSH receptor can interact (suitably under conditions that allow interaction of a TSH receptor with such autoantibodies or lymphocytes):

amino acid numbers 32 to 41 of a TSH receptor,
amino acid numbers 36 to 42 of a TSH receptor,
amino acid numbers 247 to 260 of a TSH receptor,
amino acid numbers 277 to 296 of a TSH receptor; and
amino acid numbers 381 to 385 of a TSH receptor.

Preferably a polypeptide according to the present invention comprises, consists of or consists essentially of, amino acid numbers 277 to 296 of a TSH receptor, or one or more variants, analogs, derivatives or fragments thereof, or variants, analogs or derivatives of such fragments.

Preferably a polypeptide according to the present invention comprises, consists of or consists essentially of, amino acid numbers 246 to 260 of a TSH receptor, or one or more variants, analogs, derivatives or fragments thereof, or variants, analogs or derivatives of such fragments.

Preferably a polypeptide according to the present invention comprises, consists of or consists essentially of, amino acid numbers 247 to 260 of a TSH receptor, or one or more variants, analogs, derivatives or fragments thereof, or variants, analogs or derivatives of such fragments.

It is also preferred according to the present invention that there is provided a polypeptide with which autoantibodies and/or lymphocytes produced in response to a TSH receptor can interact (suitably under conditions that allow interaction of a TSH receptor with such autoantibodies or lymphocytes) and which comprises part or all of the primary structural conformation of TSH receptor epitopes with which autoantibodies and/or lymphocytes produced in response to a TSH receptor can interact (suitably under conditions that allow interaction of a TSH receptor with such autoantibodies or lymphocytes), which polypeptide comprises, consists of or consists essentially of:
  (i) the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments, with which autoantibodies and/or lymphocytes produced in response to a TSH receptor can interact (suitably under conditions that allow interaction of a TSH receptor with such autoantibodies or lymphocytes); and
  (ii) the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments, with which autoantibodies and/or lymphocytes produced in response to a TSH receptor can interact (suitably under conditions that allow interaction of a TSH receptor with such autoantibodies or lymphocytes);
with the exception of a full length TSH receptor.

More particularly, there is provided by the present invention a polypeptide with which autoantibodies produced in response to a TSH receptor can interact (suitably under conditions that allow interaction of a TSH receptor with such autoantibodies) and which comprises part or all of the primary structural conformation of TSH receptor epitopes with which autoantibodies produced in response to a TSH receptor can interact (suitably under conditions that allow interaction of a TSH receptor with such autoantibodies), which polypeptide comprises, consists of or consists essentially of:
  (i) the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments, with which autoantibodies produced in response to a TSH receptor can interact (suitably under conditions that allow interaction of a TSH receptor with such autoantibodies); and
  (ii) the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments, with which autoantibodies produced in response to a TSH receptor can interact (suitably under conditions that allow interaction of a TSH receptor with such autoantibodies);
with the exception of a full length TSH receptor.

Alternatively, there is provided by the present invention a polypeptide with which lymphocytes produced in response to a TSH receptor can interact (suitably under conditions that allow interaction of a TSH receptor with such lymphocytes) and which comprises part or all of the primary structural conformation of TSH receptor epitopes with which lymphocytes produced in response to a TSH receptor can interact (suitably under conditions that allow interaction of a TSH receptor with such lymphocytes), which polypeptide comprises, consists of or consists essentially of:
  (i) the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments, with which lymphocytes produced in response to a TSH receptor can interact (suitably under conditions that allow interaction of a TSH receptor with such lymphocytes); and
  (ii) the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments, with which lymphocytes produced in response to a TSH receptor can interact (suitably under conditions that allow interaction of a TSH receptor with such lymphocytes);
with the exception of a full length TSH receptor.

The present invention further provides a polypeptide with which autoantibodies and/or lymphocytes produced in response to a TSH receptor can interact (suitably under conditions that allow interaction of a TSH receptor with such autoantibodies or lymphocytes) and which comprises part or all of the primary structural conformation of epitopes of a TSH receptor with which autoantibodies and/or lymphocytes produced in response to a TSH receptor can interact (suitably under conditions that allow interaction of a TSH receptor with such autoantibodies or lymphocytes), which polypeptide comprises, consists of or consists essentially of:
  (i) the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments, with which autoantibodies and/or lymphocytes produced in response to a TSH receptor can interact (suitably under conditions that allow interaction of a TSH receptor with such autoantibodies or lymphocytes); and
  (ii) the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments, with which autoantibodies and/or lymphocytes produced in response to a TSH receptor can interact (suitably under conditions that allow interaction of a TSH receptor with such autoantibodies or lymphocytes);
with the exception of a fill length TSH receptor.

More particularly, the present invention further provides a polypeptide with which autoantibodies produced in response to a TSH receptor can interact (suitably under conditions that allow interaction of a TSH receptor with such autoantibodies) and which comprises part or all of the primary structural conformation of TSH rector epitopes with which autoantibodies produced in response to a TSH receptor can interact (suitably under conditions that allow interaction of a TSH receptor with such autoantibodies), which polypeptide comprises, consists of or consists essentially of:
  (i) the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments, with which autoantibodies produced in response to a TSH receptor can interact (suitably under conditions that allow interaction of a TSH receptor with such autoantibodies); and
  (ii) the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments, with which autoantibodies produced in response to a TSH receptor can interact (suitably under conditions that allow interaction of a TSH receptor with such autoantibodies);
with the exception of a full length TSH receptor.

The present invention further provides a polypeptide with which lymphocytes produced in response to a TSH receptor can interact (suitably under conditions that allow interaction of a TSH receptor with such lymphocytes) and which comprises part or all of the primary structural conformation of TSH receptor epitopes with which lymphocytes produced in response to a TSH receptor can interact (suitably under conditions that allow interaction of a TSH receptor with such lymphocytes), which polypeptide comprises, consists of or consists essentially of:
  (i) the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments, with which lymphocytes produced in response to a TSH receptor can interact (suitably under conditions that allow interaction of a TSH receptor with such lymphocytes); and
  (ii) the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments, with which lymphocytes produced in response to a TSH receptor can interact (suitably under conditions that allow interaction of a TSH receptor with such lymphocytes);
with the exception of a full length TSH receptor.

It is also preferred according to the present invention that there is provided a polypeptide with which autoantibodies and/or lymphocytes produced in response to a TSH receptor can interact (suitably under conditions that allow interaction of a TSH receptor with such autoantibodies or lymphocytes) and which comprises part or all of the primary structural conformation of TSH receptor epitopes with which autoantibodies and/or lymphocytes produced in response to a TSH receptor can interact (suitably under conditions that allow interaction of a TSH receptor with such autoantibodies or lymphocytes), which polypeptide comprises, consists of or consists essentially of:
  (i) the primary structural conformation of amino acid numbers 277 to 296 of a TSH receptor, or one or more variants, analogs, derivatives or fragments of amino acid numbers 277 to 296 of a TSH receptor, or variants, analogs or derivatives of such fragments, with which autoantibodies and/or lymphocytes produced in response to a TSH receptor can react (suitably under conditions that allow interaction of a TSH receptor with such autoantibodies or lymphocytes);
  (ii) the primary structural conformation of amino acid numbers 246 to 260 of a TSH receptor, or one or more variants, analogs, derivatives or fragments of amino acid numbers 246 to 260 of a TSH receptor, or variants, analogs or derivatives of such fragments, with which autoantibodies and/or lymphocytes produced in response to a TSH receptor can interact (suitably under conditions that allow interaction of a TSH receptor with such autoantibodies or lymphocytes); and
  (iii) the primary structural conformation of amino acid numbers 381 to 385 of a TSH receptor, or one or more variants, analogs, derivatives or fragments of amino acid numbers 381 to 385 of a TSH receptor, or variants, analogs or derivatives of such fragments, with which autoantibodies and/or lymphocytes produced in response to a TSH receptor can interact (suitably under conditions that allow interaction of a TSH receptor with such autoantibodies or lymphocytes);
with the exception of a full length TSH receptor.

More particularly, the present invention further provides a polypeptide with which autoantibodies and/or lymphocytes produced in response to a TSH receptor can interact (suitably under conditions that allow interaction of a TSH receptor with such autoantibodies or lymphocytes) and which comprises part or all of the primary structural conformation of epitopes of a TSH receptor with which autoantibodies and/or lymphocytes produced in response to a TSH receptor can interact (suitably under conditions that allow interaction of a TSH receptor with such autoantibodies or lymphocytes), which polypeptide comprises, consists of or consists essentially of:
  (i) the primary structural conformation of amino acid numbers 277 to 296 of a TSH receptor as depicted in any one of the amino acid sequences of FIG. 5, or one or more variants, analogs, derivatives or fragments of amino acid numbers 277 to 296 of a TSH receptor as depicted in any one of the amino acid sequences of FIG. 5, or variants, analogs or derivatives of such fragments, with which autoantibodies and/or lymphocytes produced in response to a TSH receptor can interact (suitably under conditions that allow interaction of a TSH receptor with such autoantibodies or lymphocytes);
  (ii) the primary structural conformation of amino acid numbers 246 to 260 of a TSH receptor as depicted in any one of the amino acid sequences of FIG. 3, or one or more variants, analogs, derivatives or fragments of amino acid numbers 246 to 260 of a TSH receptor as depicted in any one of the amino acid sequences of FIG. 3, or variants, analogs or derivatives of such fragments, with which autoantibodies and/or lymphocytes produced in response to a TSH receptor can interact (suitably under conditions that allow interaction of a TSH receptor with such autoantibodies or lymphocytes);
  (iii) the primary structural conformation of amino acid numbers 381 to 385 of a TSH receptor as depicted in any one of the amino acid sequences of FIG. 7, or one or more variants, analogs, derivatives or fragments of amino acid numbers 381 to 385 of a TSH receptor as depicted in any one of the amino acid sequences of FIG. 7, or variants, analogs or derivatives of such fragments, with which autoantibodies and/or lymphocytes produced in response to a TSH receptor can interact (suitably under conditions that allow interaction of a TSH receptor with such autoantibodies or lymphocytes);
with the exception of a full length TSH receptor.

As will be appreciated from the accompanying Figures, such amino acid sequences can be of human, porcine, bovine, canine, feline, mouse, rat or ovine origin, and the specific amino acid sequences in each of the above mentioned species are hereinafter described in greater detail with reference to FIGS. 1, 3, 5, and 7. Suitably, in the case where polypeptides according to the second aspect of the present invention comprise amino acid sequences corresponding to part or all of the primary structural conformation of more than one epitope of a TSH receptor, the respective amino acid sequences corresponding to part or all of the primary structural conformation of respective epitopes may be separated by linker amino acid sequences so as to preferably provide the respective amino acid sequences in a conformation, arrangement or sequence that resembles or substantially resembles a conformation, arrangement or sequence of amino acids as present in an active site of a TSH receptor, and/or can be effective in providing the above referred to respective amino acid sequences of a TSH receptor in a conformation, arrangement or sequence optimal for interaction with autoantibodies and/or lymphocytes as described herein.

Preferred polypeptide sequences and polypeptides according to the present invention comprise, consist of, or consist essentially of, the specifically referred to amino acid numbered sequences of a TSH receptor as respectively shown in any of accompanying FIG. 1, 3, 5 or 7. As indicated above, however, the present invention also covers "variants", "analogs", "derivatives" and "fragments" of specific amino acid sequences described herein and the terms "variants", "analogs", "derivatives" and "fragments" as used herein when referring to polypeptide sequences and polypeptides according to the present invention (such as polypeptides having a primary structural conformation of specified amino acids as described herein with reference to the accompanying Figures) can be characterised as polypeptide sequences and polypeptides which retain essentially the same biological function or activity (in terms of autoantibody and/or lymphocyte interaction as described herein) as polypeptide sequences and polypeptides having a primary structural conformation of specified amino acids as described herein with reference to the accompanying Figures. Suitably, variants, analogs, derivatives and fragments, or variants, analogs or derivatives of the fragments as described herein can have a primary structural conformation of amino acids as seen in the accompanying Figures in which several or a few (such as 5 to 10, 1 to 5 or 1 to 3) amino acid residues are substituted, deleted or added, in any combination. Especially preferred among these are silent substitutions, additions are deletions which do not alter or substantially alter the biological activity or function of polypeptides according to the present invention as specifically described above. Conservative substitutions can be preferred as hereinafter described in greater detail.

More particularly, variants, analogs or derivatives of polypeptides having a primary structural conformation of specified amino acids as described herein with reference to the accompanying Figures may be:
  (i) ones in which one or more of the amino acid residues are substituted with a conserved or non-conserved amino acid residue (preferably a conserved amino acid residue); or
  (ii) ones in which one or more of the amino acid resides includes a substituent group; or
  (iii) ones which further comprise additional amino acids that can be effective in providing the above referred to amino acid numbers of a TSH receptor that are present in a polypeptide of the present invention in a conformation, arrangement or sequence that resembles or substantially resembles a conformation, arrangement or sequence of amino acids as present in an active site of a TSH receptor, and/or can be effective in providing the above referred to amino acid numbers of a TSH receptor that are present in a polypeptide of the present invention in a conformation, arrangement or sequence optimal for interaction with autoantibodies and/or lymphocytes as described herein.

Such variants, derivatives and analogs are deemed to be within the scope of those skilled in the art from the teachings herein.

Typically, variants, analogs or derivatives can be those that vary from a reference (such as polypeptides having a primary structural conformation of specified amino acids as described herein with reference to the accompanying Figures) by conservative amino acid substitutions. Such substitutions are those that substitute a given amino acid in a polypeptide by another amino acid of like characteristics. Typically seen as conservative substitutions are the replacements, one for another, among the aliphatic amino acids A, V, L and J; among the hydroxyl residues S and T; among the acidic residues D and E; among the amide residues N and Q; among the basic residues K and R; and among the aromatic residues F and Y.

It may be preferred that variants, analogs or derivatives as provided by the present invention are ones which further comprise additional amino acids that can be effective in providing the above referred to amino acid numbers of a TSH receptor that are present in a polypeptide of the present invention in a conformation, arrangement or sequence that resembles or substantially resembles a conformation, arrangement or sequence of amino acids as present in an active site of a TSH receptor, and/or can be effective in providing the above referred to amino acid numbers of a TSH receptor that are present in a polypeptide of the present invention in a conformation, arrangement or sequence optimal for interaction with autoantibodies and/or lymphocytes as described herein.

More particularly, the term "fragment" as used herein denotes a polypeptide having an amino acid sequence that entirely is the same as part but not all of the amino acid sequence of a polypeptide having a primary structural conformation of specified amino acids—as described herein with reference to the accompanying Figures, and variants or derivatives thereof and such fragments may be "free standing", i.e. not part of or fused to other amino acids or polypeptides, or they may be comprised within a larger polypeptide of which they form a part or region. As will be appreciated, fragments according to the present invention comprise or contain the primary structural conformation of amino acids present in one or more epitopes of a TSH receptor as described herein so as to be capable of interaction with autoantibodies and/or lymphocytes as described herein.

Polypeptides of the present invention, therefore, include polypeptides having a primary structural conformation of specified amino acids as described herein with reference to the accompanying Figures as well as polypeptides (namely variants, analogs and derivatives as referred to above) having at least 70% identity to polypeptides having a primary structural conformation of specified amino acids as described herein with reference to the accompanying Figures, preferably at least 80% identity to the polypeptides having a primary structural conformation of specified amino acids as described herein with reference to the accompanying Figures, and more preferably at least 90% identity to polypeptides having a primary structural conformation of specified amino acids as described herein with reference to the accompanying Figures and still more preferably at least 95% identity to polypeptides having a primary structural conformation of specified amino acids as described herein with reference to the accompanying Figures and also includes fragments of such polypeptides substantially as referred to above.

A polypeptide according to the present invention is suitably obtained by, or is obtainable by, expression of a polynucleotide according to the present invention substantially as hereinafter described. Alternatively, the polypeptides of the invention can be synthetically produced by conventional peptide synthesisers employing techniques which are well known in the art. A polypeptide according to the present invention so obtained can be advantageous in being free from association with other eukaryotic polypeptides or contaminants which might otherwise be associated therewith in its natural environment.

Polypeptides according to the present invention substantially as herein described can be expressed in various systems generating recombinant proteins. For example, for expression in *E. coli*, cDNA coding for the appropriate polypeptides according to the present invention can be cloned into a vector, such as pET22, pMEX8, pGEX2T or pQE81L His or an equivalent. In the case of expression in yeast (for example *Saccharomyces cerevisiae* or *Schizosaccharomyces pombe*), vectors such as pYES2, pESP2 or pYES2/CT or an equivalent, can be employed. AcMNPV (Bac-N-Blue) vector or an equivalent can be used for expression in insect cells and pRC/CMV, pcDNA3.1 vectors or an equivalent can be used for expression in mammalian cells, such as Chinese Hamster Ovary (CHO) cells. A polypeptide according to the present invention can be expressed as a discrete protein, or as a fusion protein linked to, for example, glutathione S transferase (GST) or poly histidine linker. For a discrete protein, affinity column chromatography purification using a mouse monoclonal antibody to the relevant part of a polypeptide according to the present invention coupled to a Sepharose particle can be used. If a polypeptide according to the present invention is fused to GST, glutathione Sepharose chromatography purification can be used to isolate the fusion protein. Specific proteases can be used to separate GST from a polypeptide according to the present invention and a second round of glutathione Sepharose chromatography can be used to separate GST from a polypeptide according to the present invention. In the case of peptides linked to poly histidine linker, the purification can be carried out using immobilised metal affinity chromatography.

The present invention further provides a process of preparing a polypeptide substantially as hereinbefore described, which process comprises:
(i) providing a host cell substantially as hereinbefore described;
(ii) growing the host cell; and
(iii) recovering a polypeptide according to the present invention therefrom.

Recovery of a polypeptide according to the present invention can typically employ conventional isolation and purification techniques, such as chromatographic separations or immunological separations, known to one of ordinary skill in the art.

In accordance with a further aspect of the present invention, there is provided a polynucleotide comprising:
(i) a nucleotide sequence encoding a polypeptide substantially as hereinbefore described;
(ii) a nucleotide sequence encoding a polypeptide substantially as hereinbefore described, which polypeptide comprises an amino acid sequence or sequences of specified amino acid numbers of a TSH receptor which is or arm defined by reference to any of FIGS. 1, 3, 5 and 7;
(iii) a nucleotide sequence encoding a polypeptide of (ii), which nucleotide sequence comprises nucleotide bases encoding the above mentioned specified amino acid numbers of a TSH receptor which are defined by reference to any of FIGS. 1, 3, 5, and 7, and which nucleotide bases are defined by reference to any of FIGS. 2, 4, 6 and 8;
(iv) a nucleotide sequence differing from the sequence of (iii) in codon sequence due to the degeneracy of the genetic code;
(v) a nucleotide sequence comprising an allelic variation of the sequence of (iii);
(vi) a nucleotide sequence comprising a fragment of any of the sequences of (i), (ii), (iii), (iv) or (v); or
(vii) a nucleotide sequence which hybridizes under stringent conditions to any of the sequences of (i), (ii), (iii), (iv), (v) or (vi).

The nucleotide bases of a polynucleotide according to the present invention, encoding the above mentioned epitope regions of a polypeptide according to the present invention, can be summarised as follows.

| Amino Acid Numbers | Nucleotide Numbers |
|---|---|
| 22-91 | 64-273 |
| 32 1 | 94-123 |
| 36 2 | 106-126 |
| 246-260 | 736-780 |
| 247-260 | 739-780 |
| 260-363 | 778-1089 |
| 277-296 | 829-888 |
| 380-418 | 1138-1254 |
| 381-385 | 1141-1155 |

Polynucleotides of the present invention may be in the form of DNA, including, for instance, cDNA, synthetic DNA and genomic DNA appropriately obtained by cloning or produced by chemical synthetic techniques or by a combination thereof A preferred embodiment of the present invention preferably comprises cDNA or synthetic DNA.

The coding sequence which encodes a polypeptide according to the present invention may be identical to the coding sequence of a polynucleotide as referred to above in (iii) and defined by reference to any of FIGS. 2, 4, 6 and 8. It also may be a polynucleotide with a different sequence, which, as a result of the redundancy (degeneracy) of the genetic code, encodes a polypeptide according to the present invention.

The present invention further relates to variants of the herein above described polynucleotides which encode for polypeptides having a primary structural conformation of specified amino acids as described herein with reference to the accompanying Figures, variants, analogs, derivatives or fragments thereof, or variants, analogs or derivatives of the fragments and substantially as hereinbefore described in greater detail. A variant of the polynucleotide may be a naturally occurring variant such as a naturally occurring allelic variant, or it may be a variant that is not known to occur naturally. Such non-naturally occurring variants of the polynucleotide may be made by mutagenesis techniques.

Among the variants in this regard are variants that differ from the aforementioned polynucleotides by nucleotide substitutions, deletions or additions. The substitutions, deletions or additions may involve one or more nucleotides. Alterations in the coding regions may produce conservative or non-conservative amino acid substitutions, deletions or additions, again substantially as hereinbefore described.

Variant polynucleotides according to the present invention are suitably at least 70% identical over their entire length to a polynucleotide encoding polypeptides having a primary structural conformation of specified amino acids as described herein with reference to the accompanying Figures, and polynucleotides which are complementary to, or hybridise to, such polynucleotides. Alternatively, most highly preferred are polynucleotides that comprise a region that is at least 80% identical over its entire length to a polynucleotide encoding a polypeptides having a primary structural conformation of specified amino acids as described herein with reference to the accompanying Figures and polynucleotides which are complementary to, or hybridise to, such polynucleotides. In this regard, polynucleotides at least 90% identical over their entire length to the same are particularly preferred, and among these particularly preferred polynucleotides, those with at least 95% identity are especially preferred. Furthermore, those with at least 97% identity are highly preferred among those with at least 95% identity, and among these those with at least 98% identity and at least 99% identity are particularly highly preferred, with at least 99% identity being the more preferred.

Substantially as hereinbefore described the present invention further relates to polynucleotides that hybridise to the herein above-described sequences. In this regard, the present invention especially relates to polynucleotides which hybridise under stringent conditions to the herein above-described polynucleotides. As herein used, the term "stringent conditions" means hybridisation will occur only if there is at least 95% and preferably at least 97% complementary identity between the sequences.

The present invention also relates to vectors, which comprise a polynucleotide or polynucleotides of the present invention, host cells which are genetically engineered with vectors of the invention and the production of polypeptides of the invention by recombinant techniques.

The present invention, therefore, further provides a biologically functional vector system which carries a polynucleotide substantially as hereinbefore described and which is capable of introducing the polynucleotide into the genome of a host organism.

Host cells can be genetically engineered to incorporate polynucleotides and express polypeptides of the present invention and the present invention further provides a host cell which is transformed or transfected with a polynucleotide, or one or more polynucleotides, or a vector system, each substantially as herein described. The appropriate DNA sequence may be inserted into the vector by any of a variety of well-known and routine techniques.

According to a particularly preferred embodiment of the present invention, there is also provided a method of screening for autoantibodies or lymphocytes produced in response to a TSH receptor in a sample of body fluid obtained from a subject (in particular a human) suspected of suffering from, susceptible to, having or recovering from autoimmune disease associated with an immune reaction to a TSH receptor, said method comprising:

(a) providing either (i) said sample of body fluid from said subject or (ii) lymphocytes isolated from said sample;

(b) contacting said sample or isolated lymphocytes with a polypeptide according to the present invention substantially as hereinbefore described (suitably under conditions that allow interaction of a TSH receptor with autoantibodies or lymphocytes produced in response to a TSH receptor) so as to permit said polypeptide to interact with autoantibodies, or lymphocytes, produced in response to a TSH receptor, and present in, or isolated from, said sample; and (c) monitoring the degree, or effect, of interaction of said polypeptide with either said autoantibodies, or said lymphocytes, produced in response to a TSH receptor and present in, or isolated from, said sample, thereby providing an indication of the presence of said autoantibodies, or said lymphocytes, in said sample, or isolated from said sample.

Substantially as described above, a method according to the present invention is suitable for screening for autoantibodies or lymphocytes produced in response to a TSH receptor in a sample of body fluid obtained from a subject. A method according to the present invention can, however, be particularly adapted for use in screening for autoantibodies produced in response to a TSH receptor in a sample of body fluid obtained from a subject substantially as hereinafter described in greater detail.

There is in particular provided by the present invention, therefore, a method of screening for autoantibodies produced in response to a TSH receptor in a sample of body fluid obtained from a subject (in particular a human) suspected of suffering from, susceptible to, having or recovering from autoimmune disease associated with an immune reaction to a TSH receptor, said method comprising:

(a) providing said sample of body fluid from said subject;

(b) contacting said sample with a polypeptide according to the present invention substantially as hereinbefore described (suitably under conditions that allow interaction of a TSH receptor with autoantibodies produced in response to a TSH receptor) so as to permit said polypeptide to interact with autoantibodies produced in response to a TSH receptor and present in said sample; and (c) monitoring the degree of interaction of said polypeptide with said autoantibodies produced in response to a TSH receptor and present in said sample, thereby providing an indication of the presence of said autoantibodies in said sample.

A method according to the present invention may typically employ a control, such as a sample of body fluid from a normal subject, in other words a subject known to be without autoimmune disease associated with an immune reaction to a TSH receptor.

A method of screening for autoantibodies to a -TSH receptor according to the present invention may comprise directly monitoring interaction of (i) autoantibodies to a TSH receptor present in the sample of body fluid from the subject and (ii) a polypeptide, as provided by the present invention substantially as hereinbefore described, typically by employing non-competitive sandwich type assay techniques known in the art.

Typically, in a method according to the present invention employing non-competitive techniques, monitoring of the degree of interaction of (i) autoantibodies to a TSH receptor present in the sample and (ii) a polypeptide according to the present invention substantially as hereinbefore described, can comprise providing labelling means either to a polypeptide according to the present invention substantially as hereinbefore described, or to a binding partner for autoantibodies to a TSH receptor, either of which technique would enable monitoring of the above described interaction. For example, a method according to the present invention may comprise directly or indirectly labelling a polypeptide according to the present invention substantially as hereinbefore described; contacting the thus labelled polypeptide with a sample of body fluid being screened for TSH receptor autoantibodies so as to provide a mixture thereof; and adding to the mixture a binding partner for autoantibodies to a TSH receptor (such as an anti-IgG reagent) present in the sample of body fluid, so as to cause precipitation of any complexes of labelled polypeptide and TSH receptor autoantibodies present in the mixture. Alternatively, it may be preferred that a method according to the present invention further comprises adding a labelled binding partner for TSH receptor autoantibodies (such as a labelled anti-IgG reagent, for example protein A or anti-human IgG, or labelled full length TSH receptor or an epitope thereof) to a mixture obtained by contacting (i) a polypeptide according to the present invention substantially as hereinbefore described immobilised to a support and (ii) a sample of body fluid being screened for autoantibodies to a TSH receptor.

It may alternatively be preferred that a method of screening for autoantibodies to a TSH receptor in the sample of body fluid according to the present invention, utilises the principles employed in known competitive assays. For example, a method according to the present invention may employ at least one competitor capable of competing with autoantibodies to a TSH receptor in the interaction thereof with a polypeptide according to the present invention substantially as hereinbefore described.

Typically, a competitor as employed in a competitive assay method according to the present invention may comprise one or more antibodies, which may be natural or partly or wholly synthetically produced. A competitor as employed in the present invention may alternatively comprise any other protein (for example TSH) having a binding domain or region which is capable of competing with autoantibodies to a TSH receptor in the interaction thereof with a polypeptide according to the present invention substantially as hereinbefore described. Preferably, however, a competitor as employed in the present invention comprises a monoclonal, recombinant or polyclonal antibody (especially a monoclonal antibody), capable of competing with TSH receptor autoantibodies in the interaction thereof with a polypeptide according to the present invention substantially as hereinbefore described.

Typically, therefore, a competitive assay method according to the present invention may further comprise providing at least one competitor, such as a monoclonal or polyclonal antibody, whereby in step (b) of a method as herein described a polypeptide according to the present invention substantially as hereinbefore described can interact with either a competitor, such as a monoclonal or polyclonal antibody, or autoantibodies to a TSH receptor present in said sample.

Typically monitoring in a competitive assay method according to the present invention comprises comparing:

(i) interaction of a polypeptide according to the present invention substantially as hereinbefore described and one or more competitors substantially as hereinbefore described (typically a monoclonal or polyclonal antibody), in the absence of said sample of body fluid being screened (that is a suspected disease sample), optionally in the presence of a sample of body fluid from a normal subject, typically a subject known to be without autoimmune disease associated with an immune reaction to a TSH receptor; with (ii) interaction of a polypeptide according to the present invention substantially as hereinbefore described and one or more competitors substantially as hereinbefore described (typically a monoclonal or polyclonal antibody), in the presence of said sample of body fluid being screened.

Typically, the comparison involves observing a decrease in interaction of a polypeptide according to the present invention substantially as hereinbefore described and the competitor in (ii) compared to (i) so as to provide an indication of the presence of autoantibodies to a TSH receptor in said sample. Typically, the decrease in interaction can be observed by directly or indirectly labelling the competitor and monitoring any change in the interaction of the thus labelled competitor with a polypeptide according to the present invention substantially as hereinbefore described in the absence and in the presence of a sample of body fluid being screened for autoantibodies to a TSH receptor. Suitably a polypeptide according to the present invention substantially as hereinbefore described may be immobilised to facilitate the above mentioned monitoring.

Alternatively, there is also provided by the present invention a method of screening for autoantibodies to a TSH receptor in a sample of body fluid obtained from a subject (in particular a human) suspected of suffering from, susceptible to, having or recovering from autoimmune disease associated with an immune reaction to a TSH receptor, said method comprising:

(a) providing said sample of body fluid from said subject;

(b) contacting said sample with
   (i) a full length TSH receptor (typically a recombinantly obtained full length TSH receptor), and (ii) at least one competitor capable of competing with autoantibodies to a TSH receptor in the interaction thereof with a polypeptide according to the present invention substantially as hereinbefore described,
(suitably under conditions that allow interaction of a TSH receptor with autoantibodies to a TSH receptor), so as to permit said fill length TSH receptor to interact with either autoantibodies to a TSH receptor present in said sample, or said competitor; and
(c) monitoring the interaction of said full length TSH receptor with said autoantibodies present in said sample, thereby providing an indication of the presence of said autoantibodies to a TSH receptor in said sample.

The full length TSH receptor can typically be of human, porcine, bovine, canine, feline, mouse, rat or ovine origin and more preferably a recombinantly obtained full length TSH receptor. A competitor for use in such an assay typically comprises a monoclonal or polyclonal antibody (preferably monoclonal) substantially as hereinbefore described.

Suitably a detectable label that can be employed in a method according to the present invention can be selected from the group consisting of enzymic labels, isotopic labels, chemiluminescent labels, fluorescent labels, dyes and the like.

In the case where an isotopic label (such as $^{125}I$, $^{14}C$, $^{3}H$ or $^{35}S$) is employed, monitoring may therefore comprise measuring radioactivity dependent on binding of a polypeptide according to the present invention substantially as hereinbefore described. Radioactivity is generally measured using a gamma counter, or liquid scintillation counter.

In the case of a method of screening for lymphocytes according to the present invention, it is generally preferred that lymphocytes are initially isolated from a sample of body fluid from a subject using techniques well known to one of ordinary skill in the art, followed by contact with a polypeptide according to the present invention so as to stimulate the proliferation of the isolated lymphocytes. Monitoring of the effect of interaction of a polypeptide according to the present invention and such proliferating lymphocytes, typically employs means known in the art for monitoring such proliferation of lymphocytes.

According to a further particularly preferred embodiment of the present invention, there is provided a kit for screening for autoantibodies or lymphocytes produced in response to a TSH receptor in a sample of body fluid obtained from a subject (in particular a human) suspected of suffering from, susceptible to, having or recovering from autoimmune disease associated with an immune reaction to a TSH receptor, said kit comprising:
(a) a polypeptide according to the present invention substantially as hereinbefore described;
(b) means for contacting either (i) a sample of body fluid obtained from said subject, or (ii) lymphocytes isolated from a sample of body fluid obtained from said subject, with said polypeptide according to the present invention substantially as hereinbefore described (suitably under conditions that allow interaction of a TSH receptor with autoantibodies or lymphocytes produced in response to a TSH receptor) so as to permit said polypeptide to interact with autoantibodies, or lymphocytes, produced in response to a TSH receptor, and present in, or isolated from, said sample; and
(c) means for monitoring the degree, or effect, of interaction of said polypeptide with either said autoantibodies, or said lymphocytes, produced in response to a TSH receptor and present in, or isolated from, said sample, thereby providing an indication of the presence of said autoantibodies, or lymphocytes, in said sample or isolated from said sample.

Substantially as described above, a kit according to the present invention is suitable for screening for autoantibodies or lymphocytes produced in response to a TSH receptor in a sample of body fluid obtained from a subject. A kit according to the present invention can, however, be particularly adapted for use in screening for autoantibodies produced in response to a TSH receptor in a sample of body fluid obtained from a subject substantially as hereinafter described in greater detail.

There is in particular provided by the present invention, therefore, a kit for screening for autoantibodies produced in response to a TSH receptor in a sample of body fluid obtained from a subject (in particular a human) suspected of suffering from, susceptible to, having or recovering from autoimmune disease associated with an immune reaction to a TSH receptor, said kit comprising:
(a) a polypeptide according to the present invention substantially as hereinbefore described;
(b) means for contacting a sample of body fluid obtained from said subject with said polypeptide according to the present invention substantially as hereinbefore described (suitably under conditions that allow interaction of a TSH receptor with autoantibodies produced in response to a TSH receptor) so as to permit said polypeptide to interact with autoantibodies produced in response to a TSH receptor and present in said sample; and
(c) means for monitoring the degree of interaction of said polypeptide with said autoantibodies produced in response to a TSH receptor and present in said sample, thereby providing an indication of the presence of said autoantibodies in said sample.

A kit according to the present invention may typically further comprise control means, such as means for providing a sample of body fluid from a normal subject, in other words a subject known to be without autoimmune disease associated with an immune reaction to a TSH receptor.

A kit for screening for autoantibodies to a TSH receptor according to the present invention may comprise means for directly monitoring interaction of (i) autoantibodies to a TSH receptor present in the sample of body fluid from the subject and (ii) a polypeptide, as provided by the present invention substantially as hereinbefore described, typically comprising non-competitive sandwich type assay means known in the art.

Typically, in a kit according to the present invention comprising non-competitive assay means, means are provided for monitoring the degree of interaction of (i) autoantibodies to a TSH receptor present in the sample and (ii) a polypeptide according to the present invention substantially as hereinbefore described, and can comprise labelling means provided either to a polypeptide according to the present invention substantially as hereinbefore described, or to a binding partner for autoantibodies to a TSH receptor, either of which would enable monitoring of the above described interaction. For example, a kit according to the present invention may comprise means for directly or indirectly labelling a polypeptide according to the present invention substantially as hereinbefore described; means for contacting the thus labelled polypeptide with a sample of body fluid being screened for a TSH receptor autoantibodies so as to provide a mixture thereof; a binding partner for autoantibodies to a TSH receptor (such as an anti-Ig reagent) present in the sample of body fluid; and means for adding the binding partner to the mixture so as to cause precipitation of any complexes of labelled polypeptide and TSH receptor autoantibodies present in the mixture. Alternatively, it may be preferred that a kit according to the present invention further comprises a labelled binding partner for TSH receptor autoantibodies (such as a labelled anti-IgG reagent, for example protein A or anti-human IgG, or labelled full length a TSH receptor or an epitope thereof) and means for adding the labelled binding partner to a mixture obtained by contacting (i) a polypeptide according to the present invention substantially as hereinbefore described immobilised to a support and (ii) a sample of body fluid being screened for autoantibodies to a TSH receptor.

It may alternatively be preferred that a kit for screening for autoantibodies to a TSH receptor in the sample of body fluid according to the present invention, comprises known competitive assay means. For example, a kit according to the present invention may further comprise at least one competitor capable of competing with autoantibodies to a TSH receptor in the interaction thereof with a polypeptide according to the present invention substantially as hereinbefore described.

Typically, a competitor as employed in a competitive assay kit according to the present invention may comprise one or more antibodies, which may be natural or partly or wholly synthetically produced. A competitor as employed in the present invention may alternatively comprise any other protein having a binding domain or region which is capable of competing with autoantibodies to a TSH receptor in the interaction thereof with a polypeptide according to the present invention substantially as hereinbefore described. Preferably, however, a competitor as employed in the present invention comprises a monoclonal or polyclonal antibody (especially a monoclonal antibody), capable of competing with TSH receptor autoantibodies in the interaction thereof with a polypeptide according to the present invention substantially as hereinbefore described.

Typically, therefore, a competitive assay kit according to the present invention may further comprise at least one competitor, such as a monoclonal or polyclonal antibody, whereby a polypeptide according to the present invention substantially as hereinbefore described can interact with either a competitor, such as a monoclonal or polyclonal antibody, or autoantibodies to a TSH receptor present in a sample of body fluid being screened.

Typically monitoring means in a competitive assay kit according to the present invention comprise means for comparing:

(i) interaction of a polypeptide according to the present invention substantially as hereinbefore described and one or more competitors substantially as hereinbefore described (typically a monoclonal or polyclonal antibody), in the absence of said sample of body fluid being screened (that is a suspected disease sample), optionally in the presence of a sample of body fluid from a normal subject, typically a subject known to be without autoimmune disease associated with an immune reaction to a TSH receptor; with (ii) interaction of a polypeptide according to the present invention substantially as hereinbefore described and one or more competitors substantially as hereinbefore described (typically a monoclonal or polyclonal antibody), in the presence of said sample of body fluid being screened.

Typically, the comparison involves observing a decrease in interaction of a polypeptide according to the present invention substantially as hereinbefore described and the competitor in (ii) compared to (i) so as to provide an indication of the presence of autoantibodies to a TSH receptor in said sample. Typically, the decrease in interaction can be observed by directly or indirectly labelling the competitor and monitoring any change in the interaction of the thus labelled competitor with a polypeptide according to the present invention substantially as hereinbefore described in the absence and in the presence of a sample of body fluid being screened for autoantibodies to a TSH receptor. Suitably a polypeptide according to the present invention substantially as hereinbefore described may be immobilised to facilitate the above mentioned monitoring.

Alternatively, there is also provided by the present invention a kit for screening for autoantibodies to a TSH receptor in a sample of body fluid obtained from a subject (in particular a human) suspected of suffering from, susceptible to, having or recovering from autoimmune disease associated with an immune reaction to a TSH receptor, said kit comprising:

(a) a full length TSH receptor (typically a recombinantly obtained full length TSH receptor);

(b) at least one competitor capable of competing with autoantibodies to a TSH receptor in the interaction thereof with a polypeptide according to the present invention substantially as hereinbefore described, (c) means for contacting said sample of body fluid from said subject, said fall length TSH receptor and said competitor (suitably under conditions that allow interaction of a TSH receptor with autoantibodies to a TSH receptor), so as to permit said full length TSH receptor to interact with either autoantibodies to a TSH receptor present in said sample, or said competitor; and (d) means for monitoring the interaction of said full length TSH receptor with said autoantibodies present in said sample, thereby providing an indication of the presence of said autoantibodies to a TSH receptor in said sample.

The full length TSH receptor can typically be of human, porcine, bovine, canine, feline, mouse, rat or ovine origin and more preferably a recombinantly obtained full length TSH receptor. A competitor for use in such an assay kit typically comprises a monoclonal or polyclonal antibody (preferably monoclonal) substantially as hereinbefore described.

Suitably a detectable label that can be employed in a kit according to the present invention can be selected from the group consisting of enzymic labels, isotopic labels, chemiluminescent labels, fluorescent labels, dyes and the like.

In the case where an isotopic label (such as $^{125}I$, $^{14}C$, $^{3}H$ or $^{35}S$) is employed, monitoring means may therefore comprise means for measuring radioactivity dependent on binding of a polypeptide according to the present invention substantially as hereinbefore described. Radioactivity is generally measured using a gamma counter, or liquid scintillation counter.

In the case of a kit for screening for lymphocytes according to the present invention, it is generally preferred that means are provided for initially isolating lymphocytes from a sample of body fluid from a subject, using techniques well known to one of ordinary skill in the art, and means are also provided for contacting a polypeptide according to the present invention with such isolated lymphocytes so as to stimulate proliferation of the latter by the former. Means (again known to one of ordinary skill in the art) for monitoring the effect of interaction of a polypeptide according to the present invention and such proliferating lymphocytes, are also provided in such a kit according to the present invention.

It will be appreciated from the foregoing description that the present invention provides assay methods and kits for detecting autoantibodies (in particular) or lymphocytes produced in response to a TSH receptor in a sample of body fluid substantially as hereinbefore described. The detection of such autoantibodies and/or lymphocytes produced in response to a TSH receptor in the sample of body fluid (or at least the level of such autoantibodies and/or lymphocytes in the sample) is indicative of the presence of autoimmune disease associated with an immune reaction to a TSH receptor in the subject from which the sample was obtained and can, therefore, enable the diagnosis of the likely onset or presence of autoimmune disease associated with an immune reaction to a TSH receptor.

There is, therefore, further provided by the present invention a method of diagnosing the likely onset or presence of autoimmune disease associated with an immune reaction to a TSH receptor in a subject (in particular a human) suspected of suffering from, susceptible to, having or recovering from, autoimmune disease associated with an immune reaction to a TSH receptor, the method comprising detecting autoantibodies or lymphocytes produced in response to a TSH receptor in a sample of body fluid from the subject substantially as hereinbefore described, and whereby the detected autoantibodies and/or lymphocytes can provide a diagnosis of the likely onset or presence of autoimmune disease associated with an immune reaction to a TSH receptor in the subject.

There is still further provided by the present invention a method of delaying or preventing the onset of autoimmune disease associated with an immune reaction to a TSH receptor in an animal subject (in particular a human subject) suspected of suffering from, susceptible to or recovering from autoimmune disease associated with an immune reaction to a TSH receptor, which method comprises initially detecting autoantibodies or lymphocytes indicative of the onset or presence of autoimmune disease associated with an immune reaction to a TSH receptor in a sample of body fluid obtained from the subject substantially as hereinbefore described, thereby providing a diagnosis of the likely onset of autoimmune disease associated with an immune reaction to a TSH receptor in the subject, and thereafter therapeutically treating the subject so as to delay the onset and/or prevent autoimmune disease associated with an immune reaction to a TSH receptor.

A polypeptide according to the present invention substantially as hereinbefore described is particularly suitable for use in the therapeutic treatment of autoimmune disease associated with an immune reaction to a TSH receptor. For example, tolerance can be achieved by administering a polypeptide according to the present invention substantially as hereinbefore described to a subject (in particular a human subject) suspected of suffering from, susceptible to, having or recovering from autoimmune disease associated with an immune reaction to a TSH receptor.

There is, therefore, further provided by the present invention a pharmaceutical composition comprising a polypeptide according to the present invention substantially as hereinbefore described, together with a pharmaceutically acceptable carrier, diluent or excipient therefor, wherein the polypeptide can interact with autoantibodies and/or lymphocytes produced in response to a TSH receptor.

The present invention further provides a polypeptide according to the present invention substantially as hereinbefore described for use in the manufacture of a medicament for the treatment of Graves' disease.

Compositions or medicaments according to the present invention should contain a therapeutic or prophylactic amount of at least one polypeptide according to the present invention in a pharmaceutically-acceptable carrier. The pharmaceutical carrier can be any compatible, non-toxic substance suitable for delivery of the polypeptides to the patient. Sterile water, alcohol, fats, waxes, and inert solids may be used as the carrier. Pharmaceutically-acceptable adjuvants, buffering agents, dispersing agents and the like, may also be incorporated into the pharmaceutical compositions. Such compositions can contain a single polypeptide or may contain two or more polypeptides according to the present invention.

It may be desirable to couple a polypeptide according to the present invention to immunoglobulins, e.g. IgG, or to lymphoid cells from the patient being treated in order to promote tolerance. Such an approach is described in Bradley-Mullen, *Activation of Distinct Subsets of T Suppressor Cells with Type III Pneutnococcal Polysaccharide Coupled to Syngeneic Spleen Cells*, in: IMMUNOLOGICAL TOLERANCE TO SELF AND NON-SELF, Buttisto et al, eds., Annals N.Y. Acad. Sci. Vol. 392, pp 156-166, 1982. Alternatively, the polypeptides may be modified to maintain or enhance binding to the MHC while reducing or eliminating binding to the associated T-cell receptor. In this way, the modified polypeptides may compete with natural a TSH receptor to inhibit helper T-cell activation and thus inhibit the immune response. In all cases, care should be taken that administration of the pharmaceutical compositions of the present invention ameliorate but do not potentiate the autoimmune response.

Pharmaceutical compositions according to the present invention are useful for parenteral administration. Preferably, the compositions will be administered parenterally, i.e. subcutaneously, intramuscularly, or intravenously. Thus, the invention provides compositions for parenteral administration to a patient, where the compositions comprise a solution or dispersion of the polypeptides in an acceptable carrier, as described above. The concentration of the polypeptides in the pharmaceutical composition can vary widely, i.e. from less than about 0.1% by weight, usually being at least about 1% by weight to as much as 20% by weight or more. Typical pharmaceutical compositions for intramuscular injection would be made up to contain, for example, 1 ml of sterile buffered water and 1 to 100/ug of a purified polypeptide of the present invention. A typical composition for intravenous infusion could be made up to contain 100 to 500 ml of sterile Ringer's solution and 100 to 500 mg of a purified polypeptide of the present invention. Actual methods for preparing parenterally administrable compositions are well known in the art and described in more detail in various sources, including, for example, *Remington's Pharmaceutical Science*, 15th Edition, Mack Publishing Company, Easton, Pa. (1980).

In addition to using a polypeptide according to the present invention directly in pharmaceutical compositions, it is also possible to use a polypeptide according to the present invention to enhance tolerance to a TSH receptor in a subject suspected of suffering from, susceptible to, having or recovering from autoimmune disease associated with an immune reaction to a TSH receptor, employing the following principles. More particularly, peripheral blood lymphocytes can be collected from the subject in a conventional manner and stimulated by exposure to a polypeptide according to the present invention, as defined above. Usually, other mitogens and growth enhancers will be present, e.g., phytohemagglutinin, interleukin 2, and the like. Proliferating T-helper cells may be isolated and cloned, also under the stimulation of a polypeptide according to the present invention. Clones which continue to proliferate may then be used to prepare therapeutic compositions for the subject. The cloned T-cells may be attenuated, e.g. by exposure to radiation, and administered to the subject in order to induce tolerance. Alternatively, the T-cell receptor or portions thereof may be isolated by conventional protein purification methods from the cloned T-cells and administered to the individual. Such immunotherapy methods are described generally in Sinha et al. (1990) *Science* 248:1380-1388.

In some cases, after a T-helper cell has been cloned as described above, it may be possible to develop therapeutic peptides from the T-cell receptor, where the peptides would be beneficial for treating a patient population suspected of suffering from, susceptible to, having or recovering from autoimmune disease associated with an immune reaction to a TSH receptor. In such cases, the T-cell receptor gene may be isolated and cloned by conventional techniques and peptides based on the receptor produced by recombinant techniques as described above. The recombinantly-produced peptides may then be incorporated in pharmaceutical compositions as described above.

There is also provided by the present invention a method of cloning lymphocytes produced in response to a TSH receptor, which method comprises:
  providing a source of lymphocytes;
  contacting the lymphocytes with a polypeptide according to the present invention substantially as hereinbefore described, so as to effect proliferation of said lymphocytes; and
  isolating and cloning the proliferating lymphocytes.

The present invention also provides the use of cloned lymphocytes prepared as above, in the therapeutic treatment of autoimmune disease associated with an immune reaction to a TSH receptor. There is provided, therefore, a pharmaceutical composition comprising cloned lymphocytes prepared as above, together with a pharmaceutically acceptable carrier, diluent or excipient therefor and the use of such cloned lymphocytes in the manufacture of a medicament for the treatment of autoimmune disease associated with an immune reaction to a TSH receptor, in particular Graves' disease.

There is also provided by the present invention one or more therapeutic agents identified as providing a therapeutic effect by interaction with amino acids comprising part or all of the primary conformation of amino acids of one or more epitopes of a TSH receptor substantially as hereinbefore described, and the present invention further provides one or more therapeutic agents for use in therapeutically interacting with amino acids comprising part or all of the primary conformation of amino acids of one or more epitopes of a TSH receptor substantially as hereinbefore described and as such for use in the therapeutic treatment of an autoimmune disease associated with an immune reaction to a TSH receptor.

There is, therefore, still further provided by the present invention a method of treating autoimmune disease associated with an immune reaction to a TSH receptor in a subject, which method comprises initially detecting autoantibodies or lymphocytes produced in response to a TSH receptor in a sample of body fluid obtained from the subject substantially as hereinbefore described, thereby providing a diagnosis of autoimmune disease in the subject, and administering to the subject a therapeutically effective amount of at least one therapeutic agent effective in the treatment of such autoimmune disease, such as a polypeptide according to the present invention substantially as hereinbefore described.

The present invention also provides a method of treating autoimmune disease associated with an immune reaction to a TSH receptor in a subject (in particular a human subject), which method comprises administering to the subject a therapeutically effective amount of a therapeutic agent identified as providing a therapeutic effect by interaction with amino acids comprising part or all of the primary conformation of amino acids of one or more epitopes of a TSH receptor substantially as hereinbefore described The amount of therapeutic agent administered will depend on the specific autoimmune disease state being treated, possibly the age of the patient and will ultimately be at the discretion of an attendant physician.

There is still further provided by the present invention, in combination, a kit substantially as hereinbefore described, together with a therapeutically effective amount of at least one therapeutic agent effective in the treatment of autoimmune disease associated with an immune reaction to a TSH receptor substantially as hereinbefore described.

Substantially as hereinbefore described, the sample of body fluid being screened by the present invention will typically comprise blood samples or other fluid blood fractions, such as in particular serum samples or plasma samples, but the sample may in principle be another biological fluid, such as saliva or urine or solubilised tissue extracts, or may be obtained by needle biopsy.

There is still further provided by the present invention a binding partner for a TSH receptor, such as an antibody to a TSH receptor, or a fragment of an antibody to a TSH receptor, which binding partner can interact with one or more epitopes to a TSH receptor substantially as hereinbefore described, in particular amino acid numbers 277 to 296 of a TSH receptor. Suitably, antibodies provided by the present invention can be monoclonal (preferred), recombinant or polyclonal. Typically an antibody, such as a monoclonal antibody, as provided by the present invention is in substantially purified form.

More specifically, a monoclonal antibody as provided by the present invention can comprise any of monoclonal antibodies 3C7, 2B4, 8E2, 18C5, 4D7, 16E5, 17D2, 3B3 and 14D3 or active fragments thereof, as described in the Examples and further illustrated by the accompanying Figures. Antibodies such as 2B4, 8E2, 118C5, 4D7, 16E5, 17D2, 3B3 and 14D3, or active fragments thereof, as described in the Examples preferably have a high affinity for a TSH receptor, such as at least about 108 molar~1. There is, therefore, further provided by the present invention a monoclonal antibody having an affinity of at least about 10 molar"1 for one or more epitopes of a TSH receptor and which epitope is provided by any one of the following amino acid sequences of a TSH receptor:
  amino acids 22 to 91 of a TSH receptor; or
  amino acids 246 to 260 of a TSH receptor;
or more particularly, consists essentially of any one of the following amino acid sequences of a TSH receptor:
  amino acids 36 to 42 of a TSH receptor; or
  amino acids 247 to 260 of a TSH receptor.

There is also provided by the present invention a monoclonal antibody having an affinity of at least about $10^8$ molar$^{-1}$ for one or more epitopes of a TSH receptor and which epitope is provided by any one of the following amino acid sequences of a TSH receptor:
  amino acids 32 to 41 of a TSH receptor; or
  amino acids 277 to 296 of a TSH receptor.

According to a particularly preferred embodiment of the present invention there is provided a binding partner for a TSH receptor, which binding partner is capable of binding to a TSH receptor so as to stimulate the TSH receptor, which binding partner does not comprise TSH or naturally produced autoantibodies to the TSH receptor.

Preferably the binding partner comprises an antibody, in particular a monoclonal or recombinant (preferably monoclonal) antibody, capable of binding to a TSH receptor so as to stimulate the TSH receptor. Examples of monoclonal antibodies disclosed herein which stimulate a TSH receptor in this way include 4D7, 16E5, 17D2 and 14D3.

In a preferred case the present invention provides a binding partner for a TSH receptor, which binding partner is capable of binding to the TSH receptor so as to stimulate the TSH receptor and which comprises:
an antibody $V_H$ domain selected from the group consisting of:
  $V_H$ domains as shown in any one of FIG. 10, 14, 18, 22, 42, 46 or 50, a $V_H$ domain comprising one or more $V_H$ CDRs with an amino acid sequence corresponding to a $V_H$ CDR as shown in FIG. 10, a $V_H$ domain comprising one or more $V_H$ CDRs with an amino acid sequence corresponding to a $V_H$ CDR as shown in FIG. 14, a $V_H$ domain comprising one or more $V_H$ CDRs with an amino acid sequence corresponding to a $V_H$ CDR as shown in FIG. 18, a $V_H$ domain comprising one or more $V_H$ CDRs with an amino acid sequence corresponding to a $V_H$ CDR as shown in FIG. 22, a $V_H$ domain comprising one or more $V_H$ CDRs with an amino acid sequence corresponding to a $V_H$ CDR as shown in FIG. 42, a $V_H$ domain comprising one or more $V_H$ CDRs with an amino acid sequence corresponding to a $V_H$ CDR as shown in FIG. 46, and a $V_H$ domain comprising one or more $V_H$ CDRs with an amino acid sequence corresponding to a $V_H$ CDR as shown in FIG. 50; and/or an antibody $V_L$ domain selected from the group consisting of: $V_L$ domains as shown in any one of FIG. 12, 16, 20, 24, 44, 48 or 52, a $V_L$ domain comprising one or more $V_L$ CDRs with an amino acid sequence corresponding to a $V_L$ CDR as shown in FIG. 12, a $V_L$ domain comprising one or more $V_L$ CDRs with an amino acid sequence corresponding to a $V_L$ CDR as shown in FIG. 16, a $V_L$ domain comprising one or more $V_L$ CDRs with an amino acid sequence corresponding to a $V_L$ CDR as shown in FIG. 20, a $V_L$ domain comprising one or more $V_L$ CDRs with an amino acid sequence corresponding to a $V_L$ CDR as shown in FIG. 24, a $V_L$ domain comprising one or more $V_L$ CDRs with an amino acid sequence corresponding to a $V_L$ CDR as shown in FIG. 44, a $V_L$ domain comprising one or more $V_L$ CDRs with an amino acid sequence corresponding to a $V_L$ CDR as shown in FIG. 48, and a $V_L$ domain comprising one or more $V_L$ CDRs with an amino acid sequence corresponding to a $V_L$ CDR as shown in FIG. 52.

It may be preferred according to the present invention that a binding partner substantially as hereinbefore described comprises an antibody $V_H$ domain substantially as hereinbefore described paired with an antibody $V_L$ domain substantially as hereinbefore described to provide an antibody binding site comprising both $V_H$ and $V_L$ domains for a TSH receptor, although as discussed further an antibody $V_H$ domain, or an antibody $V_L$ domain, may be independently used to bind a TSH receptor. It will be appreciated, therefore, that a binding partner substantially as hereinbefore described can comprise an antibody $V_H$ domain substantially as hereinbefore described in the absence of an antibody $V_L$ domain. It will also be appreciated, therefore, that a binding partner substantially as hereinbefore described can comprise an antibody $V_L$ domain substantially as hereinbefore described in the absence of an antibody $V_H$ domain Alternatively, a binding partner substantially as hereinbefore described can comprise an antibody $V_H$ domain paired with an antibody $V_L$ domain substantially as hereinbefore described to provide an antibody binding site comprising both $V_H$ and $V_L$ domains for a TSH receptor.

Preferred embodiments according to the present invention can thus include a binding partner substantially as hereinbefore described comprising an antibody $V_H$ domain as shown in FIG. 10 paired with an antibody $V_L$ domain as shown in FIG. 12 to provide an antibody binding site, comprising both these $V_H$ and $V_L$ domains for a TSH receptor; or a binding partner substantially as hereinbefore described comprising an antibody $V_H$ domain as shown in FIG. 14 paired with an antibody $V_L$ domain as shown in FIG. 16 to provide an antibody binding site, comprising both these $V_H$ and $V_L$ domains for a TSH receptor; or a binding partner substantially as hereinbefore described comprising an antibody $V_H$ domain as shown in FIG. 18 paired with an antibody $V_L$ domain as shown in FIG. 20 to provide an antibody binding site comprising both these $V_H$ and $V_L$ domains for a TSH receptor; or a binding partner substantially as hereinbefore described comprising an antibody $V_H$ domain as shown in FIG. 22 paired with an antibody $V_L$ domain as shown in FIG. 24 to provide an antibody binding site comprising both $V_H$ and $V_L$ domains for a TSH receptor; or a binding partner substantially as hereinbefore described comprising an antibody $V_H$ domain as shown in FIG. 42 paired with an antibody $V_L$ domain as shown in FIG. 44 to provide an antibody binding site comprising both $V_H$ and $V_L$ domains for a TSH receptor, or a binding partner substantially as hereinbefore described comprising an antibody $V_H$ domain as shown in FIG. 46 paired with an antibody $V_L$ domain as shown in FIG. 48 to provide an antibody binding site comprising both $V_H$ and $V_L$ domains for a TSH receptor, or a binding partner substantially as hereinbefore described comprising an antibody $V_H$ domain as shown in FIG. 50 paired with an antibody $V_L$ domain as shown in FIG. 52 to provide an antibody binding site comprising both $V_H$ and $V_L$ domains for a TSH receptor.

It is further envisaged according to the present invention that $V_H$ domains substantially as hereinbefore described may be paired with $V_L$ domains other than those specifically described herein. It is also further envisaged according to the present invention that $V_L$ domains substantially as hereinbefore described may be paired with $V_H$ domains other than those specifically described herein.

According to an alternative embodiment of the present invention there is provided a binding partner substantially as hereinbefore described for a TSH receptor, which binding partner is capable of binding to the TSH receptor so as to stimulate the TSH receptor and which can comprise:

an antibody $V_H$ domain comprising:
  a $V_H$ domain comprising one or more $V_H$ CDRs with an amino acid sequence corresponding to a $V_H$ CDR as shown in FIG. 10, or a $V_H$ domain comprising one or more $V_H$ CDRs with an amino acid sequence corresponding to a $V_H$ CDR as shown in FIG. 14, or a $V_H$ domain comprising one or more $V_H$ CDRs with an amino acid sequence corresponding to a $V_H$ CDR as shown in FIG. 18, or a $V_H$ domain comprising one or more $V_H$ CDRs with an amino acid sequence corresponding to a $V_H$ CDR as shown in FIG. 22, or a $V_H$ domain comprising one or more $V_H$ CDRs with an amino acid sequence corresponding to a $V_H$ CDR as shown in FIG. 42, or a $V_H$ domain comprising one or more $V_H$ CDRs with an amino acid sequence corresponding to a $V_H$ CDR as shown in FIG. 46, or a $V_H$ domain comprising one or more $V_H$ CDRs with an amino acid sequence corresponding to a $V_H$ CDR as shown in FIG. 50; and/or an antibody $V_L$ domain comprising:
  a $V_L$ domain comprising one or more $V_L$ CDRS with an amino acid sequence corresponding to a $V_L$ CDR as shown in FIG. 12, or a $V_L$ domain comprising one or more $V_L$ CDRs with an amino acid sequence corresponding to a $V_L$ CDR as shown in FIG. 16, or a $V_L$ domain comprising one or more $V_L$ CDRs with an amino acid sequence corresponding to a $V_L$ CDR as shown in FIG. 20, or a $V_L$ domain comprising one or more $V_L$ CDRs with an amino acid sequence corresponding to a $V_L$ CDR as shown in FIG. 24, or a $V_L$ domain comprising one or more $V_L$ CDRs with an amino acid sequence corresponding to a $V_L$ CDR as shown in FIG. 44, or a $V_L$ domain comprising one or more $V_L$ CDRs with an amino acid sequence corresponding to a $V_L$ CDR as shown in FIG. 48, or a $V_L$ domain comprising one or more $V_L$ CDRs with an amino acid sequence corresponding to a $V_L$ CDR as shown in FIG. 52.

One or more CDRs as referred to above may be taken from the hereinbefore described $V_H$ and $V_L$ domains and incorporated into a suitable framework. For example, the amino acid sequence of one or more CDRs substantially as hereinbefore described may be incorporated into framework regions of antibodies differing from those specifically disclosed herein, such antibodies thereby incorporating the one or more CDRs and being capable of binding to the TSH receptor, preferably to stimulate the TSH receptor substantially as hereinbefore described. Alternatively, a binding partner according to the present invention may comprise a polypeptide capable of binding to the TSH receptor so as to stimulate the TSH receptor substantially as hereinbefore described and comprising the primary structural conformation of amino acids as represented by one or more CDRs as specifically described herein, optionally together with further amino acids, which further amino acids may enhance the binding affinity of one or more CDRs as described herein for a TSH receptor or may have substantially no role in affecting the binding properties of the polypeptide for a TSH receptor.

Preferably a binding partner according to the present invention includes an antibody. The term "antibody" as used herein describes an immunoglobulin whether natural or partly or wholly synthetically produced. The term also covers any polypeptide having a binding domain which is, or is substantially homologous to, an antibody binding domain. Examples of antibodies are the immunoglobulin isotypes and their isotypic subclasses and fragments which comprise an antigen binding domain such as Fab, scFv or the like.

In particular, fragments of antibodies specifically as herein described form an important aspect of the present invention. In this way, where a binding partner according to the present invention comprises an antibody substantially as hereinbefore described, the antibody may comprise any of the following fragments: (i) the Fab fragment consisting of $V_L$, $V_H$, $C_L$ and $C_H1$ domains; (ii) the Fd fragment consisting of the $V_H$ and $C_H1$ domains; (iii) the Fv fragment consisting of the $V_L$ and $V_H$ domains; (iv) the dAb fragment which consists of a $V_H$ domain; (v) isolated CDR regions; (vi) F(ab')2 fragments, a bivalent fragment comprising two linked Fab fragments; and (vii) single chain Fv molecules (scFv), wherein a $V_H$ domain and a $V_L$ domain are linked by a peptide linker which allows the two domains to associate to form an antigen binding site.

Alternatively, in the case where a binding partner according to the present invention comprises an antibody, the antibody may comprise a whole antibody, whereby the antibody includes variable and constant regions, which variable and constant regions can be further illustrated for the antibodies provided by the present invention by reference to any of FIG. 9 to 24, or 41 to 52.

The present invention, also encompasses variants, analogs and derivatives of the specific binding partners, antibodies, $V_H$ domains, $V_L$ domains, CDRs and polypeptides disclosed herein, which variants, analogs and derivatives retain the ability to bind to the TSH receptor so as to stimulate the TSH receptor substantially as hereinbefore described. The terms variants, analogs and derivatives are substantially herein before further described in greater detail with respect to polypeptides according to the present invention and what is meant by these terms as hereinbefore described applies also to variants, analogs and derivatives of the specific binding partners according to the present invention.

The present invention also provides a further binding partner capable of binding to the TSH receptor so as to stimulate the TSH receptor substantially as hereinbefore described, and which further binding partner can compete for binding to the TSH receptor with any specific binding partner disclosed herein, which further binding partner does not comprise TSH or autoantibodies to a TSH receptor. In particular this further binding partner may comprise a further antibody having a binding site for an epitope region of a TSH receptor suitably as hereinbefore described, which further antibody is capable of binding to the TSH receptor so as to stimulate the TSH receptor substantially as hereinbefore described and can compete for binding to the TSH receptor with any specific binding partner disclosed herein.

There is also provided by the present invention a polynucleotide comprising:

(i) a nucleotide sequence as shown in any of FIG. 25 to 40, or 53 to 64; or parts of such sequences as shown in FIG. 26, 28, 30, 32, 34, 36, 38, 40, 54, 56, 58, 60, 62, or 64, encoding an amino acid sequence of an antibody $V_H$ domain, an antibody $V_L$ domain or CDR as shown in any of FIG. 10, 12, 14, 16, 18, 20, 22, 24, 42, 44, 46, 48, 50 or 52;

(ii) a nucleotide sequence encoding a binding partner substantially as hereinbefore described, or encoding an amino acid sequence of an antibody $V_H$ domain, an antibody $V_L$ domain or CDR of a binding partner substantially as hereinbefore described;

(iii) a nucleotide sequence encoding a binding partner having a primary structural conformation of amino acids as shown in any of FIG. 9 to 24 or 41 to 52, or encoding an amino acid sequence of an antibody $V_H$ domain, an antibody $V_L$ domain or CDR as shown in any of FIG. 10, 12, 14, 16, 18, 20, 22, 24, 42, 44, 46, 48, 50 or 52;

(iv) a nucleotide sequence differing from any sequence of (i) in codon sequence due to the degeneracy of the genetic code;

(v) a nucleotide sequence comprising an allelic variation of any sequence of (i);

(vi) a nucleotide sequence comprising a fragment of any of the sequences of (i), (ii), (iii), (iv) or (v), and in particular a nucleotide sequence comprising a fragment of any of the sequences of (i), (ii), (iii), (iv) or (v) and encoding a Fab fragment, aFd fragment, a Fv fragment, a dAb fragment, an isolated CDR region, F(ab')2 fragments or a scFv fragment, of a binding partner substantially as hereinbefore described;

(vii) a nucleotide sequence differing from the any sequence of (i) due to mutation, deletion or substitution of a nucleotide base and encoding a binding partner substantially as hereinbefore described, or encoding an amino acid sequence of an antibody $V_H$ domain, an antibody $V_L$ domain or CDR of a binding partner substantially as hereinbefore described.

Variant polynucleotides according to the present invention are suitably at least 70% identical over their entire length to any polynucleotide sequence of (i), most highly preferred are polynucleotides that comprise a region that is at least 80% identical over its entire length to any polynucleotide sequence of (i), polynucleotides at least 90% identical over their entire length to any polynucleotide sequence of (i) are particularly preferred, and among these particularly preferred polynucleotides, those with at least 95% identity are especially preferred. What is meant by variants of specific polynucleotide sequences described herein is hereinbefore described in greater detail.

The present invention further provides a biologically functional vector system which carries a polynucleotide substantially as hereinbefore described and which is capable of introducing the polynucleotide into the genome of a host organism.

The present invention also relates to host cells which are transformed with polynucleotides of the invention and the production of binding partners of the invention by recombinant techniques. Host cells can be genetically engineered to incorporate polynucleotides and express binding partners of the present invention.

A binding partner substantially as hereinbefore described may have diagnostic and therapeutic applications, and may advantageously interact or bind with one or more epitope regions of a TSH receptor substantially as hereinbefore described.

Accordingly, a binding partner substantially as hereinbefore described can be employed in screening methods for detecting autoantibodies substantially as hereinbefore described and also in diagnostic methods substantially as hereinbefore described. In this way, binding partners according to the present invention can be employed in place of competitors hitherto described for use in screening methods for detecting autoantibodies substantially as hereinbefore described and also in diagnostic methods substantially as hereinbefore described. Similarly, binding partners according to the present invention can be employed in place of competitors hitherto described for use in kits for use in detecting autoantibodies substantially as hereinbefore described.

The present invention also provides a method of screening for autoantibodies to a TSH receptor in a sample of body fluid obtained from a subject suspected of suffering from, susceptible to, having or recovering from autoimmune disease associated with an immune reaction to a TSH receptor, said method comprising:
(a) providing said sample of body fluid from said subject;
(b) contacting said sample with
 (i) a full length TSH receptor, one or more epitopes thereof or a polypeptide comprising one or more epitopes of a TSH receptor, and
 (ii) one or more binding partners substantially as hereinbefore described;
 (suitably under conditions that allow interaction of a TSH receptor with autoantibodies produced in response to a TSH receptor) so as to permit said TSH receptor, said one or more epitopes thereof or said polypeptide, to interact with either autoantibodies to a TSH receptor present in said sample, or said one or more binding partners; and
(c) monitoring the interaction of said TSH receptor, said one or more epitopes thereof or said polypeptide, with said autoantibodies present in said sample, thereby providing an indication of the presence of said autoantibodies to a TSH receptor in said sample.

Preferably, a method according to the present invention as referred to above, further comprises providing labelling means for the one or more binding partners, suitable labelling means being substantially as hereinbefore described.

The present invention also provides a method of screening for autoantibodies produced in response to a TSH receptor in a sample of body fluid obtained from a subject suspected of suffering from, susceptible to, having or recovering from autoimmune disease associated with an immune reaction to a TSH receptor, said method comprising:
(a) providing said sample of body fluid from said subject;
(b) contacting said sample with
 (i) a full length TSH receptor, one or more epitopes thereof or a polypeptide comprising one or more epitopes of a TSH receptor, and
 (ii) one or more binding members for a TSH receptor;
 (suitably under conditions that allow interaction of a TSH receptor with autoantibodies produced in response to a TSH receptor) so as to permit said TSH receptor, said one or more epitopes thereof or said polypeptide, to interact with either autoantibodies to a TSH receptor present in said sample, or said one of more binding members; and
(c) monitoring the interaction of said TSH receptor, said one or more epitopes thereof or said polypeptide, with said autoantibodies present in said sample, thereby providing an indication of the presence of said autoantibodies to a TSH receptor in said sample;
 wherein said one or more binding members are directly or indirectly immobilised to a surface either prior to, or after step (b).

Typically the one or more binding members comprise one or more binding partners according to the present invention substantially as hereinbefore described. Suitably, labelling means are provided for the TSH receptor, the one or more epitopes thereof or the polypeptide.

The present invention also provides a kit for screening for autoantibodies to a TSH receptor in a sample of body fluid obtained from a subject suspected of suffering from, susceptible to, having or recovering from autoimmune disease associated with an immune reaction to a TSH receptor, said kit comprising:
(a) a full length TSH receptor, one or more epitopes thereof or a polypeptide comprising one or more epitopes of a TSH receptor;
(b) one or more binding partners substantially as hereinbefore described;
(c) means for contacting said sample of body fluid from said subject, said TSH receptor, said one or more epitopes thereof or said polypeptide, and said one or more binding partners, (suitably under conditions that allow interaction of a TSH receptor with autoantibodies produced in response to a TSH receptor) so as to permit said TSH receptor, said one or more epitopes thereof or said polypeptide, to interact with either autoantibodies to a TSH receptor present in said sample, or said one or more binding partners; and
(d) means for monitoring the interaction of said TSH receptor, said one or more epitopes thereof or said polypeptide, with said autoantibodies present in said sample, thereby providing an indication of the presence of said autoantibodies to a TSH receptor in said sample.

Suitably, a kit as referred to above further comprises labelling means for the one or more binding partners, suitable labelling means being substantially as hereinbefore described.

The present invention also provides a kit for screening for autoantibodies to a TSH receptor in a sample of body fluid obtained from a subject suspected of suffering from, susceptible to, having or recovering from autoimmune disease associated with an immune reaction to a TSH receptor, said kit comprising:
(a) a full length TSH receptor, one or more epitopes thereof or a polypeptide comprising one or more epitopes of a TSH receptor;
(b) one or more binding members for a TSH receptor;
(c) means for contacting said sample of body fluid from said subject, said TSH receptor, said one or more epitopes thereof or said polypeptide, and said one or more binding members, (suitably under conditions that allow interaction of a TSH receptor with autoantibodies produced in response to a TSH receptor) so as to permit said TSH receptor, said one or more epitopes thereof or said polypeptide, to interact with either autoantibodies to a TSH receptor present in said sample, or said one or more binding members;

(d) means for directly or indirectly immobilising said one or more members to a surface, either before or after contacting said one or more binding members with said sample of body fluid from said subject and said TSH receptor, said one or more epitopes thereof or said polypeptide; and (e) means for monitoring the interaction of said TSH receptor, said one or more epitopes thereof or said polypeptide, with said autoantibodies present in said sample, thereby providing an indication of the presence of said autoantibodies to a TSH receptor in said sample.

Typically the one or more binding members comprise one or more binding partners according to the present invention substantially as hereinbefore described. Suitably, labelling means are provided for the TSH receptor, the one or more epitopes thereof or the polypeptide.

Suitably a method or kit as referred to above can employ a polypeptide or epitope according to the present invention substantially as hereinbefore described.

Substantially as hereinbefore described, in the presence of autoantibodies to the TSH receptor, binding of the TSH receptor to the immobilised binding member or binding partner will be decreased. Such a method and kit for screening for autoantibodies to a TSH receptor can be advantageous in alleviating problems that can be associated with TSH receptor when immobilised to a surface.

A binding partner substantially as hereinbefore described can also be usefully employed in therapy. There is, therefore, further provided by the present invention methods of treatment comprising administration of a specific binding partner substantially as hereinbefore described, pharmaceutical compositions comprising a specific binding partner substantially as hereinbefore described (together with one or more pharmaceutically acceptable carriers, diluents or excipients therefor), and use of a specific binding partner substantially as hereinbefore described in the manufacture of a medicament or composition, in particular a medicament or composition for use in stimulating thyroid tissue, and/or tissue containing a TSH receptor. In particular, a specific binding partner according to the present invention can be employed in oncology, and in particular for use in the diagnosis, management and treatment of thyroid cancer.

Pharmaceutical compositions according to the present invention include those suitable for oral, parenteral and topical administration, although the most suitable route will generally depend upon the condition of a patient and the specific disease being treated. The precise amount of a binding partner substantially as hereinbefore described to be administered to a patient will be the responsibility of an attendant physician, although the dose employed will depend upon a number of factors, including the age and sex of the patient, the specific disease being treated and the route of administration substantially as described above.

There is further provided by the present invention a method of stimulating thyroid tissue, and/or tissue containing a TSH receptor, which method comprises administering to a patient in need of such stimulation a diagnostically or therapeutically effective amount of a binding partner substantially as hereinbefore described.

The present invention also provides in combination, a binding partner substantially as hereinbefore described, together with one or more further agents capable of stimulating thyroid tissue, and/or tissue containing a TSH receptor, for simultaneous, separate or sequential use in stimulating thyroid tissue, and/or tissue containing a TSH receptor. Preferably the one or more further agents comprise recombinant human TSH and/or one or more variants, analogs, derivatives or fragments thereof, or variants, analogs or derivatives of such fragments. Alternatively, the one or more further agents can act independently of binding to the TSH receptor.

The following illustrative explanations are provided to facilitate understanding of certain terms used herein. The explanations are provided as a convenience and are not limitative of the invention BINDING PARTNER, or BINDING MEMBER, FOR A TSH RECEPTOR, describes a molecule having a binding specificity for a TSH receptor. A binding partner or binding member as described herein may be naturally derived or wholly or partially synthetically produced. Such a binding partner or binding member has a domain or region which specifically binds to and is therefore complementary to one or more epitope regions of a TSH receptor.

C DOMAIN denotes a region of relatively constant amino acid sequence in antibody molecules.

CDR denotes complementary determining regions which are present on both heavy and light chains of antibody molecules and represent regions of most sequence variability. CDRs represent approximately 15 to 20% of variable domains and represent antigen binding sites of an antibody.

FR denotes framework regions and represent the remainder of the variable light domains and variable heavy domains not present in CDRs.

HC denotes part of a heavy chain of an antibody molecule comprising the heavy chain variable domain and the first domain of an IgG constant region.

HOST CELL is a cell which has been transformed or transfected, or is capable of transformation or transfection by an exogenous polynucleotide sequence.

IDENTITY, as known in the art, is the relationship between two or more polypeptide sequences, or two or more polynucleotide sequences, as determined by comparing the sequences.

LC denotes a light chain of an antibody molecule.

STIMULATION OF A TSH RECEPTOR by a binding partner or binding member as described herein denotes the ability of the binding partner or binding member to bind to a TSH receptor and to thereby effect, for example, production of cyclic AMP as a result of such binding to the TSH receptor. Such stimulation is analogous to the responses seen on binding of TSHE or TSH receptor autoantibodies, to a TSH receptor and in this way a binding partner or binding member as described herein mimics the effect of TSH, or TSH receptor autoantibody, binding to a TSH receptor.

V DOMAIN denotes a region of highly variable amino acid sequence in antibody molecules.

$V_H$ DOMAIN denotes variable regions or domains in heavy chains of antibody molecules.

$V_L$ DOMAIN denotes variable regions or domains in light chains of antibody molecules.

The present invention will now be illustrated by the following Figures and Examples, which do not limit the scope of the invention in any way.

FIG. 1 lists amino acids 1 to 200 of (in the following order) human (HTSHR.PRO; SEQ ID NO:1), porcine (PTSHR.PRO; SEQ ID NO:2), bovine (BTSHR.PRO; SEQ ID NO:3), feline (CTSHR.PRO; SEQ ID NO:4), canine (DTSHR.PRO; SEQ ID NO:5), mouse (MTSHR.PRO; SEQ ID NO:6), rat (RTSHR.PRO; SEQ ID NO:7) and ovine (STSHRP.PRO; SEQ ID NO:8) TSH receptors. Majority (SEQ ID NO: 93) represents the consensus sequence.

FIG. 2 lists nucleotide bases 1 to 300 coding for regions of (in the following order) feline (CAT.SEQ; SEQ ID NO:9), bovine (COW.SEQ; SEQ ID NO:10), canine (DOG.SEQ; SEQ ID NO:11), mouse (MOUSE.SEQ; SEQ ID NO:12), porcine (PTSHR.SEQ; SEQ ID NO:13), rat (RAT.SEQ; SEQ ID NO:14), ovine (SHEEP.SEQ; SEQ ID NO:15) and human (HTSHR.SEQ; SEQ ID NO:16) TSH receptors. Majority (SEQ ID NO: 94) represents the consensus sequence.

FIG. 3 lists amino acids 200 to 300 of (in the following order) human (HTSHR.PRO; SEQ ID NO:17), porcine (PTSHR.PRO; SEQ ID NO:18), bovine (BTSHR.PRO; SEQ ID NO:19), feline (CTSHR.PRO; SEQ ID NO:20), canine (DTSHR.PRO; SEQ ID NO:21), mouse (MTSHR.PRO; SEQ ID NO:22), rat (RTSHR.PRO; SEQ ID NO:23) and ovine (STSHRP.PRO; SEQ ID NO:24) TSH receptors. Majority (SEQ ID NO: 95) represents the consensus sequence.

FIG. 4 lists nucleotide bases 700 to 899 coding for regions of (in the following order) feline (CAT.SEQ; SEQ ID NO:25), bovine (COW.SEQ; SEQ ID NO:26), canine (DOG.SEQ; SEQ ID NO:27), mouse (MOUSE.SEQ; SEQ ID NO:28), porcine (PTSHR.SEQ; SEQ ID NO:29), rat (RAT.SEQ; SEQ ID NO:30), ovine (SHEEP.SEQ; SEQ ID NO:31) and human (HTSHR.SEQ; SEQ ID NO:32) TSH receptors. Majority (SEQ ID NO: 96) represents the consensus sequence.

FIG. 5 lists amino acids 250 to 449 of (in the following order) human (HTSHR.PRO; SEQ ID NO:33), porcine (PTSHR.PRO; SEQ ID NO:34), bovine (BTSHR.PRO; SEQ ID NO:35), feline (CTSHR.PRO; SEQ ID NO:36), canine (DTSHR.PRO; SEQ ID NO:37), mouse (MTSHR.PRO; SEQ ID NO:38), rat (RTSHR.PRO; SEQ ID NO:39) and ovine (STSHRP.PRO; SEQ ID NO:40) TSH receptors. Majority (SEQ ID NO: 97) represents the consensus sequence.

FIG. 6 lists nucleotide bases 750 to 1100 coding for regions of (in the following order) feline (CAT.SEQ; SEQ ID NO:41), bovine (COW.SEQ; SEQ ID NO:42), canine (DOG.SEQ; SEQ ID NO:43), mouse (MOUSE.SEQ; SEQ ID NO:44), porcine (PTSHR.SEQ; SEQ ID NO:45), rat (RAT.SEQ; SEQ ID NO:46), ovine (SHEEP.SEQ; SEQ ID NO:47) and human (HTSHR.SEQ; SEQ ID NO:48) TSH receptors. Majority (SEQ ID NO: 98) represents the consensus sequence.

FIG. 7 lists amino acids 350 to 500 of (in the following order) human (HTSHR.PRO; SEQ ID NO:49), porcine (PTSHR.PRO; SEQ ID NO:50), bovine (BTSHR.PRO; SEQ ID NO:51), feline (CTSHR.PRO; SEQ ID NO:52), canine (DTSHR.PRO; SEQ ID NO:53), mouse (MTSHR.PRO; SEQ ID NO:54), rat (RTSHR.PRO; SEQ ID NO:55) and ovine (STSHRP.PRO; SEQ ID NO:56) TSH receptors. Majority (SEQ ID NO: 99) represents the consensus sequence.

FIG. 8 lists nucleotide bases 1100 to 1299 coding for regions of (in the following order) feline (CAT.SEQ; SEQ ID NO:57), bovine (COW.SEQ; SEQ ID NO:58), canine (DOG.SEQ; SEQ ID NO:59), mouse (MOUSE.SEQ; SEQ ID NO:60), porcine (PTSHR.SEQ; SEQ ID NO:61), rat (RAT.SEQ; SEQ ID NO:62), ovine (SHEEP.SEQ; SEQ ID NO:63) and human (HTSHR.SEQ; SEQ ID NO:64) TSH receptors. Majority (SEQ ID NO: 100) represents the consensus sequence.

FIG. 9 lists amino acids of the heavy chain (HC) of 4D7 (SEQ ID NO:65).

FIG. 10 lists amino acids of the heavy chain (HC) of 4D7 (SEQ ID NO:65), showing the variable region or domain (namely amino acid numbers 10 to 115), the CDRs (namely CDR1 amino acid numbers 31 to 35, CDRII amino acid numbers 50 to 66 and CDRIII amino acid numbers 99 to 104) and the constant region or domain (namely amino acid numbers 116 to 200).

FIG. 11 lists amino acids of the light chain (LC) of 4D7 (SEQ ID NO:66).

FIG. 12 lists amino acids of the light chain (LC) of 4D7 (SEQ ID NO:66), showing the variable region or domain (namely amino acid numbers 9 to 111), the CDRs (namely CDR1 amino acid numbers 24 to 38, CDRII amino acid numbers 54 to 60 and CDRIII amino acid numbers 93 to 101) and the constant region or domain (namely amino acids numbers 112 to 211).

FIG. 13 lists amino acids of the heavy chain (HC) of 16E5 (SEQ ID NO:67).

FIG. 14 lists amino acids of the heavy chain (HC) of 16E5 (SEQ ID NO:67), showing the variable region or domain (namely amino acid numbers 9 to 120), the CDRs (namely CDR1 amino acid numbers 31 to 35, CDRII amino acid numbers 50 to 66 and CDRIII amino acid numbers 99 to 109) and the constant region or domain (namely amino acid numbers 121 to 205).

FIG. 15 lists amino acids of the light chain (LC) of 16E5 (SEQ ID NO:68).

FIG. 16 lists amino acids of the light chain (LC) of 16E5 (SEQ ID NO:68), showing the variable region or domain (namely amino acid numbers 9 to 107), the CDRs (namely CDR1 amino acid numbers 24 to 34, CDRII amino acid numbers 50 to 56 and CDRIII amino acid numbers 89 to 97) and the constant region or domain (namely amino acids numbers 108 to 207).

FIG. 17 lists amino acids of the heavy chain (HC) of 17D2 (SEQ ID NO:69).

FIG. 18 lists amino acids of the heavy chain (HC) of 17D2 (SEQ ID NO:69), showing the variable region or domain (namely amino acid numbers 9 to 120), the CDRs (namely CDR1 amino acid numbers 31 to 35, CDRII amino acid numbers 50 to 66 and CDRIII amino acid numbers 99 to 109) and the constant region or domain (namely amino acid numbers 121 to 205).

FIG. 19 lists amino acids of the light chain (LC) of 17D2 (SEQ ID NO:70).

FIG. 20 lists amino acids of the light chain (LC) of 17D2 (SEQ ID NO:70), showing the variable region or domain (namely amino acid numbers 9 to 107), the CDRs (namely CDR1 amino acid numbers 24 to 34, CDRII amino acid numbers 50 to 56 and CDRIII amino acid numbers 89 to 97) and the constant region or domain (namely amino acids numbers 108 to 207).

FIG. 21 lists amino acids of the heavy chain (HC) of 14D3 (SEQ ID NO:71).

FIG. 22 lists amino acids of the heavy chain (HC) of 14D3 (SEQ ID NO:71), showing the variable region or domain (namely amino acid numbers 9 to 120), the CDRs (namely CDR1 amino acid numbers 31 to 35, CDRII amino acid numbers 50 to 66 and CDRIII amino acid numbers 99 to 109) and the constant region or domain (namely amino acid numbers 121 to 205).

FIG. 23 lists amino acids of the light chain (LC) of 14D3 (SEQ ID NO:72).

FIG. 24 lists amino acids of the light chain (LC) of 14D3 (SEQ ID NO:72), showing the variable region or domain (namely amino acid numbers 9 to 107), the CDRs (namely CDR1 amino acid numbers 24 to 34, CDRII amino acid numbers 50 to 56 and CDRIII amino acid numbers 89 to 97) and the constant region or domain (namely amino acids numbers 108 to 207).

FIG. 25 lists nucleotide bases encoding amino acids of the heavy chain (HC) of 4D7 (SEQ ID NO:73) as shown in FIG. 9.

FIG. 26 lists nucleotide bases encoding amino acids of the heavy chain (HC) of 4D7 (SEQ ID NO:73) as shown in FIG. 9, and shows the nucleotide bases encoding the variable region or domain, the CDRs and the constant region or domain as shown in FIG. 10.

FIG. 27 lists nucleotide bases encoding amino acids of the light chain (LC) of 4D7 (SEQ ID NO:74) as shown in FIG. 11.

FIG. 28 lists nucleotide bases encoding amino acids of the light chain (LC) of 4D7 (SEQ ID NO:74) as shown in FIG. 11, and shows the nucleotide bases encoding the variable region or domain, the CDRs and the constant region or domain as shown in FIG. 12.

FIG. 29 lists nucleotide bases encoding amino acids of the heavy chain (HC) of 16E5 (SEQ ID NO:75) as shown in FIG. 13.

FIG. 30 lists nucleotide bases encoding amino acids of the heavy chain (HC) of 16E5 (SEQ ID NO:75) as shown in FIG. 13, and shows the nucleotide bases encoding the variable region or domain, the CDRs and the constant region or domain as shown in FIG. 14.

FIG. 31 lists nucleotide bases encoding amino acids of the light chain (LC) of 16E5 (SEQ ID NO:76) as shown in FIG. 15.

FIG. 32 lists nucleotide bases encoding amino acids of the light chain (LC) of 16E5 (SEQ ID NO:76) as shown in FIG. 15, and shows the nucleotide bases encoding the variable region or domain, the CDRs and the constant region or domain as shown in FIG. 16.

FIG. 33 lists nucleotide bases encoding amino acids of the heavy chain (HC) of 17D2 (SEQ ID NO:77) as shown in FIG. 17.

FIG. 34 lists nucleotide bases encoding amino acids of the heavy chain (HC) of 17D2 (SEQ ID NO:77) as shown in FIG. 17, and shows the nucleotide bases encoding the variable region or domain, the CDRs and the constant region or domain as shown in FIG. 18.

FIG. 35 lists nucleotide bases encoding amino acids of the light chain (LC) of 17D2 (SEQ ID NO:78) as shown in FIG. 19.

FIG. 36 lists nucleotide bases encoding amino acids of the light chain (LC) of 17D2 (SEQ ID NO:78) as shown in FIG. 19, and shows the nucleotide bases encoding the variable region or domain, the CDRs and the constant region or domain as shown in FIG. 20.

FIG. 37 lists nucleotide bases encoding amino acids of the heavy chain (HC) of 14D3 (SEQ ID NO:79) as shown in FIG. 21.

FIG. 38 lists nucleotide bases encoding amino acids of the heavy chain (HC) of 14D3 (SEQ ID NO:79) as shown in FIG. 21, and shows the nucleotide bases encoding the variable region or domain, the CDRs and the constant region or domain as shown in FIG. 22.

FIG. 39 lists nucleotide bases encoding amino acids of the light chain (LC) of 14D3 (SEQ ID NO:80) as shown in FIG. 23.

FIG. 40 lists nucleotide bases encoding amino acids of the light chain (LC) of 14D3 (SEQ ID NO:80) as shown in FIG. 23, and shows the nucleotide bases encoding the variable region or domain, the CDRs and the constant region or domain as shown in FIG. 24.

FIG. 41 lists amino acids of the heavy chain (HC) of 3B3 (SEQ ID NO:81).

FIG. 42 lists amino acids of the heavy chain (HC) of 3B3 (SEQ ID NO:81), showing the variable region or domain (namely amino acid numbers 8 to 112), the CDRs (namely CDR1 amino acid numbers 31 to 35, CDRII amino acid numbers 50 to 66 and CDRIII amino acid numbers 99 to 101) and the constant region or domain (namely amino acid numbers 113 to 196).

FIG. 43 lists amino acids of the light chain (LC) of 3B3 (SEQ ID NO:82).

FIG. 44 lists amino acids of the light chain (LC) of 3B3 (SEQ ID NO:82), showing the variable region or domain (namely amino acid numbers 9 to 111), the CDRs (namely CDR1 amino acid numbers 24 to 38, CDRII amino acid numbers 54 to 60 and CDRIII amino acid numbers 93 to 101) and the constant region or domain (namely amino acids numbers 112 to 211).

FIG. 45 lists amino acids of the heavy chain (HC) of 3C7 (SEQ ID NO:83).

FIG. 46 lists amino acids of the heavy chain (HC) of 3C7 (SEQ ID NO:83), showing the variable region or domain (namely amino acid numbers 10 to 115), the CDRs (namely CDR1 amino acid numbers 31 to 35, CDRII amino acid numbers 50 to 66 and CDRIII amino acid numbers 99 to 104) and the constant region or domain (namely amino acid numbers 116 to 200).

FIG. 47 lists amino acids of the light chain (LC) of 3C7 (SEQ ID NO:84).

FIG. 48 lists amino acids of the light chain (LC) of 3C7 (SEQ ID NO:84), showing the variable region or domain (namely amino acid numbers 9 to 111), the CDRs (namely CDR1 amino acid numbers 24 to 38, CDRII amino acid numbers 54 to 60 and CDRIII amino acid numbers 93 to 101) and the constant region or domain (namely amino acids numbers 112 to 211).

FIG. 49 lists amino acids of the heavy chain (HC) of 2B4 (SEQ ID NO:85).

FIG. 50 lists amino acids of the heavy chain (HC) of 2B4 (SEQ ID NO:85), showing the variable region or domain (namely amino acid numbers 9 to 122), the CDRs (namely CDR1 amino acid numbers 31 to 35, CDRII amino acid numbers 50 to 66 and CDRIII amino acid numbers 99 to 111) and the constant region or domain (namely amino acid numbers 123 to 207).

FIG. 51 lists amino acids of the light chain (LC) of 2B4 (SEQ ID NO:86).

FIG. 52 lists amino acids of the light chain (LC) of 2B4 (SEQ ID NO:86), showing the variable region or domain (namely amino acid numbers 9 to 112), the CDRs (namely CDR1 amino acid numbers 24 to 39, CDRII amino acid numbers 78 to 82 and CDRIII amino acid numbers 94 to 102) and the constant region or domain (namely amino acids numbers 113 to 212).

FIG. 53 lists nucleotide bases encoding amino acids of the heavy chain (HC) of 3B3 (SEQ ID NO:87) as shown in FIG. 41.

FIG. 54 lists nucleotide bases encoding amino acids of the heavy chain (HC) of 3B3 (SEQ ID NO:87) as shown in FIG. 41, and shows the nucleotide bases encoding the variable region or domain, the CDRs and the constant region or domain as shown in FIG. 42.

FIG. 55 lists nucleotide bases encoding amino acids of the light chain (LC) of 3B3 (SEQ ID NO:88) as shown in FIG. 43.

FIG. 56 lists nucleotide bases encoding amino acids of the light chain (LC) of 3B3 (SEQ ID NO:88) as shown in FIG. 43, and shows the nucleotide bases encoding the variable region or domain, the CDRs and the constant region or domain as shown in FIG. 44.

FIG. 57 lists nucleotide bases encoding amino acids of the heavy chain (HC) of 3C7 (SEQ ID NO:89) as shown in FIG. 45.

FIG. 58 lists nucleotide bases encoding amino acids of the heavy chain (HC) of 3C7 (SEQ ID NO:89) as shown in FIG. 45, and shows the nucleotide bases encoding the variable region or domain, the CDRs and the constant region or domain as shown in FIG. 46.

FIG. 59 lists nucleotide bases encoding amino acids of the light chain (LC) of 3C7 (SEQ ID NO:90) as shown in FIG. 47.

FIG. 60 lists nucleotide bases encoding amino acids of the light chain (LC) of 3C7 (SEQ ID NO:90) as shown in FIG. 47, and shows the nucleotide bases encoding the variable region or domain, the CDRs and the constant region or domain as shown in FIG. 48.

FIG. 61 lists nucleotide bases encoding amino acids of the heavy chain (HC) of 2B4 (SEQ ID NO:91) as shown in FIG. 49.

FIG. 62 lists nucleotide bases encoding amino acids of the heavy chain (HC) of 2B4 (SEQ ID NO:91) as shown in FIG. 49, and shows the nucleotide bases encoding the variable region or domain, the CDRs and the constant region or domain as shown in FIG. 50.

FIG. 63 lists nucleotide bases encoding amino acids of the light chain (LC) of 2B4 (SEQ ID NO:92) as shown in FIG. 51.

FIG. 64 lists nucleotide bases encoding amino acids of the light chain (LC) of 2B4 (SEQ ID NO:92) as shown in FIG. 51, and shows the nucleotide bases encoding the variable region or domain, the CDRs and the constant region or domain as shown in FIG. 52.

More specifically, the FIGS. 1 to 8 illustrate the following:

FIG. 1 lists amino acids 1 to 200 of TSH receptors in the above mentioned species, which include the following amino acid sequences employed in the present invention:
amino acids 22 to 91 of a TSH receptor,
amino acids 32 to 41 of a TSH receptor, and
amino acids 36 to 42 of a TSH receptor.

FIG. 2 lists nucleotide bases 1 to 300 in the above mentioned species, which include coding regions for the above mentioned amino acid sequences present in FIG. 1.

FIG. 3 lists amino acids 200 to 300 of TSH receptors in the above mentioned species, which include the following amino acid sequences employed in the present invention:
amino acids 246 to 260 of a TSH receptor, and
amino acids 247 to 260 of a TSH receptor.

FIG. 4 lists nucleotide bases 700 to 899 in the above mentioned species, which include coding regions for the above mentioned amino acid sequences present in FIG. 3.

FIG. 5 lists amino acids 250 to 449 of TSH receptors in the above mentioned species, which include the following amino acid sequences employed in the present invention:
amino acids 260 to 363 of a TSH receptor; and
amino acids 277 to 296 of a TSH receptor.

FIG. 6 lists nucleotide bases 750 to 1100 in the above mentioned species, which include coding regions for the above mentioned amino acid sequences present in FIG. 5.

FIG. 7 lists amino acids 350 to 500 of TSH receptors in the above mentioned species, which include the following amino acid sequences employed in the present invention:
amino acids 380 to 418 of a TSH receptor; and
amino acids 381 to 385 of a TSH receptor.

FIG. 8 lists nucleotide bases 1100 to 1299 in the above mentioned species, which include coding regions for the above mentioned amino acid sequences present in FIG. 7.

EXAMPLE 1

(1) Production of Mouse Monoclonal Antibodies to the TSH Receptor

BALB/c mice were immunised with a recombinant, highly purified mature form of the TSH receptor expressed in CHO cells. [Y Oda, J Sanders, M Evans, A Kiddie, A Munkley, C James, T Richards, J Wills, J Furmaniak, B Rees Smith "Epitope analysis of the human thyrotrophin (TSH) receptor using monoclonal antibodies." Thyroid 2000 10(12): 1051-1059.] Mouse antibodies were also raised by DNA immunization technique with full length human TSHR cDNA cloned in pcDNA3.1. MAbs were cloned using standard techniques and IgGs were purified from culture supernatants by affinity chromatography on Protein A Sepharose. The reactivity of MAbs with the TSH receptor was tested by (a) Western blotting with partially purified receptors, (b) inhibition of TSH binding to the TSH receptor, and (c) immunoprecipitation of $^{35}$S-labelled TSH receptors produced in an in vitro transcription/translation system as described in Y Oda, J Sanders, S Roberts, M Maruyama, R Kato, M Perez, V B Peteresen, N Wedlock, J Furmaniak, B Rees Smith "Binding characteristics of antibodies to the TSH receptor." Journal of Molecular Endocrinology 1998 20: 233-244.

(2) Inhibition of $^{125}$I-TSH Binding to the TSH Receptor

The inhibition of $^{125}$I-TSH binding to the TSH receptor was analysed in an assay where, 50 μL of detergent solubilised TSH receptor was preincubated with 50 μL of MAb purified as described in step (1) for 15 minutes at room temperature before addition of 100 μL of $^{125}$I-TSH (30,000 cpm) followed by incubation at 37° C. for one hour. The complexes of $^{125}$I-TSH/TSH receptor were precipitated by addition of 2 mL 16.5% polyethylene glycol and 25 μL healthy blood donor serum, centrifuged at 1500×g for 30 minutes at 4° C., aspirated and the radioactivity of the pellets counted using known techniques.

MAbs termed: 2B4 MAb (at IgG concentration of 5 μg/mL), 8E2 Mab (at IgG concentration of 1 ug/mL) and 18C5 Mab (at IgG concentration 1 mg/mL) showed 76%, 38% and 91% inhibition of TSH binding, respectively. Fab fragments were produced from 2B4 Mab, 8E2 Mab and 18C5 Mab IgGs by digestion with L-cysteine/papain or pepsin, followed by the separation of Fc and Fab on Protein A column.

(3) Epitope Recognition by MAbs

Western blotting analysis [Y Oda, J Sanders, M Evans, A Kiddie, A Munkley, C James, T Richards, J Wills, J Furmaniak, B Rees Smith "Epitope analysis of the human thyrotrophin (TSH) rector using monoclonal antibodies." Thyroid 2000 10(12): 1051-1059.] showed that 2B4 MAb bound to an epitope between amino acid (aa) 380 and 418, 8E2 MAb to an epitope between aa 22 and 91 and 18C5 MAb to an epitope between aa 246 and 260 of the TSH receptor sequence. Analysis with overlapping TSH receptor peptides covering these regions [Y Oda, J Sanders, M Evans, A Kiddie, A Munkley, C James, T Richards, J Wills, J Furmaniak, B Rees Smith "Epitope analysis of the human thyrotrophin (TSH) receptor using monoclonal antibodies." Thyroid 2000 10(12): 1051-1059.] showed that 2B4 MAb reacted with the aa 381 to 385, 8E2 MAb with the aa 36 to 42 and 18C5 MAb with the aa 247 to 260.

(4) Preparation of $^{125}$I-Labelled TSH Receptor

Solubilised preparations of TSH receptor were labelled with $^{125}$I by way of $^{125}$I-labelled MAB (4E31) reactive with the C-terminal end of the TSH receptor prepared as described in J Sanders, Y Oda, S Roberts, A Kiddie, T Richards, J Bolton, V McGrath, S Walters, D Jaskolski, J Furmaniak, B Rees Smith "The interaction of TSH receptor autoantibodies with $^{125}$I-labelled TSH receptor." Journal of Clinical Endocrinology and Metabolism 1999 84(10):3797-3802. Aliquots of $^{125}$I-labelled 4E31 F(ab)$_2$ were incubated for 15 minutes at room temperature with solubilised TSH receptor and then used an immunoprecipitation assay as described in step (5).

(5) Inhibition of TSH Receptor Autoantibody (TRAb) Binding to the TSH Receptor by MAbs The inhibition of TRAb binding to the TSH receptor by MAbs was tested as follows:

10 μL of $^{125}$I-labelled TSH receptor (30,000 cpm) prepared in step (4) was preincubated with 20 μL of 2B4 Fab (5 and 10 mg/mL) for 15 minutes at room temperature followed by incubation with 20 μL of TRAb positive patient serum for one hour at room temperature. 50 μL of solid phase Protein A (an anti-human IgG reagent) was then added and incubation continued for one hour at room temperature followed by washing step and centrifugation at 1500×g at 4° C. for 30 minutes; aspiration and counting of the radioactivity of the pellets. Similar experiments were carried out with 8E2 and 18C5 Fabs and the combination of two Fabs together.

Results of Example 1

Results of the inhibition of TRAb binding to the TSH receptor are shown in Table 1.

EXAMPLE 2

Methods (1) Production of Mouse Monoclonal Antibodies to the TSH Receptor

BALB/C mice were immunised with a recombinant, highly purified mature form of the TSH receptor expressed in CHO cells (Y. Oda, J. Sanders, M. Evans, A. Kiddie, A. Munkley, C. James, T. Richards, J. Wills, J. Furmaniak, B. Rees Smith "Epitope analysis of the human thyrotropin (TSH) receptor using monoclonal antibodies" Thyroid 2000 10(12): 1051-1059). Mouse antibodies were also raised by DNA immunisation techniques with full length human TSHR cDNA cloned in pRC/CM.1. MAbs were cloned using standard techniques and IgGs were purified from culture supernatants by affinity chromatography on Protein A Sepharose.

(Fab)$_2$ fragments were produced from the purified MAb IgGs by digestion with pepsin followed by chromatography on a protein A affinity column as described in Y. Oda, J. Sanders, S. Roberts, M. Maruyama, R P Kato, M. Perez, V B Petersen, N. Wedlock, J. Furmaniak, B. Rees Smith 1998 "Binding characteristics of antibodies to the TSH receptor". Journal of Molecular Endocrinology 20: 233-244.

Fab fragments were prepared by digestion of the purified MAbs with papain as described in E. Hendry, G. Taylor, F. Grennan-Jones, A. Sullivan, N. Liddy, J. Godfrey, N. Hayakawa, M. Powell J. Furmaniak, B Rees Smith 2001 "X-ray crystal structure of a monoclonal antibody that binds to a major autoantigenic epitope on thyroid peroxidase." Thyroid 11(12): 1091-1099.

The reactivity of MAbs with the TSH receptor was tested by (a) western blotting with partially purified receptors, (b) inhibition of the TSH binding to the TSH receptor and (c) immunoprecipitation of $^{35}$S-labelled TSH receptors produced in an in vitro transcription/translation system as described in Y. Oda, J. Sanders, S. Roberts, M. Maruyama, R. Kato, M. Perez, V B. Petersen, N. Wedlock, J. Furmaniak, B. Rees Smith "Binding characteristics of antibodies to the TSH receptor" Journal of Molecular Endocrinology 1998 20: 233-244.

(2) Inhibition of $^{125}$I TSH Binding to the TSH Receptor (a) PEG Method for Use with Detergent Solubilised TSHR The inhibition of $^{125}$I TSH binding to detergent solubilised TSH receptor was analysed in an assay where 50 μL of MAb purified as described in Methods (1) above was preincubated with receptor for 15 minutes at room temperature before addition of 100 μL of $^{125}$I TSH (30,000 cpm) followed by incubation at 37° C. for one hour. The complexes of $^{125}$I TSH and TSH receptor were precipitated by addition of 2 mL 16.5% polyethylene glycol and 25 μL healthy blood donor serum, centrifuged at 1500×g for 30 minutes at 4° C., aspirated and the radioactivity of the pellets counted in a gamma counter.

(b) Method Using Tubes Coated with TSHR

In this procedure, plastic tubes are first coated with a MAb such as 4E31 which binds to a part of the TSHR unrelated to TSH or TRAb binding. Detergent solubilised TSHR preparations are then added, captured by the TSHR MAb and then become immobilised on the tube surface in such a way as to be able to bind TSH or TRAb. In particular the MAb 4E31 reactive with the TSHR C terminus (10 μg/mL F(ab)$_2$ preparation in 0.1 M Na$_2$CO$_3$ pH 9.2) was added to plastic tubes (Nune Maxisorp, 200 μL per tube) and coating allowed to proceed overnight 4° C. After washing and post-coating (10 mg/mL bovine serum albumin) the tubes were washed again with assay buffer (10 mM Tris-HCl pH 7.8, 50 mM NaCl, 1 mg/mL bovine serum albumin, 0.1% Triton X-100). 200 μL of a detergent solubilised TSHR preparation was then added and incubated overnight at 4° C. followed by aspiration and washing steps. Thereafter, 20 μL of "start" buffer (10 mM Tris-HCl pH 7.8, 50 mM NaCl, bovine serum albumin 1 mg/mL, 6 mM NaN$_3$, 1% Triton X-100) was added to the TSHR coated tubes followed by 100 μL of purified MAb IgG or patient sera and incubated at room temperature for 2 hours with gentle shaking. After aspiration, the tubes were washed twice with 1 mL of assay buffer before addition of 100 μL of $^{125}$I TSH (80,000 cpm) and incubation at room temperature for 20-60 min with shaking. The tubes were then washed twice with 1 mL of assay buffer, aspirated and counted in a gamma counter.

(3) Analysis of Thyroid Stimulating or Blocking Activities of MAbs.

The ability of MAbs to either stimulate the production of cyclic AMP in isolated porcine thyroid cells (thyroid stimulating activity) or to act as TSH antagonists by blocking TSH stimulation of cyclic AMP (blocking activity) was assessed using reagents from Yamasa Corporation, Tokyo, Japan.

In addition the ability of the MAbs to stimulate production of cyclic AMP in Chinese hamster ovary (CHO) cells expressing human TSHR was analysed as described by M. Kita, L. Ahma, P C. Marians, H. Viase, P. Unger, P. N. Graves, T. F. Davies 1999 "Regulation and transfer of a murine model of thyrotropin receptor antibody mediated Graves' disease." Endocrinology 140: 1392-1398.

(4) Binding of $^{125}$I-Labelled MAbs to the TSHR and Effect of TRAb

Purified IgG from two of the MAbs that showed thyroid simulating activity (16E5 and 14D3, table 2) were labelled with $^{125}$I followed by separation of unincorporated $^{125}$I by filtration on Sephadex G-50 as in (4) in Example 1.

Plastic tubes were coated with TSHR preparations as in 2b above. Thereafter, 100 μL of test serum (from healthy blood donors or from patients with Graves' disease) were added and tubes incubated for 2 hours at room temperature with shaking.

After this incubation, the tubes were washed 2 times with assay buffer. Then, 100 μL of $^{125}$I-labelled 16E5 or 14D3 IgG (30,000 cpm diluted in 20 mM Tris-HCl pH 7.3, 50 mM NaCl, 1 mg/mL bovine serum albumin, 0.1% Triton X-100) was added to the tubes and incubated for 1 hour at room temperature with shaking. The tubes were then washed twice with the same buffer that was used for diluting $^{125}$I-labelled MAbs and counted in a gamma counter.

(5) Binding of TSHR to MAb Coated Tubes and Effect of TRAb

Detergent solubilised TSHR preparations (20 μL were incubated for 1 hour at room temperature with 100 μL of test serum and 20 μL of start buffer (2b above). 100 μL of this mixture was then added to plastic tubes coated with TSHR MAb (as in 2b above) and incubated for 1 hour with shaking at room temperature. Then the tubes were aspirated and washed twice (2b above) and 100 μL (30,000 cpm) of $^{125}$I-labelled C-terminal TSHR MAb 4E31 F(ab)$_2$ preparation labelled with $^{125}$I as in 4 above added. After further incubation for 1 hour at room temperature with shaking, the tubes were aspirated, washed twice and the radioactivity counted with a gamma counter.

Oligonucleotide primers were designed using the sequences as described previously (Kettleborough C. A. et al "Optimization of primers for cloning libraries of mouse immunoglobulin genes using the polymerase chain reaction." European Journal of Immunology 1993 23:206-211).

Both sense and antisense primers included additional 5' restriction endonuclease site sequences to facilitate cloning of PCR products. RT-PCR products were cloned into pUC18 DNA prepared by the Qiagen method (Qiagen) and sequenced by the Sanger-Coulson method Results of Example 2

(1) Thyroid stimulating activity of the TSHR MAbs is shown in tables 2 and 3. Four of the MAbs (16E5, 14D3, 17D2, and 4D7) were able to stimulate cyclic AMP production in isolated porcine thyroid cells. In addition when Fab fragments from three of these MAbs were tested, all three also stimulated cyclic AMP production (table 2). For comparison a TRAb positive patient serum showed similar levels of stimulation to the MAbs (table 2). Also, TSHR MAb 2B4 which has the ability to inhibit TSH binding to the TSHR strongly did not show thyroid stimulating activity (table 2). Another TSHR MAb and Fab (3B3) did not stimulate cyclic AMP production nor did the Tg MAb Fab 2G2 (table 2).

In a further series of experiments some of the MABS which were able to stimulate porcine thyroid cells (16E5 and 14D3) were tested for their ability to stimulate cyclic AMP production in CHO cells expressing human TSHR (table 3). Similar results were obtained to those observed with porcine thyroid cells.

(2) In the presence of sera from healthy blood donors, $^{125}$I-labelled 16E5 bound to TSHR coated tubes is in the range from 23 to 35% of total counts added (table 4). In the presence of sera from patients with Graves' disease (all TRAb positive) the binding of $^{125}$I-labelled 16E5 was markedly reduced and was in the range from 1.9 to 7.5% (table 4).

This indicated that Graves' disease patient sera with TRAb activity inhibit the binding of TSHR MAb 16E5 to the TSHR. Further experiments with labelled 16E5 are shown in table 5 where a comparison of the effects of Graves' disease patient sera on (a) $^{125}$I-labelled 16E5 to TSHR coated tubes and (b) $^{125}$I-labelled TSH binding to TSHR coated tubes. Similar experiments to those shown in table 5 were carried out with $^{125}$I-labelled TSHR MAb 14D3 and the results are shown in table 6.

The effects of Graves' disease patient sera on TSHR coated tube binding by $^{125}$I-labelled 16E5, 14D3 or TSH were similar with strong inhibition of binding being observed in most cases (tables 5 and 6). In contrast to Graves' disease patient sera, sera from healthy blood donors had little effect on labelled MAb or labelled TSH binding to TSHR coated tubes (tables 5 and 6). Table 7 shows the effect of sera containing autoantibodies other than the TSHR autoantibodies on TSHR coated tube binding by labelled TSH, 16E5 and 14D3. As can be seen from table 7, sera containing autoantibodies to glutamic acid decarboxylase (D1 and D2) or to 21-hydroxylase (A1 and A2) had no effect on TSH or MAb binding. However, the serum G42 from a patient with Graves' disease showed a strong, dose-dependent inhibition of both TSH and MAb binding.

(3) As shown in table 8, plastic tubes coated with MAb 16E5 were able to bind TSHR and this binding was inhibited by Graves' sera containing TSHR autoantibodies. In particular, detection of TSHR binding by the $^{125}$I-labelled TSHR MAb 4E31 showed that (a) in the presence of sera from healthy blood donors, labelled 4E31 binding ranged from 13.5-17.8% of total cpm added whereas (b) in the presence of Graves' sera, labelled MAb binding ranged from 1.8-4.8% of total cpm added. Similar results were obtained with plastic tubes coated with MAb 14D3 (table 9).

Conclusions

The results shown in tables 2-9 show:
(a) we have produced TSHR MAbs and MAb Fab fragments which can stimulate isolated thyroid cells in a similar way to TRAb in patient sera and in a similar way to TSH. Different MAbs show different degrees of stimulating activity.
(b) these MAbs can be used instead of labelled TSH in assays for TSHR autoantibodies (TRAb).
(c) when the MAbs are coated onto plastic surfaces, they can bind TSHR preparations. This binding is inhibited by TRAb in patient sera, thus providing a new type of TRAb assay.
(d) the ability of the MAbs to stimulate the thyroid means that they are potentially useful as alternatives to TSH in in vivo applications.

EXAMPLE 3

Inhibition of $^{125}$I-16E5 Fab Binding to Solubilised TSH Receptor by TSH Receptor Mabs Method The inhibition of 11I-16E5 Fab binding to detergent solubilised TSH receptor was analysed in an assay where 50 μL of Mab IgG (100 μg/ml) purified as described above was incubated with receptor for 30 minutes at room temperature before addition of 100 μL of $^{125}$I-16E5 Fab (30,000 cpm) followed by incubation at room temperature for 2 hours. The complexes of $^{125}$I-16E5 Fab and TSH receptor were precipitated by addition of 2 ml 16.5% polyethylene glycol and 50 μL healthy blood donor serum, centrifuged at 1500×g for 30 minutes at 4° C., aspirated and the radioactivity of the pellets counted in a gamma counter.

The results are shown in Table 10. From Table 10 it can be seen that Mab 4D7 (which binds to epitope region 246 to 260 and stimulates isolated thyroid cells) quite strongly inhibits labelled 16E5 Fab binding to the TSH receptor (24.2% inhibition). Two other Mabs, 3C7 and 18C5 also quite strongly inhibit 16E5 Fab binding (17 and 15.7% inhibition respectively) and also bind to the epitope region 246 to 260. Weak or no inhibition is observed with the other Mabs. This suggests that epitope region 246 to 260 is involved in 16E5 binding to the TSH receptor. As the other stimulating Mabs 14D3 and 17D2 compete well with 16E5 binding to the TSH receptor as can be seen from Table 10, epitope region 246 to 260 is probably also important for TSH receptor binding by 14D3 and 17D2.

TABLE 1

Inhibition of binding of TRAb in patient serum (K3) to the TSH receptor by Mab Fabs

| | Serum K3 1/10 | |
|---|---|---|
| | Labelled TSHR immunoprecipitated (%) | % inhbition |
| Buffer | 17.5 | — |
| 2B4 (5 mg/mL) | 10.1 | 42 |
| 2B4 (10 mg/mL) | 3.9 | 77.7 |
| 18C5 (5 mg/mL) | 13.7 | 21.7 |
| 18C5 (10 mg/mL) | 9.7 | 44 |
| 8E2 (5 mg/mL) | 15.0 | 14.3 |
| 8E2 (10 mg/mL) | 13.0 | 25.7 |
| 2B4 + 18C5 (5 mg/mL) | 5.7 | 67.4 |
| 18C5 + 8E2 (5 mg/mL) | 12.4 | 29.1 |
| 2B4 + 8E2 (5 mg/mL) | 8.1 | 53.7 |
| Unlabelled TSH (2.94 mg/mL) | 7.8 | 55.4 |
| 2B4 + 8E2 + 18C5 (3.3 mg/mL) | 7.4 | 57.7 |

$$\% \text{ inhibition} = 100 - \left(\frac{A}{B} \times 100\right)$$

where
A = $^{125}$I-TSHR (cpm) immunoprecipitated in the presence of test sera and test Mab Fab as a percentage of total cpm of material added to the tube;
B = $^{125}$I-TSHR (cpm) immunoprecipitated in the presence of test sera and assay buffer as a percentage of total cpm of material added to the tube The above results show that:
(1) the sequences of the TSH receptor which are involved in the TSHR binding are also involved in TRAb binding;
(2) mouse Mab reactive with these sequences can be used effectively to inhibit TRAb binding to the TSH receptor; and
(3) one or more of the MAbs reactive with one or more of the above TSH receptor sequences can be used to detect and measure TRAb.

TABLE 2

Thyroid stimulating activity of TSHR MAbs tested using isolated porcine thyroid cells

| Test sample | | Stimulation (%)[1] | Inhibition of TSH binding (%)[2,3] |
|---|---|---|---|
| 16E5 IgG | 200 µg/ml | 466 | nt |
| | 20 µg/ml | 332 | 83.3 |
| | 2 µg/ml | 269 | 73.6 |
| | 0.2 µg/ml | 157 | nt |
| | 0.02 µg/ml | 52 | nt |
| 14D3 IgG | 200 µg/ml | 557 | nt |
| | 20 µg/ml | 351 | 76.4 |
| | 2 µg/ml | 323 | 61.0 |
| | 0.2 µg/ml | 227 | nt |
| | 0.02 µg/ml | 78 | nt |
| 17D2 IgG | 200 µg/ml | 377 | nt |
| | 20 µg/ml | 207 | 81.3 |
| | 2 µg/ml | 134 | 73.7 |
| 4D7 IgG | 200 µg/ml | 259 | 33[4] |
| | 20 µg/ml | 31 | nt |

TABLE 2-continued

Thyroid stimulating activity of TSHR MAbs tested using isolated porcine thyroid cells

| Test sample | | Stimulation (%)[1] | Inhibition of TSH binding (%)[2,3] |
|---|---|---|---|
| 3B3 IgG[a] | 200 µg/ml | 34 | 30.7 |
| | 20 µg/ml | 37 | 6.1 |
| 2B4 IgG[a] | 20 µg/ml | 100 | nt |
| | 2 µg/ml | 116 | 69.9 |
| 3C7 Fab | 1 mg/ml | 348 | 45.2 |
| 4D7 Fab | 1 mg/ml | 512 | 48.6 |
| 16E5 Fab | 200 µg/ml | 425 | 53[5] |
| 14D3 Fab | 200 µg/ml | 648 | 64[5] |
| 17D2 Fab | 200 µg/ml | 274 | 45[5] |
| 3B3 Fab[a] | 200 µg/ml | 42 | 66.5[4] |
| 2G2 Fab[6] | 1 mg/ml | 55 | 0 |
| | 200 µg/ml | 37 | 0 |
| TRAb +ve patient | dil 1:2 | 771 | 65[7] |
| | dil 1:4 | 530 | nt |
| Pool of healthy blood donor sera | | 29 | 0.6 |
| TRAb negative serum | | 70 | 0 |

Table 2 footnotes
[1]MAb IgG or Fab preparations were diluted in the pool of healthy blood donor sera. Stimulation (%) was calculated as 100x the ratio of: cyclic AMP produced in the presence of test sample to cyclic AMP produced in the presence of a pool of healthy blood donor sera. A stimulation level of >180% was assessed as positive i.e. this level of stimulation was always greater than that observed by sera from individual healthy blood donors.
[2]Inhibition of TSH binding level of >10% is positive
[3]Method = coated tube
[4]Inhibition tested at 250 µg/ml
[5]Inhibition tested at 10 µg/ml
[6]2G2 is a MAb reactive with thyroglobulin i.e. unreactive with the TSHR
[7]Inhibition with undiluted serum
[a]3B3 and 2B4 IgGs act as TSH antagonists i.e. block the ability of TSH to stimulate cyclic AMP production by isolated porcine thyroid cells.
nt = not tested at this concentration

TABLE 3

| Test sample[1] | Stimulation (%)[2] | Inhibition of TSH binding (%)[3,4] |
|---|---|---|
| 16E5 20 µg/mL | 850 | 78.5[5] |
| 14D3 20 µg/mL | 908 | 71.8[5] |
| 2B4 20 µg/mL | 111 | 84.4 |
| TRAb +ve patient | 850 | 65.0[6] |
| Pool of healthy blood donor sera | 100 | 0 |

Table 3 footnotes:
[1]All samples were diluted 1:10 prior to addition to cells.
[2]Stimulation (%) was calculated as 100x the ratio of: cyclic AMP produced in the presence of test sample to cyclic AMP produced in the presence of a pool of healthy blood donor sera.
[3]Inhibition of TSH binding level of >10% is positive.
[4]Method = coated tubes
[5]Inhibition tested at 10 µg/mL
[6]Tested for inhibition undiluted.

TABLE 4

Binding of $^{125}$I-labelled Mab 16E5 to TSHR coated tubes and effect of TRAb in patient sera

| Test Material[1] | Inhibition of TSH binding (%)[2] | $^{125}$I-16E5 bound to TSHR coated tubes (% total counts added) |
|---|---|---|
| G1 | 21 | 5.6 |
| G2 | 22.7 | 6.5 |
| G3 | 24.7 | 3.5 |
| G4 | 22.7 | 6.0 |
| G5 | 28.1 | 3.6 |
| G6 | 29.4 | 2.5 |
| G7 | 29.3 | 5.8 |
| G8 | 39 | 1.9 |
| G9 | 31.9 | 6.8 |
| G10 | 34.8 | 5.4 |
| G11 | 34.5 | 3.4 |
| G12 | 35.3 | 4.2 |

TABLE 4-continued

Binding of $^{125}$I-labelled Mab 16E5 to TSHR coated tubes and effect of TRAb in patient sera

| Test Material[1] | Inhibition of TSH binding (%)[2] | $^{125}$I-16E5 bound to TSHR coated tubes (% total counts added) |
|---|---|---|
| G13 | 35.6 | 6.2 |
| G14 | 36.9 | 2.8 |
| G15 | 30.3 | 4.3 |
| G16 | 35 | 2.2 |
| G17 | 47.6 | 3.9 |
| G18 | 43 | 3.4 |
| G19 | 53.5 | 3.7 |
| G20 | 59.2 | 7.5 |
| G21 | 58.9 | 4.9 |
| NPS | <14 | 27.5 |
| NSF 1 | <14 | 23.3 |
| NSF 2 | <14 | 30.2 |
| NSF 3 | <14 | 29.1 |
| NSF 4 | <14 | 22.8 |
| NSF 5 | <14 | 28.9 |
| NSF 6 | <14 | 31.0 |
| NSF 7 | <14 | 29.2 |
| NSF 8 | <14 | 35.3 |
| NSF 9 | <14 | 26.3 |
| NSF 10 | <14 | 25.2 |

Table 4 footnotes:
[1]sera G1-G22 are from patients with Graves' disease sera NSF 1-NSF 10 are from healthy blood donors NPS = pool of healthy blood donor sera
[2]Inhibition of TSH binding >14% is positive; PEG method used

TABLE 5

Effect of Graves' disease patient sera on $^{125}$I-16E5 binding and $^{125}$I-TSH binding to TSHR coated tubes

| Test material[1] | $^{125}$I-16E5 bound to TSHR coated tubes (% total counts added)[2] | Inhibition of $^{125}$I-16E5 binding (%)[2,3] | $^{125}$I-TSH bound to TSHR coated tubes (% total counts added)[4] | Inhibition of $^{125}$I-TSH binding (%)[3,4] |
|---|---|---|---|---|
| G23 | 13.2 | 44.0 | 8.9 | 27.1 |
| G28 | 5.8 | 75.4 | 3.8 | 68.5 |
| G29 | 13.3 | 43.6 | 8.0 | 34.4 |
| G30 | 9.2 | 61.0 | 5.3 | 56.9 |
| G32 | 11.9 | 49.6 | 7.5 | 38.4 |
| G36 | 15.5 | 34.3 | 10.1 | 17.5 |
| G38 | 16.1 | 31.8 | 10.0 | 18.3 |
| G41 | 17.8 | 24.6 | 10.8 | 11.4 |
| G43 | 5.9 | 75.0 | 4.0 | 67.2 |
| G44 | 18.6 | 21.2 | 12.4 | −ve |
| G45 | 5.1 | 78.4 | 3.5 | 71.0 |
| G46 | 3.8 | 83.9 | 2.7 | 77.9 |
| G47 | 7.2 | 69.5 | 4.3 | 64.8 |
| G48 | 6.9 | 70.8 | 4.8 | 60.8 |
| G49 | 9.1 | 61.4 | 6.1 | 49.6 |
| G50 | 8.7 | 63.1 | 6.3 | 48.4 |
| G51 | 11.9 | 49.6 | 7.9 | 35.2 |
| G52 | 12.3 | 47.9 | 7.4 | 39.0 |
| NSF 4 | 23.0 | 2.6 | 12.5 | −ve |
| NSF 5 | 25.3 | −ve | 12.3 | −ve |
| NSF 10 | 22.4 | 5.1 | 12.5 | −ve |
| NSF 16 | 23.3 | 1.3 | 12.0 | 1.8 |
| NSF 17 | 24.2 | −ve | 11.5 | 5.3 |
| NSF 18 | 19.9 | 15.7 | 11.2 | 8.0 |
| NSF 20 | 21.5 | 8.9 | 12.3 | −ve |
| NSF 21 | 23.3 | 1.3 | 12.3 | −ve |
| NSF 22 | 24.5 | −ve | 12.4 | −ve |
| NSF 26 | 26.5 | −ve | 12.8 | −ve |

Table 5 footnotes:
[1]Sera G53-G52 are from patients with Graves' disease; sera NSF are from healthy blood donors
[2]mean binding in the presence of healthy blood donor sera was 23.6% for $^{125}$I-16E5
[3]inhibition of binding was calculated using the formula $$\% \text{ inhibition} = 100 - \left(\frac{A}{B} \times 100\right)$$

where
A = binding in the presence of test serum;
B = mean binding in the presence of healthy blood donor sera
[4]mean binding in the presence of healthy blood donor sera was 12.2% for $^{125}$I-TSH

TABLE 6

Binding of $^{125}$I-labelled MAb 14D3 to TSHR coated tubes and effect of TRAb in patient sera

| Test material[1] | $^{125}$I-14D3 bound to TSHR coated tubes (% total counts added)[2] | Inhibition of $^{125}$I-14D3 binding (%)[2,3] | $^{125}$I-TSH bound to TSHR coated tubes (% total counts added)[4] | Inhibition of $^{125}$I-TSH binding (%)[3,4] |
|---|---|---|---|---|
| G23 | 13.9 | 20 | 8.9 | 26.6 |
| G24 | 11.3 | 35 | 6.9 | 43.4 |
| G25 | 14.1 | 19 | 7.2 | 40.5 |
| G26 | 7.3 | 58 | 2.6 | 78.3 |
| G27 | 12.3 | 29.7 | 7.3 | 40.1 |
| G28 | 8.0 | 54.4 | 3.8 | 68.3 |
| G29 | 13.2 | 24.4 | 8.0 | 34.0 |
| G30 | 12.5 | 28.4 | 5.3 | 56.6 |
| G31 | 9.8 | 44 | 4.3 | 64.3 |
| G32 | 11.4 | 34.8 | 7.5 | 38.0 |
| G33 | 12.7 | 27.2 | 6.1 | 49.9 |
| G34 | 10.9 | 37.5 | 7.5 | 37.8 |
| G35 | 9.8 | 43.6 | 4.3 | 64.6 |
| G36 | 13.5 | 22.8 | 10.1 | 16.9 |
| G37 | 11.9 | 31.6 | 9.3 | 23.4 |
| G38 | 11.3 | 35.4 | 10.0 | 17.6 |
| G39 | 12.3 | 29.5 | 7.9 | 34.8 |
| G40 | 9.8 | 44.0 | 7.2 | 40.9 |
| G41 | 14.0 | 19.8 | 10.8 | 10.7 |
| NSF 4 | 17.4 | 0.3 | 12.5 | –ve |
| NSF 5 | 16.5 | 9.1 | 12.3 | –ve |
| NSF 10 | 17.6 | –ve | 12.5 | –ve |
| NSF 16 | 17.7 | –ve | 12.0 | 1.1 |
| NSF 17 | 17.0 | 2.7 | 11.5 | 4.6 |
| NSF 18 | 16.6 | 8.6 | 11.2 | 7.3 |
| NSF 20 | 18.3 | –ve | 12.3 | –ve |
| NSF 21 | 16.8 | 3.6 | 12.3 | –ve |
| NSF 22 | 16.3 | 6.7 | 12.4 | –ve |
| NSF 26 | 18.4 | –ve | 12.8 | –ve |

Table 6 footnotes:
[1]Sera G23-41 are from patients with Graves' disease
Sera NSF are from healthy blood donors
[2]Mean binding in the presence of healthy blood donor sera was 17.4% for $^{125}$I-14D3.
[3]Inhibition of binding was calculated using the formula:

$$\% \text{ inhibition} = 100 - \left(\frac{A}{B} \times 100\right)$$

where
A = binding in the presence of test serum;
B = mean binding in the presence of healthy blood donor sera
[4]Mean binding in the presence of healthy blood donor sera was 12.1% for $^{125}$I-TSH.

TABLE 7

Effect of sera from various patients in TSHR coated tube binding by labelled TSH, 16E5 and 14D3

| Test sample | % inhibition of binding to TSHR coated tubes[2] using: | | |
|---|---|---|---|
| | $^{125}$I-TSH | $^{125}$I-16E5 | $^{125}$I-14D3 |
| G42/5 | 87 | 71 | 77 |
| G42/10 | 82 | 56 | 51 |
| G42/20 | 70 | 34 | 24 |
| D1/10 | 2 | 3 | 2 |
| D1/100 | –2 | 3 | 0 |
| D2/10 | 1 | 1 | –7 |
| D2/100 | –2 | 0 | 0 |
| A1/10 | –1 | 3 | 2 |
| A1/100 | –1 | 3 | –1 |
| A2/10 | 5 | 3 | 5 |
| A2/100 | 1 | 3 | 1 |

Table 7 footnotes:
[1]Serum G42 is from a patient with Graves' disease;
sera D1 and D2 are from patients with type 1 diabetes mellitus (positive for auto antibodies to glutamic acid decarboxylase);
sera A1 and A2 are from patients with Addison's disease (positive for steroid 21-hydroxylase autoantibodies)

All test sampes were diluted in a pool of serum from healthy blood donors and dilution factor shown as /5, /10, /20 or /100

[2]Inhibition of binding was calculated using the formula $$\% \text{ inhibition} = 100 - \left(\frac{A}{B} \times 100\right)$$

where
A = binding in the presence of test serum;
B = mean binding in the presence of a pool of healthy blood donor sera

TABLE 8

Effect of patient sera on binding of the TSHR to 16E5 F(ab)₂ coated tubes

| Test material[1] | $^{125}$I-43E1 labelled TSHR bound to 16E5 F(ab)₂ coated tubes (% total counts added) | Inhibition of binding[2] | Inhibition of TSH binding (%)[3] |
|---|---|---|---|
| G43 | 1.8 | 91.4 | 72.3 |
| G44 | 4.8 | 77.2 | 45.1 |
| G45 | 3.0 | 85.6 | 71.8 |
| G46 | 2.0 | 90.2 | 83.8 |
| G47 | 1.8 | 91.4 | 75.3 |
| NSF 10 | 17.8 | 14.4 | <14 |
| NSF 17 | 14.8 | 29.1 | <14 |
| NSF 21 | 13.5 | 34.9 | <14 |

Table 8 footnotes:
[1] Sera G43-47 are from patients wwith Graves' disease;
Sera NSF are from healthy blood donors
[2] Inhibition of binding was calculated using the formula:

$$\% \text{ inhibition} = 100 - \left(\frac{A}{B} \times 100\right)$$

where
A = binding 4E31 binding in the presence of test serum;
B = mean labelled 4E31 binding for healthy blood donor sera (15.4%)
[3] Inhibition of TSH binding >14% is positive; PEG method used

TABLE 9

Effect of patient sera on binding of the TSHR to 14D3 F(ab)₂ coated tubes

| Test material[1] | $^{125}$I-4E31 labelled TSHR bound to 14D3 F(ab)₂ coated tubes (% total counts added) | Inhibition of binding[2] | Inhibition of TSH binding (%)[3] |
|---|---|---|---|
| Serum A | 4.0 | 70 | 72 |
| Serum B | 6.9 | 49 | 40 |
| Serum C | 3.0 | 78 | 85 |
| Serum D | 2.6 | 81 | 80 |
| NSF 5 | 15.1 | −12 | <14 |
| NSF 17 | 14.6 | −9 | <14 |
| NSF 21 | 12.0 | 10 | <14 |
| NSF 23 | 11.8 | 12 | <14 |

Table 9 footnotes:
[1] Sera A-D are from patients with Graves' disease;
Sera NSF are from healthy blood donors
[2] Inhibition of binding was calculated using the formula:

$$\% \text{ inhibition} = 100 - \left(\frac{A}{B} \times 100\right)$$

where
A = labelled 4E31 binding in the presence of test serum;
B = mean labelled 4E31 binding for healthy blood donor sera (15.4%)
[3] Inhibition of TSH binding >14% is positive; PEG method used

TABLE 10

Inhibition of $^{125}$I-16E5 Fab binding to TSHR by TSHR MAbs

| IgG (100 μg/ml) | % inhibition | Epitope region (aa) |
|---|---|---|
| 16E5 | 70.4 | — |
| 17D3 | 68.8 | — |
| 14D3 | 67.6 | — |
| 17D2 | 69.2 | — |
| 2G2 | −ve | Thyroglobulin specific |
| 5D6 | −ve | 22-41 |
| 8E2 | −ve | 22-41 |
| 4B5 | 7.1 | 22-41 |
| 10C4 | −ve | 37-56 |
| 10D5 | −ve | 37-71 |
| 4D2 | −ve | 37-71 |
| 2E2 | −ve | 52-71 |
| 1D6 | −ve | 202-221 |
| 7B5 | −ve | 202-221 |
| 16B6 | −ve | 202-221 |
| 3C3 | 11.2 | 202-236 |
| 4B4 | −ve | 217-236 |
| 4E4 | −ve | 217-236 |
| 8D3 | −ve | 217-236 |
| 6D7 | −ve | 217-236 |
| 18C5 | 15.7 | 246-260 |
| 3C7 | 17 | 246-260 |
| 4D7 | 24.2 | 246-260 |
| 3B3 | 8.8 | 277-296 |
| 5B5 | −ve | 307-326 |
| 4E6 | −ve | 307-326 |
| 6E2 | −ve | 322-341 |
| 9C2 | −ve | 322-341 |
| 6B4 | −ve | 337-356 |
| 3E4 | −ve | 337-371 |
| 3F3 | −ve | 352-371 |
| 3B2 | −ve | 352-371 |
| 7C2 | −ve | 367-386 |
| 2B4 | −ve | 381-385 |
| 3E6 | 5.4 | 381-385 |
| 8E3 | 4.8 | 381-385 |
| 7C4 | −ve | 381-385 |
| 1D5 | 4.2 | 381-385 |
| 4E2 | −ve | 381-385 |
| 3D3 | −ve | 382-401 |
| 2C4 | −ve | 382-401 |
| 10C2 | −ve | 382-401 |
| 7E5 | −ve | 382-401 |

The invention claimed is:

1. A method of screening a sample of body fluid for TSH receptor autoantibodies wherein said sample is from a subject suspected of suffering from, susceptible to, having or recovering from autoimmune disease associated with an immune reaction to a TSH receptor, said method comprising:
   (a) contacting said sample with:
      a polypeptide comprising a full length TSH receptor so as to permit said polypeptide to bind with TSH receptor autoantibodies present in said sample; and
      one or more murine monoclonal antibodies capable of competing with autoantibodies to TSH receptor in the binding of said full length TSH receptor, wherein said one or more monoclonal antibodies is positive for thyroid stimulating activity at a concentration of 20 μg/ml in a cyclic AMP thyroid cell assay and inhibits binding of TSH to TSH receptor, said one or more monoclonal antibodies being classified as positive if the thyroid stimulating activity of said one or more monoclonal antibodies is greater than 180 percent in the cyclic AMP thyroid cell assay wherein said percent thyroid stimulating activity comprises 100 X ratio of cyclic AMP produced in the presence of said one or more monoclonal antibodies to cyclic AMP produced in the presence of sera pooled from healthy blood donors; and
   (b) detecting binding of said polypeptide with said autoantibodies thereby providing an indication of the presence of said autoantibodies in said sample.

2. A method of diagnosing the likely onset or presence of autoimmune disease associated with an immune reaction to a TSH receptor in a subject suspected of suffering from, susceptible to, having or recovering from, autoimmune disease associated with an immune reaction to a TSH receptor, the method comprising detecting autoantibodies produced in response to a TSH receptor in a sample of body fluid from the subject according to claim 1, and whereby the detected autoantibodies can provide a diagnosis of the likely onset or presence of autoimmune disease associated with an immune reaction to a TSH receptor in the subject.

3. A method according to claim 1, wherein said one or more monoclonal antibodies comprises a binding affinity of at least $10^8$ molar$^{-1}$ for TSH receptor.

4. A method according to claim 1, wherein said one or more monoclonal antibodies is positive for thyroid stimulating activity at a concentration of 2 μg/ml in the cyclic AMP thyroid cell assay.

5. A method according to claim 1, wherein said one or more monoclonal antibodies includes a monoclonal antibody comprising:
   i) a $V_H$ domain wherein CDR1 comprises amino acid residues 31 to 35 of SEQ ID NO: 67, CDR2 comprises amino acid residues 50 to 66 of SEQ ID NO:67, and CDR3 comprises amino acid residues 99 to 109 of SEQ ID NO:67; and
      a $V_L$ domain wherein CDR1 comprises amino acid residues 24 to 34 of SEQ ID NO:68, CDR2 comprises amino acid residues 50 to 56 of SEQ ID NO:68, and CDR3 comprises amino acid residues 89 to 97 of SEQ ID NO: 68;
ii) a $V_H$ domain wherein CDR1 comprises amino acid residues 31 to 35 of SEQ ID NO:69, CDR 2 comprises amino acid residues 50 to 66 of SEQ ID NO:69, and CDR 3 comprises amino acid residues 99 to 109 of SEQ ID NO:69, and
a $V_L$ domain wherein CDR1 comprises amino acid residues 24 to 34 of SEQ ID NO:70, CDR2 comprises amino acid residues 50 to 56 of SEQ ID NO:70, and CDR3 comprises amino acid residues 89 to 97 of SEQ ID NO: 70; or
iii) a $V_H$ domain wherein CDR1 comprises amino acid residues 31 to 35 of SEQ ID NO: 71, CDR2 comprises amino acid residues 50 to 66 of SEQ ID NO:71, and CDR 3 comprises amino acid residues 99 to 109 of SEQ ID NO:71, and
a $V_L$ domain wherein CDR1 comprises amino acid residues 24 to 34 of SEQ ID NO:72, CDR2 comprises amino acid residues 50 to 56 of SEQ ID NO:72, and CDR3 comprises amino acid residues 89 to 97 of SEQ ID NO: 72.

6. A method according to claim 1, wherein said one or more monoclonal antibodies includes a monoclonal antibody comprising:
i) a $V_H$ domain comprising amino acid residues 9 to 120 of SEQ ID NO:67 and a $V_L$ domain comprising amino acid residues 9 to 107 of SEQ ID NO:68;
ii) a $V_H$ domain comprising amino acid residues 9 to 120 of SEQ ID NO:69 and a $V_L$ domain comprising amino acid residues 9 to 107 of SEQ ID NO:70; or
iii) a $V_H$ domain comprising amino acid residues 9 to 120 of SEQ ID NO:71 and a $V_L$ domain comprising amino acid residues 9 to 107 of SEQ ID NO:72.

7. A method of screening a sample of body fluid for TSH receptor autoantibodies wherein said sample is from a subject suspected of suffering from, susceptible to, having or recovering from autoimmune disease associated with an immune reaction to a TSH receptor, said method comprising:
(a) providing said sample of body fluid from said subject;
(b) contacting said sample with
(i) a full length TSH receptor comprising amino acid residues 246-260, wherein the amino acid sequence of residues 246-260 comprises amino acid residues 47 to 61 of SEQ ID NO:17 or 22, and
(ii) one or more murine monoclonal antibodies capable of competing with autoantibodies to a TSH receptor in the binding of said full length TSH receptor, wherein said one or more competitor monoclonal antibodies is positive for thyroid stimulating activity at a concentration of 20 µg/ml in a cyclic AMP thyroid cell assay and inhibits binding of TSH to TSH receptor, said one or more monoclonal antibodies being classified as positive if the thyroid stimulating activity of said one or more monoclonal antibodies is greater than 180 percent in the cyclic AMP thyroid cell assay, said percent thyroid stimulating activity comprising 100× ratio of cyclic AMP produced in the presence of said one or more monoclonal competitor antibodies to cyclic AMP produced in the presence of sera pooled from healthy blood donors,
so as to permit said full length TSH receptor with either autoantibodies to TSH receptor present in said sample, or said one or more competitor monoclonal antibodies; and
(c) detecting the binding of said full length TSH receptor with said autoantibodies present in said sample, thereby providing an indication of the presence of said autoantibodies to a TSH receptor in said sample.

8. A method according to claim 7, wherein said one or more competitor monoclonal antibodies comprises a binding affinity of at least $10^8$ molar$^{-1}$ for TSH receptor.

9. A method according to claim 7, wherein said one or more monoclonal antibodies is positive for thyroid stimulating activity at a concentration of 2 µg/ml in the cyclic AMP thyroid cell assay.

10. A method according to claim 7, wherein said one or more monoclonal antibodies includes a monoclonal antibody comprising:
i) a $V_H$ domain wherein CDR1 comprises amino acid residues 31 to 35 of SEQ ID NO: 67, CDR2 comprises amino acid residues 50 to 66 of SEQ ID NO:67, and CDR3 comprises amino acid residues 99 to 109 of SEQ ID NO:67; and
a $V_L$ domain wherein CDR1 comprises amino acid residues 24 to 34 of SEQ ID NO:68, CDR2 comprises amino acid residues 50 to 56 of SEQ ID NO:68, and CDR3 comprises amino acid residues 89 to 97 of SEQ ID NO: 68;
ii) a $V_H$ domain wherein CDR1 comprises amino acid residues 31 to 35 of SEQ ID NO:69, CDR 2 comprises amino acid residues 50 to 66 of SEQ ID NO:69, and CDR 3 comprises amino acid residues 99 to 109 of SEQ ID NO:69, and
a $V_L$ domain wherein CDR1 comprises amino acid residues 24 to 34 of SEQ ID NO:70, CDR2 comprises amino acid residues 50 to 56 of SEQ ID NO:70, and CDR3 comprises amino acid residues 89 to 97 of SEQ ID NO: 70; or
iii) a $V_H$ domain wherein CDR1 comprises amino acid residues 31 to 35 of SEQ ID NO: 71, CDR2 comprises amino acid residues 50 to 66 of SEQ ID NO:71, and CDR 3 comprises amino acid residues 99 to 109 of SEQ ID NO:71, and
a $V_L$ domain wherein CDR1 comprises amino acid residues 24 to 34 of SEQ ID NO:72, CDR2 comprises amino acid residues 50 to 56 of SEQ ID NO:72, and CDR3 comprises amino acid residues 89 to 97 of SEQ ID NO: 72.

11. A method according to claim 7, wherein said one or more monoclonal antibodies includes a monoclonal antibody comprising:
i) a $V_H$ domain comprising amino acid residues 9 to 120 of SEQ ID NO:67 and a $V_L$ domain comprising amino acid residues 9 to 107 of SEQ ID NO:68;
ii) a $V_H$ domain comprising amino acid residues 9 to 120 of SEQ ID NO:69 and a $V_L$ domain comprising amino acid residues 9 to 107 of SEQ ID NO:70; or
iii) a $V_H$ domain comprising amino acid residues 9 to 120 of SEQ ID NO:71 and a $V_L$ domain comprising amino acid residues 9 to 107 of SEQ ID NO:72.

12. A method of screening a sample of body fluid for autoantibodies to a TSH receptor wherein said sample is from a subject suspected of suffering from, susceptible to, having or recovering from autoimmune disease associated with an immune reaction to a TSH receptor, said method comprising:
(a) contacting said sample with
(i) a full length TSH receptor, one or more epitopes thereof or a and
(ii) one or more murine monoclonal antibodies for the TSH receptor, wherein said one or more monoclonal antibodies:

does not comprise naturally produced autoantibodies to the TSH receptor, inhibits binding of TSH to TSH receptor, and is positive for thyroid stimulating activity at a concentration of 20 μg/ml in a cyclic AMP thyroid cell assay, said one or more monoclonal antibodies being classified as positive if the thyroid stimulating activity of said one or more monoclonal antibodies is greater than 180 percent in the cyclic AMP thyroid cell assay, wherein said percent thyroid stimulating activity comprises 100× ratio of cyclic AMP produced in the presence of said one or more monoclonal antibodies to cyclic AMP produced in the presence of sera pooled from healthy blood donors;

so as to permit said TSH receptor to bind with either autoantibodies to TSH receptor present in said sample, or said one or more monoclonal antibodies for the TSH receptor; and (b) detecting binding of said TSH receptor, with said autoantibodies present in said sample, thereby providing an indication of the presence of said autoantibodies to TSH receptor in said sample.

13. A method according to claim 12, which comprises providing labeling means for said one or more monoclonal antibodies for a TSH receptor.

14. A method according to claim 12, wherein said one or more monoclonal antibodies comprises a binding affinity of at least $10^8$ molar$^{-1}$ for TSH receptor.

15. A method according to claim 12, wherein said one or more monoclonal antibodies is positive for thyroid stimulating activity at a concentration of 2 μg/ml in the cyclic AMP thyroid cell assay.

16. A method according to claim 12, wherein said one or more monoclonal antibodies includes a monoclonal antibody comprising:

i) a $V_H$ domain wherein CDR1 comprises amino acid residues 31 to 35 of SEQ ID NO: 67, CDR2 comprises amino acid residues 50 to 66 of SEQ ID NO:67, and CDR3 comprises amino acid residues 99 to 109 of SEQ ID NO:67; and a $V_L$ domain wherein CDR1 comprises amino acid residues 24 to 34 of SEQ ID NO:68, CDR2 comprises amino acid residues 50 to 56 of SEQ ID NO:68, and CDR3 comprises amino acid residues 89 to 97 of SEQ ID NO: 68;

ii) a $V_H$ domain wherein CDR1 comprises amino acid residues 31 to 35 of SEQ ID NO:69, CDR 2 comprises amino acid residues 50 to 66 of SEQ ID NO:69, and CDR3 comprises amino acid residues 99 to 109 of SEQ ID NO:69, and a $V_L$ domain wherein CDR1 comprises amino acid residues 24 to 34 of SEQ ID NO:70, CDR2 comprises amino acid residues 50 to 56 of SEQ ID NO:70, and CDR3 comprises amino acid residues 89 to 97 of SEQ ID NO: 70; or iii) a $V_H$ domain wherein CDR1 comprises amino acid residues 31 to 35 of SEQ ID NO: 71, CDR2 comprises amino acid residues 50 to 66 of SEQ ID NO:71, and CDR3 comprises amino acid residues 99 to 109 of SEQ ID NO:71, and a $V_L$ domain wherein CDR1 comprises amino acid residues 24 to 34 of SEQ ID NO:72, CDR2 comprises amino acid residues 50 to 56 of SEQ ID NO:72, and CDR3 comprises amino acid residues 89 to 97 of SEQ ID NO: 72.

17. A method according to claim 12, wherein said one or more monoclonal antibodies includes a monoclonal antibody comprising:

i) a $V_H$ domain comprising amino acid residues 9 to 120 of SEQ ID NO:67 and a $V_L$ domain comprising amino acid residues 9 to 107 of SEQ ID NO:68;

ii) a $V_H$ domain comprising amino acid residues 9 to 120 of SEQ ID NO:69 and a $V_L$ domain comprising amino acid residues 9 to 107 of SEQ ID NO:70; or iii) a $V_H$ domain comprising amino acid residues 9 to 120 of SEQ ID NO:71 and a $V_L$ domain comprising amino acid residues 9 to 107 of SEQ ID NO:72.

18. A method of screening a sample of body fluid for TSH receptor autoantibodies wherein said sample is from a subject suspected of suffering from, susceptible to, having or recovering from autoimmune disease associated with an immune reaction to a TSH receptor, said method comprising:

(a) contacting said sample with (i) a full length TSH receptor, and (ii) one or more murine monoclonal antibodies for said TSH receptor, wherein said one or more monoclonal antibodies is positive for thyroid stimulating activity at a concentration of 20 μg/ml in a cyclic AMP thyroid cell assay and inhibits binding of TSH to TSH receptor, said one or more monoclonal antibodies being classified as positive if the thyroid stimulating activity of said one or more monoclonal antibodies is greater than 180 percent in the cyclic AMP thyroid cell assay, said percent thyroid stimulating activity comprising 100× ratio of cyclic AMP produced in the presence of said one or more monoclonal antibodies to cyclic AMP produced in the presence of sera pooled from healthy blood donors;

so as to permit said TSH receptor to bind with either autoantibodies to said TSH receptor present in said sample, or said one or more monoclonal antibodies; and (b) detecting binding of said TSH receptor with said autoantibodies present in said sample, thereby providing an indication of the presence of said autoantibodies to TSH receptor in said sample;

wherein said one or more monoclonal antibodies for said TSH receptor are directly or indirectly immobilised to a surface either prior to, or after step (a).

19. A method according to claim 18, wherein said one or more monoclonal antibodies does not comprise naturally produced autoantibodies to the TSH receptor.

20. A method according to claim 18, which comprises providing labeling means for said TSH receptor.

21. A method according to claim 18, wherein said one or more monoclonal antibodies comprises a binding affinity of at least $10^8$ molar$^{-1}$ for TSH receptor.

22. A method according to claim 18, wherein said one or more monoclonal antibodies is positive for thyroid stimulating activity at a concentration of 2 μg/ml in the cyclic AMP thyroid cell assay.

23. A method according to claim 18, wherein said one or more monoclonal antibodies includes a monoclonal antibody comprising:

i) a $V_H$ domain wherein CDR1 comprises amino acid residues 31 to 35 of SEQ ID NO: 67, CDR2 comprises amino acid residues 50 to 66 of SEQ ID NO:67, and CDR3 comprises amino acid residues 99 to 109 of SEQ ID NO:67; and a $V_L$ domain wherein CDR1 comprises amino acid residues 24 to 34 of SEQ ID NO:68, CDR2 comprises amino acid residues 50 to 56 of SEQ ID NO:68, and CDR3 comprises amino acid residues 89 to 97 of SEQ ID NO: 68;
ii) a $V_H$ domain wherein CDR1 comprises amino acid residues 31 to 35 of SEQ ID NO:69, CDR 2 comprises amino acid residues 50 to 66 of SEQ ID NO:69, and CDR3 comprises amino acid residues 99 to 109 of SEQ ID NO:69, and
a $V_L$ domain wherein CDR1 comprises amino acid residues 24 to 34 of SEQ ID NO:70, CDR2 comprises amino acid residues 50 to 56 of SEQ ID NO:70, and CDR3 comprises amino acid residues 89 to 97 of SEQ ID NO: 70; or
iii) a $V_H$ domain wherein CDR1 comprises amino acid residues 31 to 35 of SEQ ID NO: 71, CDR2 comprises amino acid residues 50 to 66 of SEQ ID NO:71, and CDR3 comprises amino acid residues 99 to 109 of SEQ ID NO:71, and
a $V_L$ domain wherein CDR1 comprises amino acid residues 24 to 34 of SEQ ID NO:72, CDR2 comprises amino acid residues 50 to 56 of SEQ ID NO:72, and CDR3 comprises amino acid residues 89 to 97 of SEQ ID NO: 72.

24. A method according to claim 18, wherein said one or more monoclonal antibodies includes a monoclonal antibody comprising:
i) a $V_H$ domain comprising amino acid residues 9 to 120 of SEQ ID NO:67 and a $V_L$ domain comprising amino acid residues 9 to 107 of SEQ ID NO:68;
ii) a $V_H$ domain comprising amino acid residues 9 to 120 of SEQ ID NO:69 and a $V_L$ domain comprising amino acid residues 9 to 107 of SEQ ID NO:70; or
iii) a $V_H$ domain comprising amino acid residues 9 to 120 of SEQ ID NO:71 and a $V_L$ domain comprising amino acid residues 9 to 107 of SEQ ID NO:72.

* * * * *